(12) United States Patent
Lefer et al.

(10) Patent No.: US 11,497,775 B2
(45) Date of Patent: Nov. 15, 2022

(54) COMPOSITIONS AND METHODS FOR TREATING CARDIAC INJURY

(71) Applicant: THE BOARD OF SUPERVISORS OF LOUISIANA STATE UNIVERSITY AND AGRICULTURAL AND MECHANICAL COLLEGE, Baton Rouge, LA (US)

(72) Inventors: David J. Lefer, Saint Bernard, LA (US); David J. Polhemus, Metairie, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 539 days.

(21) Appl. No.: 16/265,067

(22) Filed: Feb. 1, 2019

(65) Prior Publication Data
US 2019/0160106 A1  May 30, 2019

Related U.S. Application Data

(63) Continuation-in-part of application No. PCT/US2017/044818, filed on Aug. 1, 2017.
(Continued)

(51) Int. Cl.
*A61B 18/12* (2006.01)
*A61K 35/28* (2015.01)
(Continued)

(52) U.S. Cl.
CPC .............. *A61K 35/28* (2013.01); *A61B 18/12* (2013.01); *A61B 18/1206* (2013.01);
(Continued)

(58) Field of Classification Search
CPC ........ A61K 35/28; A61K 35/34; A61B 18/12; A61B 18/14; A61B 18/1442;
(Continued)

(56) References Cited

U.S. PATENT DOCUMENTS

2002/0052621 A1* 5/2002 Fried ...................... A61B 18/24
606/192
2011/0264086 A1* 10/2011 Ingle ................... A61B 18/1492
606/33

FOREIGN PATENT DOCUMENTS

| WO | 99/49015 | 9/1999 |
| WO | 2011/094367 | 8/2011 |

(Continued)

OTHER PUBLICATIONS

Babbs, Anterior-Posterior Impedance Cardiography: A New Approach to Accurate, Non-Invasive Monitoring of Cardiac Function, 2010 (Year: 2010).*
(Continued)

*Primary Examiner* — Amber R Stiles
(74) *Attorney, Agent, or Firm* — Baker Donelson

(57) ABSTRACT

This invention is directed to compositions and methods for treating a condition of the heart. In an embodiment, the invention is directed to a method of treating a subject in need thereof, wherein the method comprises ablating at least one nerve of the renal artery of the subject; and administering to the subject a therapeutically effective amount of cells.

20 Claims, 157 Drawing Sheets
(141 of 157 Drawing Sheet(s) Filed in Color)

Related U.S. Application Data

(60) Provisional application No. 62/489,537, filed on Apr. 25, 2017, provisional application No. 62/455,852, filed on Feb. 7, 2017, provisional application No. 62/369,432, filed on Aug. 1, 2016.

(51) Int. Cl.
    A61B 18/14    (2006.01)
    A61K 35/34    (2015.01)
    A61B 18/00    (2006.01)

(52) U.S. Cl.
    CPC .......... *A61B 18/14* (2013.01); *A61B 18/1442* (2013.01); *A61B 18/1492* (2013.01); *A61K 35/34* (2013.01); *A61B 2018/0063* (2013.01); *A61B 2018/0072* (2013.01); *A61B 2018/00404* (2013.01); *A61B 2018/00434* (2013.01); *A61B 2018/00511* (2013.01); *A61B 2018/00577* (2013.01); *A61B 2018/00648* (2013.01); *A61B 2018/00732* (2013.01); *A61B 2018/00767* (2013.01); *A61B 2018/00779* (2013.01); *A61B 2018/00875* (2013.01); *A61B 2018/00994* (2013.01); *A61B 2018/1455* (2013.01)

(58) Field of Classification Search
    CPC ............ A61B 18/1206; A61B 18/1492; A61B 2018/1455; A61B 2018/00875; A61B 2018/0063; A61B 2018/00767; A61B 2018/00779; A61B 2018/00994; A61B 2018/00732; A61B 2018/0072; A61B 2018/00648; A61B 2018/00404; A61B 2018/00434; A61B 2018/00511; A61B 2018/00577
    See application file for complete search history.

(56) References Cited

FOREIGN PATENT DOCUMENTS

| | | |
|---|---|---|
| WO | 2013/059735 | 4/2013 |
| WO | 2017/066121 | 6/2017 |

OTHER PUBLICATIONS

Grogan, Ejection Fraction: What Does It Measure?, 2014, Mayoclinic online, available at https://www.mayoclinic.org/ejection-fraction/expert-answers/faq-20058286. (Year: 2014).*

Eirin et al., Intrarenal Delivery of Mesenchymal Stem Cells and Endothelieal Progentiro Cells Attenuates Hypertensive Cardiomyopathy in Experimental Renovascular Hypertension, 2015, Cell Transplantation, vol. 24, pp. 2041-2053. (Year: 2015).*

Abdel-Latif, Ahmed, et al. "Adult bone marrow-derived cells for cardiac repair: a systematic review and meta-analysis." Archives of internal medicine 167.10 (2007): 989-997.

Anand-Srivastava, Madhu B. "Enhanced expression of inhibitory guanine nucleotide regulatory protein in spontaneously hypertensive rats. Relationship to adenylate cyclase inhibition." Biochemical Journal 288.1 (1992): 79-85.

Azizi, Michel, et al. "Endovascular ultrasound renal denervation to treat hypertension (Radiance-HTN SOLO): a multicentre, international, single-blind, randomised, sham-controlled trial." The Lancet 391.10137 (2018): 2335-2345.

Bhatt, Deepak L., et al. "A controlled trial of renal denervation for resistant hypertension." N Engl J Med 370 (2014): 1393-1401.

Bhushan, Shashi, et al. "Nitrite therapy improves left ventricular function during heart failure via restoration of nitric oxide-mediated cytoprotective signaling." Circulation research 114.8 (2014): 1281-1291.

Bolli, Roberto. "Repeated cell therapy: a paradigm shift whose time has come." Circulation research 120.7 (2017): 1072-1074.

Booz, George W. "Putting the brakes on cardiac hypertrophy: exploiting the NO-cGMP counter-regulatory system." Hypertension 45.3 (2005): 341-346.

Brouri, Fazia, et al. "Blockade of ß1-and desensitization of ß2-adrenoceptors reduce isoprenaline-induced cardiac fibrosis." European journal of pharmacology 485.1-3 (2004): 227-234.

Burchfield, Jana S., and Stefanie Dimmeler. "Role of paracrine factors in stem and progenitor cell mediated cardiac repair and tissue fibrosis." Fibrogenesis & tissue repair 1.1 (2008): 1-11.

Cargnoni, Anna, et al. "Role of bradykinin and eNOS in the anti-ischaemic effect of trandolapril." British journal of pharmacology 133.1 (2001): 145.

Carpenter, Todd C., and Kurt R. Stenmark. "Hypoxia decreases lung neprilysin expression and increases pulmonary vascular leak." American Journal of Physiology-Lung Cellular and Molecular Physiology 281.4 (2001): L941-L948.

Chade AR, et al. Endothelial progenitor cells restore renal function in chronic experimental renovascular disease. Circulation. Feb. 3, 2009;119(4):547-57.

Chakravarty T, et al. ALLogeneic Heart STem Cells to Achieve Myocardial Regeneration (ALLSTAR) Trial: Rationale and Design. Cell Transplant. Feb. 16, 2017;26(2):205-214.

Chatterjee, Neal A., and Jagmeet P. Singh. "Novel interventional therapies to modulate the autonomic tone in heart failure." JACC: Heart Failure 3.10 (2015): 786-802.

Chavakis, Emmanouil, Masamichi Koyanagi, and Stefanie Dimmeler. "Enhancing the outcome of cell therapy for cardiac repair: progress from bench to bedside and back." Circulation 121.2 (2010): 325-335.

Chen, Liwen, et al. "Paracrine factors of mesenchymal stem cells recruit macrophages and endothelial lineage cells and enhance wound healing." PloS one 3.4 (2008): e1886.

Chen, Shao-Liang, et al. "Effect on left ventricular function of intracoronary transplantation of autologous bone marrow mesenchymal stem cell in patients with acute myocardial infarction." The American journal of cardiology 94.1 (2004): 92-95.

Colucci, Wilson S., et al. "Intravenous nesiritide, a natriuretic peptide, in the treatment of decompensated congestive heart failure." New England Journal of Medicine 343.4 (2000): 246-253.

De Couto, Geoffrey, et al. "Exosomal microRNA transfer into macrophages mediates cellular postconditioning." Circulation 136.2 (2017): 200-214.

De Couto, Geoffrey, et al. "Macrophages mediate cardioprotective cellular postconditioning in acute myocardial infarction." The Journal of clinical investigation 125.8 (2015): 3147-3162.

Deddish, Peter A., et al. "Neprilysin inhibitors potentiate effects of bradykinin on B2 receptor." Hypertension 39.2 (2002): 619-623.

Eirin, Alfonso, et al. "Intrarenal delivery of mesenchymal stem cells and endothelial progenitor cells attenuates hypertensive cardiomyopathy in experimental renovascular hypertension." Cell transplantation 24.10 (2015): 2041-2053.

Fala, Loretta. "Entresto (Sacubitril/Valsartan): first-in-class angiotensin receptor neprilysin inhibitor FDA approved for patients with heart failure." American health & drug benefits 8.6 (2015): 330.

Feola, Mauro, et al. "Cardiotoxicity after anthracycline chemotherapy in breast carcinoma: effects on left ventricular ejection fraction, troponin I and brain natriuretic peptide." International journal of cardiology 148.2 (2011): 194-198.

Fisher, Sheila A., et al. "Meta-analysis of cell therapy trials for patients with heart failure." Circulation research 116.8 (2015): 1361-1377.

Flather, Marcus D., et al. "Long-term ACE-inhibitor therapy in patients with heart failure or left-ventricular dysfunction: a systematic overview of data from individual patients." The Lancet 355.9215 (2000): 1575-1581.

Francis GS, Felker GM, Tang WH. A Test in Context: Critical Evaluation of Natriuretic Peptide Testing in Heart Failure. J Am Coll Cardiol. Jan. 26, 2016;67(3):330-7.

Gallet, Romain, et al. "Exosomes secreted by cardiosphere-derived cells reduce scarring, attenuate adverse remodelling, and improve function in acute and chronic porcine myocardial infarction." European heart journal 38.3 (2017): 201-211.

(56) References Cited

OTHER PUBLICATIONS

Garbern, Jessica C., and Richard T. Lee. "Cardiac stem cell therapy and the promise of heart regeneration." Cell stem cell 12.6 (2013): 689-698.
Garg, Rekha, et al. "Overview of randomized trials of angiotensin-converting enzyme inhibitors on mortality and morbidity in patients with heart failure." Jama 273.18 (1995): 1450-1456.
Geiger, Adolf, Audrey Walker, and Erwin Nissen. "Human fibrocyte-derived exosomes accelerate wound healing in genetically diabetic mice." Biochemical and biophysical research communications 467.2 (2015): 303-309.
Gnecchi, Massimiliano, et al. "Paracrine mechanisms in adult stem cell signaling and therapy." Circulation research 103.11 (2008): 1204-1219.
Gonzales, Christine, and Thierry Pedrazzini. "Progenitor cell therapy for heart disease." Experimental cell research 315.18 (2009): 3077-3085.
Goodchild, Traci, et al. "Safety of intramyocardial injection of autologous bone marrow cells to treat myocardial ischemia in pigs." Cardiovascular Revascularization Medicine 7.3 (2006): 136-145.
Guo, Yiru, et al. "Repeated doses of cardiac mesenchymal cells are therapeutically superior to a single dose in mice with old myocardial infarction." Basic research in cardiology 112.2 (2017): 18.
Gyöngyösi, Mariann, et al. "Meta-Analysis of Cell-based CaRdiac stUdiEs (ACCRUE) in patients with acute myocardial infarction based on individual patient data." Circulation research 116.8 (2015): 1346-1360.
Hajjar, Roger J., et al. "Modulation of ventricular function through gene transfer in vivo." Proceedings of the National Academy of Sciences 95.9 (1998): 5251-5256.
Hastings, Conn L., et al. "Drug and cell delivery for cardiac regeneration." Advanced drug delivery reviews 84 (2015): 85-106.
Hodgkinson, Conrad P., et al. "Emerging concepts in paracrine mechanisms in regenerative cardiovascular medicine and biology." Circulation research 118.1 (2016): 95-107.
Hong, Kyung U., et al. "c-kit+ Cardiac stem cells alleviate post-myocardial infarction left ventricular dysfunction despite poor engraftment and negligible retention in the recipient heart." PloS one 9.5 (2014): e96725.
Huang ZM, Gao E, Chuprun JK, Koch WJ. GRK2 in the heart: a GPCR kinase and beyond. Antioxid Redox Signal. Nov. 10, 2014;21(14):2032-43.
Hunt, P. J., et al. "The role of the circulation in processing pro-brain natriuretic peptide (proBNP) to amino-terminal BNP and BNP-32." Peptides 18.10 (1997): 1475-1481.
International Search Report for PCT/US2017/044818, dated Oct. 6, 2017.
James, Paul A., et al. "2014 evidence-based guideline for the management of high blood pressure in adults: report from the panel members appointed to the Eighth Joint National Committee (JNC 8)." Jama 311.5 (2014): 507-520.
Janssens S, et al. Autologous bone marrow-derived stem-cell transfer in patients with ST-segment elevation myocardial infarction: double-blind, randomised controlled trial. Lancet. Jan. 14, 2006;367(9505):113-21.
Jones, Steven P., et al. "The NHLBI-Sponsored Consortium for preclinicAl assESsment of cARdioprotective Therapies (CAESAR) A New Paradigm for Rigorous, Accurate, and Reproducible Evaluation of Putative Infarct-Sparing Interventions in Mice, Rabbits, and Pigs." Circulation research 116.4 (2015): 572-586.
Kandzari, D. E., et al. "Investigators SH-OMT. Effect of renal denervation on blood pressure in the presence of antihypertensive drugs: 6-month efficacy and safety results from the SPYRAL HTN-ON MED proof-of-concept randomised trial." Lancet 391. 10137 (2018): 2346-2355.
Kapoun, Ann M., et al. "B-type natriuretic peptide exerts broad functional opposition to transforming growth factor-ß in primary human cardiac fibroblasts: fibrosis, myofibroblast conversion, proliferation, and inflammation." Circulation research 94.4 (2004): 453-461.

Karlsberg, Ronald P., et al. "Rapid activation of the sympathetic nervous system following coronary artery occlusion: relationship to infarct size, site, and haemodynamic impact." Cardiovascular research 13.9 (1979): 523-531.
Kearney, Patricia M., et al. "Global burden of hypertension: analysis of worldwide data." The lancet 365.9455 (2005): 217-223.
Khan M, et al. Embryonic stem cell-derived exosomes promote endogenous repair mechanisms and enhance cardiac function following myocardial infarction. Circ Res. Jun. 19, 2015;117(1):52-64.
King, Adrienne L., et al. "Hydrogen sulfide cytoprotective signaling is endothelial nitric oxide synthase-nitric oxide dependent." Proceedings of the National Academy of Sciences 111.8 (2014): 3182-3187.
Krum, Henry, et al. "Catheter-based renal sympathetic denervation for resistant hypertension: a multicentre safety and proof-of-principle cohort study." The Lancet 373.9671 (2009): 1275-1281.
Lapchak PA, et al. Intravenous xenogeneic human cardiosphere-derived cell extracellular vesicles (exosomes) improves behavioral function in small-clot embolized rabbits. Exp Neurol 2018.
Lefer, David J., and Eduardo Marbán. "Is cardiopratection dead?." Circulation 136.1 (2017): 98-109.
Levin, Ellis R., David G. Gardner, and Willis K. Samson. "Natriuretic peptides." New England Journal of Medicine 339.5 (1998): 321-328.
Limas, Catherine, and Constantinos J. Limas. "Reduced number of ß-adrenergic receptors in the myocardium of spontaneously hypertensive rats." Biochemical and biophysical research communications 83.2 (1978): 710-714.
Linz, Wolfgang, Gabriele Wiemer, and Bernward A. Schölkens. "ACE-inhibition induces NO-formation in cultured bovine endothelial cells and protects isolated ischemic rat hearts." Journal of molecular and cellular cardiology 24.8 (1992): 909-919.
Lu, Bao, et al. "The control of microvascular permeability and blood pressure by neutral endopeptidase." Nature medicine 3.8 (1997): 904-907.
Mahfoud, Felix, et al. "Expert consensus document from the European Society of Cardiology on catheter-based renal denervation." European Heart Journal 34.28 (2013): 2149-2157.
Makkar, Raj R., et al. "Intracoronary cardiosphere-derived cells for heart regeneration after myocardial infarction (CADUCEUS): a prospective, randomised phase 1 trial." The Lancet 379.9819 (2012): 895-904.
Malliaras, Konstantinos, et al. "Intracoronary cardiosphere-derived cells after myocardial infarction: evidence of therapeutic regeneration in the final 1-year results of the CADUCEUS trial (CArdiosphere-Derived aUtologous stem CElls to reverse ventricUlar dySfunction)." Journal of the American College of Cardiology 63.2 (2014): 110-122.
Marbán, Eduardo. "A mechanistic roadmap for the clinical application of cardiac cell therapies." Nature biomedical engineering 2.6 (2018): 353-361.
Martin-Rendon, Enca, et al. "Autologous bone marrow stem cells to treat acute myocardial infarction: a systematic review." European heart journal 29.15 (2008): 1807-1818.
McMurray, John JV, et al. "Angiotensin-neprilysin inhibition versus enalapril in heart failure." N Engl J Med 371 (2014): 993-1004.
McMurray, John JV, et al. "Effects of candesartan in patients with chronic heart failure and reduced left-ventricular systolic function taking angiotensin-converting-enzyme inhibitors: the CHARM-Added trial." The Lancet 362.9386 (2003): 767-771.
Menasché P, et al. The Myoblast Autologous Grafting in Ischemic Cardiomyopathy (MAGIC) trial: first randomized placebo-controlled study of myoblast transplantation. Circulation. Mar. 4, 2008;117(9):1189-200.
Mohan, Puneet, et al. "Myocardial contractile response to nitric oxide and cGMP." Circulation 93.6 (1996): 1223-1229.
Moro C, Lafontan M. Natriuretic peptides and cGMP signaling control of energy homeostasis. Am J Physiol Heart Circ Physiol. Feb. 1, 2013;304(3):H358-68.
Morstyn, G. and W. Sheridan, Cell Therapy: Stem Cell Transplantation, Gene Therapy, and Cellular Immunotherapy, Cambridge University Press, 1996.

(56) References Cited

OTHER PUBLICATIONS

Mozaffarian D, et al. Heart disease and stroke statistics—2015 update: a report from the American Heart Association. Circulation. Jan. 27, 2015;131(4):e29-322.
Mozaffarian D, et al. Heart Disease and Stroke Statistics—2016 Update: A Report From the American Heart Association Circulation. Jan. 26, 2016;133(4):e38-360.
Murry, Charles E., Loren J. Field, and Philippe Menasche'. "Cell-based cardiac repair: reflections at the 10-year point." Circulation 112.20 (2005): 3174-3183.
Nishikimi T, Maeda N, Matsuoka H. The role of natriuretic peptides in cardiopratection. Cardiovasc Res. Feb. 1, 2006;69(2):318-28.
Oliver, Paula M., et al. "Hypertension, cardiac hypertrophy, and sudden death in mice lacking natriuretic peptide receptor A." Proceedings of the National Academy of Sciences 94.26 (1997): 14730-14735.
Packer M, et al. Angiotensin receptor neprilysin inhibition compared with enalapril on the risk of clinical progression in surviving patients with heart failure. Circulation Jan. 6, 2015;131(1):54-61.
Packer, Milton, et al. "The effect of carvedilol on morbidity and mortality in patients with chronic heart failure." New England Journal of Medicine 334.21 (1996): 1349-1355.
Palazzuoli, Alberto, et al. "Natriuretic peptides (BNP and NT-proBNP): measurement and relevance in heart failure." Vascular health and risk management 6 (2010): 411.
Pankow, Kristin, et al. "Successive action of meprin A and neprilysin catabolizes B-type natriuretic peptide." Circulation research 101.9 (2007): 875-882.
Pereira, Naveen L., et al. "Natriuretic peptide pharmacogenetics: membrane metallo-endopeptidase (MME): common gene sequence variation, functional characterization and degradation." Journal of molecular and cellular cardiology 49.5 (2010): 864-874.
Perin, Emerson C., et al. "Adipose-derived regenerative cells in patients with ischemic cardiomyopathy: The PRECISE Trial." American heart journal 168.1 (2014): 88-95.
Polhemus, David J., et al. "Radiofrequency renal denervation protects the ischemic heart via inhibition of GRK2 and increased nitric oxide signaling." Circulation research 119.3 (2016): 470-480.
Polhemus, David J., et al. "Renal sympathetic denervation protects the failing heart via inhibition of neprilysin activity in the kidney." Journal of the American College of Cardiology 70.17 (2017): 2139-2153.
Potter, Lincoln R. "Natriuretic peptide metabolism, clearance and degradation." The FEBS journal 278.11 (2011): 1808-1817.
Potter, Lincoln R., et al. "Natriuretic peptides: their structures, receptors, physiologic functions and therapeutic applications." cGMP: Generators, Effectors and Therapeutic Implications (2009): 341-366.
Principles of Laboratory Animal Care formulated by the National Society of Medical Research and the Guide for the Care and Use of Laboratory Animals published by the NIH (Revised 2011).
Reich, Heidi, et al. "Repeated transplantation of allogeneic cardiosphere-derived cells boosts therapeutic benefits without immune sensitization in a rat model of myocardial infarction." The Journal of Heart and Lung Transplantation 35.11 (2016): 1348-1357.
Reinhardt, Christopher P., et al. "Stable labeled microspheres to measure perfusion: validation of a neutron activation assay technique." American Journal of Physiology-Heart and Circulatory Physiology 280.1 (2001): H108-H116.
Ripa RS, et al. Stem cell mobilization induced by subcutaneous granulocyte-colony stimulating factor to improve cardiac regeneration after acute ST-elevation myocardial infarction: result of the double-blind, randomized, placebo-controlled stem cells in myocardial infarction (STEMMI) trial. Circulation. Apr. 25, 2006;113(16):1983-92.
Ruskoaho, Heikki. "Atrial natriuretic peptide: synthesis, release and metabolism." Pharmacol Rev 44 (1992): 479-601.
Russo, Valerio, et al. "Mesenchymal stem cell delivery strategies to promote cardiac regeneration following ischemic injury." Biomaterials 35.13 (2014): 3956-3974.
Saito, Takashi, et al. "Somatostatin regulates brain amyloid ß peptide Aß 42 through modulation of proteolytic degradation." Nature medicine 11.4 (2005): 434-439.
Sanganalmath, Santosh K., and Roberto Bolli. "Cell therapy for heart failure: a comprehensive overview of experimental and clinical studies, current challenges, and future directions." Circulation research 113.6 (2013): 810-834.
Schächinger, Volker, et al. "Pilot trial on determinants of progenitor cell recruitment to the infarcted human myocardium." Circulation 118.14 (2008): 1425-1432.
Seino, Yoshihiko, et al. "Application of NT-proBNP and BNP measurements in cardiac care: a more discerning marker for the detection and evaluation of heart failure." European journal of heart failure 6.3 (2004): 295-300.
Sharp III, Thomas E., et al. "Renal denervation prevents heart failure progression via inhibition of the renin-angiotensin system." Journal of the American College of Cardiology 72.21 (2018): 2609-2621.
Solomon, Scott D., et al. "The angiotensin receptor neprilysin inhibitor LCZ696 in heart failure with preserved ejection fraction: a phase 2 double-blind randomised controlled trial." The Lancet 380.9851 (2012): 1387-1395.
Stephenson, Sally L., and A. John Kenny. "The hydrolysis of a-human atrial natriuretic peptide by pig kidney microvillar membranes is initiated by endopeptidase-24.11." Biochemical Journal 243.1 (1987): 183-187.
Symplicity HTN-2 Investigators. "Renal sympathetic denervation in patients with treatment-resistant hypertension (The Symplicity HTN-2 Trial): a randomised controlled trial." The Lancet 376.9756 (2010): 1903-1909.
Townsend, Raymond R., et al. "Catheter-based renal denervation in patients with uncontrolled hypertension in the absence of antihypertensive medications (SPYRAL HTN-OFF MED): a randomised, sham-controlled, proof-of-concept trial." The Lancet 390.10108 (2017): 2160-2170.
Triposkiadis F, et al. The sympathetic nervous system in heart failure physiology, pathophysiology, and clinical implications. J Am Coll Cardiol. Nov. 3, 2009;54(19):1747-62.
Troughton, Richard W., et al. "Treatment of heart failure guided by plasma aminoterminal brain natriuretic peptide (N-BNP) concentrations." The Lancet 355.9210 (2000): 1126-1130.
Vodovar, Nicolas, et al. "Post-translational modifications enhance NT-proBNP and BNP production in acute decompensated heart failure." European heart journal 35.48 (2014): 3434-3441.
Voigt, Jeff, et al. "A reevaluation of the costs of heart failure and its implications for allocation of health resources in the United States." Clinical cardiology 37.5 (2014): 312-321.
Vu, Duc Thang, and Theo Kofidis. "Myocardial restoration: is it the cell or the architecture or both?." Cardiology research and practice 2012 (2012).
Wang, Thomas J. "The natriuretic peptides and fat metabolism." New England Journal of Medicine 367.4 (2012): 377-378.
Watson AM, et al. Mechanisms of sympathetic activation in heart failure. Clin Exp Pharmacol Physiol. Dec. 2006;33(12):1269-74.
Weber, Michael, and Christian Hamm. "Role of B-type natriuretic peptide (BNP) and NT-proBNP in clinical routine." Heart 92.6 (2006): 843-849.
White, Ian A., et al. "Sympathetic reinnervation is required for mammalian cardiac regeneration." Circulation research 117.12 (2015): 990-994.
Worthley, Stephen G., et al. "Safety and efficacy of a multi-electrode renal sympathetic denervation system in resistant hypertension: the EnligHTN I trial." European heart journal 34.28 (2013): 2132-2140.
Written Opinion of the International Searching Authority for PCT/US2017/044818, dated Oct. 6, 2017.
Yamaguchi, Toru, Hiroshi Kido, and Nobuhiko Katunuma. "A membrane-bound metallo-endopeptidase from rat kidney: Characteristics of its hydrolysis of peptide hormones and neuropeptides." European journal of biochemistry 204.2 (1992): 547-552.

\* cited by examiner

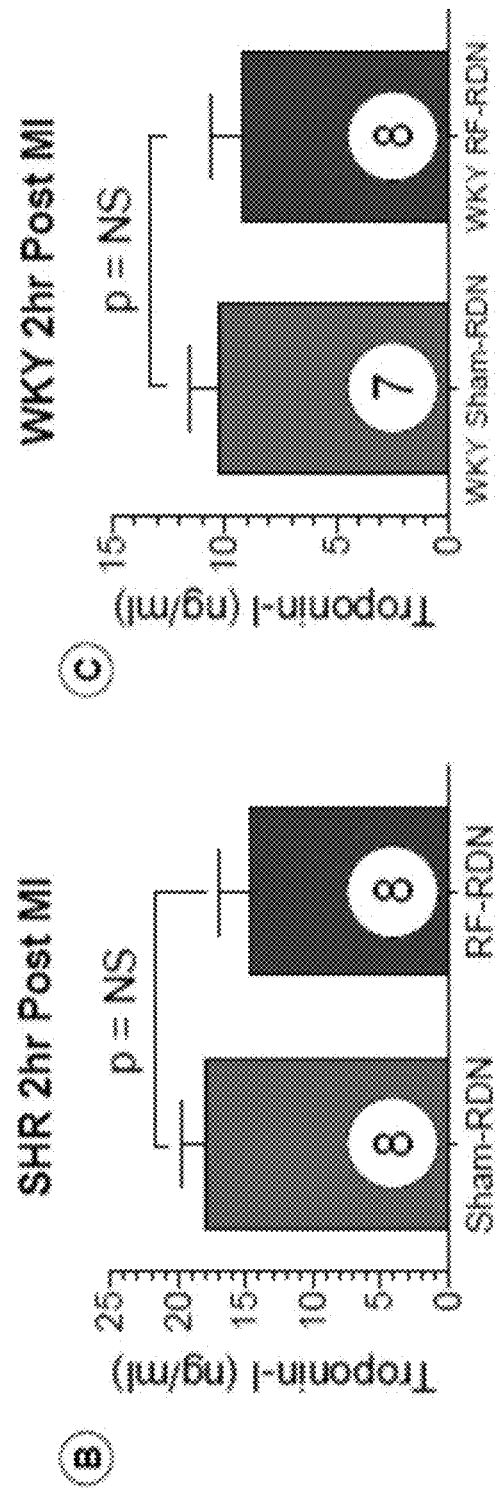
*FIG. 11 CON'T*

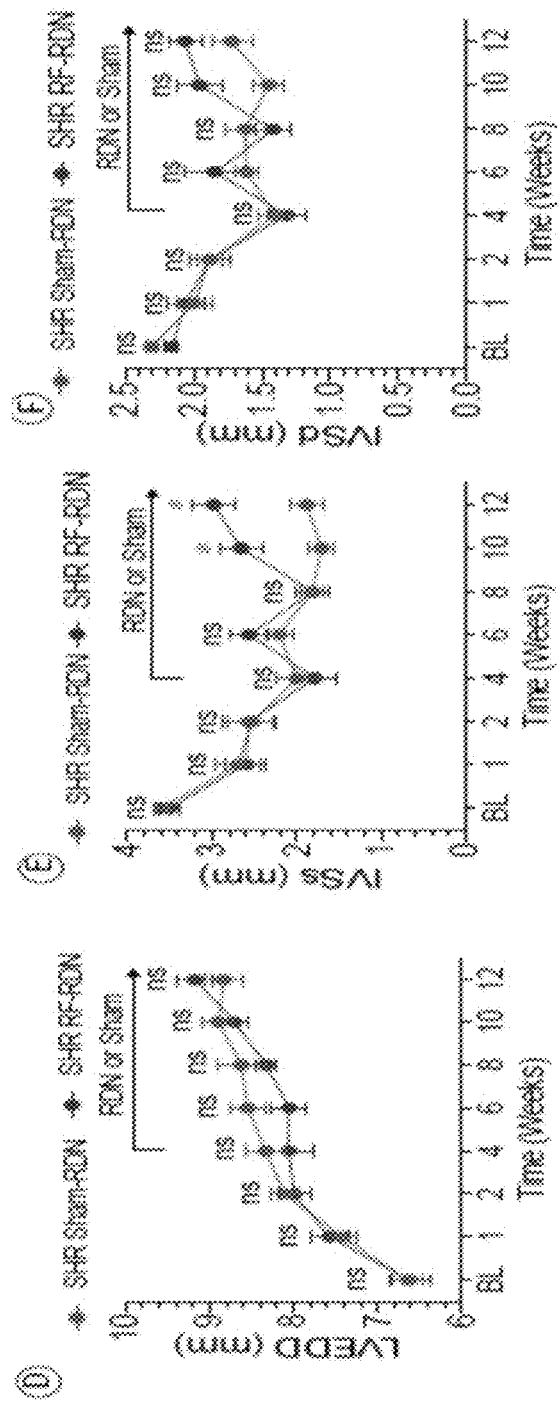
FIG. 13 CON'T

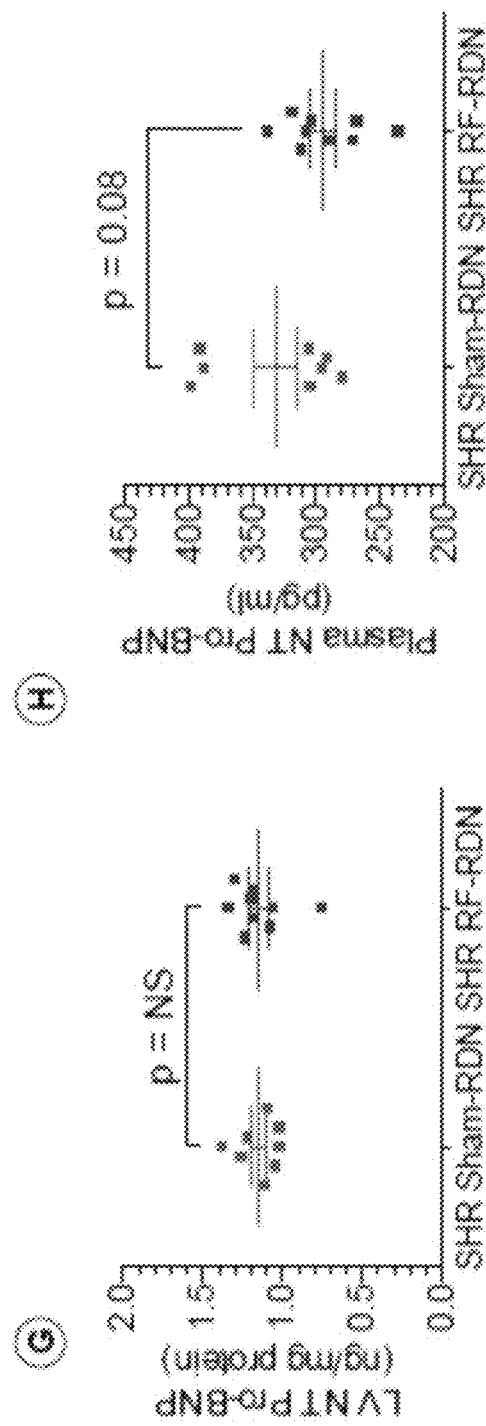
FIG. 14 CON'T

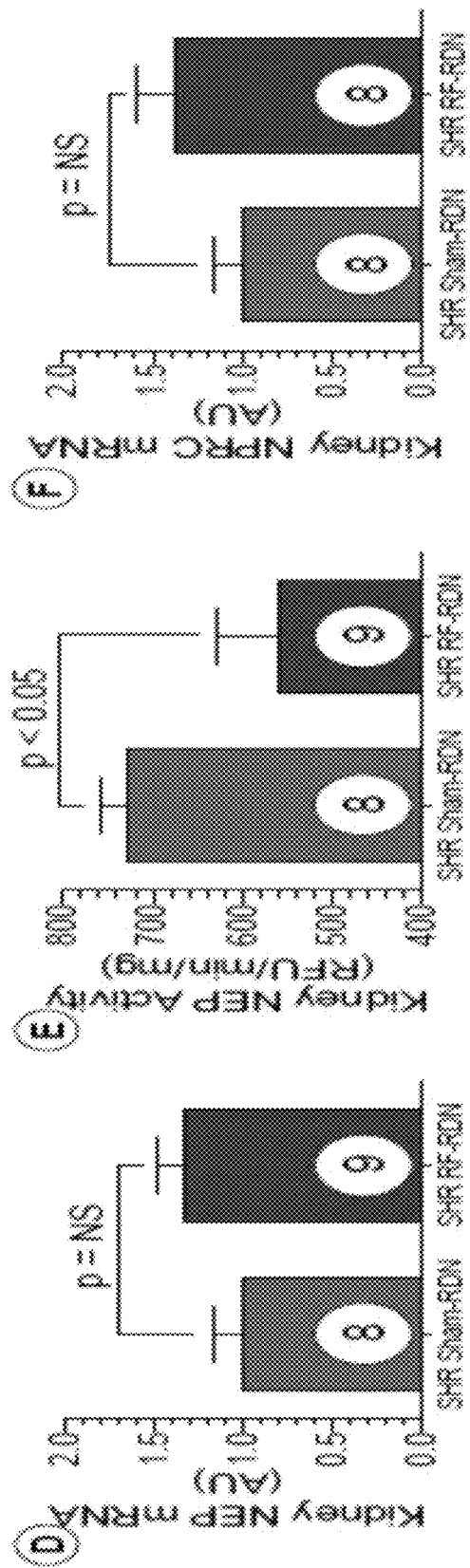
FIG. 15 CON'T

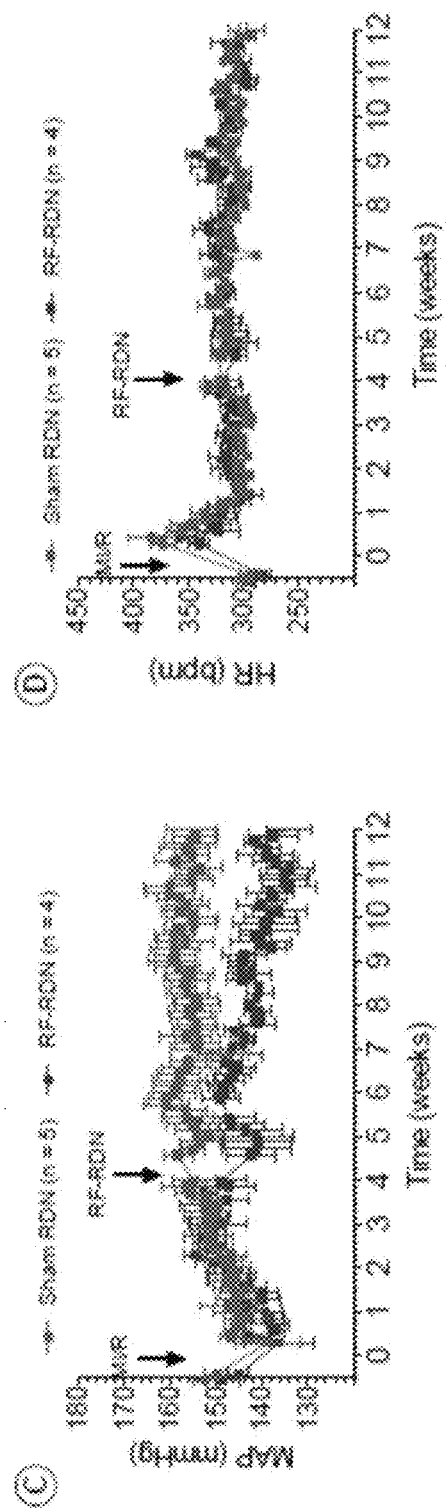
FIG. 17 CON'T

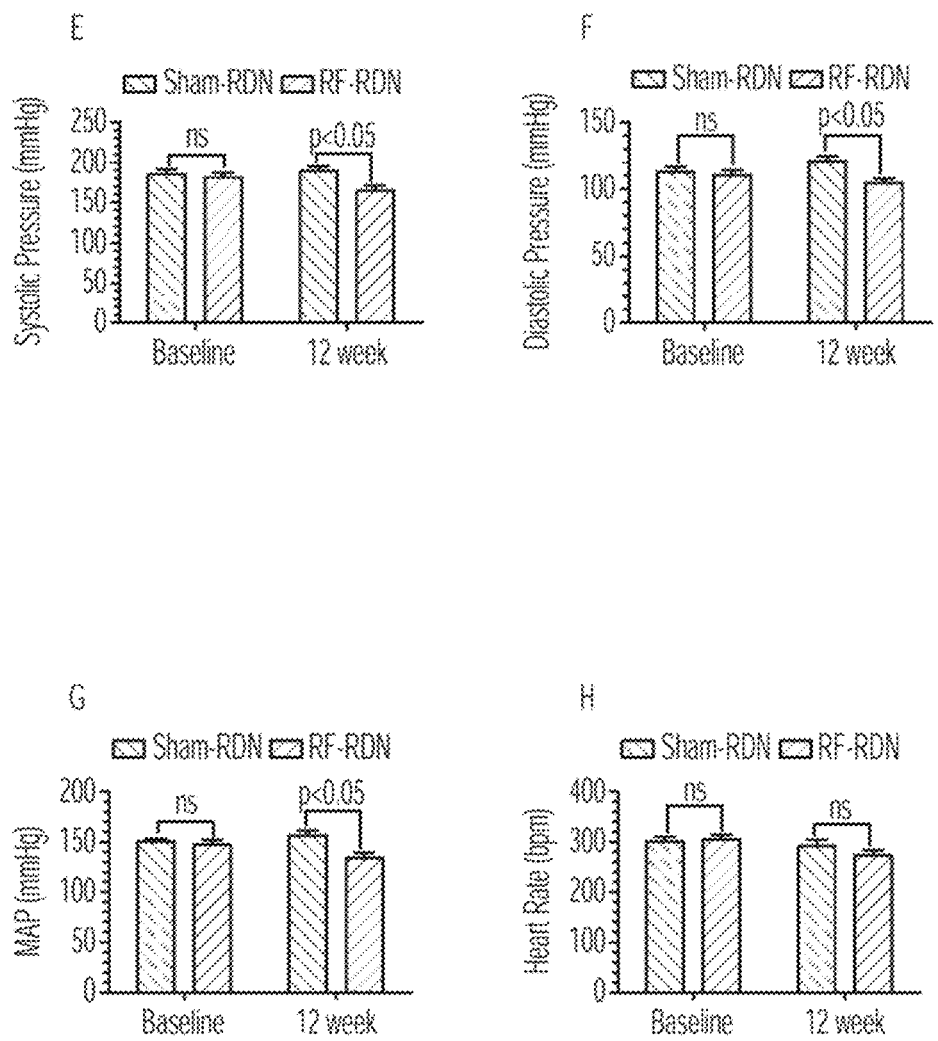
*FIG. 17 CON'T*

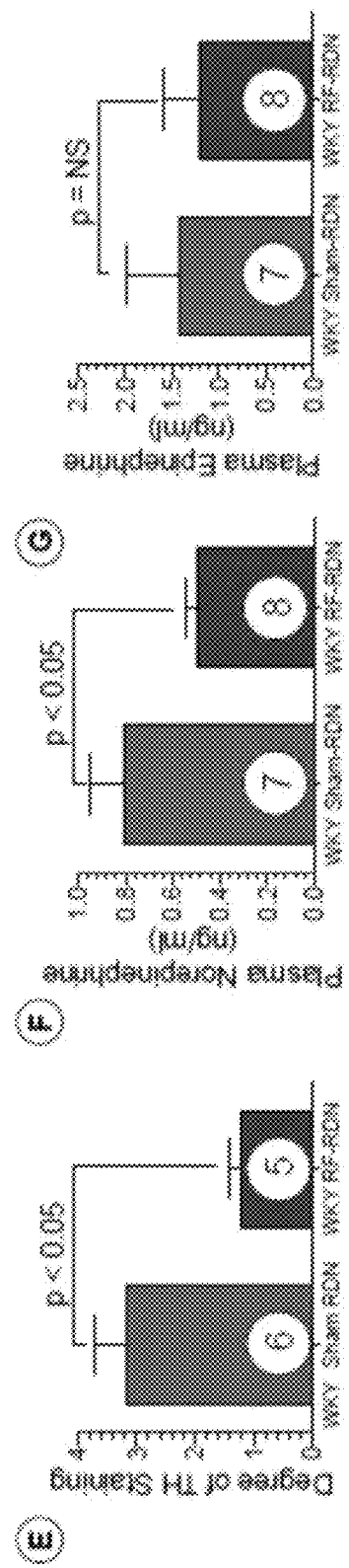
FIG. 18 CON'T

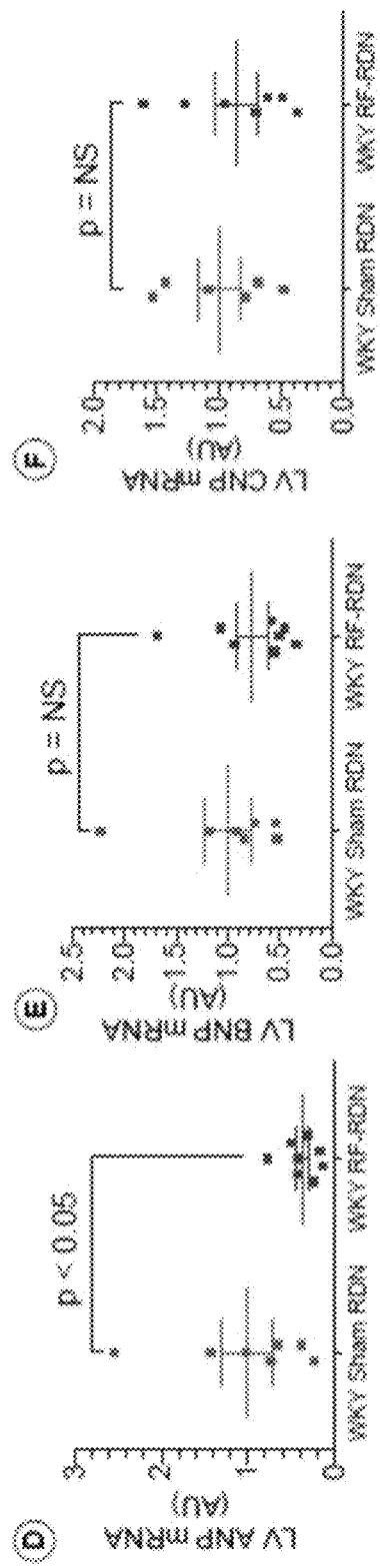
FIG. 20 CON'T

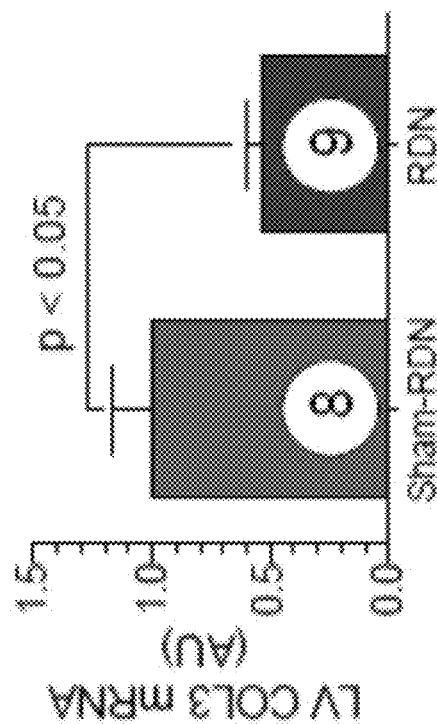
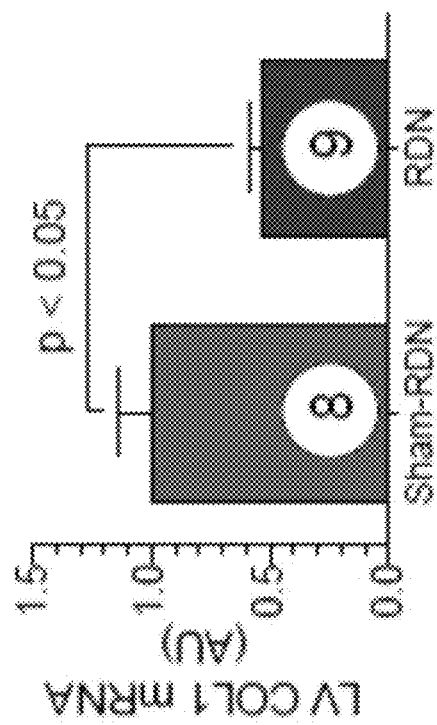
FIG. 25 CON'T

Sham RDN

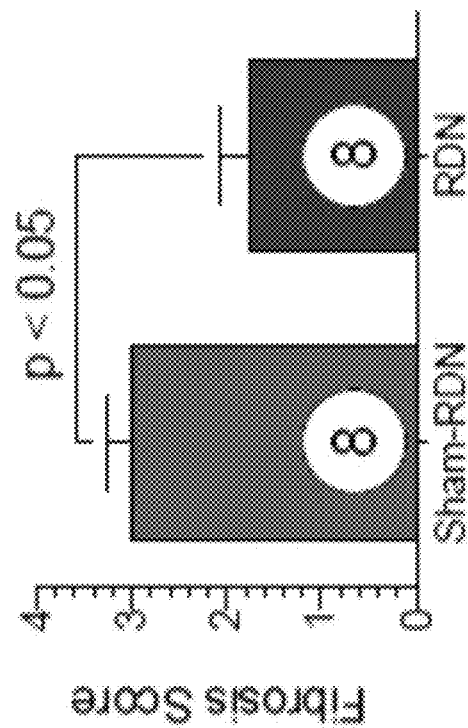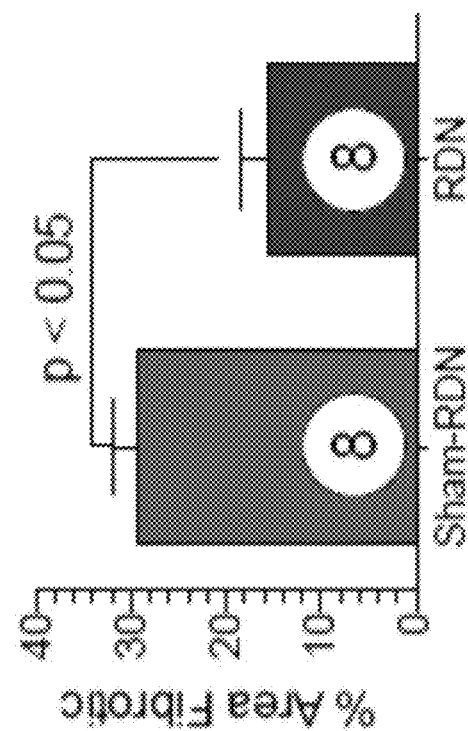
*FIG. 37 CON'T*

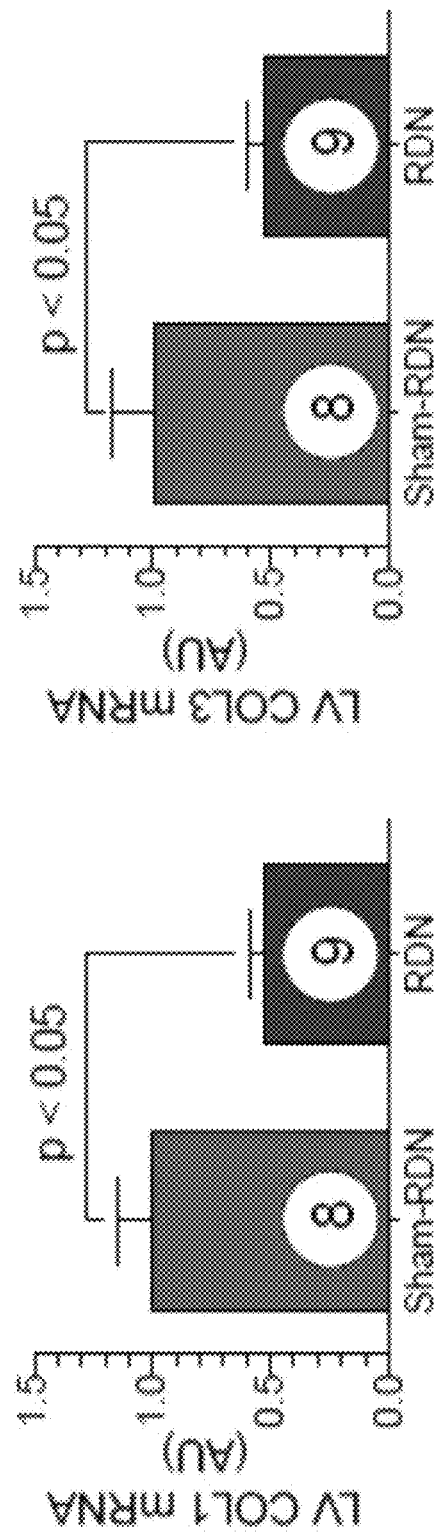
FIG. 37 CON'T

*Anitoxid Redox Signal. 2014 Nov 10; 21(14): 2032-2403*

WKY Sham-RDN    WKY RF-RDN

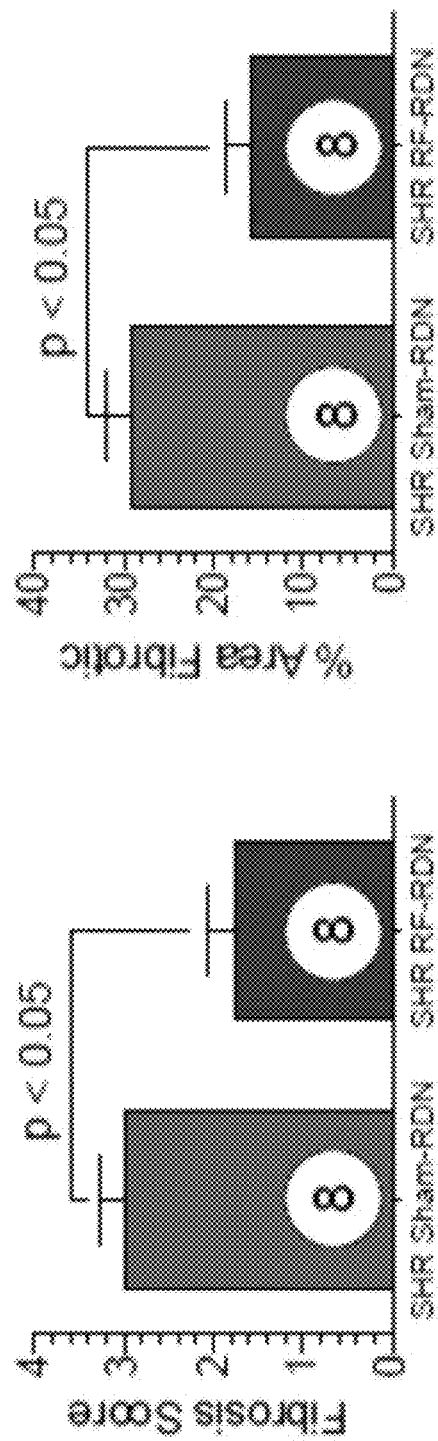
FIG. 73 CON'T

| 24 hours | Sham-RDN | RF-RDN | p-value |
|---|---|---|---|
| Food Intake (g) | 13.86 ± 0.87 | 15.03 ± 0.56 | 0.42 |
| Water Intake (ml) | 22.68 ± 1.92 | 25.50 ± 0.61 | 0.12 |
| Urine Volume (ml) | 4.94 ± 0.91 | 4.17 ± 2.66 | 0.16 |
| Urinary Na+ Excretion (mEq) | 0.28 ± 0.06 | .31 ± 0.05 | 0.63 |
| Urinary K+ Excretion (mEq) | 0.85 ± 0.11 | 0.68 ± 0.03 | 0.09 |

*FIG. 90*

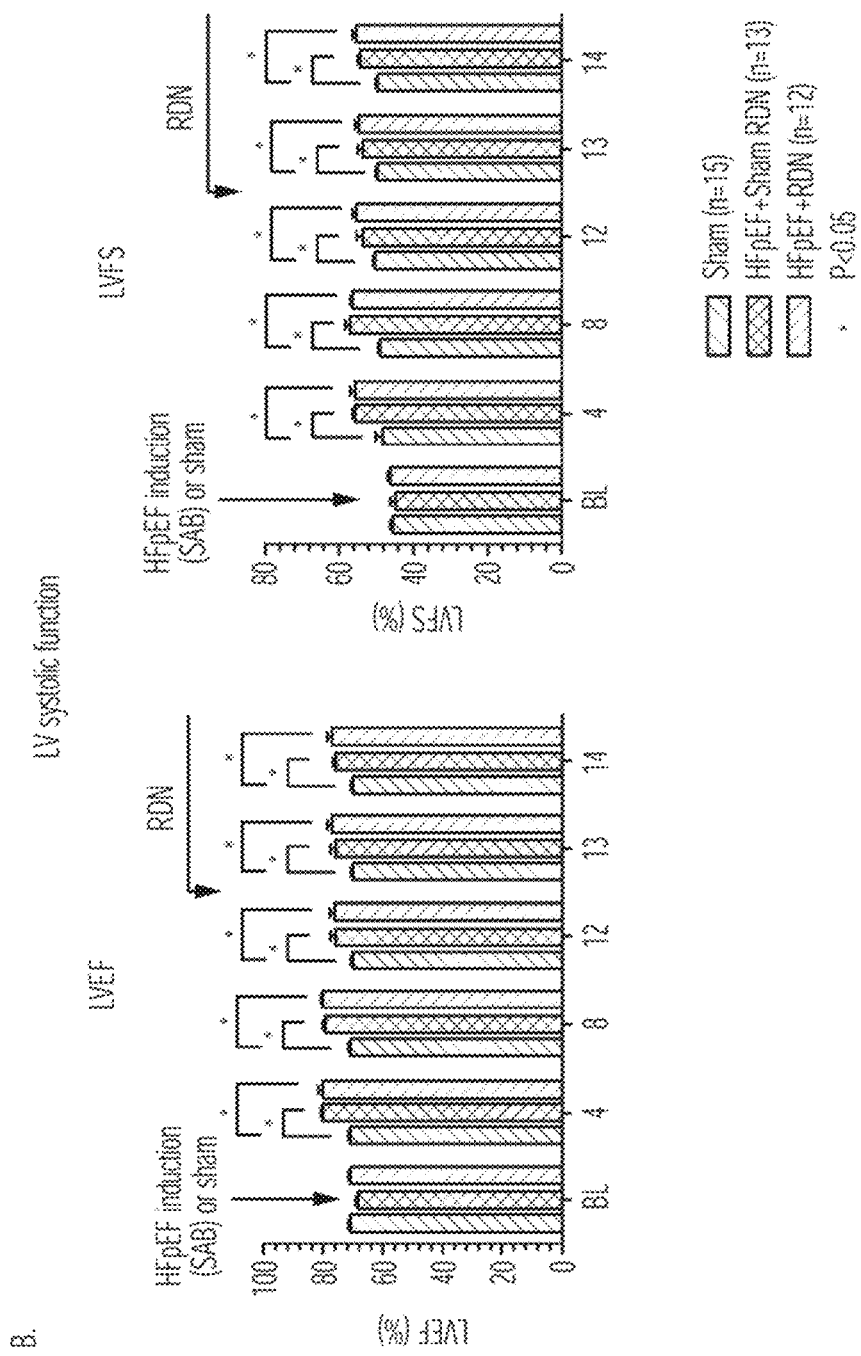
FIG. 103 CON'T

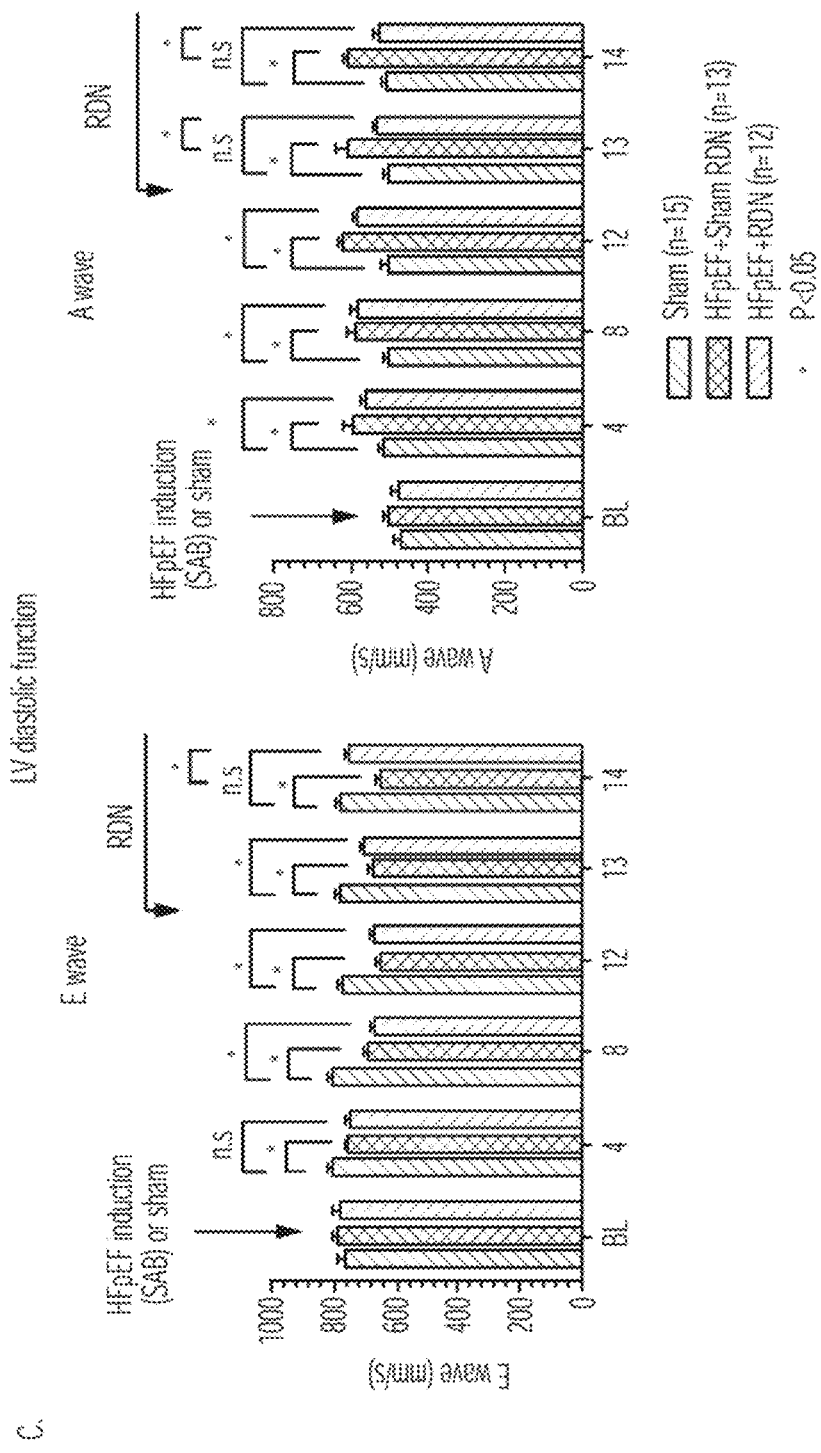
FIG. 103 CON'T

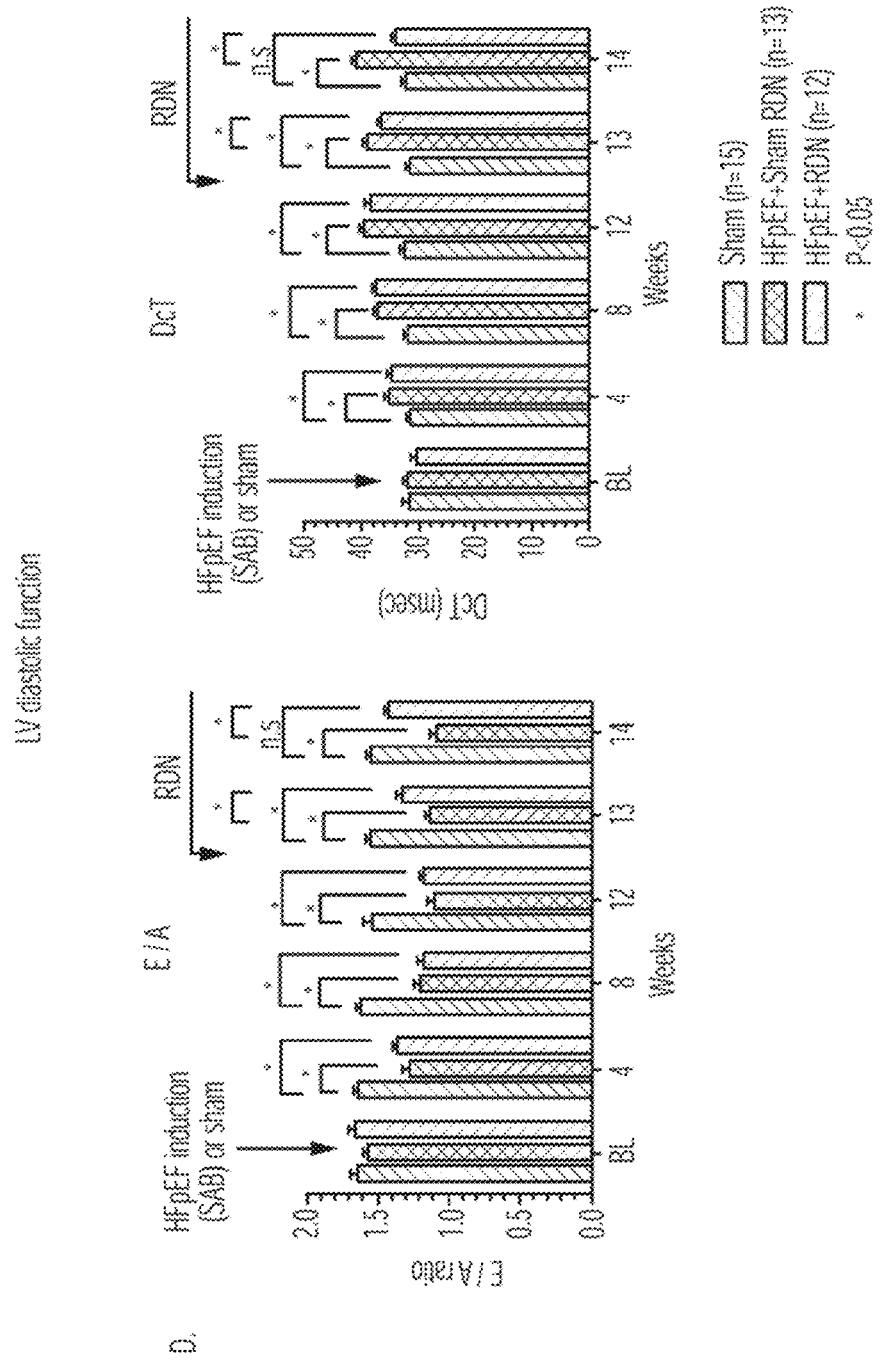
FIG. 103 CON'T

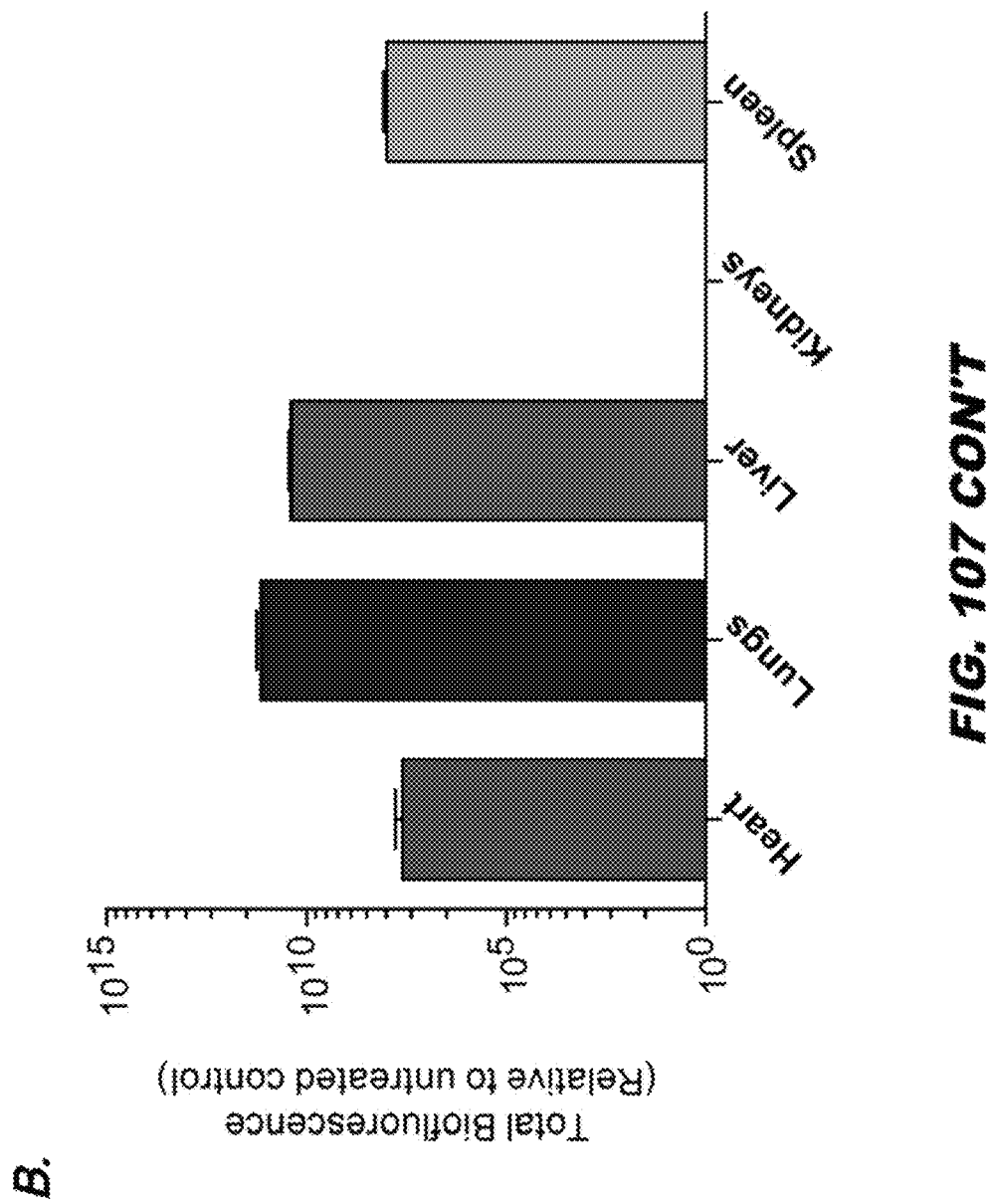
FIG. 107 CON'T

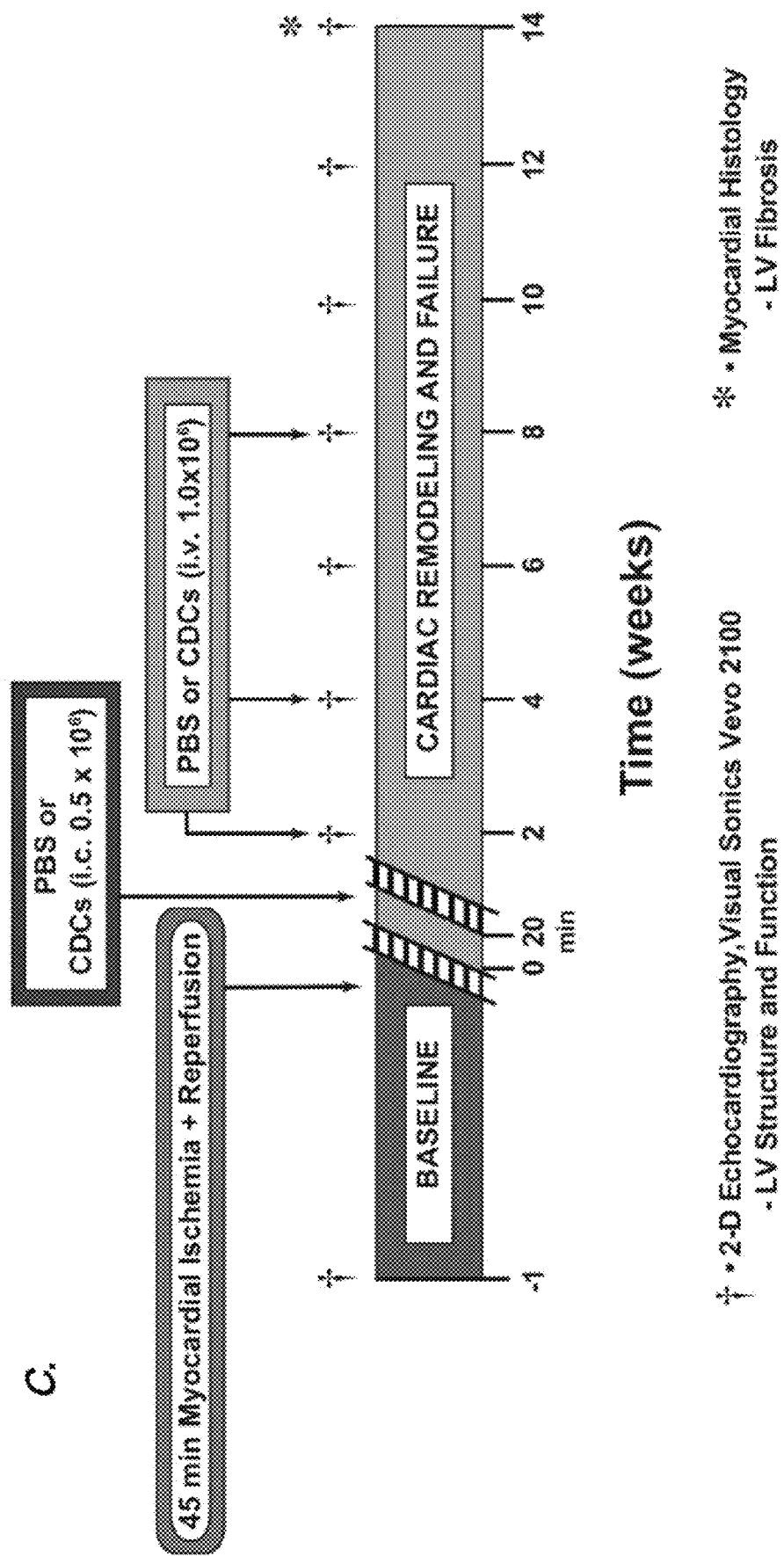
FIG. 107 CON'T

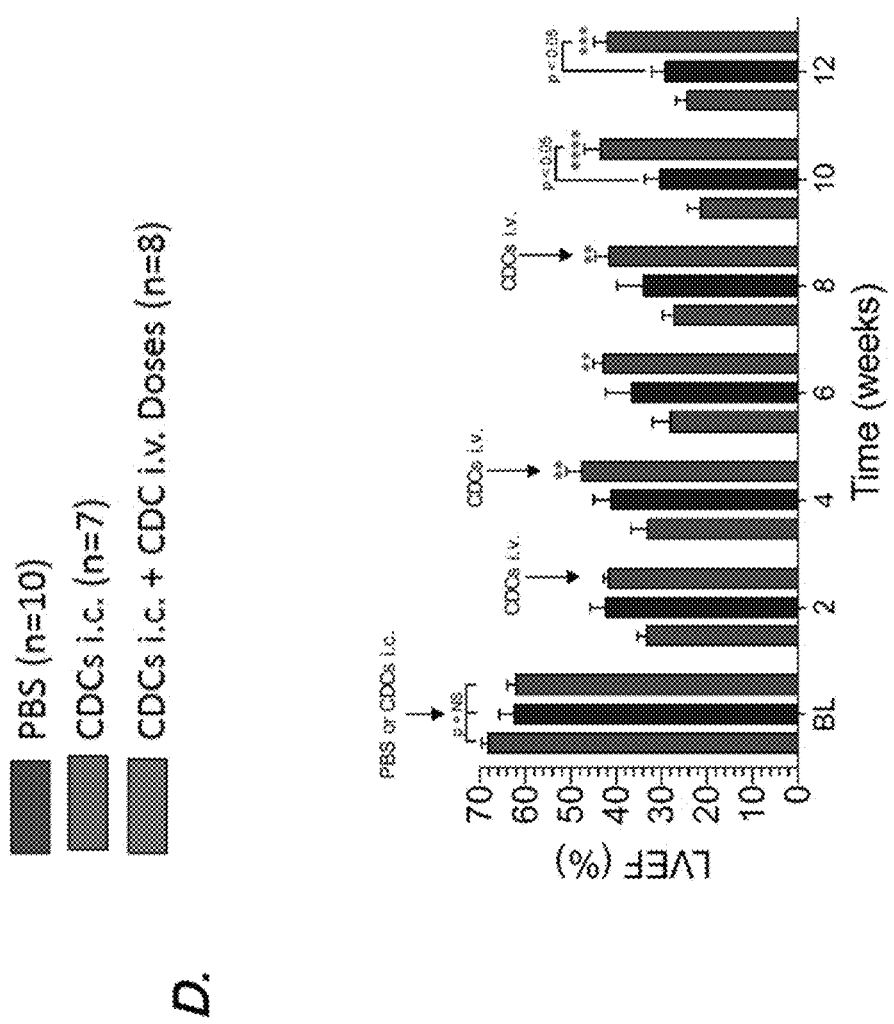
FIG. 107 CON'T

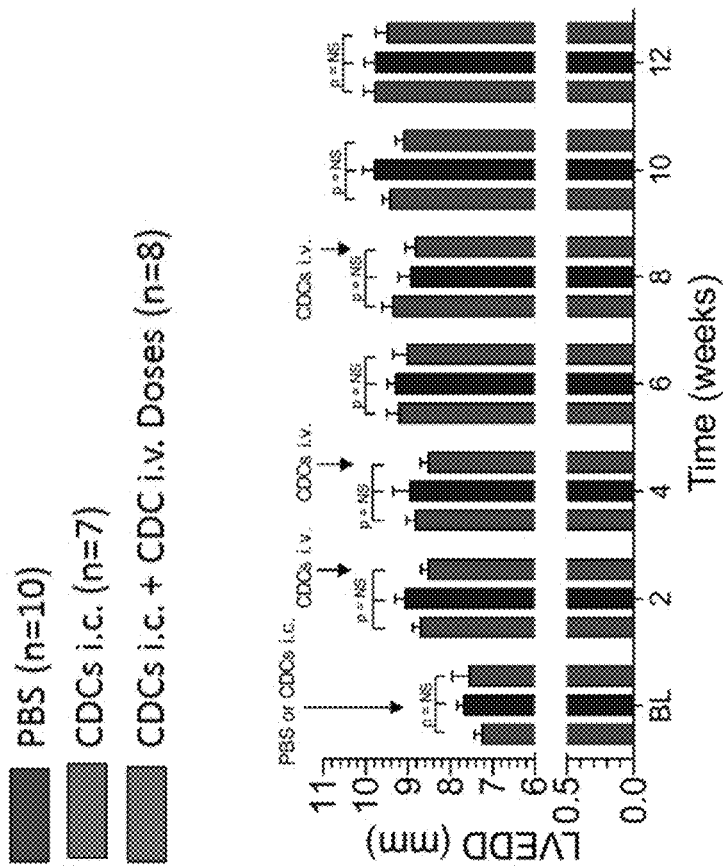
FIG. 107 CON'T

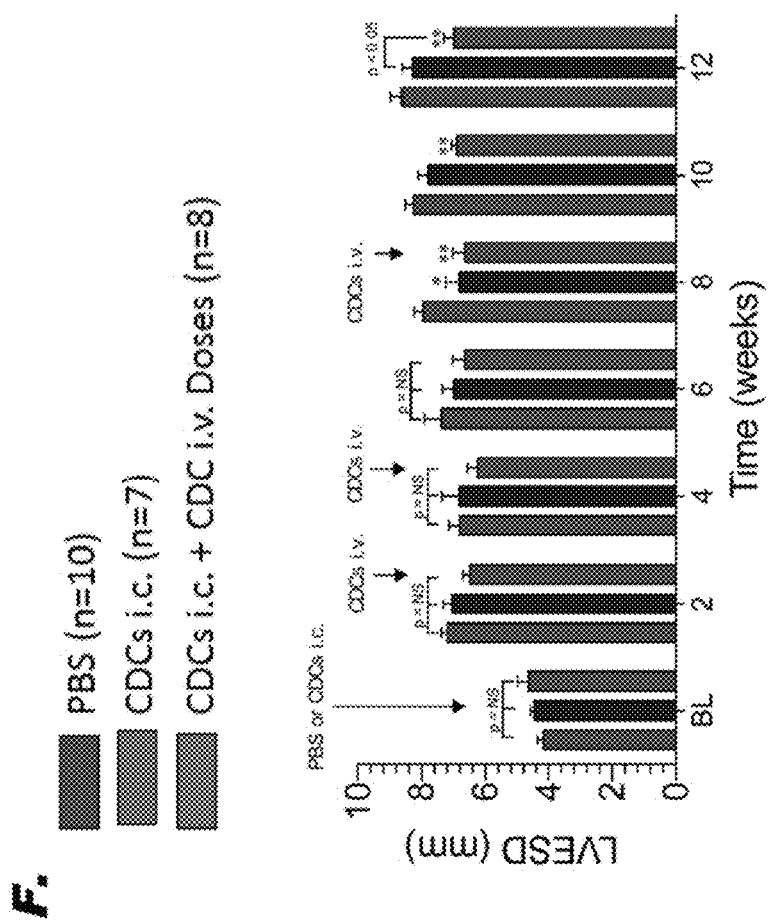
FIG. 107 CON'T

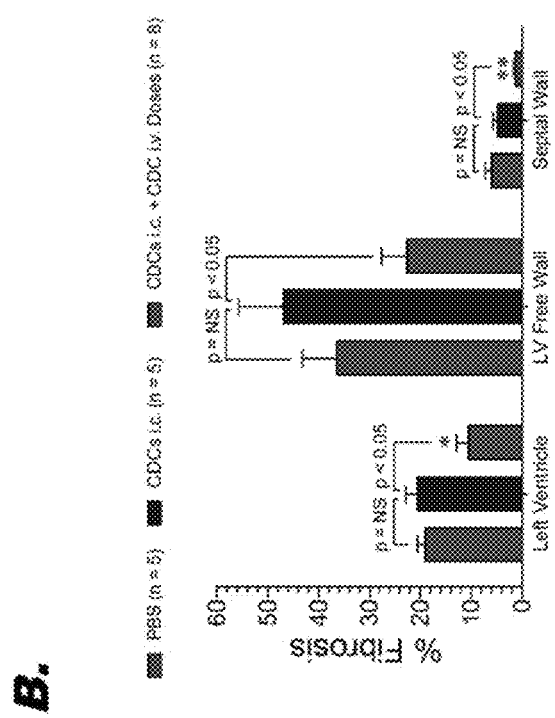
FIG. 108 CON'T

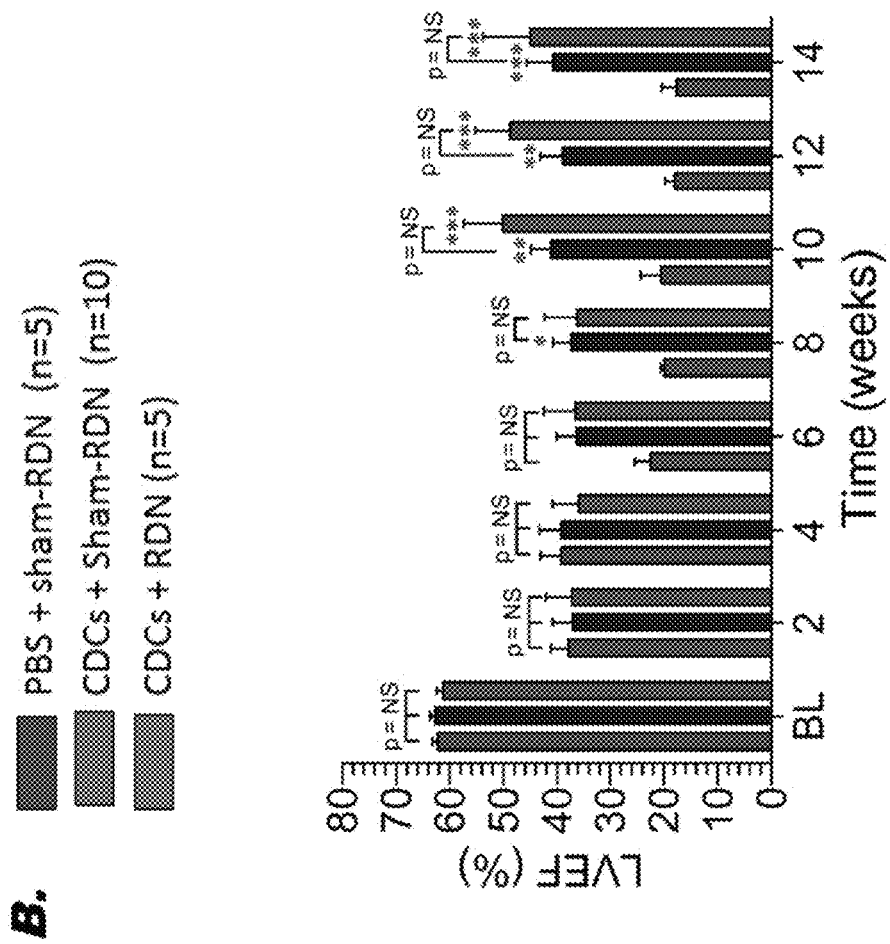
FIG. 109 CON'T

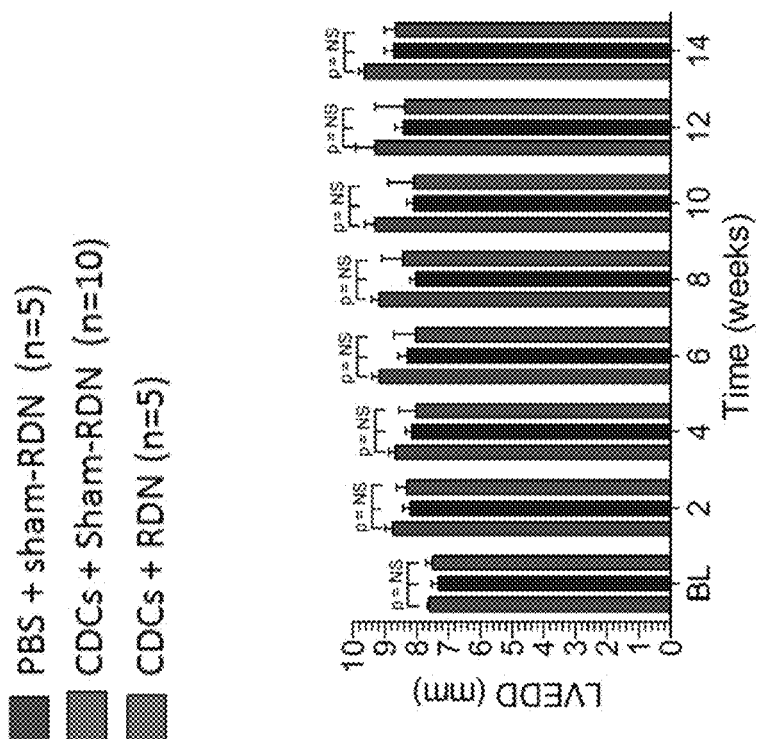
FIG. 109 CON'T

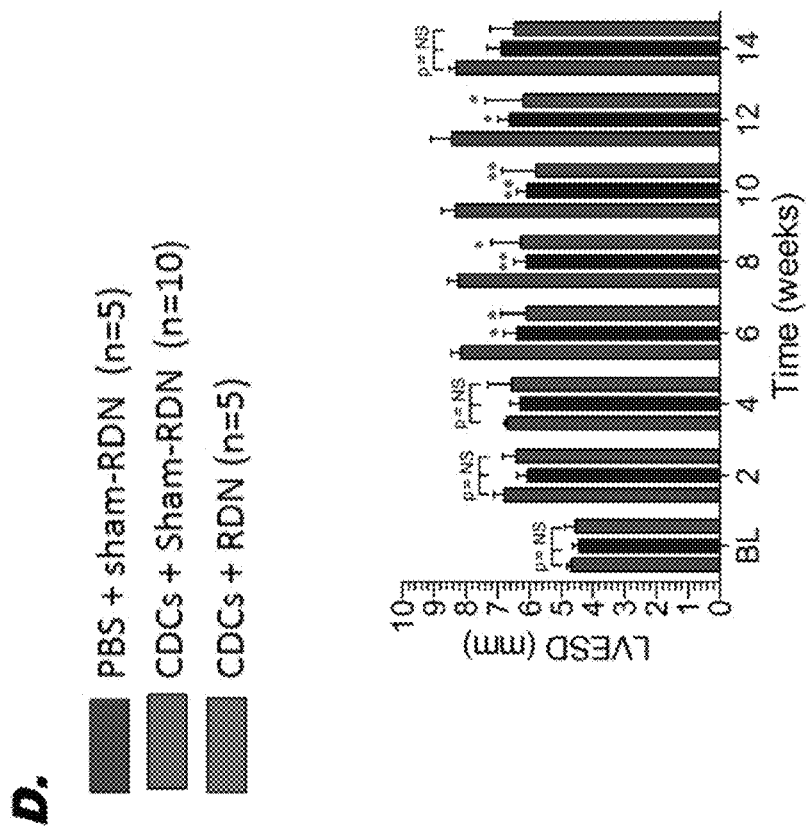
FIG. 109 CON'T

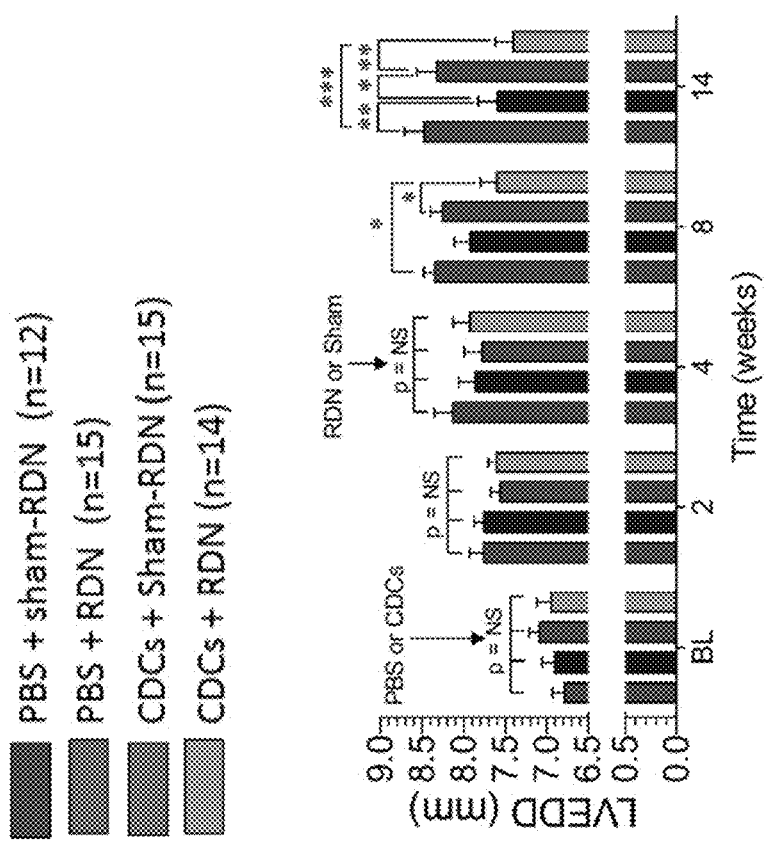
FIG. 111 CON'T

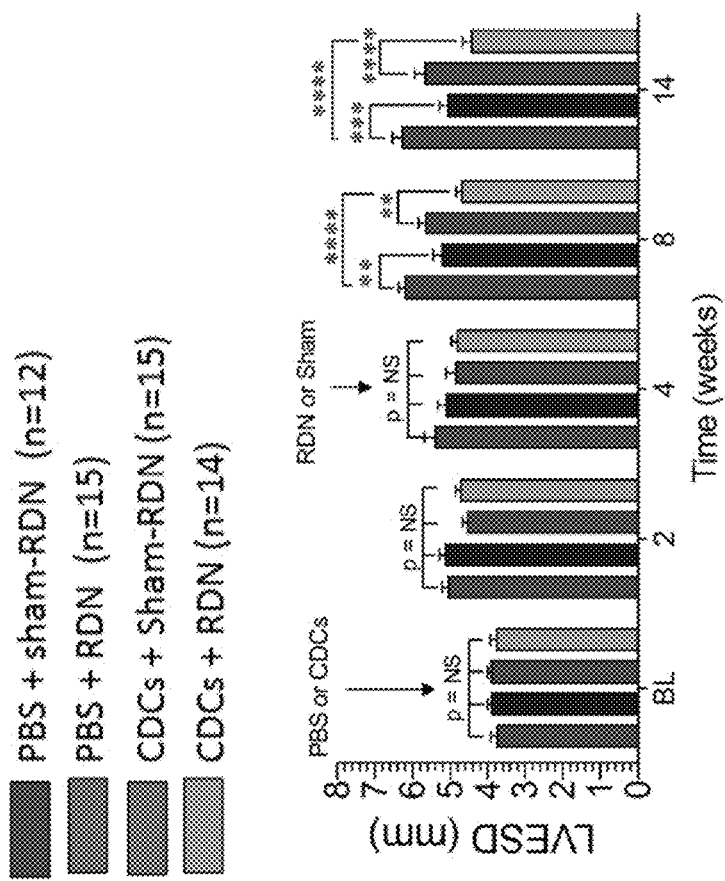
FIG. 111 CON'T

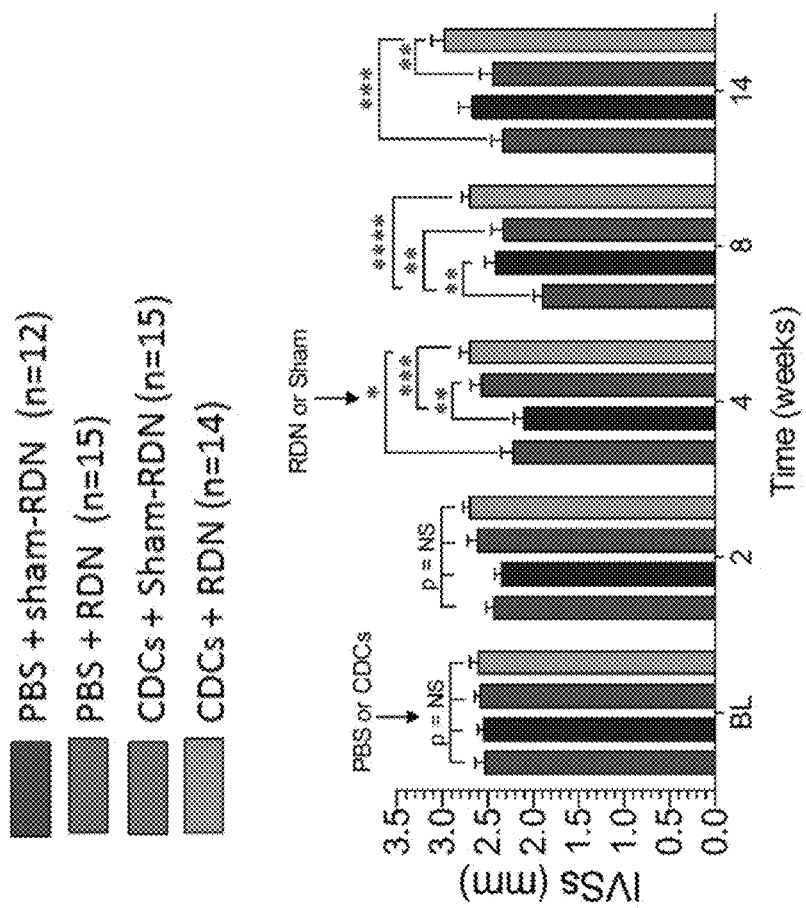
FIG. 111 CON'T

A.

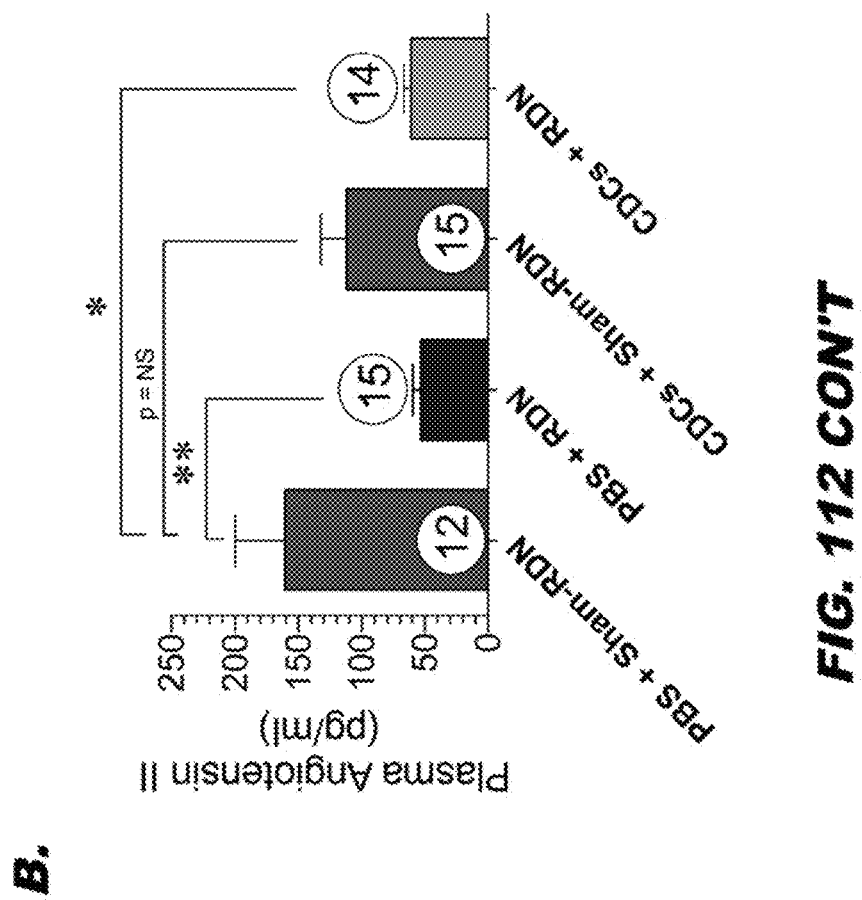
FIG. 112 CON'T

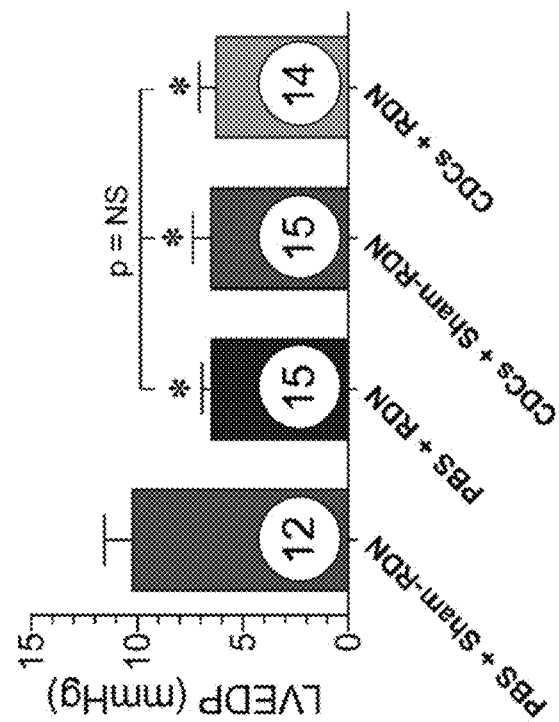
FIG. 113 CON'T

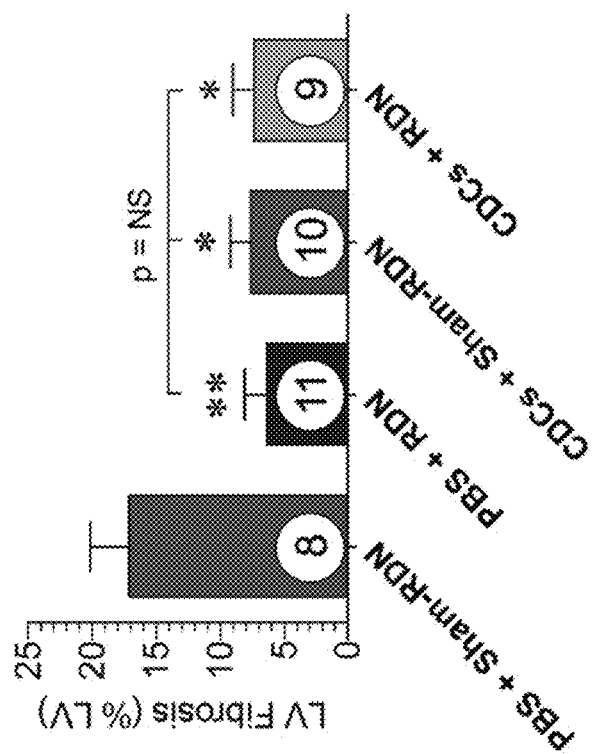
*FIG. 114 CON'T*

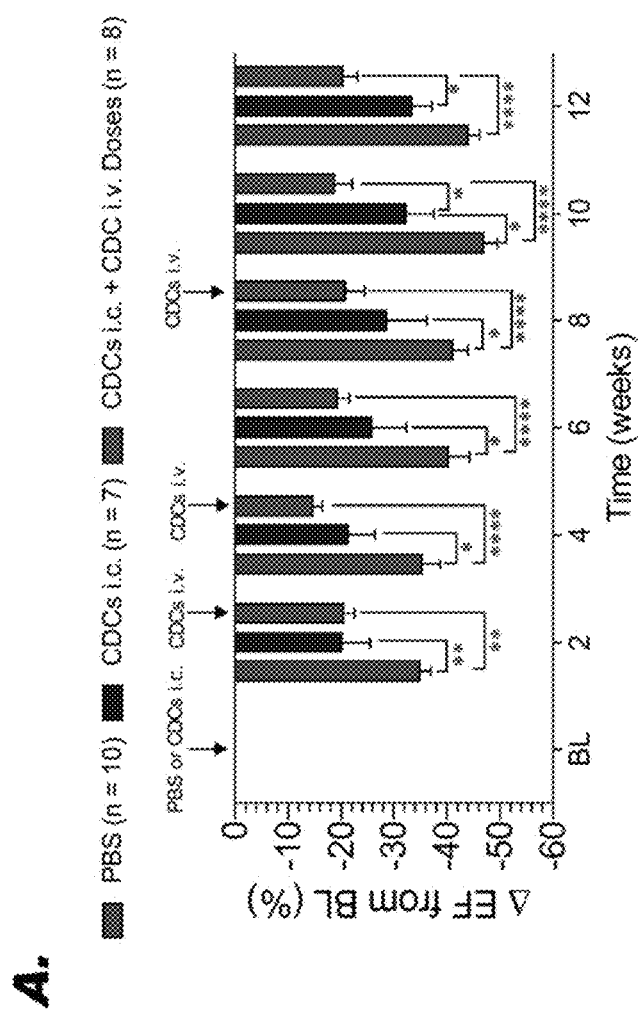
FIG.115 CON'T

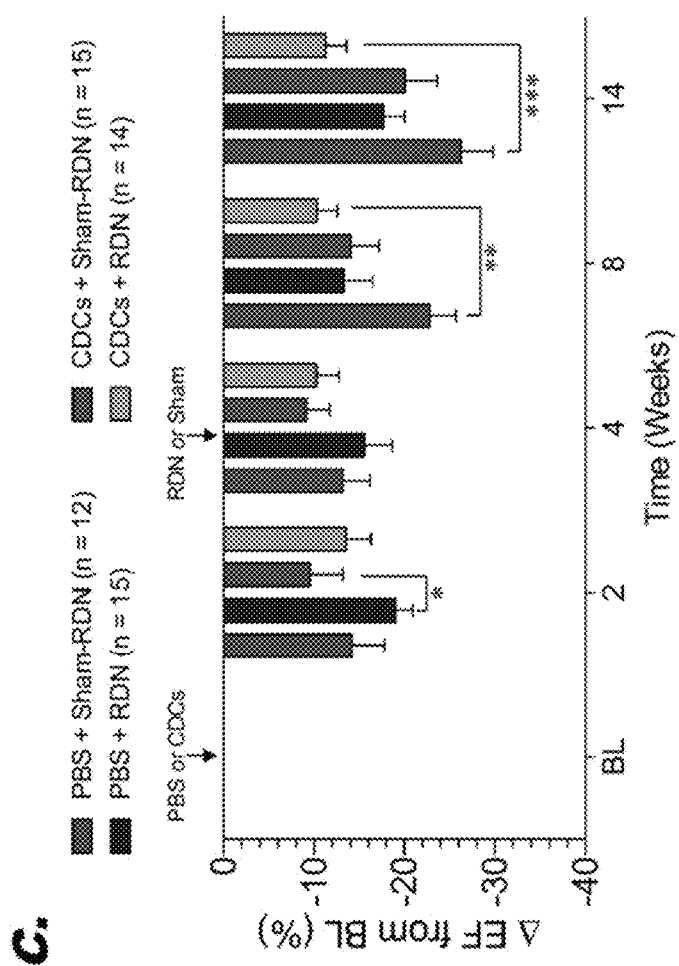
*FIG. 115 CON'T*

COMPOSITIONS AND METHODS FOR TREATING CARDIAC INJURY

This application is a Continuation in Part of International Application No. PCT/US2017/044818, filed on Aug. 1, 2017, which claims priority from U.S. Provisional Application No. 62/369,432, filed on Aug. 1, 2016, U.S. Provisional Application No. 62/455,852, filed on Feb. 7, 2017, and U.S. Provisional Application No. 62/489,537, filed on Apr. 25, 2017, the entire contents of each which are incorporated herein by reference.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to compositions and methods for treating a condition of the heart.

BACKGROUND OF THE INVENTION

Following acute myocardial infarction (MI), cardiac structure undergoes adverse remodeling leading to a progressive decline in cardiac function. However, while timely coronary revascularization therapy is effective for acute MI, maximizing reperfusion is not associated with a maximized cardioprotective effect. Not only does unrelieved ischemia cause permanent damage to the cardiac tissue, reperfusion of the tissue leads to significant injury of the myocardium. Once the myocardium has been damaged by the initial ischemic insult and further by reperfusion injury, there is a progressive decline in cardiac function and heart failure (HF) ensues. The development of compositions and methods for treating cardiac injury can improve the ability of healthcare professionals to treat subjects suffering from cardiac injury, and can ultimately improve the prognosis of subjects suffering from cardiac injury.

SUMMARY OF THE INVENTION

The present invention provides a method of treating a subject, wherein the method comprises ablating at least one nerve of the renal artery of the subject, and administering to the subject a therapeutically effective amount of cells.

In embodiments, the cells can be administered before, concurrently with, at about the same time as, or after the nerve is ablated. For example, the cells can be administered about 1, 2, 3, 4, 5, 6, 7, 8, 9, 10, 11, 12, 24, 52, or more than 52 weeks before the nerve is ablated (See FIG. 98). Alternatively, the cells can be administered about 1, 2, 3, 4, 5, 6, 7, 8, 9, 10, 11, 12, 24, 52, or more than 52 weeks after the nerve is ablated. In embodiments, the cells can be administered as a single dose. In other embodiments, 2, 3, 4, 5, 6, 7, 8, 9, 10, or more than 10 doses of cells are administered.

In embodiments, the cells can be administered before, concurrently with, at about the same time as, or after the onset of a heart disease. In embodiments, the cells can be administered before, concurrently with, at about the same time as, or after the modulation of a nerve, such as denervation or attenuation of the renal nerve. For example, the cells can be administered before, concurrently with, at about the same time as, or after the myocardial ischemia and reperfusion event. For example, the cells can be administered about 1, 5, 10, 15, 16, 17, 18, 19, 20, 21, 22, 23, 24, 25, 30, 45, 60, or more than 60 minutes after the onset of a myocardial ischemia and reperfusion event (See FIG. 99). For example, cells can be administered about 1, 6, 12, 24, 36, 48, 60, 72, 84, 96, or more than 96 hours after the onset of a myocardial ischemia and reperfusion event. For example, cells can be administered about 1, 4, 6, 8, 10, 12 or more than 12 weeks after the onset of a myocardial ischemia and reperfusion event (See FIG. 98). In embodiments, the cells can be administered as a single dose. In other embodiments, 2, 3, 4, 5, 6, 7, 8, 9, 10, or more than 10 doses of cells are administered. In still other embodiments, the cells can be administered as a continuous dose, such as an infusion, over a period of time. For example, the cells can be administered continuously for about 5 minutes, about 10 minutes, about 15 minutes, about 30 minutes, about 1 hour, about 2 hours, about 4 hours, about 8 hours, about 12 hours, or about 24 hours.

In embodiments, the cells can be administered before, concurrently with, at about the same time as, or after the modulation of a nerve, such as denervation or attenuation of the renal nerve. For example, the cells can be administered about 1, 5, 10, 15, 16, 17, 18, 19, 20, 21, 22, 23, 24, 25, 30, 45, 60, or more than 60 minutes after a renal denervation procedure. For example, cells can be administered about 1, 6, 12, 24, 36, 48, 60, 72, 84, 96, or more than 96 hours after a renal denervation procedure. For example, cells can be administered about 1, 4, 6, 8, 10, 12 or more than 12 weeks after a renal denervation procedure. In embodiments, the cells can be administered as a single dose. In other embodiments, 2, 3, 4, 5, 6, 7, 8, 9, 10, or more than 10 doses of cells are administered.

In embodiments, the autonomic nervous system is modulated. For example, the sympathetic nervous system can be inhibited, such as by ablation, or the parasympathetic nervous system can be stimulated, such as by electrical impulse or chemical stimulation. For example, the parasympathetic nervous system can be stimulated by acetylcholine, or analogs or derivatives thereof such as a cholinomimetic drug or a cholinergic drug. Non-limiting examples of parasympathetic stimulants comprise acetylcholine, bethanechol, carbachol, methacholine, arecoline, nicotine, muscarine, pilocarpine, donepezil, edrophonium, neostigmine, phjysostigmine, pyridostigmine, rivastigmine, tacrine, caffeine, huperzine A, echothiphate, isoflurophate, malathion, cisapride, droperidol, domperidone, metoclopramide, risperidone, paliperidone, or trazodone. In embodiments, the sympathetic nervous system is inhibited, for example with an alcohol based neurotoxin, and the parasympathetic nervous system is stimulated, such as by acetylecholine.

In embodiments, the nerve can be a sympathetic nerve. In embodiments, the subject can be suffering from a heart disease. In embodiments, the heart disease can be a myocardial injury, myocardial infarction, heart failure, induced by an anti-cancer agent, congenital heart defects (such as hypoplastic left heart syndrome, septal defects, patent ductus arteriosus), structural heart diseases (such as valvular disease), diseases and/or complications associated with left ventricular device (LVAD) implantation, inflammation mediated heart disease, heart failure induced by hypertension or any combination thereof. In embodiments, the heart disease is not myocardial infarction. Non-limiting examples of anti-cancer agents that can induce heart failure comprise anthracyclines and anthraquinolones, capecitabine, paclitaxel, vinca alkaloids, imatinib, trastuzumab, thorax irradiation, or doxorubicin.

Non-limiting examples of methods for ablating a nerve thermal necrosis (e.g., using energy such as thermal energy, radiofrequency electrical current, direct current, microwave, ultrasound, high intensity focused ultrasound, and laser), cryogenic ablation, electroporation, selective denervation, embolization (e.g., occlusion of blood vessels feeding the gland), artificial sclerosing of blood vessels, mechanical impingement or crushing, surgical removal, chemical ablation, or application of radiation causing controlled necrosis (e.g., brachytherapy).

Non-limiting examples of methods for attenuating a nerve comprises vagus nerve stimulation (VNS), spinal cord stimulation (SCS), baroreceptor stimulation, renal denervation, tragus stimulation, endovascular stimulation, endovascular cardiac plexus stimulation or a combination thereof.

In embodiments, heart failure can be heart failure with reduced ejection fraction (HFrEF) or heart failure with preserved ejection fraction (HFpEF). In embodiments, the heart failure can be artificially induced by a composition administered to a subject, such as an anti-cancer agent, can be induced by a metabolic syndrome, is naturally-occurring, or a combination of both. The composition can be an anti-cancer agent. The anti-cancer agent can be an anthracycline, such as doxorubicin. In embodiments, the cells can be administered to the subject prior to, concurrent, at about the same time as, or subsequent to nerve ablation. The method can further comprise the step of determining a cardiac function of the subject, such as an improvement in cardiac function. In embodiments, the cardiac function can be left ventricular ejection fraction, left ventricular diastolic function, or a combination of both. In embodiments, determining a cardiac function can comprise measuring a myocardial peptide marker, a circulating peptide marker, a heart pump function, a heart gross morphology, an enzymatic activity, or a combination thereof can be used to determine an improvement in cardiac function of a subject. In embodiments, the peptide marker can comprise ANP, BNP, or CNP; the heart pump function can be of the left ventricle; dimensions of heart pump function can be captured; gross morphology can comprise myocardial fibrosis, myocardial vascularity, or a combination thereof; the enzymatic activity can comprise neprilysin activity; and heart pump function can be measured by echocardiogram. In embodiments, the myocardial injury can result from heart failure, myocardial infarction, ischemia/reperfusion, or a combination thereof. In embodiments, the ablation of at least one nerve of the renal artery can comprise radiofrequency denervation, chemical ablation, or a combination thereof. In embodiments, the radiofrequency denervation can be catheter-based. In embodiments, the cells can be administered intracoronarilly, intramyocardially, or a combination thereof. In embodiments, at least one sympathetic nerve of the renal artery can be ablated by radio frequency renal denervation. In embodiments, the cells can be autologous cells, homologous cells, heterologous cells, allogenic cells, syngeneic cells, or any combination thereof. In embodiments, the cells can be stem cells, stem cell-like cells, stem cell-derived releasing factors, or any combination thereof. In embodiments, the cells can be cardiospheres, cardiosphere-derived cells, cardiac stem cells, bone marrow derived cells, adipose derived mesenchymal cells, hematopoietic stem cells, bone marrow derived mesenchymal cells cardiac, mesenchymal, endothelial, induced pluripotent stem cells, exosomes derived from progenitor cells, cardiac-derived myocytes, bone-derived stem cells or any combination thereof. In embodiments, the stem cell-derived releasing factors can be exosomes, microRNAs, nucleotides, lipids, short peptides, proteins, cytoprotective cytokines (for example, IL-10, IL-13, hepatocyte growth factor (HGF) and stromal cell-derived factor-1 alpha (CXCL12)), stem cell derived factors (for example, SDF) or any combination thereof. In some embodiments, stem cell-derived releasing factors comprise exosomes and/or components thereof (e.g., hepatocyte growth factor (HGF), insulin-like growth factor-1 (IGF1), nerve growth factor (NGF), and stromal-derived growth factor-1 (SDF1)); proangiogenic miRNAs (e.g., miR-126, miR-130a, miR-132) and anti-inflammatory miRNAs (e.g., miR124a, miR-125b); miRNAs that regulate collagen deposition (e.g., miR-21); stem cell derived factors (e.g., IGF-1, VEGF, TGF-β1, HGF, FGF-2, PDGF-BB, BMP-2, and SDF); nucleotides encoding any of the exosome components, growth factors, and/or stem cell derived factors described herein; short peptides and/or fragments (e.g., at least 10, 15, 20, 25, 30, 35, 40, 45, 50 amino acids in length) comprising the exosome components, growth factors, and/or stem cell derived factors described herein; proteins corresponding to exosome components, growth factors, and/or stem cell derived factors described herein; lipids, cytoprotective cytokines (i.e., IL-10, IL-13, hepatocyte growth factor (HGF) and stromal cell-derived factor-1 alpha (CXCL12)); or any combination thereof (see, for example, Geiger A.; Walker A.; Nissen E. (2015). "Human fibrocyte-derived exosomes accelerate wound healing in genetically diabetic mice". *Biochemical and Biophysical Research Communications* 467(2): 303-309).

Embodiments as described herein can be administered to subject concurrently with or about the same time as left ventricular device (LVAD) implantation.

Another embodiment provides a method for improving a cardiac function of a subject comprising ablating at least one nerve of the renal artery and administering to the subject a therapeutically effective amount of cells. In embodiments, the cells can be administered before, concurrently with, at about the same time as, or after the nerve is ablated. In embodiments, the nerve can be a sympathetic nerve. In embodiments, the method can further comprise the step of measuring left ventricular ejection fraction, left ventricular diastolic function, or both. In embodiments, an improved cardiac function can be indicated by an increase in the left ventricular ejection fraction. In embodiments, the subject can be suffering from a heart disease. In embodiments, the heart disease can be a myocardial injury, myocardial infarction, heart failure or any combination thereof. In embodiments, the heart disease is not myocardial infarction. In embodiments, heart failure can be heart failure with reduced ejection fraction (HFrEF). In embodiments, the heart failure can be artificially induced by a composition administered to a subject, such as an anti-cancer agent, can be induced by a metabolic syndrome, is naturally-occurring, or a combination of both. In embodiments, the anti-cancer agent can be an anthracycline, such as doxorubicin. In embodiments, the administering of the cells can occur prior to, concurrent, at about the same time as or subsequent to nerve ablation. In embodiments, the ablation of at least one nerve of the renal artery can comprise radiofrequency denervation, chemical ablation, or a combination thereof. In embodiments, radiofrequency denervation is catheter-based. In embodiments, the sympathetic nerve can be denervated by radiofrequency renal denervation. In embodiments, a nerve, such as the sympathetic nerve, can be denervated by non-invasive procedures, such as by using ultrasound energy. For example, the source of the ultrasound energy can be either an internal or external source. In embodiments, both radiofrequency renal denervation and non-invasive procedures such as ultrasound energy, can be used to denervate a nerve, such as the sympathetic nerve. Non-limiting examples of methods for ablating a nerve thermal necrosis (e.g., using energy such as thermal energy, radiofrequency electrical current, direct current, microwave, ultrasound, high intensity focused ultrasound, and laser), cryogenic ablation, electroporation, selective denervation, embolization (e.g., occlusion of blood vessels feeding the gland), artificial sclerosing of blood vessels, mechanical impingement or crushing, surgical removal, chemical ablation, or application of radiation causing controlled necrosis (e.g., brachytherapy). In embodiments, the cells can be administered intracoronarilly, intramyocardially, or a combination thereof. In embodiments, the cells can be autologous cells, homologous cells, heterologous cells, allogenic cells, syngeneic cells, or any combination thereof. In embodiments, the cells can be stem cells, stem cell like cells, stem cell-derived releasing factors, or any combination thereof. In embodiments, the cells can be cardiospheres, cardiosphere-derived cells, cardiac stem cells, bone marrow derived cells, adipose derived mesenchymal cells, hematopoietic stem cells, bone marrow derived mesenchymal cells cardiac, mesenchymal, endothelial, induced pluripotent stem cells, exosomes derived from progenitor cells, cardiac-derived myocytes, bone-derived stem cells, or any combination thereof. In embodiments, the stem cell-derived releasing factors can be exosomes, microRNAs, nucleotides, lipids, short peptides, proteins, cytoprotective cytokines (for example, IL-10, IL-13, hepatocyte growth factor (HGF) and stromal cell-derived factor-1 alpha (CXCL12)), stem cell derived factors (for example, SDF) or any combination thereof. In some embodiments, stem cell-derived releasing factors comprise exosomes and/or components thereof (e.g., hepatocyte growth factor (HGF), insulin-like growth factor-1 (IGF1), nerve growth factor (NGF), and stromal-derived growth factor-1 (SDF1)); proangiogenic miRNAs (e.g., miR-126, miR-130a, miR-132) and anti-inflammatory miRNAs (e.g., miR124a, miR-125b); miRNAs that regulate collagen deposition (e.g., miR-21); stem cell derived factors (e.g., IGF-1, VEGF, TGF-β1, HGF, FGF-2, PDGF-BB, BMP-2, and SDF); nucleotides encoding any of the exosome components, growth factors, and/or stem cell derived factors described herein; short peptides and/or fragments (e.g., at least 10, 15, 20, 25, 30, 35, 40, 45, 50 amino acids in length) comprising the exosome components, growth factors, and/or stem cell derived factors described herein; proteins corresponding to exosome components, growth factors, and/or stem cell derived factors described herein; lipids, cytoprotective cytokines (i.e., IL-10, IL-13, hepatocyte growth factor (HGF) and stromal cell-derived factor-1 alpha (CXCL12)); or any combination thereof (see, for example, Geiger A.; Walker A.; Nissen E. (2015). "Human fibrocyte-derived exosomes accelerate wound healing in genetically diabetic mice". *Biochemical and Biophysical Research Communications* 467(2): 303-309).

Another embodiment provides for a method for improving left ventricular ejection fraction in a subject following a myocardial infarction comprising ablating at least one nerve of the renal artery, administering a therapeutically effective amount of cells to the subject, and measuring a left ventricular ejection fraction using echocardiogram, wherein an increase in the ejection fraction indicates an improved cardiac function. In embodiments, the cells can be administered before, concurrently with, at about the same time as, or after the nerve is ablated. In embodiments, the nerve can be a sympathetic nerve. In embodiments, the subject can be suffering from a heart disease. In embodiments, the heart disease can be a myocardial injury, myocardial infarction, heart failure or any combination thereof. In embodiments, the heart disease is not myocardial infarction. In embodiments, the heart failure can be artificially induced by a composition administered to a subject, such as an anti-cancer agent, can be induced by a metabolic syndrome, is naturally-occurring, or a combination of both. In embodiments, the anti-cancer agent can be an anthracycline, such as doxorubicin. In embodiments, the cells can be administered prior to, concurrent, at about the same time as, or subsequent to nerve ablation. In embodiments, the ablation of at least one nerve of the renal artery can comprise radiofrequency denervation, chemical ablation, or a combination thereof. In embodiments, the radiofrequency denervation can be catheter-based. In embodiments, the cells can be administered intracoronarilly, intramyocardially, or a combination thereof. In embodiments, the cells can be autologous cells, homologous cells, heterologous cells, allogenic cells, syngeneic cells, or any combination thereof. In embodiments, the cells can be cardiac derived stem cells. In embodiments, the cells can be stem cells, stem cell like cells, stem cell-derived releasing factors, or any combination thereof. In embodiments, the cells can be cardiospheres, cardiosphere-derived cells, cardiac stem cells, bone marrow derived cells, adipose derived mesenchymal cells, hematopoietic stem cells, bone marrow derived mesenchymal cells cardiac, mesenchymal, endothelial, induced pluripotent stem cells, exosomes derived from progenitor cells, cardiac-derived myocytes, bone-derived stem cells or any combination thereof. In embodiments, the stem cell-derived releasing factors can be exosomes, microRNAs, nucleotides, lipids, short peptides, proteins, cytoprotective cytokines (for example, IL-10, IL-13, hepatocyte growth factor (HGF) and stromal cell-derived factor-1 alpha (CXCL12)), stem cell derived factors (for example, SDF) or any combination thereof. In some embodiments, stem cell-derived releasing factors comprise exosomes and/or components thereof (e.g., hepatocyte growth factor (HGF), insulin-like growth factor-1 (IGF1), nerve growth factor (NGF), and stromal-derived growth factor-1 (SDF1)); proangiogenic miRNAs (e.g., miR-126, miR-130a, miR-132) and anti-inflammatory miRNAs (e.g., miR124a, miR-125b); miRNAs that regulate collagen deposition (e.g., miR-21); stem cell derived factors (e.g., IGF-1, VEGF, TGF-β1, HGF, FGF-2, PDGF-BB, BMP-2, and SDF); nucleotides encoding any of the exosome components, growth factors, and/or stem cell derived factors described herein; short peptides and/or fragments (e.g., at least 10, 15, 20, 25, 30, 35, 40, 45, 50 amino acids in length) comprising the exosome components, growth factors, and/or stem cell derived factors described herein; proteins corresponding to exosome components, growth factors, and/or stem cell derived factors described herein; lipids, cytoprotective cytokines (i.e., IL-10, IL-13, hepatocyte growth factor (HGF) and stromal cell-derived factor-1 alpha (CXCL12)); or any combination thereof (see, for example, Geiger A.; Walker A.; Nissen E. (2015). "Human fibrocyte-derived exosomes accelerate wound healing in genetically diabetic mice". *Biochemical and Biophysical Research Communications* 467(2): 303-309).

Another embodiment provides for a method for improving left ventricular diastolic function in a subject comprising ablating at least one nerve of the renal artery, administering a therapeutically effective amount of cells to the subject, and measuring a left ventricular ejection fraction using echocardiogram, wherein an increase in the ejection fraction indicates an improved cardiac function. In embodiments, the cells can be administered before, concurrently with, at about the same time as, or after the nerve is ablated. In embodiments, the nerve can be a sympathetic nerve. In embodiments, the subject can be suffering from a heart disease. In embodiments, the heart disease can be a myocardial injury, myocardial infarction, heart failure or any combination thereof. In embodiments, the heart disease is not myocardial infarction. In embodiments, heart failure can be heart failure with reduced ejection fraction (HFrEF) or heart failure with preserved ejection fraction (HFpEF). In embodiments, the heart failure can be artificially induced by a composition administered to a subject, such as an anti-cancer agent, can be induced by a metabolic syndrome, can be naturally-occurring, or a combination of both. In embodiments, the anti-cancer agent can be an anthracycline, such as doxorubicin. In embodiments, the administering of the cells occurs prior to, concurrent, at about the same time as, or subsequent to nerve ablation. In embodiments, the ablation of at least one nerve of the renal artery comprises radiofrequency denervation, chemical ablation, or a combination thereof. In embodiments, the at least one sympathetic nerve can be ablated by radiofrequency renal denervation. In embodiments, radiofrequency denervation can be catheter-based. In embodiments, the cells can be administered intracoronarilly, intramyocardially, or a combination thereof. In embodiments, the cells can be cardiac derived stem cells. In embodiments, the cells can be autologous cells, homologous cells, heterologous cells, allogenic cells, syngeneic cells, or any combination thereof. In embodiments, the cells can be stem cells, stem cell like cells, stem cell derived releasing factors, or any combination thereof. In embodiments, the cells can be cardiospheres, cardiosphere-derived cells, cardiac stem cells, bone marrow derived cells, adipose derived mesenchymal cells, hematopoietic stem cells, bone marrow derived mesenchymal cells cardiac, mesenchymal, endothelial, induced pluripotent stem cells, exosomes derived from progenitor cells, cardiac-derived myocytes, bone-derived stem cells, or any combination thereof. In embodiments, the stem cell-derived releasing factors can be exosomes, microRNAs, nucleotides, lipids, short peptides, proteins, cytoprotective cytokines (for example, IL-10, IL-13, hepatocyte growth factor (HGF) and stromal cell-derived factor-1 alpha (CXCL12)), stem cell derived factors (for example, SDF) or any combination thereof. In some embodiments, stem cell-derived releasing factors comprise exosomes and/or components thereof (e.g., hepatocyte growth factor (HGF), insulin-like growth factor-1 (IGF1), nerve growth factor (NGF), and stromal-derived growth factor-1 (SDF1)); proangiogenic miRNAs (e.g., miR-126, miR-130a, miR-132) and anti-inflammatory miRNAs (e.g., miR124a, miR-125b); miRNAs that regulate collagen deposition (e.g., miR-21); stem cell derived factors (e.g., IGF-1, VEGF, TGF-β1, HGF, FGF-2, PDGF-BB, BMP-2, and SDF); nucleotides encoding any of the exosome components, growth factors, and/or stem cell derived factors described herein; short peptides and/or fragments (e.g., at least 10, 15, 20, 25, 30, 35, 40, 45, 50 amino acids in length) comprising the exosome components, growth factors, and/or stem cell derived factors described herein; proteins corresponding to exosome components, growth factors, and/or stem cell derived factors described herein; lipids, cytoprotective cytokines (i.e., IL-10, IL-13, hepatocyte growth factor (HGF) and stromal cell-derived factor-1 alpha (CXCL12)); or any combination thereof (see, for example, Geiger A.; Walker A.; Nissen E. (2015). "Human fibrocyte-derived exosomes accelerate wound healing in genetically diabetic mice". *Biochemical and Biophysical Research Communications* 467(2): 303-309).

Another embodiment provides for a kit comprising a means for ablating at least one nerve of the renal artery of a subject, a means for administering cells to the subject, and instructions for use thereof. In embodiments, the means for ablating can be selected from the group consisting of a means for chemical denervation, a means for radio frequency denervation, or a combination thereof. In embodiments, the cells can be cardiac derived stem cells. In embodiments, the cells can comprise cardiospheres, cardiosphere-derived cells, cardiac stem cells, bone marrow derived cells, adipose derived mesenchymal cells, hematopoietic stem cells, bone marrow derived mesenchymal cells cardiac, mesenchymal, endothelial, induced pluripotent stem cells, exosomes derived from progenitor cells, cardiac-derived myocytes, bone-derived stem cells, stem cell-derived releasing factors, or any combination thereof. In embodiments, the stem cell-derived releasing factors can be exosomes, microRNAs, nucleotides, lipids, short peptides, proteins, cytoprotective cytokines (for example, IL-10, IL-13, hepatocyte growth factor (HGF) and stromal cell-derived factor-1 alpha (CXCL12)), stem cell derived factors (for example, SDF) or any combination thereof. In some embodiments, stem cell-derived releasing factors comprise exosomes and/or components thereof (e.g., hepatocyte growth factor (HGF), insulin-like growth factor-1 (IGF1), nerve growth factor (NGF), and stromal-derived growth factor-1 (SDF1)); proangiogenic miRNAs (e.g., miR-126, miR-130a, miR-132) and anti-inflammatory miRNAs (e.g., miR124a, miR-125b); miRNAs that regulate collagen deposition (e.g., miR-21); stem cell derived factors (e.g., IGF-1, VEGF, TGF-β1, HGF, FGF-2, PDGF-BB, BMP-2, and SDF); nucleotides encoding any of the exosome components, growth factors, and/or stem cell derived factors described herein; short peptides and/or fragments (e.g., at least 10, 15, 20, 25, 30, 35, 40, 45, 50 amino acids in length) comprising the exosome components, growth factors, and/or stem cell derived factors described herein; proteins corresponding to exosome components, growth factors, and/or stem cell derived factors described herein; lipids, cytoprotective cytokines (i.e., IL-10, IL-13, hepatocyte growth factor (HGF) and stromal cell-derived factor-1 alpha (CXCL12)); or any combination thereof (see, for example, Geiger A.; Walker A.; Nissen E. (2015). "Human fibrocyte-derived exosomes accelerate wound healing in genetically diabetic mice". *Biochemical and Biophysical Research Communications* 467(2): 303-309). In embodiments, the nerve can be at least one sympathetic nerve.

Another embodiment provides for a method of treating a subject in need thereof, wherein the method comprises attenuating the activity of the sympathetic nervous system of the subject, and administering to the subject a therapeutically effective amount of cells. In embodiments, the sympathetic nervous system is attenuated by no more than 25%, by no more than 50%, by no more than 75%, or by no more than 100% as compared to the subject prior to the sympathetic nervous system being attenuated. In embodiments the sympathetic nervous system can be attenuated by vagal nerve stimulation (VNS), spinal cord stimulation (SCS), baroreceptor stimulation, renal denervation, tragus stimulation, endovascular stimulation, endovascular cardiac plexus stimulation or a combination thereof. In embodiments, a device implanted within the subject attenuates the activity of the sympathetic nervous system. In embodiments, the device stimulates the vagal nerve, stimulates the spinal cord, or a combination thereof. In embodiments, baroreceptor stimulation comprises carotid baroreceptor stimulation. In embodiments, attenuating the sympathetic nervous system comprises reduction in plasma neurepinephrine levels. In embodiments, attenuation of the sympathetic nervous system can be measured by microneurography, positron emission tomography (PET), heart rate, heart rate viability, heart rate recovery following exercise, baroreflex sensitivity, catecholamine (norepinephrine, epinephrine, dopamine) concentrations, concentration of BDNF, or a combination thereof. In embodiments, the subject can be suffering from a heart disease. In embodiments, the heart disease can comprise a myocardial injury, myocardial infarction, heart failure or any combination thereof. In embodiments, heart failure can comprise heart failure with reduced ejection fraction (HFrEF) or heart failure with preserved ejection fraction (HFpEF). In embodiments, the heart failure can be artificially induced from a composition administered to a subject, can be induced by a metabolic syndrome, is naturally occurring, or a combination thereof. In embodiments, the composition comprises an anti-cancer agent. In embodiments, the anti-cancer agent can comprise an anthracycline, such as doxorubicin. In embodiments, the administering of the cells can occur prior to, concurrently with, or subsequent to attenuation. In embodiments, the method can further comprise the step of determining cardiac function of the subject. In embodiments, the cardiac function can comprise left ventricular ejection fraction, left ventricular diastolic function, or a combination thereof. In embodiments, determining the cardiac function can comprise measuring a myocardial peptide marker, a circulating peptide marker, a heart pump function, a heart gross morphology, an enzymatic activity, or a combination thereof. In embodiments, the peptide marker can comprise ANP, BNP, or CNP. In embodiments, the heart pump function can be of the left ventricle. In embodiments, the dimensions of heart pump function can be captured digitally, electronically, or a combination thereof. In embodiments, gross morphology can comprise a myocardial fibrosis, myocardial vascularity, or a combination thereof. In embodiments, the enzymatic activity can comprise neprilysin activity. In embodiments, heart pump function can be measured by echocardiogram. In embodiments, myocardial injury can be heart failure, myocardial infarction, ischemia/reperfusion, or a combination thereof. In embodiments, the cells can be administered intracoronarilly, intramyocardially, intravenously, intraarterially, or a combination thereof. In embodiments, the cells can be autologous cells, homologous cells, heterologous cells, allogenic cells, syngenic cells, or any combination thereof. In embodiments, the cells can be stem cells, stem cell-like cells, stem cell-derived releasing factors, or any combination thereof. In embodiments, the cells can be cardiospheres, cardiosphere-derived cells, cardiac stem cells, bone marrow derived cells, adipose derived mesenchymal cells, hematopoietic stem cells, bone marrow derived mesenchymal cells cardiac, mesenchymal, endothelial, induced pluripotent stem cells, exosomes derived from progenitor cells, cardiac-derived myocytes, bone-derived stem cells, or any combination thereof. In embodiments, the cells can be stem cell-derived releasing factors are microRNAs, exosomes, nucleotides, lipids, short peptides, proteins, or any combination thereof.

Other objects and advantages of this invention will become readily apparent from the ensuing description.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 90 shows sodium and water excretion in SHR following RF-RDN in heart failure.

DETAILED DESCRIPTION OF THE INVENTION

Abbreviations and Definitions

Figure 1:
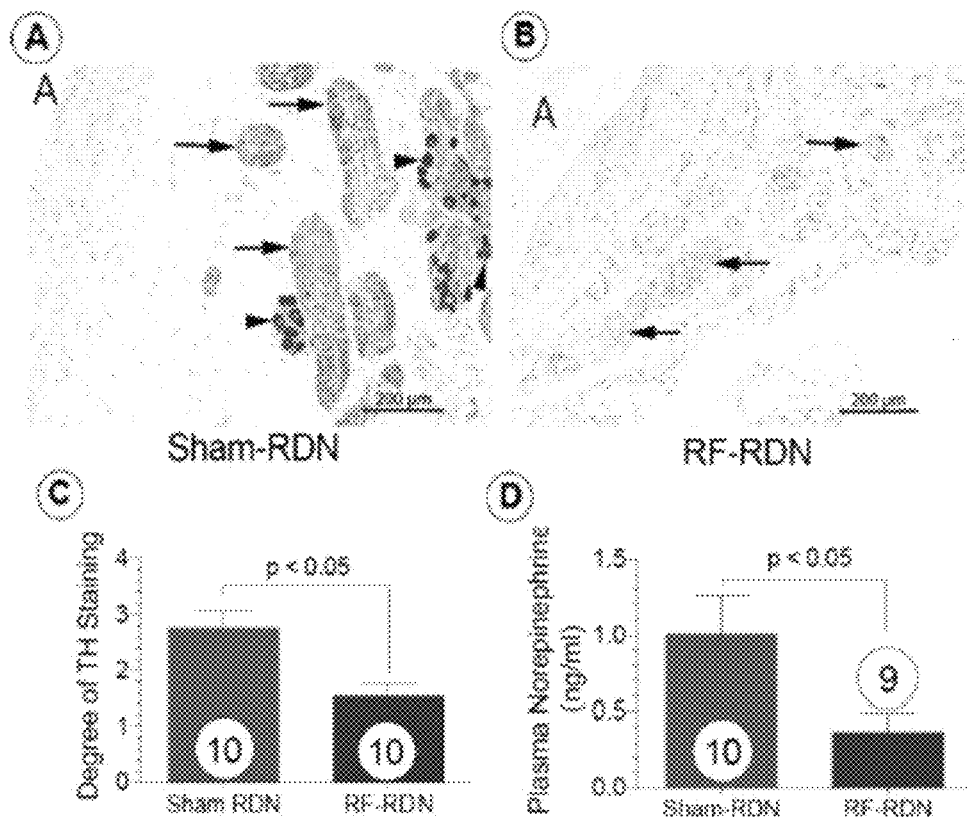
FIG. 1 shows the renal artery nerve staining and catecholamine spillover following RF-RDN in SHR. Tyrosine hydroxylase (TH) immunostaining of renal artery sections 35 days following Sham-RDN (A) or RF-RDN (B). Results of histopathologic assessment of the degree of TH immunostaining are shown (C). Plasma norepinephrine levels (D) 28 days following Sham or RF-RDN are shown. Arrows=normal nerves showing TH staining; Arrowheads=ganglion cells showing full intensity cytoplasmic TH staining; A=renal artery lumen. Values are mean±SEM. Circles denote number of animals per group. $*p<0.05$ between groups.

Detailed descriptions of one or more embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Methods of Treatment

Aspects of the invention can comprise the step of determining an improvement in cardiac function of the subject by measuring a myocardial peptide marker, a circulating peptide marker, a heart pump function, a heart gross morphology, an enzymatic activity, or a combination thereof.

Aspects of the invention are directed towards a method of treating a subject in need thereof by ablating at least one nerve of the renal artery of the subject and administering to the subject a therapeutically effective amount of cells.

Aspects are further directed towards a method of treating a subject in need thereof by attenuating the activity of the sympathetic nervous system of the subject, administering to the subject a therapeutically effective amount of cells.

The term "treating" can refer to partially or completely alleviating, ameliorating, improving, relieving, delaying onset of, inhibiting progression of, reducing severity of, and/or reducing incidence of one or more symptoms, features, or clinical manifestations of a particular disease, disorder, and/or condition. For example, "treating" heart failure can refer to increasing the left ventricular ejection fraction, which can serve as an indicator of improved cardiac function. Treatment can be administered to a subject who does not exhibit signs of a disease, disorder, and/or condition (e.g., prior to an identifiable disease, disorder, and/or condition), and/or to a subject who exhibits only early signs of a disease, disorder, and/or condition for the purpose of decreasing the risk of developing pathology associated with the disease, disorder, and/or condition. In some embodiments, treatment comprises ablating or attenuating the activity of a renal nerve and administering to the subject a therapeutically effective amount of cells.

The term "subject" or "patient" can refer to any organism to which aspects of the invention can be administered, e.g., for experimental, diagnostic, prophylactic, and/or therapeutic purposes. Typical subjects to which methods of the present disclosure may be administered will be mammals, particularly primates, especially humans. For veterinary applications, a wide variety of subjects can be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals can be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

The term "ablate," "ablation"," or "ablating" (generally referred to as "ablation") can refer to an intervention that alters a tissue to suppress or inhibit its biological function or ability to respond to stimulation permanently or for an extended period of time, such as greater than 3 weeks, greater than 6 months, greater than a year, for several years, or for the remainder of the patient's life. In some embodiments ablation refers to an intervention that is intended to permanently suppress or inhibit natural nerve functioning. Ablation can involve, but is not limited to, thermal necrosis (e.g., using energy such as thermal energy, radiofrequency electrical current, direct current, microwave, ultrasound, high intensity focused ultrasound, and laser), cryogenic ablation, electroporation, selective denervation, embolization (e.g., occlusion of blood vessels feeding the gland), artificial sclerosing of blood vessels, mechanical impingement or crushing, surgical removal, chemical ablation, or application of radiation causing controlled necrosis (e.g., brachytherapy).

The term "attenuate" or "attenuation" can refer to any reduction in the strength of the biological function or ability to respond to stimulation, whether permanently, for a short period of time, or for an extended period of time, such as greater than 3 weeks, greater than 6 months, greater than a year, for several years, or for the remainder of the patient's life. In some embodiments attenuation refers to an intervention that is intended to temporarily suppress or inhibit natural nerve functioning, and in other embodiments attenuation is a permanent reduction in biological function or ability to respond to stimulation. In some embodiments, attenuation can refer to a reduction in the strength of the biological function by about 10%, about 20%, about 30%, about 40%, about 50%, about 60%, about 70%, about 80%, or about 90%. For example, attenuation a renal nerve can be achieved by vagal nerve stimulation (VNS), spinal cord stimulation (SCS), baroreceptor stimulation, renal denervation, tragus stimulation, endovascular stimulation, endovascular cardiac plexus stimulation or a combination thereof.

The term "administration" refers to introducing a substance, such as cells or a pharmaceutical composition comprising cells, into a subject. In general, any route of administration may be utilized including, for example, intracoronarilly, intramyocardially, intravenously, intraarterially, or any combination thereof. For example, the cells, such as cardiac derived stem cells, can be administered to the subject prior to, concurrent with, or subsequent to nerve ablation, such as renal nerve ablation. In another embodiments, the cells, such as cardiac derived stem cells, can be administered in a continuous fashion.

The term "therapeutically effective" can refer to the amount of a pharmaceutically active composition, such as cells or a composition comprising the same, that will result in a measurable desired medical or clinical benefit to a subject, as compared to the subject's baseline status or to the status of an untreated or placebo-treated (e.g., not treated with the cells) subject. For example, the clinical benefit to the subject can be improved heart pump function, as demonstrated by an improvement in heart ejection fraction.

In embodiments, the nerve comprises a nerve of the sympathetic nervous system. The term "sympathetic nervous system" can refer to the thoracolumbar division of the autonomic nervous system, which is responsible for helping to regulate a variety of body functions, including heart rate, breathing, sweating, and digestion.

Aspects of the invention are further directed towards methods for improving cardiac function of a subject comprising ablating or attenuating at least one nerve of the renal artery and administering to the subject a therapeutically effective amount of cells.

"Cardiac function" can refer to the function of the heart and, further, to the cardio-vascular system. In most species, the heart comprises a muscle which repeatedly contracts to pump blood through vascular network. Cardiac function can be impacted by a variety of factors including age, stress, disease, overall health, and the like. Cardiac function can also be affected by environmental conditions such as altitude and pressure. Non-limiting examples of cardiac functions comprise left ventricular ejection fraction, left ventricular diastolic function, right ventricular function, atrial function, valvular function, or a combination thereof.

Aspects of the invention comprise the use of left ventricular ejection fraction as an indicator of heart pump function. For example, an increase in left ventricular ejection fraction as demonstrated by echocardiogram can be used as an indicator of improved heart pump function following treatment with methods as described herein. Aspects can use other measurements and indicators as an indicator of heart pump function. Non-limiting examples of indicators of pump function comprise left ventricle developed pressure, contractility, left ventricle end-diastolic pressure, the detection of regional wall movement abnormalities (such as by doplar imagine, or stress echocardiography. In embodiments, mechanical performance is not only be evaluated at rest, but also in response to stimulation.

Aspects of the invention comprise the use of heart gross morphology measurements as an indicator of cardiac function. For example, the heart gross morphology may be left ventricular end-systolic diameter or can be left ventricular end-diastolic diameter as an indicator of cardiac function. A decrease in left ventricular end-systolic diameter (LVESD) following the methods as described herein can indicate improved left ventricular systolic function following acute myocardial infarction and heart failure.

As described herein, radiofrequency renal denervation (RF-RDN) significantly increases the thickness of the interventricular septal wall at end-systole following ischemic injury, indicating that RF-RDN promotes myocardial tissue thickening of the infarcted wall. For example, an increase in the thickness of the interventricular septal wall can indicate less cardiac myocyte loss and less pathological remodeling following acute myocardial infarction and heart failure.

In vivo left ventricle pressure measurements indicate that RF-RDN has no significant effect on LV end systolic pressure or the rate of pressure development during contraction. However, the LV rate of decreased pressure during relaxation (LV Min dP/dT) was significantly improved in the RF-RDN treated animals. The LV relaxation time constant, Tau, had a trending improvement in the RF-RDN group compared to Sham-RDN treated animals. An increase in LV pressure measurements following the methods as described herein can indicate improved left ventricular performance.

As described herein, left ventricular end-diastolic diameter (LVEDD) is significantly reduced following RF-RDN. Aspects of the invention comprise the use of a reduction in left ventricular end-diastolic diameter, for example, as an indicator of improved left ventricular function and a reduction in adverse cardiac remodeling.

Embodiments can further comprise measuring cardiac function of the subject such as by measuring a myocardial peptide marker, a circulating peptide marker, a heart pump function, a heart gross morphology, an enzymatic activity, or a combination thereof. For example, a heart pump function can be measured by echocardiogram, and an increase in the left ventricular ejection fraction indicates an improved cardiac function. A cardiac function can be measured by, for example, microneurography, positron emission tomography (PET), heart rate, heart rate viability, heart rate recovery following exercise, baroreflex sensitivity, or a combination thereof.

Aspects of the invention comprise the use of peptide markers as an indicator of improved cardiac function and overall health. For example, peptide markers can be a circulating marker or a myocardial peptide marker. For example, circulating markers can be nitric oxide, and myocardial peptide markers can be ANP, BNP, CNP, cardiac troponin. In aspects of the invention, the peptide markers can be natriuretic peptides, such as ANP, BNP, and CNP. For example, an increase in natriuretic peptides, such as ANP, BNP and CNP, following the methods as described herein can result in improved cardiac function and improved blood circulation.

Additional peptide markers comprise cardioprotective and vasculoprotective markers, such as Substance P and Bradykinin (BK). NEP degrades these and other cardioprotective and vasculoprotective peptides. As described herein, RF-RDN promotes BK levels in circulation, in part because RF-RDN inhibits NEP activity. It is well established that BK promote nitric oxide (NO) levels by activating endothelial nitric oxide synthase (eNOS). Increased LV nitrite levels following RF-RDN indicate improved NO signaling and may provide another mechanism of cardioprotection.

Aspects of the invention comprise the use of enzymes, enzyme levels, enzymatic activity, or any combination thereof, as an indicator of cardiac function. For example, the enzyme may be Neprilysin, a metalo-endopeptidase that degrades NPs. Neprilysin (NEP) is NEP is present in a wide variety of tissues, but is particularly abundant in the kidney. As described herein, plasma ANP, BNP and CNP levels were markedly elevated 12 weeks after RF-RDN in part due to inhibition of renal neprilysin activity. For example, a decrease in neprilysin activity or neprilysin levels can indicate improvements in left ventricular function and improved function of the circulatory system.

As described herein, RF-RDN reduced left ventricular (LV) fibrosis score and % area fibrotic of the LV following ischemic injury. One aspect of the present invention comprises the methods as described herein to reduce left ventricular fibrosis. A reduction in left ventricular fibrosis, for example, is an indicator of reduced pathological left ventricular remodeling.

As described herein, RF-RDN also inhibits transition zone expansion of the infarcted region, in part by reducing pro-fibrotic signaling. Another aspect of the invention comprises the methods as described herein to reduce transition zone expansion. Reduction in transition zone expansion, for example, is an indicator of improved cardiac structure and reduced pathological cardiac remodeling.

Aspects of the invention can be applicable to subjects suffering from a heart disease. "Heart disease" can refer to acute and/or chronic cardiac dysfunctions. Heart disease is often associated with a decrease in cardiac contractile function and may be associated with an observable decrease in blood flow to the myocardium (e.g., as a result of coronary artery disease). Manifestations of heart disease include myocardial ischemia, which may result in angina, heart attack and/or congestive heart failure.

Non-limiting examples of heart disease comprise a myocardial injury, myocardial infarction, heart failure, a congenital heart defect, a structural heart disease, an inflammation-mediated heart disease, hypertension-induced heart failure, or any combination thereof.

The term "myocardial injury" can refer to a contusion or bruising of the myocardium, such as from blunt trauma, as well as to injury, such as ischemic injury, to the myocardium, such as results from angina (including unstable angina) or myocardial infarction, heart failure, ischemia/reperfusion, or any combination thereof.

"Myocardial ischemia" is a condition in which the heart muscle does not receive adequate levels of oxygen and nutrients, which is typically due to inadequate blood supply to the myocardium (e.g., as a result of coronary artery disease).

"Heart failure" is clinically defined as a condition in which the heart does not provide adequate blood flow to the body to meet metabolic demands. Symptoms include breathlessness, fatigue, weakness, leg swelling, and exercise intolerance. On physical examination, patients with heart failure tend to have elevations in heart and respiratory rates, rales (an indication of fluid in the lungs), edema, jugular venous distension, and, in many cases, enlarged hearts. Patients with severe heart failure suffer a high mortality; typically 50% of the patients die within two years of developing the condition. In some cases, heart failure is associated with severe coronary artery disease ("CAD"), typically resulting in myocardial infarction and either progressive chronic heart failure or an acute low output state. In other cases, heart failure is associated with dilated cardiomyopathy without associated severe coronary artery disease. Heart failure can be metabolic-syndrome induced, artificially induced from a composition administered to a subject, such as an anti-cancer agent, naturally occurring, or a combination thereof.

The ejection fraction (EF) is an important measurement in determining how well a subject's heart is pumping out blood, and can be used in diagnosing and tracking heart failure. Ejection fraction can be measured as a percent measurement of how much blood the left ventricle pumps out with each contraction. For example, an ejection fraction of 60% means that 60% of the total amount of blood in the left ventricle is pushed out with each heartbeat. A normal heart's ejection fraction may be between 50% and 70%. A measurement of under 40% may be evidence of heart failure or cardiomyopathy. An ejection fraction from 41% to 49% may be considered "borderline" but does not always indicate that a person is developing heart failure. It may indicate damage, perhaps from a previous heart attack. An ejection fraction of higher than 75% may indicate a heart condition like hypertrophic cardiomyopathy.

Heart failure can comprise heart failure with reduced ejection fraction (HFrEF) or heart failure with preserved ejection fraction (HFpEF). In a subject with heart failure with preserved ejection fraction, also referred to as diastolic heart failure, the heart muscle contracts normally but the ventricles do not relax as they should during ventricular filling (or when the ventricles relax). If the heart muscle has become so thick and stiff that the ventricle holds a smaller-than-usual volume of blood, it might still seem to pump out a normal percentage of the blood that enters it. In reality, though, the total amount of blood pumped isn't enough to meet the body's needs. In a subject with heart failure with reduced ejection fraction, also referred to as systolic heart failure, the heart muscle does not contract effectively and less oxygen-rich blood is pumped out to the body.

Non-limiting clinical examples of methods to measure ejection fraction comprise an echocardiogram, MUGA scan, CAT scan, cardiac catheterization or a nuclear stress test.

Hypertension is a major risk factor for stroke, ischemic heart disease, and the development of heart failure. As used herein, the term "hypertension" can refer to abnormally high blood pressure, such as arterial blood pressure, when compared to prior blood pressure readings, and the abnormally high value is maintained over a specified time period, such as 3-6 months. The increase can be observed in systolic pressure, diastolic pressure, or both. Conventionally, hypertension is defined as a blood pressure of equal to or greater than 140/90 mm Hg. Blood pressure can be measured by any method known in the art, such as direct arterial puncture, oscillometry, Doppler ultrasonography, and a sphygmomanometer. Blood pressure is measured in millimeters of mercury (mm Hg). Hypertension-induced heart failure is usually preceded by the development of left ventricular hypertrophy (LVH), which represents an adaptive and compensatory response to the increased cardiac workload.

Aspects of the invention can be directed towards both hypertensive subjects and normotensive subjects. Much of the cardioprotective effects of RDN therapy can be due to reduction in pressure, which reduces the afterload of the heart. However, as described herein, left ventricular function and cardiac remodeling is improved in normotensive animals following RF-RDN. Furthermore, left ventricular end-diastolic diameter (LVEDD) was also significantly reduced. Aspects of the invention can have be used to treat both normotensive and hypertensive subjects.

A "congenital heart defect," also known as a "congenital heart anomaly" or "congenital heart disease," can refer to a defect of the heart, such as a structural defect, that is present at birth. Complications, such as heart failure, can result from congenital heart defects. Signs and symptoms vary depending on the specific defect of the hear, and can include rapid breathing, bluish skin, poor weight gain, and feeling tired. Non-limiting examples of congenital heart defects comprise atrial septal defect, patent foramen ovale, and coarctation of the aorta.

A congenital heart defect can include a "structural heart disease," which refers to abnormalities in the structure of the heart, such as abnormalities of the valves, in the heart wall itself, or of a chamber of the heart. Such structural defects can also develop with normal aging and wear on the heart.

"Inflammation-mediated heart disease" can refer to diseases caused by inflammation of structural components of the heart, such as of the heart muscle or heart wall. Non-limiting examples of "inflammation-mediated heart disease" comprises cardiac allograft rejection, atherosclerosis, and myocarditis.

The Cells

Aspects of the invention are directed towards a method of treating a subject in need thereof by modulating the activity of or ablating at least one nerve of the renal artery of the subject and administering to the subject a therapeutically effective amount of cells. The term "cell" refers to cytoplasm bound by a membrane that contains DNA within. A cell may be either a prokaryotic or eukaryotic cell.

In embodiments, autologous cells, homologous cells, allogenic cells, heterologous cells, or a combination thereof can be administered to the subject. Autologous cells, for example, can be collected from the subject and subsequently re-administered to the subject. Homologous cells, also referred to allogenic cells, can be collected from a compatible donor, such as an immunocompatible donor, prior to administration to the subject. Heterologous cells can be collected from a species different than that of the subject, and subsequently administered to the subject. Withdrawal, storage, preservation, preparation and administration of the cells can be optimized as desired, such as based on cell type, route of administration, subject, or disease type.

In some methods, the recipient patient of stem cells and the donor from which the cells are obtained are HLA-matched to reduce allotypic rejections. In other methods, cells are administered under cover of an immunosuppressive regime to reduce the risk of rejection. Immunosuppressive agents that can be used include cyclosporin, corticosteroids, and OKT3. In other methods, immune responses are avoided by obtaining stem cells from the patient that is to be treated. Cardiac derived stems cells, for example, can be obtained by biopsy of heart tissue, and expanded in vitro before re-administration. Alternatively, given the present provision of isolated cardiac-derived stem cells, differentiation markers can be identified for these cells, and the cells can be isolated from the blood of the patient to be treated (see PCT/US1999/006356, the entire contents of which are incorporated herein by reference).

In embodiments, stem cells or stem cell-like cells are administered to the subject. The term "stem cell" refers to a progenitor as defined herein further capable of self-renewal, i.e., which can under appropriate conditions proliferate without differentiation. The term encompasses stem cells capable of substantially unlimited self-renewal, i.e., wherein at least a portion of the stem cell's progeny substantially retains the unspecialized or relatively less specialized phenotype, the differentiation potential, and the proliferation capacity of the mother stem cell; as well as stem cells which display limited self-renewal, i.e., wherein the capacity of the stem cell's progeny for further proliferation and/or differentiation is demonstrably reduced compared to the mother cell.

Non-limiting examples of cells which can be administered to a subject in embodiments of the invention comprise cardiospheres, cardiosphere-derived cells, cardiac stem cells, bone marrow derived cells, adipose derived mesenchymal cells, hematopoietic stem cells, bone marrow derived mesenchymal cells cardiac cells, mesenchymal cells, endothelial cells, induced pluripotent stem cells, exosomes derived from progenitor cells, cardiac-derived myocytes, bone-derived stem cells, or any combination thereof.

Conditions as described herein can be treated by administration of cells as described herein, such as cardiac-derived stem cells. The cells can be administered intracoronarilly, intramyocardially, intravenously, intraarterially, or any combination thereof. For example, a catheter can be used for administration. Cells can be administered in a therapeutically effective dosage. For example, such a dosage of cardiac-derived stem cells is sufficient to generate significant numbers of new cardiocytes cells in the heart, and/or at least partially replace necrotic heart tissue, and/or produce a clinically significant change in heart function. A clinically significant improvement in heart performance can be determined by measuring a heart pump function, such as the left ventricular ejection fraction, prior to, and after administration of cells, and determining an increase, such as at least a 5% increase or, for example, a 10% or more increase, in the total ejection fraction. Standard procedures are available to determine ejection fraction, as measured by blood ejected per beat. Dosages can vary from about 100-$10^7$, 1000-$10^6$ or $10^4$-$10^5$ cells. Cells can be administered as pharmaceutical compositions, which can also include, depending on the formulation desired, pharmaceutically-acceptable, typically sterile, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers and the like Administration of stem cells can be preceded, accompanied or followed by modulation of a nerve as described herein, such as renal nerve denervation.

Embodiments as described herein comprise cardiac-derived stem cells. Methods of isolating, processing, maintaining, evaluating, see PCT/US1999/006356, the entirety of which is incorporated herein by reference.

In certain embodiments, stem cell-derived releasing factors can be administered to the subject. Non-limiting examples of such comprise microRNAs, exosomes, nucleotides, lipids, short peptides, proteins, or any combination thereof.

Exosomes from different sources contain different structural proteins and lipids. The payloads are even more diverse. According to the current version of the exosome content database, ExoCarta (version 4; http://www.exocarta.org), from the 146 studies of different cell types and organisms, 4,563 proteins, 1,639 mRNAs, 764 miRNAs, and 194 species of lipids have been identified in exosomes.

Exosomes are bounded by a lipid bilayer membrane consisting of cholesterol, diglycerides, sphingolipids, phospholipids, glycerophospholipids, and polyglycerophospholipids. The lipid composition of exosomes differs from that of the plasma membrane, which explains the difference in the physical properties, including the exceptional rigidity of exosome membranes compared with that of the plasma membrane. Some of these lipids also serve extrastructural functions, including trafficking during biogenesis (particularly trafficking of ceramide, which is critical for budding into the endosome), recognition, and internalization. Aside from structural and trafficking components, exosomes also contain bioactive lipids, including prostaglandins, leukotrienes, and active enzymes that can generate these lipids.

The most commonly occurring proteins belong to classes of membrane transport and fusion proteins, including tetraspanins (e.g., CD63, CD9, and CD81), heat shock proteins (e.g., Hspa8, Hsp90), GTPases (e.g., EEF1A1, EEF2), and endosomal proteins and markers (e.g., Alix). Other proteins commonly found on exosomes include cytoskeletal, metabolic, signaling, and carrier proteins and albumin. Relative expression levels depend largely on the cell type of origin and may change under different environmental conditions. Other markers of note are major histocompatibility complexes (MHCs). MHC class I is ubiquitously expressed on all exosomes, whereas MHC II expression is confined to exosomes derived from antigen-presenting cells, including dendritic cells, macrophages, B cells, microglia, and intestinal epithelial cells.

Given the incredible diversity of cells, generalizations regarding exosome cargo should not be viewed dogmatically. The payload of each exosome population varies greatly according to the cell and tissue type of the secreting population. Nevertheless, certain features are common. Given the small size of exosomes, organelles such as ribosomes and mitochondria are generally absent; likewise, DNA is rarely found in exosomes in any abundance, unlike the case for cancer-derived EVs, which are typically larger than exosomes and contain double-stranded DNA. Proteins are present and vary greatly with the cell of origin. Exosomes can contain enzymes, transcription factors, and structural proteins. Perhaps the greatest source of signaling diversity is in the plentiful RNA content, which includes not only transcripts but also abundant noncoding RNA species such as miRs and transfer RNAs. Exosome RNA content varies dramatically according to the cell type of origin, but it does not merely parrot the RNA profile of the secreting cell. Sorting processes are at play in determining what RNA species are packaged into exosomes. Furthermore, the unique signature of miRs derived from tumor exosomes has generated increasing interest in the use of exosomes as diagnostic and prognostic biomarkers.

As used herein, the qualifier "pluripotent" denotes a stem cell capable of giving rise to cell types originating from all three germ layers of an organism, i.e., mesoderm, endoderm, and ectoderm, and potentially capable of giving rise to any and all cell types of an organism, although not able of growing into the whole organism.

A progenitor or stem cell is said to "give rise" to another, relatively more specialized cell when, for example, the progenitor or stem cell differentiates to become said other cell without previously undergoing cell division, or if said other cell is produced after one or more rounds of cell division and/or differentiation of the progenitor or stem cell. The term "mammalian pluripotent stem cell" or "mPS" cell generally refers to a pluripotent stem cell of mammalian origin. The term "mammal" refers to any animal classified as such, including, but not limited to, humans, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes.

The invention also provides a pharmaceutical composition or formulation comprising cells, such as those described herein. For example, the pharmaceutical composition comprising cells, such as cardiac derived stem cells, can be administered to a subject before, concurrently with, or subsequent to modulation of a renal nerve.

The pharmaceutical composition may contain components ensuring the viability of the cells therein. In particular, the cells can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996, the entire contents of which is incorporated herein by reference in its entirety. Choice of the cellular excipient and any accompanying elements of the composition will be adapted in accordance with the device used for administration. For example, the composition may comprise a suitable buffer system to suitable pH, e.g., near neutral pH (e.g., phosphate or carbonate buffer system), and may comprise sufficient salt to ensure iso-osmotic conditions for the cells, i.e., preventing osmotic stress. For example, suitable solution for these purposes may be phosphate-buffered saline (PBS) as known in the art. Further, the composition may comprise a carrier protein, e.g., albumin, which may increase the viability of the cells. To ensure exclusion of non-human animal material, the albumin may be of human origin (e.g., isolated from human material or produced recombinantly). Suitable concentrations of albumin are generally known.

Pharmaceutical compositions according to the present invention, and for use in accordance with the present invention, may comprise, in addition to the cells, a pharmaceutically acceptable excipient, carrier, buffer, preservative, stabilizer, anti-oxidant or other material well known to those skilled in the art. Such materials should be non-toxic and should not interfere with the activity of the cells. The precise nature of the carrier or other material will depend on the route of administration. The composition may include one or more of protective molecules, growth factor, anti-apoptotic factor, or factor that regulates gene expression in the cells of the invention. Such substances may render the cells independent of its environment. The invention also encompasses methods of producing said pharmaceutical compositions by mixing the cells of the invention with one or more additional components as above. Liquid pharmaceutical compositions generally include a liquid carrier such as water, petroleum, animal or vegetable oils, mineral oil or synthetic oil. Physiological saline solution, tissue or cell culture media, dextrose or other saccharide solution or glycols such as ethylene glycol, propylene glycol or polyethylene glycol may be included.

The composition may be in the form of a parenterally acceptable aqueous solution, which is pyrogen-free and has suitable pH, isotonicity and stability. Those of relevant skill in the art are well able to prepare suitable solutions using, for example, isotonic vehicles such as Sodium Chloride, Ringer's Injection, or Lactated Ringer's Injection. A composition may be prepared using biological fluids, such as artificial cerebrospinal fluid. In a further aspect, the invention relates to an arrangement comprising a surgical instrument for administration of a composition at a site of tissue dysfunction or lesion and further comprising the pharmaceutical composition as defined above, wherein the arrangement is adapted for administration of the pharmaceutical composition at the site of tissue dysfunction or lesion. For example, a suitable surgical instrument or intravenous catheter may be capable of injecting a liquid composition comprising cells of the present invention at the site of cardiac dysfunction or structural defects. Cells may be implanted into a patient by any technique known in the art (Hastings, Conn L., et al. "Drug and cell delivery for cardiac regeneration." *Advanced drug delivery reviews* 84 (2015): 85-106, the entirety of which is incorporated herein by reference). To date, the majority of clinical studies and a significant number of preclinical studies have utilized relatively simple delivery methods for regenerative therapeutics, such as simple systemic administration or local injection in saline carrier vehicles. Other methods include (i) delivery of therapeutic agents in biomaterial carriers, (ii) nanoparticulate encapsulation, (iii) multimodal therapeutic strategies and (iv) localized, minimally invasive delivery via percutaneous transcatheter systems. Where administration of the cells to a patient is contemplated, the cells should be selected such as to maximize the tissue compatibility between the patient and the administered cells, thereby reducing the chance of rejection of the administered cells by patient's immune system (graft vs. host rejection). For example, advantageously the cell lines may be typically selected which have either identical HLA haplotypes (including one or more HLA-A, HLA-B, HLA-C, HLA-D, HLA-DR, HLA-DP and HLA-DQ; for example, one or all HLA-A, HLA-B and HLA-C) to the patient, or which have the most HLA antigen alleles common to the patient and none or the least of HLA antigens to which the patient contains pre-existing anti-HLA antibodies The Kit Aspects of the invention can be directed towards a kit comprising a means for attenuating or ablating at least one nerve of the renal artery of a subject, a means for administering cells to the subject, and instructions for use thereof. Optionally, the kit can comprise the cells to be administered to the subject, such as provided in a preservation solution, and/or instruments and reagents for isolating cells from a subject and purifying and culturing said cells.

Non-limiting examples of means for ablating a nerve thermal necrosis (e.g., using energy such as thermal energy, radiofrequency electrical current, direct current, microwave, ultrasound, high intensity focused ultrasound, and laser), cryogenic ablation, electroporation, selective denervation, embolization (e.g., occlusion of blood vessels feeding the gland), artificial sclerosing of blood vessels, mechanical impingement or crushing, surgical removal, chemical ablation, or application of radiation causing controlled necrosis (e.g., brachytherapy). For example, the kit may comprise means for chemical ablation, such as alcohol-based neurotoxins.

Non-limiting examples of means for attenuating a nerve comprises vagus nerve stimulation (VNS), spinal cord stimulation (SCS), baroreceptor stimulation, renal denervation, tragus stimulation, endovascular stimulation, endovascular cardiac plexus stimulation or a combination thereof. For example, the kit can contain an implantable device that delivers an electrical impulse to the vagal nerve.

Non-limiting examples of means for administering the cells to a subject comprises equipment and instruments known in the art for administering the cells and compositions containing the same intracoronarilly, intramyocardially, intravenously, intraarterially, or any combination thereof. Non-limiting examples of such equipment comprises a cannula, an infusion pump, a syringe, a catheter, and the like. For example, if to be administered intracoronarilly, cells such as CDCs can be infused through an over-the-wire angioplasty catheter, with the balloon inflated at the (stented) site of the previous blockage in the infarct-related artery (see Makkar, Raj R., et al. "Intracoronary cardiosphere-derived cells for heart regeneration after myocardial infarction (CADUCEUS): a prospective, Randomised phase 1 trial." *The Lancet* 379.9819 (2012): 895-904, which is incorporated herein by reference in its entirety). In such an example, cells can be infused over 15 min in three boluses, in a saline solution containing heparin (100 U/mL) and nitroglycerin (50 μg/mL). As other examples, cells can be administered intramyocardially by needle injection directly into the myocardium, can be administered by IV injection through an IV line, or can be administered arterially by syringe and arterial line.

The kit can further comprise the cells themselves, such as those described herein, and optionally preservatives and the like for growing and/or maintaining the cells. Non-limiting examples of which comprise cardiospheres, cardiosphere-derived cells, cardiac stem cells, bone marrow derived cells, adipose derived mesenchymal cells, hematopoietic stem cells, bone marrow derived mesenchymal cells cardiac, mesenchymal cells, endothelial cells, induced pluripotent stem cells, exosomes derived from progenitor cells, cardiac-derived myocytes, stem cell-derived releasing factors, bone-derived stem cells or any combination thereof.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

New approaches to reduce myocardial infarct size have stalled in translation. Clinical treatment for acute myocardial infarction is dominated by a rush to open the infarct related artery. Adjunctive therapies which work at the time of, or after, reperfusion are highly desirable. Recently, stem cell therapy has been examined as a therapy given after reperfusion to regenerate cardiac muscle and reduce scar size. However, clinical trials have had limited success due to sub-optimal stem cell delivery, cell viability, cell-engraftment, cell replication, and regenerative capacity of the ischemic region of tissue.

Renal Denervation (RDN) is a minimally invasive endovascular procedure by which an energy source (eg. Radiofrequency) ablates the sympathetic nerves of the renal artery. Studies in our lab show that RDN has infarct sparing effects by inhibiting pro-death signaling pathways, improving redox status, and enhancing nitric oxide (NO) signaling in cardiac myocytes (Polhemus et al. Circulation Research 2016). We have also found that following myocardial infarction injury, RDN reduces infarct size and promotes left ventricular wall thickening (Attached data). Hence, RDN has a unique ability to preserve myocardial cell viability, promote myocardial regeneration and create a healthy cellular environment for cell based therapies to improve cell retention, viability, and tissue regeneration.

Without wishing to be bound by theory, the use of RDN before, or at the time of, delivery of cell therapy can optimally reduce scar size and maximize tissue regeneration following ischemic injury.

Example 2

Specific Aims

Following acute myocardial infarction (MI), cardiac structure undergoes adverse remodeling leading to a progressive decline in cardiac function. However, while timely coronary revascularization therapy is effective for acute MI, maximizing reperfusion is not associated with a maximized cardioprotective effect. Not only does unrelieved ischemia cause permanent damage to the cardiac tissue, reperfusion of the tissue leads to significant injury of the myocardium. Once the myocardium has been damaged by the initial ischemic insult and further by reperfusion injury, there is a progressive decline in cardiac function and heart failure (HF) ensues.

The application of regenerative therapies aimed at preserving or restoring lost myocardial function post-MI is still evolving. Over the last decade, clinical trials have assessed the ability of stem and progenitor cells from various tissue niches to prevent or reverse these effects in the post-reperfusion phase. Modest improvements in cardiac function reported in many of these trials have tempered initial optimism for cardiac regenerative therapeutics. In addition, several issues concerning cardiac cell therapy including efficacy and cell retention have been raised.

Catheter-based radiofrequency renal denervation (RF-RDN) is currently under development for the treatment of resistant hypertension and is thought to reduce blood pressure via interruption of sympathetic pathways that modulate cardiovascular function. The sympathetic nervous system also plays a critical role in the pathogenesis of acute MI and heart failure. Previous studies in our laboratory have demonstrated significant cardioprotective actions of RF-RDN in rodent models of acute MI and HF. The proposed studies will evaluate the cardioprotective effects of RF-RDN and cardiac derived stem cells (CDCs) in a clinically relevant model of heart failure.

These studies will provide data necessary to further translation of this highly promising therapeutic regimen to the clinical arena. We will evaluate the effects of RF-RDN together with CDCs on the infarct size following myocardial ischemia and reperfusion injury. The overall goal of this project is to develop a new method using device technology with targeted biologics that modulate cardiac repair in heart failure and improve patient outcomes.

Together, without wishing to be bound by theory, the findings of these studies will provide essential information regarding the underlying neural, humoral and anatomical pathways that are altered in the myocardium by RF-RDN allowing for better CDC engraftment. Using an established rodent model of hypertension and acute MI, information generated from this study may then be translated to human studies to further treat the HF in chronic resistant hypertensive patients.

Specific Aim 1: To Evaluate the Effects of RF-RDN on Left Ventricular (LV) Remodeling and Function Following the Onset of Heart Failure Studies will measure LV function and dimensions, myocardial and circulating ANP, BNP, and CNP levels, myocardial fibrosis, myocardial vascularity, LV hemodynamics, and neprilysin activity in a porcine model of heart failure. These studies will involve a control group and a group treated with RF-RDN at 4 weeks post myocardial infarction.

Specific Aim 2: To Evaluate the Effects of RF-RDN+Cardiac Derived Stem Cells (CDCs) on Left Ventricular (LV) Remodeling and Function Following the Onset of Heart Failure Studies will measure LV function and dimensions, myocardial and circulating ANP, BNP, and CNP levels, myocardial fibrosis, myocardial vascularity, LV hemodynamics, and renal neprilysin activity in a porcine model of heart failure. These studies will involve a control group, a group treated with CDCs at 4 weeks post myocardial infarction, and a group treated with RF-RDN+CDCs at 4 weeks post-myocardial infarction.

The significance of this project lies in its goal to address two major challenges in medical therapy for acute MI. First, the number of patients progressing to HF could be reduced by limiting infarct size and improving cardiac function following acute MI. Secondly, RF-RDN and CDC therapies have only shown modest clinical benefit and patient morbidity and mortality remains high. The combination of RDN and CDC treatment has the potential to mitigate both those pathologies. This application is innovative because of its focus on the concept that it combines two technologies targeting different cardiac repair mechanisms which could have transformative therapeutic utility. The experiments herein will herald a new methodology that could be exploited in cardiovascular diseases wherein the sympathetic nervous system plays a pathogenic role.

Research Strategy (a) Significance

The proposed experiments will lead to improved patient outcomes following acute MI when treated using RF-RDN and CDC combination therapy. This proposal differs from previous efforts to develop devices and biologics for the treatment of acute MI. This strategy emphasizes the use of a new method combination approach in the setting of acute myocardial infarction. Coronary heart disease (CHD) was the leading cause of death in approximately 1 of every 7 deaths in the United States in 2013 [A1]. We do not propose a new standalone therapy for CHD. Our therapy builds on effective proven treatment: revascularization. However, while timely coronary revascularization therapy is effective for acute MI, maximizing reperfusion is not associated with a maximized cardioprotective effect. Not only does unrelieved ischemia cause permanent damage to the cardiac tissue, reperfusion of the tissue leads to significant injury of the myocardium. Once the myocardium has been damaged by the initial ischemic insult and further by reperfusion injury, it is replaced by fibrous scar tissue. Since scar tissue does not contribute to myocardial contraction, global cardiac function progressively declines and heart failure (HF) ensues. Projections show that the prevalence of HF will increase 46% from 2012 to 2030, resulting in greater than 8 million American adults living with HF and over 50% of the people dying within 5 years following diagnosis of HF [A1]. The success of coronary revascularization has resulted in a paradigm shift in MI research with the current focus on new therapies to limit progression to HF.

High blood pressure, known as hypertension (HTN), is a major cause for cardiovascular diseases and remains uncontrolled in many individuals despite advanced drug therapies. There is consensus that increased activity of the sympathetic nervous system plays a major role in producing hypertension, as well as in the development of heart failure. Over the past 3 years clinical studies in humans have demonstrated remarkable success in lowering blood pressure in drug-resistant hypertensive patients by a new non-pharmacological approach. This procedure involves ablation (destruction) of the renal nerves by using angiographic guidance to place a catheter inside the renal arteries that delivers radio-frequency energy through the arterial wall.

As hypertension and cardiovascular disease rates rise in the developed world [A2], effective interventions and pharmacotherapies are required to optimally manage blood pressure and impede the development of comorbidities associated with hypertension. Recent enthusiasm for the treatment of resistant hypertension arose from preliminary clinical trials that reported effective, sustained reductions in blood pressure following catheter-based radiofrequency renal denervation (RF-RDN), which inhibits activity of renal sympathetic efferent and afferent nerves that lie within and immediately adjacent to the wall of the renal artery [A3-A5]. However, data from the SYMPLICITY HTN-3 trial, which was the first randomized, sham-controlled trial, failed to show significant reductions of systolic blood pressure in patients with resistant hypertension 6 months after RDN as compared to control [A6].

Cell therapy has emerged as a promising alternative strategy, since it involves the delivery of cells with regenerative potential, mainly through the release of paracrine and autocrine important factors that contribute to cell survival, angiogenesis, and tissue remodeling [A7-A9]. The different lineages of stem cells, which have shown therapeutic potential for cardiovascular disease, can be broadly classified as bone marrow derived cell (BMDC) [A10] bone marrow derived mesenchymal stem cells (MSC) [A11], adipose derived mesenchymal cell (ADSC) [A12], hematopoietic stem cells (HSC) [A13], and cardiac stem cells (CSC) [A14]. Despite the progress made since the first clinical trial conducted by Menasché et al. [A15] cell therapy is far from being an established treatment for patients with myocardial infarction. The lack of robust results due to the low rate of survival and poor retention of transplanted cells in the injured tissue [A16] as well as the cell type and route of administration seem to affect the treatment success [A17, A18].

The significance of this project lies in its goal to address two major challenges in medical therapy for acute MI. First, the number of patients progressing to HF could be reduced by limiting infarct size and improving cardiac function following acute MI. Secondly, RDN and CDC therapies have only shown modest clinical benefit and patient morbidity and mortality remains high. The combination of RDN and CDC treatment has the potential to mitigate both those pathologies.

The results from this study will be very important to the general public since information gained from these studies will guide future therapy for heart failure patients. The scientific community will be very interested in these results since data obtained from these studies will further elucidate the pathophysiology of heart failure. Data obtained from these studies will allow us to be competitive for NIH research grants from the Heart Lung and Blood Institute, The American Heart Association, and from a number of device companies. The results of the proposed studies will provide us with the necessary preliminary data to successfully compete for extramural funding from a number of sources.

(b) Innovation

The proposed studies on RF-RDN and CDC therapy in a clinically relevant large animal model will both expand the basic understanding of the pathogenesis of heart failure and lead to a new methodology for treatment. For years, physicians have controlled excessive sympathetic nervous system activity associated with cardiovascular disease using pharmacological approaches. However, many of the pharmacological agents have unintended and undesirable off-target side effects and their ultimate effectiveness is limited by the complex pathology of hypertension and by patient compliance. Renal denervation (RDN) is currently under clinical investigation as a strategy to significantly means to reduce blood pressure in resistant hypertensive patients by disruption of the sympathetic nerves that lie within and around the renal artery. We utilized a "reverse translational" approach to investigate the effects of complete renal denervation on myocardial injury in the setting of hypertension and acute myocardial infarction. Given that the sympathetic nervous system plays a critical role in the pathogenesis of myocardial infarction, we examined whether RF-RDN could protect the heart against myocardial ischemia/reperfusion injury in the setting of established hypertension.

Revascularization therapies including percutaneous coronary intervention (PCI), emergency coronary artery bypass grafting and fibrinolysis for patients suffering from acute MI have the primary aim of salvaging viable tissue within the ischemic risk zone; however, reperfusion has a deleterious effect on cardiac tissue. Cell therapy has emerged as a promising option to treat myocardial infarction or heart failure; more than 1500 patients with cardiovascular diseases are treated with adult progenitor cells worldwide [A19]. A number of plausible reasons have been discussed to explain the modest effects, sending researchers back to the bench to elucidate strategies to overcome the limitations of cell therapy and to develop more efficient approaches. Successful cardiac cell therapy in clinical practice also depends on the efficient delivery and the appropriate integration and alignment of injected or infused cells. The low rate of cell homing, retention, and survival is one of the major limitations in current experimental and clinical studies with all different types of cells available. Basically, 2 strategies might be used to augment cell engraftment. First, one may consider pretreating the cells to stimulate adhesion, migration, survival, or differentiation. Second, pretreatment of the target tissue to provide the appropriate milieu for progenitor cell recruitment, long-term engraftment, and differentiation might be an option, particularly when cells are delivered to patients with chronic heart failure and established scars in whom homing was shown to be extremely poor [A20].

The studies detailed in this application are innovative because of their focus on the concept that it combines two technologies targeting different signaling mechanisms cardiac repair which could have transformative therapeutic utility. Pretreatment of a distal organ using RF-RDN will provide a less hostile myocardial environment and thereby allowing for better stem cell retention and engraftment. The experiments proposed herein will herald a new methodology that could be exploited in cardiovascular diseases wherein the sympathetic nervous system plays a pathogenic role.

(c) Approach

Figure 2:
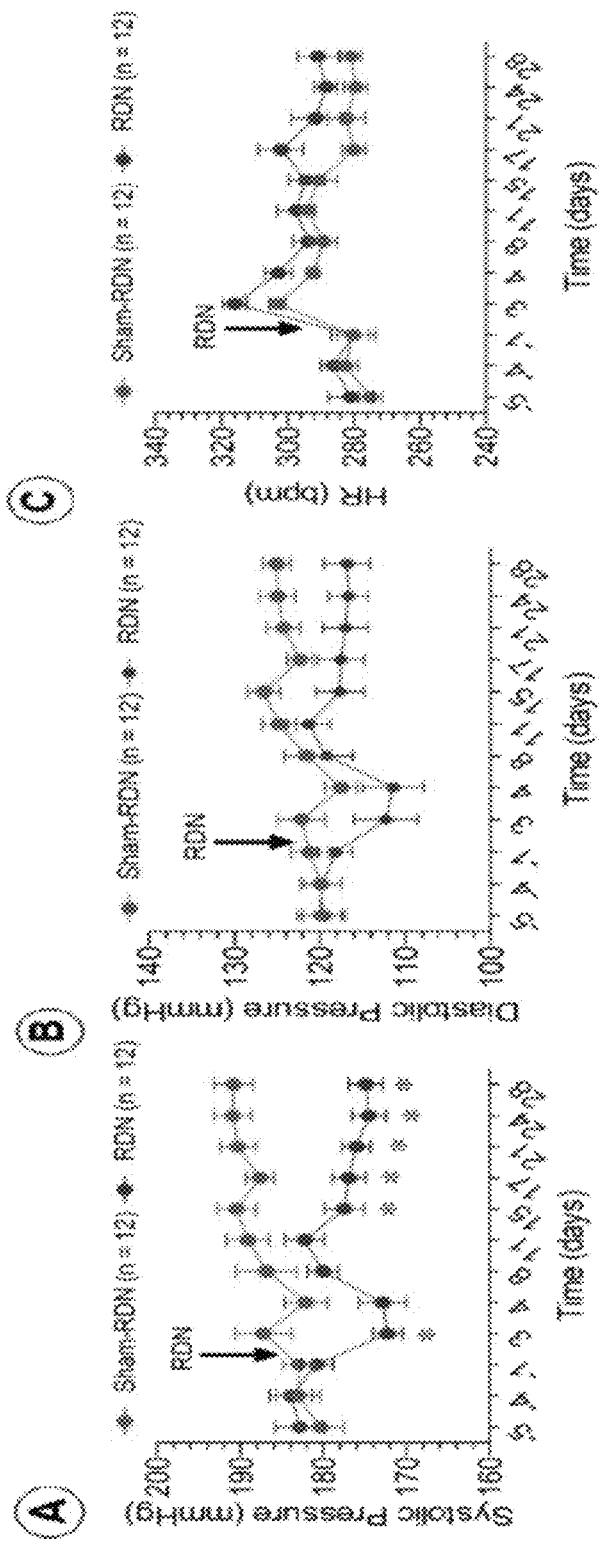
FIG. 2 shows the arterial blood pressure in SHR following RF-RDN or Sham-RDN. Systolic (A) and diastolic (B) pressures (mmHg) and heart rate (C; beats per minute) in 20-week-old male SHR before and for 4 weeks after treatment. RF-RDN and Sham-RDN procedures were performed on day 0 when rats were 20 weeks of age. Values are mean±SEM. $*p<0.05$ between groups.

Proof-of-concept studies performed in rat models of acute myocardial infarction and heart failure demonstrate that radiofrequency-renal denervation therapy reduces myocardial infarct size and improves cardiac function. Studies in our laboratory have demonstrated significant cardioprotective actions of RF-RDN in in vivo rodent models of myocardial ischemia and reperfusion (MI/R). In the initial experiments, renal nerves were denervate the renal sympathetic nerves were denervated using radiofrequency (RF) ablation applied via an electrode at the catheter tip. Renal artery nerve tyrosine hydroxylase immunostaining at 35 days following RFRDN or Sham-RDN in SHR rats revealed significantly reduced, but somewhat variable reductions in renal nerve viability following RF-RDN as compared to sham-RDN procedures (FIG. 1). As a marker of sympathetic nerve function, spillover norepinephrine (NE) and epinephrine levels were measured 28 days following RF-RDN or Sham-RDN. There was a significant reduction in circulating NE following RF-RDN compared to the sham-RDN. 20-week-old male SHR were subjected to either bilateral RF-RDN or Sham-RDN of the nerves surrounding the renal arteries. RF-RDN produced a small, but significant decrease in systolic blood pressure as compared to Sham-RDN at days 15-28 following the procedure, but systolic blood pressures remained significantly elevated (i.e., >170 mmHg) compared to normotensive animals (FIG. 2). Furthermore, systolic blood pressures in SHR treated with RF-RDN were not significantly reduced when compared to baseline values in the SHR group. RF-RDN did not result in a significant reduction in diastolic pressure in aged SHR rats compared to the sham-RDN procedure. Mean arterial blood pressure was significantly lower at days 24-28 following RF-RDN ($p<0.05$ vs. Sham-RDN). Heart rate remained unchanged between groups (FIG. 2).

Figure 3:
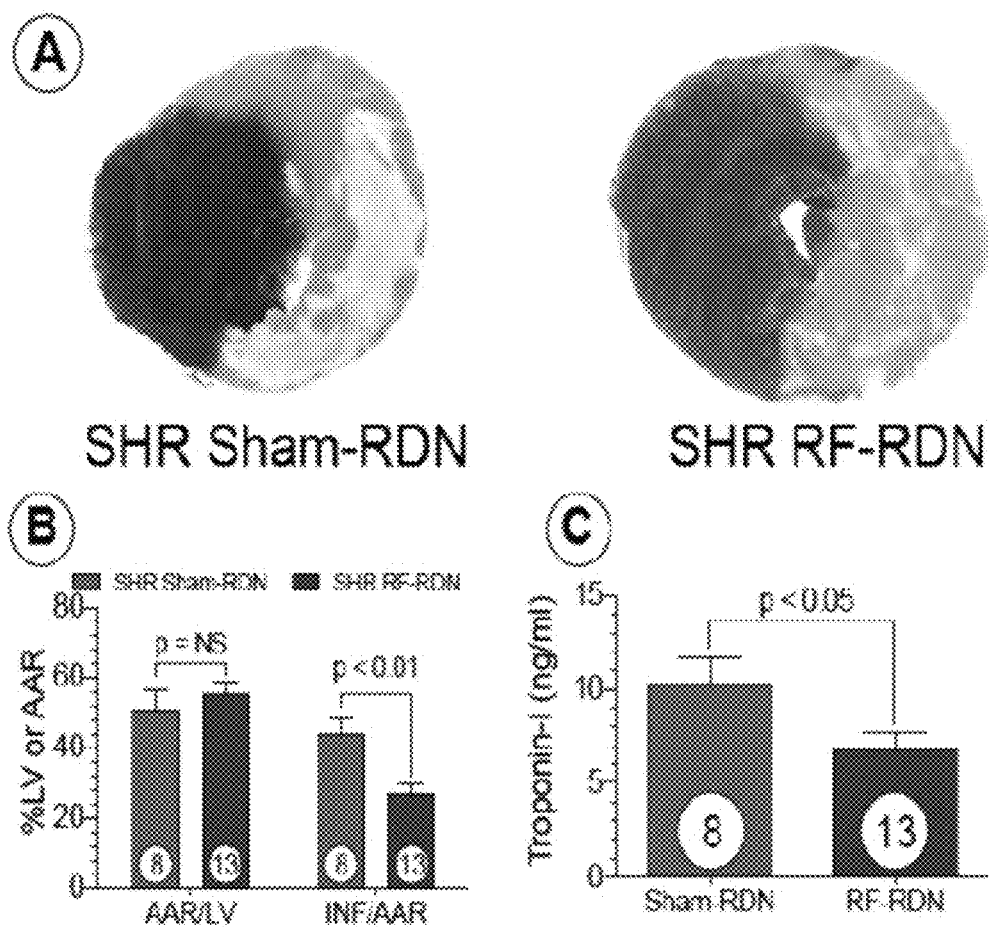
FIG. 3 shows that RF-RDN protects against myocardial ischemia/reperfusion injury and improves LV function in SHR. Representative mid-ventricular photomicrographs of rat hearts (A) after 30 min of myocardial ischemia and 24 h reperfusion. Bar graphs of myocardial AAR/LV and INF/AAR (B). Cardiac troponin-I levels (C) after 4 h reperfusion. Values are mean±SEM. Circles denote number of animals per group. $*p<0.05$ between groups.

We then evaluated whether RF-RDN would protect against myocardial ischemia-reperfusion injury. At 4 weeks following RF-RDN, SHR rats were subjected to 30 minutes of left anterior descending (LAD) ligation followed by 24 hours reperfusion. RF-RDN rats displayed a significant reduction in myocardial infarct size (INF) per area at-risk (AAR) and reduced plasma troponin-I levels compared to the Sham-RDN group (FIG. 3). These data indicate that a single administration of RF-RDN exerts cardioprotective actions that are sustained over a 4-week period using a rat model of acute MI.

Figure 4:
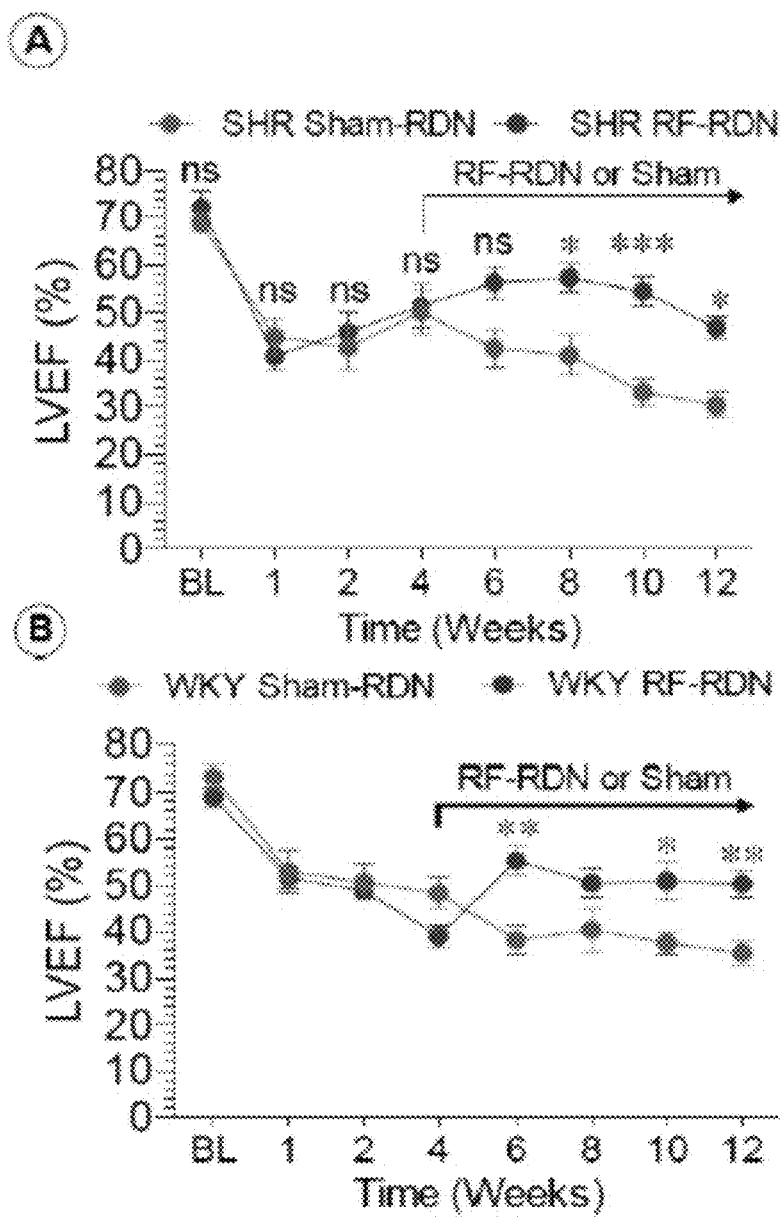
FIG. 4 shows that RF-RDN improves cardiac function in SHR and WKY. Left ventricular ejection fraction was measured in SHR (A) and WKY (B) rats 8 wks post-RDN. Values are mean±SEM. Circles denote number of animals per group. $*p<0.05$ between groups.
Figure 5:
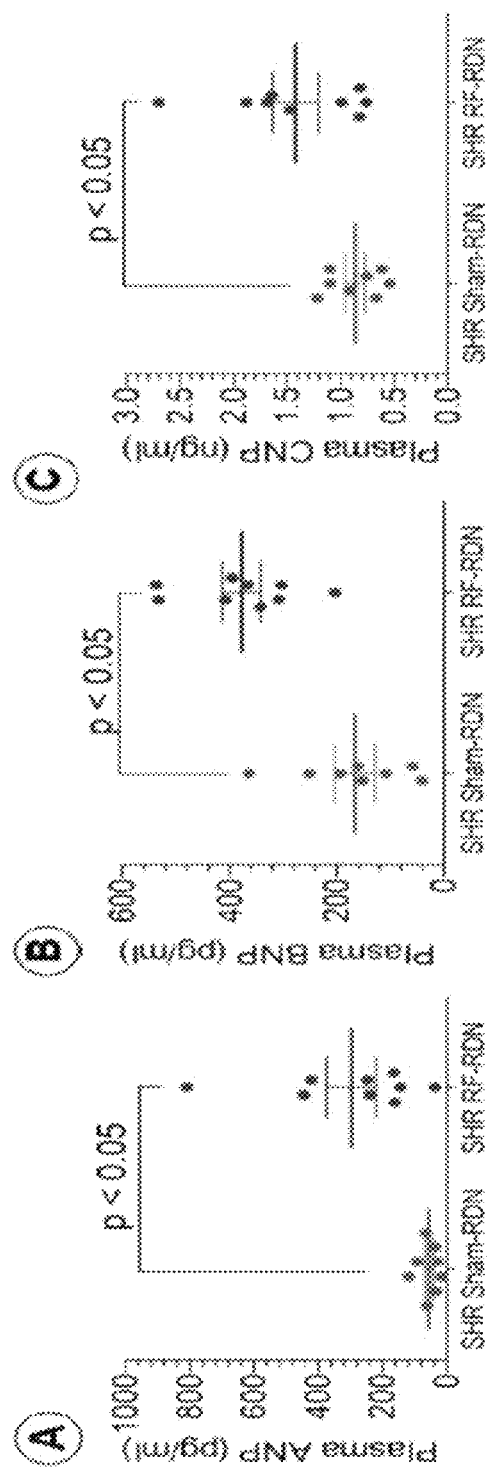
FIG. 5 shows that RF-RDN increases circulating ANP, BNP and CNP in SHR and WKY. Circulating atrial (A), brain (B and D) and cardiac (C and E) natriuretic peptides were measured in the plasma of SHR (A, B, C) and WKY (D, E) rats 8 wks post-RDN. Values are mean±SEM. Circles denote number of animals per group. $*p<0.05$ between groups.
Figure 5:
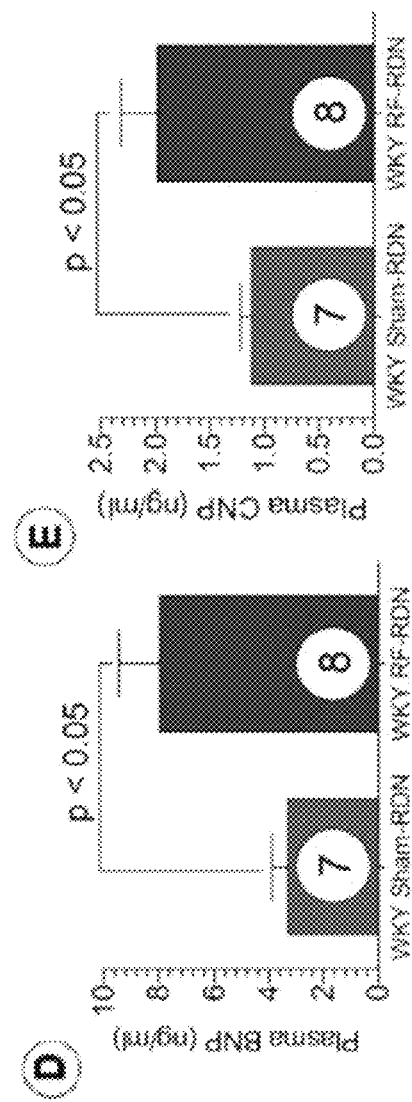

We next investigated the protective actions of RF-RDN in a rat model of severe HF following MI/R injury. These data are presented in FIG. 4. When RF-RDN was delayed until 4 wks following MI/R injury, RF-RDN significantly increased LV ejection fraction in hypertensive SHR and normotensive WKY rats. We next determined We next evaluated whether RF-RDN impacted circulating natriuretic peptides in both the hypertensive (SHR) and normotensive (WKY) rats (FIG. 5). At 4 weeks following RF-RDN, SHR and WKY rats were subjected to 30 minutes of left anterior descending (LAD) ligation followed by 8 weeks of reperfusion. Plasma levels of natriuretic peptides were significantly increased in SHR and WKY rats 4 weeks following RFRDN as compared to Sham-RDN. Kidney tissue neprilysin activity was also significantly decreased following RF-RDN compared to Sham-RDN (data not shown).

Taken together, these data indicate that a single administration of RF-RDN exerts cardiotherapeutic actions that are sustained over a 8-week period using a rat model heart failure.

Overall Study Design

These studies will be performed at the LSUHSC CV Center Translational Research Laboratory in collaboration with the Ochsner clinic. The experiments will involve a well-established swine model of acute myocardial infarction and heart failure. The research teams at Ochsner and LSUHSC have previously worked together on an Ochsner OTRMI funded project using this same model system. The study protocol involves 75 minutes of coronary artery occlusion using a balloon catheter followed by 12 weeks heart failure. Bilateral RF-RDN will be performed using percutaneous techniques with clinical RF-RDN devices. In additional studies porcine cardiac stem cells will be provided by Dr. Eduardo Marban at Cedars Sinai Heart Institute (Los Angeles, Calif.) in collaboration with our research team. We will evaluate cardiac structure and function using two-dimensional echocardiography. Circulating levels of ANP, BNP, and CNP will be determined using commercially available ELISA kits. Myocardial fibrosis and histological determinations will be performed under contract with Alizee Pathology (Thurmont, MD). We will also perform molecular analyses of renal and myocardial tissue to evaluate molecular mechanisms of RF-RDN mediated cardioprotection.

Specific Aim 1: To Evaluate the Effects of RF-RDN on Left Ventricular (LV) Remodeling and Function Following the Onset of Heart Failure This Specific Aim has 3 objectives. The first objective, designated as Exp. 1.1, is to verify the effectiveness of RF-RDN in a clinically relevant large animal model of heart failure. The second objective, designated as Exp. 1.2, is to ascertain the ability of RF-RDN treatment to increase circulating ANP, BNP, and CNP levels and decrease neprilysin activity in a porcine model of heart failure. The third objective, designated as Exp. 1.3 is to determine if RF-RDN can improve LV function and dimensions, myocardial and, myocardial fibrosis, myocardial vascularity and LV hemodynamics in swine with established heart failure.

These experiments will validate further development of RF-RDN and CDCs for cardiac indications. Critical data regarding the timing of the RF-RDN and CDC therapies will be determined for the subsequent combination treatment. Resolution of Specific Aim 1 in will permit advancement to Specific Aim 2 for determination of CDC retention within the ischemic myocardial tissue.

Without wishing to be bound by theory, the experiments of Specific Aim 1 will: (1) verify the effectiveness of RF-RDN observed in the previous rodent SHR studies using a pig model of HF; and, (2) ascertain the optimal timing of RF-RDN pretreatment and CDC administration to improve cardiac function and circulating biomarkers.

Specific Aim 2: To Evaluate the Effects of RF-RDN+Cardiac Derived Stem Cells (CDCs) on Left Ventricular (LV) Remodeling and Function Following the Onset of Heart Failure This Specific Aim has 3 objectives. The first designated as Exp. 2.1, will be performed to determine whether CDCs together with RF-RDN can improve cardiac function in large animal model once heart failure has ensued. The second objective, designated as Exp. 2.2 will be to determine if RF-RDN enhanced subcellular localization and accumulation of CDCs within the ischemic pig myocardium. The third objective will be to examine the favorable effect RF-RDN has on the myocardial tissue architecture. These experiments will verify a key aspect of the mechanism by which RF-RDN therapy can alter the ischemic myocardial milieu and without CDC deposition in normal uninjured myocardium.

Without wishing to be bound by theory, the experiments of Specific Aim 2 will: (1) determine the effectiveness of RF-RDN and CDC to improve cardiac function; and, (2) ascertain the impact RF-RDN treatment to enhance CDC retention within the ischemic myocardium and on the ischemic myocardial environment allowing for increased stem cell engraftment.

Outcomes for Specific Aims 1 and 2: Based on our previous rat experiments in which RFRDN administered 4 weeks before myocardial ischemia reperfusion injury resulted in a 50% reduction in infarct size (FIG. 3B) and reduction in cardiac troponin I (FIG. 3C), along with improvement in LVEF when administered 4 weeks post-MI (FIGS. 4 A and B), we expect RF-RDN delivered 4 weeks post-MI/R injury to exhibit a similar improvement in LV function in the proposed pig experiments. Administration of CDCs after 4 weeks of reperfusion may result in a further improvement in cardiac function as that achieved by either RFRDN or CDCs alone. If the improvement in cardiac function is similar between the 3 treatment groups (RFRDN, CDCs, and RF-RDN+CDC) pig experiments, a higher dose of CDCs will be utilized in future studies. Additionally, we will store blood and tissue samples from this study for further analysis of circulating CDC levels to better understand the distribution of CDCs.

Limitations and Alternatives for Specific Aims 1 and 2 of this Grant Application All experiments proposed in Specific Aim 1 involve a well-established model of LAD coronary artery balloon-occlusion and reperfusion injury in normal Yucatan swine. The animals we propose to use in this study are healthy adult Yucatan miniswine that lack the co-morbidities commonly associated with acute myocardial infarction including atherosclerosis and hypertension. Future experiments could include the evaluation of the cardioprotective effect of RF-RDN and CDCs in atherosclerotic miniswine lacking the low-density lipoprotein receptor (Exemplar Genetics, Sioux City Iowa).

Figure 6:
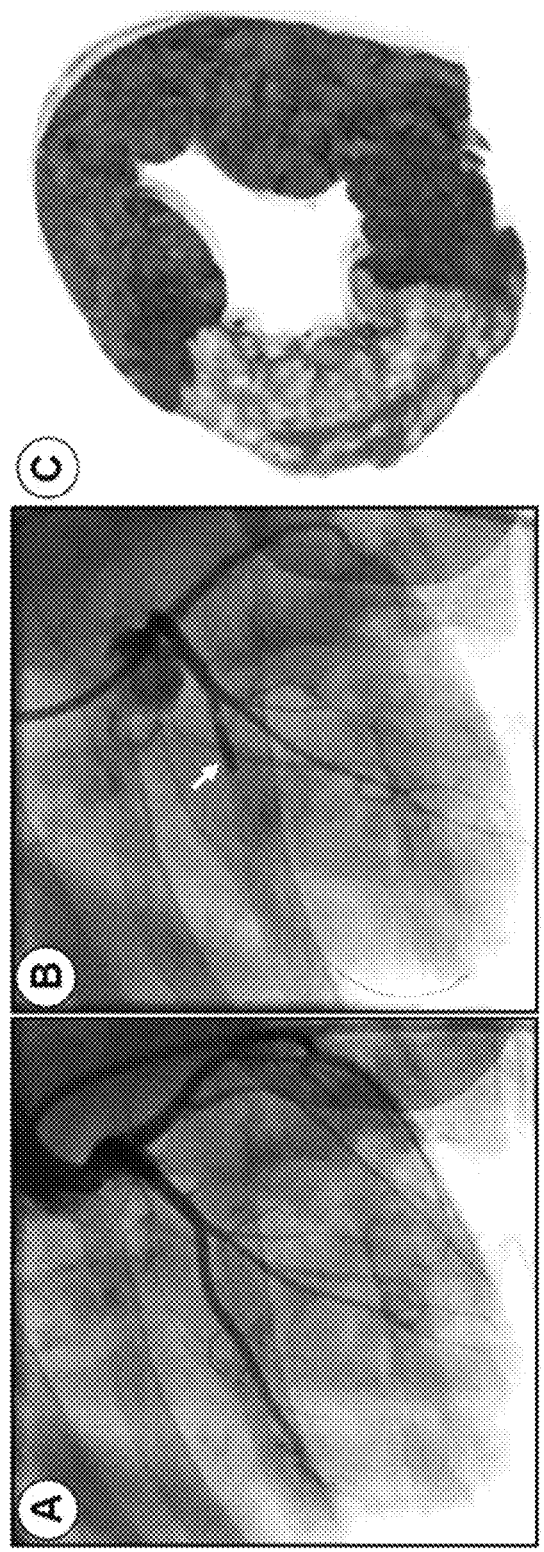
FIG. 6 shows a model of acute myocardial infarction in swine. Angiographic images of the left anterior descending coronary artery (LAD) at baseline (A) and during 75 min occlusion (B) achieved by inflation of an angioplasty balloon-catheter (arrow) deployed distal to the first diagonal artery. Following 48 h reperfusion, the resulting large transmural infarct stains white following TTC infusion within the area at risk defined as red myocardium lacking phthalo blue staining (C). The LAD balloon-occlusion generation of acute myocardial infarction in swine is a clinically relevant translational model.
Figure 7:
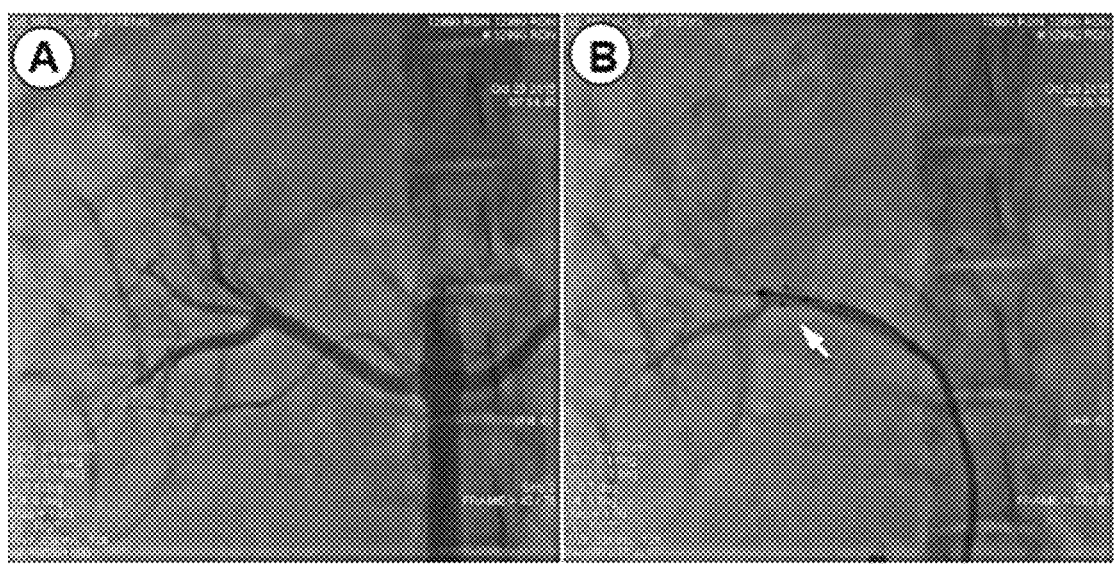
FIG. 7 shows radiofrequency renal denervation in swine. Angiographic images of the right renal artery at baseline (A) and RF-RDN (B) achieved using the St. Jude EnligHTN catheter (arrow) deployed distally for the first RD-RDN treatment. The RF-RDN cardiotherapeutic potential will be determined in a clinically relevant translational swine model of heart failure.
Figure 8:
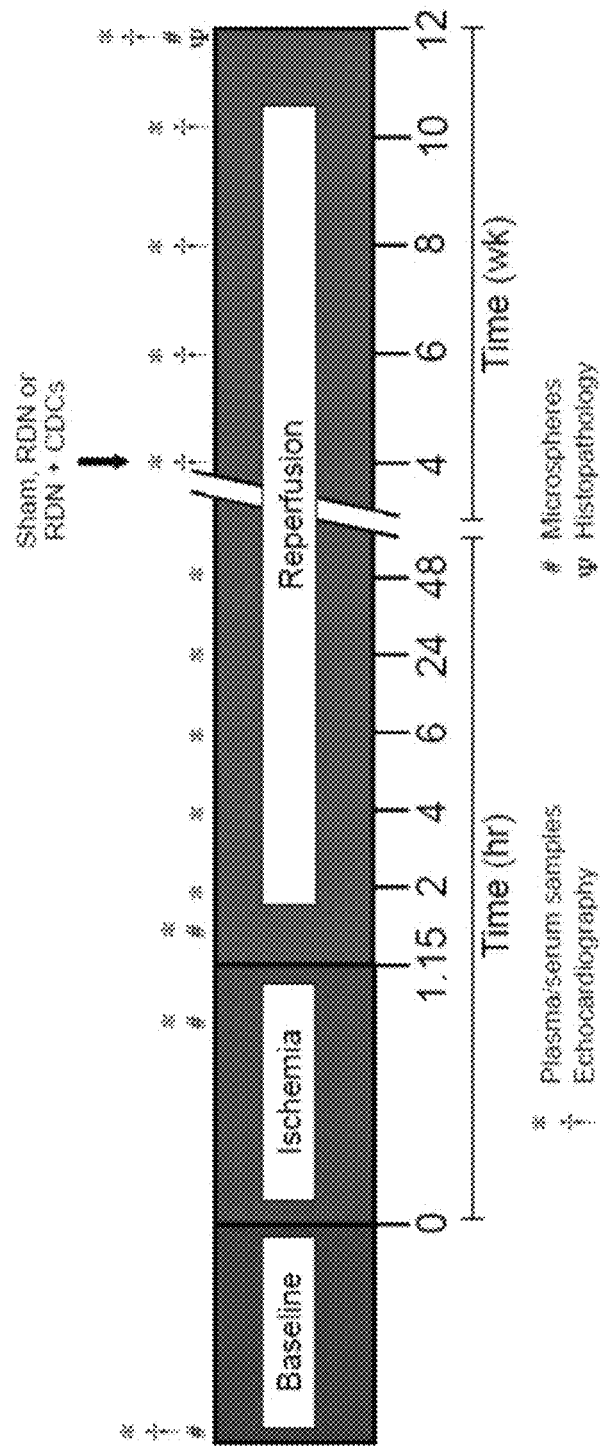
FIG. 8 shows a schematic.
Figure 9:
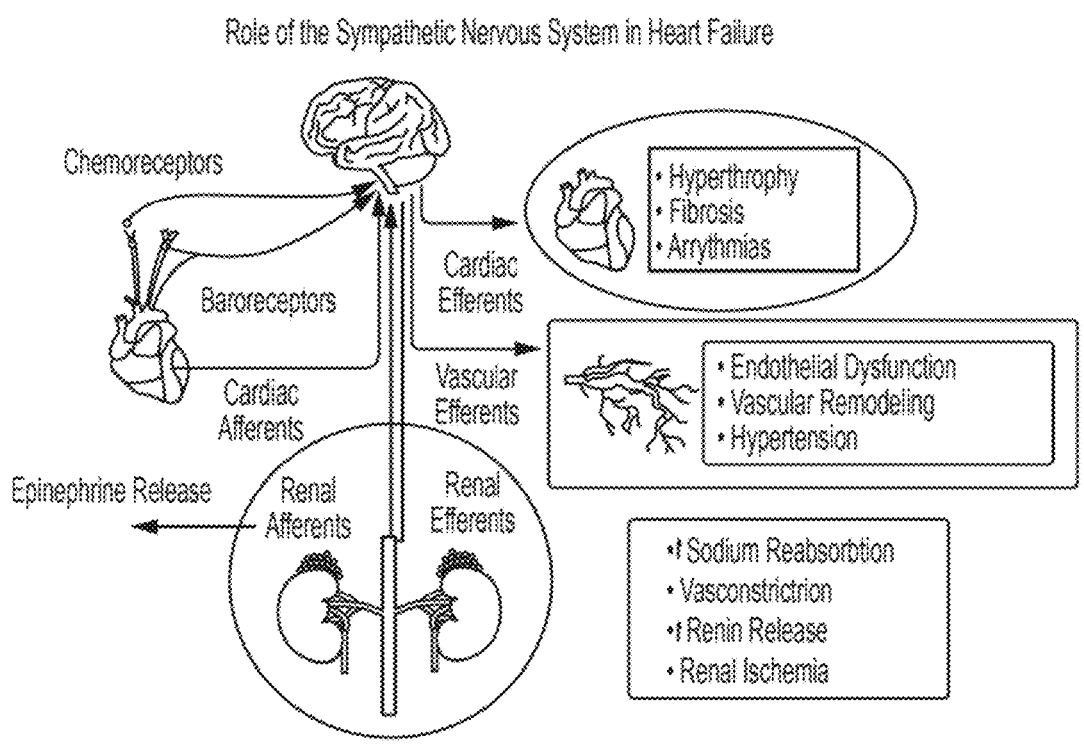
FIG. 9 shows the role of the sympathetic nervous system in heart failure.
Figure 10:
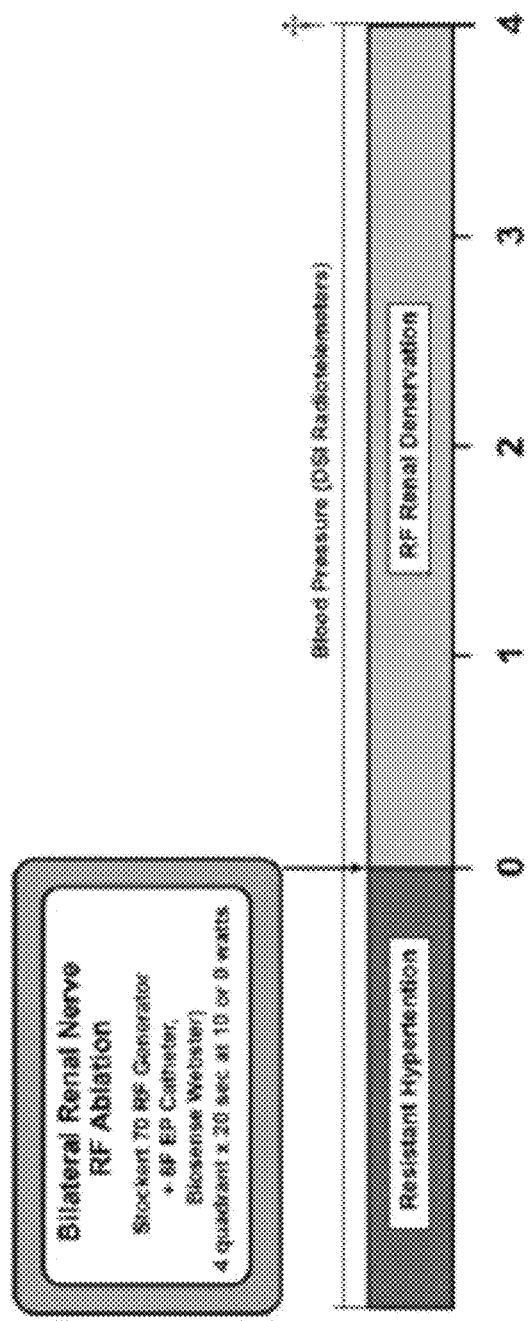
FIG. 10 shows a schematic of the renal nerve radiofrequency ablation protocol in SHR hypertensive rats.

Overview: Studies in the proposal will verify the effectiveness of the clinical product RF-RDN to treat the severe cardiac dysfunction associated with heart failure following acute MI. The cardiotherapeutic effects of RF-RDN will be tested in a porcine model of heart failure initiated from MI/R injury by subjecting adult miniswine to 75 minutes of ischemia by inflating a balloon-angioplasty catheter positioned in the LAD coronary artery (FIG. 6). Treatment with RF-RDN will be delayed until 4 weeks post-reperfusion when severe LV dysfunction evidenced by a significant reduction in LV ejection fraction (i.e., <40%). Upon confirmation of heart failure with reduced ejection fraction, swine will be randomized to receive Sham-RDN, RF-RDN or RFRDN+CDCs. Echocardiography for measurement of LV ejection fraction and LV end-systolic and end-diastolic diameters will be performed at baseline, and 4, 6, 8, 10 and 12 weeks of reperfusion. Serial blood samples will be obtained to measure circulating cardiac troponin I (cTnI) as a marker of acute cardiac injury at baseline, 60 min. into ischemia, and 2, 4, 6, 24 and 48 hr. of reperfusion. Microsphere injections will be performed for myocardial blood flow determination at baseline, 60 minutes into ischemia to confirm LAD occlusion, 15 minutes into reperfusion for LAD patency verification, and at 12 weeks of reperfusion to assess improvements in myocardial blood flow with treatment. At 12 weeks of reperfusion, myocardial tissue samples obtained from normal and ischemic regions will be processed for assessment of angiogenesis, vasculogenesis and myocardial salvage by immunohistochemical staining. Myocardial tissue samples obtained from normal and ischemic regions will be processed for histopathologic assessment by standard chemical staining. The results from experiments described under Specific Aims 1 and 2 will provide information regarding cardiotherapeutic efficacy and safety of RF-RDN and CDCs in a preclinical translational large animal model of heart failure.

Swine model of myocardial ischemia reperfusion injury. Acute myocardial infarction will be induced in swine as previously described [21]. Adult female Yucatan mini-pigs weighing 40-50 Kg will be utilized in three basic protocols: one protocol will utilize 15 animals for evaluation of RF-RDN given once as at 4 weeks post MI/R injury. This protocol is intended to mimic the strategies for the treatment for heart failure.

Radiofrequency renal denervation procedure. A 6-9F arterial sheath will be placed via the right or left femoral arteries (cut-down or percutaneous access). Heparin (300 U/kg IV) will be administered to achieve an intraprocedural activated clotting time (ACT) >250 sec. Renal angiography (contrast injections) will be performed in two planes to evaluate vessel anatomy. Catheter-based RDN will be performed by endovascular delivery into each renal artery of a 5-6F compatible electrode catheter. Low-power radiofrequency (RF), typically 4-6 min, 2-min low power RF ablations will be performed in each renal artery starting distally with subsequent ablations performed after repositioning the catheter and moving proximately in the vessel lumen. The generator automatically delivers the RF energy, using a proprietary algorithm with temperature and impedance feedback. Follow-up angiography will be performed immediately post and 6 wks. after RDN to assess for filling defects, stenosis, thrombosis, or any abnormalities. Each kidney will be examined by angiography to assess for perfusion defects.

Measurement of regional myocardial blood flow. For measurement of regional myocardial blood flow (RMBF), BioPAL microspheres (BioPhysics Assay Laboratory, Inc., Worcester, Mass.) will be used as described previously [22]. Microspheres will be injected at baseline, during coronary occlusion, 15 min. after reperfusion, and at scheduled follow-up time point after reperfusion. Absolute RMBF will be computed and expressed as ml/min per gram of tissue.

Cardiac troponin assay. Serial blood samples (~1.0 mL) will be obtained at baseline and 2, 4, 6, 24, and 48 hrs. of reperfusion. Plasma cardiac troponin I (cTnI) levels will be measured with cTnI ELISA kits (Life Diagnostics, West Chester, Pa.).

Myocardial infarct size determination. The heart will be mounted onto a dual perfusion system. The LAD will be cannulated at the site of previous occlusion to perfuse the area-at-risk (AAR). The aortic root will be cannulated to perfuse the non-ischemic myocardium retrogradely. The LAD cannula will be perfused with 2,3,5-triphenyltetrazolium chloride (TTC) solution and the aortic cannula with Phthalo blue dye. Myocardial infarct size will be determined as described previously [A22].

Swine cardiac derived stem cell injection. At 4 weeks of reperfusion, pig CDCs (10 million) will be administered into the LAD ischemic region by. They will be delivered with a 31 G needle to minimize cardiac bleeding. The CDCs will be sex-mismatched (i.e. male cells into female recipients) for subsequent in situ hybridization localization.

Echocardiography. Trans-thoracic echocardiographic studies including two-dimensional (2-D), and three-dimensional (3-D) echocardiography will be performed at baseline (before MI/R injury), 4, 6, 8, 10 and 12 weeks. A GE vivid E9 ultrasound system will be used to acquire echocardiographic data with a multi-frequency imaging transducer (S5 probe for 2-D images or X3 probe for 3-D images) as described previously [A23].

Brain natriuretic peptide levels, chemistries and complete blood counts. Blood samples for B-type natriuretic peptide (BNP) levels as a marker of chronic cardiac injury along with clinical pathology (serum chemistries and complete blood counts) assessment will be obtained at baseline, 24, 48 hours and 4, 6, 8, 10 and 12 weeks of reperfusion. Blood samples for complete blood counts (CBC) and differential, and blood chemistry will be collected and shipped to Antech for analysis. Serum for BNP testing will be separated, stored frozen and measured by EIA (Porcine BNP-32; Phoenix Pharmaceutics, Inc.).

Disposition and localization of CDCs. Pig hearts will be removed, embedded in optimal cutting temperature (OCT), snap-frozen in liquid nitrogen, and stored at −80C. Serial sections (5 um) of the OCT blocks will be collected on slides and fixed with 4% paraformaldehyde at 4 C for 5 min. Fluorescence in situ hybridization (FISH) will be performed to detect male MSCs in the female pigs using a synthetic probe specific for the rat Y chromosome sry gene. Finally, the nuclei will be stained with PI (red) and observed with an epifluorescent microscope.

REFERENCES CITED IN THIS EXAMPLE

A1. Mozaffarian D, Benjamin E J, Go A S, Arnett D K, Blaha M J, Cushman M, Das S R, de Ferranti S, Desprs J-P, Fullerton H J, Howard V J, Huffman M D, Isasi C R, Jimnez M C, Judd S E, Kissela B M, Lichtman J H, Lisabeth L D, Liu S, Mackey R H, Magid D J, McGuire D K, Mohler ER III, Moy C S, Muntner P, Mussolino M E, Nasir K, Neumar R W, Nichol G, Palaniappan L, Pandey D K, Reeves M J, Rodriguez C J, Rosamond W, Sorlie P D, Stein J, Towfighi A, Turan T N, Virani S S, Woo D, Yeh R W, Turner M B; on behalf of the American Heart Association Statistics Committee and Stroke Statistics Subcommittee. Heart disease and stroke statistics—2016 update: A report from the American Heart Association. Circulation. 2016; 133:e38-e360.

A2. Kearney, P. M., Whelton, M., Reynolds, K., Muntner, P., Whelton, P. K., and He, J. 2005. Global burden of hypertension: analysis of worldwide data. Lancet 365: 217-223.

A3. Krum, H., Schlaich, M., Whitbourn, R., Sobotka, P. A., Sadowski, J., Bartus, K., Kapelak, B., Walton, A., Sievert, H., Thambar, S., et al. 2009. Catheter-based renal sympathetic denervation for resistant hypertension: a multicentre safety and proof-of-principle cohort study. Lancet 373:1275-1281.

A4. Symplicity, H. T. N. I., Esler, M. D., Krum, H., Sobotka, P. A., Schlaich, M. P., Schmieder, R. E., and Bohm, M. 2010. Renal sympathetic denervation in patients with treatment-resistant hypertension (The Symplicity HTN-2 Trial): a randomised controlled trial. Lancet 376:1903-1909.

A5. Worthley, S. G., Tsioufis, C. P., Worthley, M. I., Sinhal, A., Chew, D. P., Meredith, I. T., Malaiapan, Y., and Papademetriou, V. 2013. Safety and efficacy of a multi-electrode renal sympathetic denervation system in resistant hypertension: the EnligHTN I trial. Eur Heart J 34:2132-2140.

A6. Bhatt, D. L., Kandzari, D. E., O'Neill, W. W., D'Agostino, R., Flack, J. M., Katzen, B. T., Leon, M. B., Liu, M., Mauri, L., Negoita, M., et al. 2014. A controlled trial of renal denervation for resistant hypertension. N Engl J Med 370:1393-1401.

A7. Chen L., Tredget E. E., Wu P. Y. G., Wu Y., Wu Y. Paracrine factors of mesenchymal stem cells recruit macrophages and endothelial lineage cells and enhance wound healing. PLoS ONE. 2008; 3(4).

A8. Gnecchi M., Zhang Z., Ni A., Dzau V. J. Paracrine mechanisms in adult stem cell signaling and therapy. Circulation Research. 2008; 103(11):1204-1219.

A9. Burchfield J. S., Dimmeler S. Role of paracrine factors in stem and progenitor cell mediated cardiac repair and tissue fibrosis. Fibrogenesis and Tissue Repair. 2008; 1(1, article 4) doi: 10.1186/1755-1536-1-4.

A10. Abdel-Latif A., Bolli R., Tleyjeh I. M., et al. Adult bone marrow-derived cells for cardiac repair: a systematic review and meta-analysis. Archives of Internal Medicine. 2007; 167(10): 989-997.

A11. Chen S.-L., Fang W.-W., Ye F., et al. Effect on left ventricular function of intracoronary transplantation of autologous bone marrow mesenchymal stem cell in patients with acute myocardial infarction. The American Journal of Cardiology. 2004; 94(1): 92-95 .

A12. Perin E. C., Sanz-Ruiz R., Sánchez P. L., et al. Adipose-derived regenerative cells in patients with ischemic cardiomyopathy: the PRECISE Trial. American Heart Journal. 2014; 168(1):88.e2-95.e2.

A13. Murry C. E., Field L. J., Menasché P. Cell-based cardiac repair reflections at the 10-year point. Circulation. 2005; 112(20):3174-3183.

A14. Garbern J. C., Lee R. T. Cardiac stem cell therapy and the promise of heart regeneration. Cell Stem Cell. 2013; 12(6):689-698.

A15. Menasché P., Alfieri O., Janssens S., et al. The myoblast autologous grafting in ischemic cardiomyopathy (MAGIC) trial: first randomized placebo-controlled study of myoblast transplantation. Circulation. 2008; 117(9): 1189-1200.

A16. Vu D. T., Kofidis T. Myocardial restoration: is it the cell or the architecture or both? Cardiology Research and Practice. 2012; 2012:11.

A17. Russo V., Young S., Hamilton A., Amsden B. G., Flynn L. E. Mesenchymal stem cell delivery strategies to promote cardiac regeneration following ischemic injury. Biomaterials. 2014; 35(13):3956-3974.

A18. Gonzales C., Pedrazzini T. Progenitor cell therapy for heart disease. Experimental Cell Research. 2009; 315 (18):3077-3085.

A19. Chavakis E., Koyanagi M., Dimmeler S. Enhancing the outcome of cell therapy for cardiac repair; Progress from bedside and back. Circulation. 2010; 121: 325-335.

A20. Schachinger V, Aicher A, Dobert N, Rover R, Diener J, Fichtlscherer S, Assmus B, Seeger F H, Menzel C, Brenner W, Dimmeler S, Zeiher A M. Pilot trial on determinants of progenitor cell recruitment to the infarcted human myocardium. Circulation. 2008; 118: 1425-1432.

A21. Jones S P, Tang X L, Guo Y, Steenbergen C, Lefer D J, Kukrej a R C, Kong M, Li Q, Bhushan S, Zhu X, Du J, Nong Y, Stowers H L, Kondo K, Hunt G N, Goodchild T T, Orr A, Chang C C, Ockaili R, Salloum F N and Bolli R. The NHLBI-sponsored Consortium for preclinic A1 assESsment of cARdioprotective therapies (CAESAR): a new paradigm for rigorous, accurate, and reproducible evaluation of putative infarct-sparing interventions in mice, rabbits, and pigs. Circulation Res. 2015; 116:572-86.

A22. Reinhardt C P, Dalhberg S, Tries M A, Marcel R, Leppo J A. Stable labeled microspheres to measure perfusion: validation of a neutron activation assay technique. Am J Physiol Heart Circ Physiol. 2001; 280:H108-H116.

A23. Goodchild T, Pang W, Tondato F, Cui J, Otsuka Y, Frowein S, Ungs M, Robinson K, Poznansky M, Chronos N. Safety of intramyocardial injection of autologous bone

Example 3

Abstract

Sustained pathological sympathetic activation that accompanies heart failure contributes to the progression of myocardial injury, cardiac fibrosis, and left ventricular (LV) dysfunction. Neprilysin (NEP) degrades natriuretic peptides (NP) and attenuates the beneficial effects of natriuretic peptide signaling. We utilized radiofrequency renal nerve denervation (RF-RDN) in a rodent model of heart failure to investigate whether renal efferent activity regulates NEP activity, modulates NP levels and signaling, attenuates and improves ventricular function. Spontaneously hypertensive rats (SHR) and normotensive Wistar-Kyoto rats (WKY) were subjected to 45 minutes of coronary artery ligation and reperfusion (Rep) for 12 weeks. At 4 weeks post-Rep, SHR and WKY underwent either bilateral RF-RDN or Sham-RDN procedure. RF-RDN reduced left ventricular (LV) fibrosis and inhibited transition zone expansion of the infarcted region. Despite improved LV function and remodeling in SHR and WKY rats, 12-week plasma NP levels were significantly elevated in the RF-RDN treated group, while RF-RDN inhibited renal NEP activity. We have identified a new link between the sympathetic nervous system and endogenous regulation of cardioprotective NPs. Sympathetic inhibition by RF-RDN reduces cardiac fibrosis and inhibits renal NEP activity resulting in increased levels of NPs, thereby resulting in cardiac protection in heart failure.

Introduction

Heart failure (HF) continues to grow as an insufficiently managed healthcare burden that affects nearly 6 million people in the United States alone (1). Although the current pharmacotherapies have improved mortality rates, heart failure prevalence is projected to double by 2030 (B1). Improved survival rates accompanied by increased HF diagnoses have led to an exponential growth of HF-related costs in the US, estimated to range between $30-60 billion annually (B2).

Overactive sympathetic nervous system activity accompanying HF initially serves as a compensatory response to maintain cardiac output via positive inotropic and chemotropic effects. However, chronic sympathetic inputs lead to the progression of myocardial dysfunction, pro-death intracellular signaling cascades, and the formation of interstitial fibrosis (B3, B4). Current HF pharmacotherapies targeting the autonomic nervous system, such as Beta-blockers and renin-angiotensin-aldosterone system (RAAS) inhibitors, have proven to improve morbidity and mortality (B5-B8). The newest FDA approved drug for the treatment of HF with reduced ejection fraction, Entresto, is a combination formula of an angiotensin receptor blocker (Valsartan) and a neprilysin (NEP) inhibitor (sacubitril)(B9, B10). In the PARADIGM-HF trial, Entresto outperformed enalapril by reducing risk of cardiovascular death and limiting HF hospitalizations (9). NEP inhibition has now emerged as a beneficial therapeutic approach by preventing the degradation of cardio and vasculoprotective plasma peptides such as B-type natriuretic peptide (BNP)(B11).

Current pharmacological strategies are not without limitations. They have a wide range of off-target side-effects, their effectiveness is regulated by patient compliance, and they bear a significant cost burden on heart failure patients who are living longer than ever. As such, alternative interventional therapeutic approaches are under investigation to replace or supplement contemporary pharmacologic strategies (B12). Renal nerve denervation (RDN) is a minimally invasive endovascular procedure whereby radiofrequency (RF) energy is used to ablate the sympathetic nerves of the renal artery (B13). Developed for the treatment of resistant hypertension, mixed clinical trial results have sparked debate over whether this strategy effectively lowers blood pressure (B13-B16). We sought to examine whether RF-RDN induced sympathetic inhibition could improve left ventricular post infarction remodeling in a clinically relevant animal model of cardiovascular disease, the spontaneously hypertensive rat. We also examined the effect of the sympathetic nervous system on NEP activity as an endogenous regulator of cardioprotective natriuretic peptides (NPs).

Methods

Experimental Animals

Male Spontaneously Hypertensive Rats (SHR) and male Wistar-Kyoto Rats (WKY) 19-20 weeks of age (Charles River Laboratories) were used in the present study. All animals were housed in a temperature-controlled animal facility with a 12-hour light/dark cycle, with water and rodent chow provided ad libitum. All animals received humane care in compliance with the Principles of Laboratory Animal Care formulated by the National Society of Medical Research and the Guide for the Care and Use of Laboratory Animals published by the NIH (Publication No. 85-23, Revised 1996). The LSUHSC New Orleans IACUC approved all animal procedures.

Myocardial Ischemia/Reperfusion

Rats were fully anesthetized with 2% isoflurane. The animals were then attached to a surgical board, orally intubated, and connected to a model 683 rodent ventilator (Harvard Apparatus; Natick, Mass.). The tidal volume was set at 3.5 ml, and the respiratory rate was set at 80 breaths/min. A median sternotomy was performed and the proximal left anterior descending (LAD) coronary artery was visualized and completely ligated with 6-0 silk suture mounted on a tapered needle (Ethicon). Rats were subjected to 45 minutes of ischemia and 12 weeks of reperfusion.

Radiofrequency Renal Denervation Procedure

SHR and WKY were randomly divided into either a RF-RDN or sham-RDN groups 4 weeks after reperfusion. Rats were anesthetized with isoflurane (2%) and a flank incision was made to expose the left renal artery. For RF-RDN, a segment (~3 mm in length) of the proximal renal artery adjacent to the renal artery ostium (i.e., bifurcation from the aorta) was carefully dissected leaving any visible extra-vascular nerves intact. A small piece of plastic cut in the shape of a triangle was then placed under the renal artery as a platform /and to protect underlying tissue. The tip of the radiofrequency probe (6F, Celsius electrophysiology catheter) was then applied to 4-quadrants (circumferential) of the renal artery for 20 s each at 10 Watts for the RF-RDN group or 0 Watts for the Sham-RDN group (Stockert 70 radiofrequency generator and probes graciously provided by Biosense Webster). During RF-RDN the temperature of the probe was not permitted to be higher than 65° C. Following completion of the RF-RDN or Sham-RDN procedure the plastic was removed and the muscle and skin were sutured closed in layers. The same RF-RDN or Sham-RDN procedure was then performed on the contralateral renal artery.

Plasma Troponin Measurements

At 2 hours following reperfusion, plasma was collected and cardiac troponin-I levels were measured as previously described (B17).

Blood Pressure Telemetry Measurements

At 19 weeks of age SHR were implanted with a radiotelemetry transmitter (Data Sciences International, DSI, St. Paul, Minn.) for measurement of blood pressure and heart rate. Under anesthesia (2% Isoflurane), an incision was made to expose the right femoral artery. The tip of the transmitter catheter was advanced into the abdominal aorta and secured into position via the femoral artery access. The wound was sutured closed and rats were given 1 week to recover. Baseline blood pressure recording was then performed for two consecutive days. After the MI/R procedure, blood pressure recording continued daily for 4 weeks. Following ischemia-reperfusion, Sham-RDN or RF-RDN procedures were performed and telemetry recoding continued for the remainder of the study (weeks 4-12). Telemetry data was analyzed with Dataquest ART Acquisition Software (version 4.33). The average arterial blood pressure and heart rate for each day were calculated from values recorded during a 15-minute period every 2 hours of the day.

Echocardiography

Prior to myocardial infarction, baseline parasternal long axis echocardiogram was performed using MS250 13-24-MHz probe on a Vevo 2100 (Visualsonics) under anesthesia with isoflurane (1%) supplemented with 100% $O_2$. Serial echocardiography was also performed in the same manner at 1, 2, 4, 6, 8, 10, and 12 week time points. To determine cardiac structure and function, LV end diastolic dimension (LVEDD), LV end systolic dimension (LVESD), systolic interventricular septal diameter (IVSs) and diastolic interventricular septal diameter (IVSd), and LV fractional shortening analyzed from EKV™ (ECG-Gated Kilohertz Visualization) generated M-mode long-axis images. LV ejection fraction (LVEF) was determined using LV Trace from an EKV™ generated long axis B-mode image.

Plasma Norepinephrine and Epinephrine Measurement

At 4 weeks following Sham-RDN or RF-RDN, plasma was collected and catecholamine levels were measured using ELISA technique according to the manufacturer's recommendations (Abnova Co.)

Tyrosine Hydroxylase Staining of Renal Arteries

At 8 weeks following Sham-RDN or RF-RDN (12 weeks after reperfusion), renal arteries were excised, fixed (paraformaldehyde, 4.0%), paraffin-embedded and sectioned (3 µm). Sections were deparaffinized and antigen retrieval was performed. Sections were incubated with rabbit polyclonal anti-tyrosine hydroxylase (TH) (Millipore AB152), followed by biotinylated anti-rabbit IgG. In a blinded fashion, stain intensity (degree of TH staining) was scored as 0=negative; 1=weak (blush); 2=mild; 3=moderate; or 4=strong. Proportion of nerves showing decreased TH staining was scored as 1=~1-25%; 2=~25-50%; 3=~50-75%; 4=~75-100%.

Myocardial Measurements of $NO_2$

Nitrite concentrations were quantified as previously described (18) using an automated ion chromatography system (ENO30 Analyzer, Eicom).

RNA Isolation and Reverse Transcriptase RT-PCR mRNA levels were assessed by using quantitative real-time RT-PCR (qPCR). Total RNA was extracted from LV tissue. Purified RNA was quantified and cDNA was synthesized using an I-script cDNA synthesis kit (Bio-Rad). TaqMan primers from Life Technology were used to amplify qPCR. 18s was used as a housekeeping gene and $2^{\Delta\Delta CT}$ was used for data analysis.

Natriuretic Peptide Quantification

At 12 weeks following reperfusion, LV and plasma is collected from SHR and WKY rats. Brain natriuretic peptide-32 (BNP), atrial natriuretic peptide (ANP), c-type natriuretic peptide (CNP), Bradykinin, and Substance P were quantified using ELISA technique (Phoenix Peptides). NT Pro-BNP levels were quantified according to the manufacturer's instructions (My Bio Source).

Neprilysin Activity Assay

NEP enzyme activity was determined as previously described (19). Using the substrate 3-dansyl-d-Ala-Gly-p-Phe-Gly (DAGNPG), which is principally degraded by NEP, and to a smaller extent by ACE. 100 µg tissue homogenate is incubated with 50 µM GAGNPG and 1 um captopril at 37 C. Reactions are stopped by heating samples to 100 C for 5 min. Samples are spun (5000 g×5 min) and fluorescence is determined using 342 nm excitation and 562 emission wavelengths.

LV Pressure Catheter

In vivo analyses of LV pressures were quantified using a Millar pressure catheter and data acquisition monitor (Transonic SciSense). At the 12-week endpoint under isoflurane (2%), the right carotid artery was isolated and the pressure catheter was advanced into the aorta and then the LV lumen to determine aortic pressure, LV pressure, dP/dT, and tau.

Histology of Cardiac Fibrosis

Hearts were collected at the 12-week endpoint and fixed in 4% paraformaldehyde, embedded in paraffin, sectioned at one level, cut twice and stained for Masson's Trichrome and Picrosirius Red to detect fibrosis. Fibrosis score was determined in a blinded fashion as 0=not present; 1=present, but minimal feature; 2=notable feature, mild; 3=prominent feather that does not disrupt tissue architecture and is not overwhelming, moderate; or 4=overwhelming feature or feature that effaces or disrupts tissue architecture, severe. Infarct area of LV was calculated as total fibrotic area/myocardium area×100.

Statistical Analysis

All data in this study are expressed as the mean±SEM. Differences in data between the groups were compared using Prism 6 (GraphPad Software) with Student's unpaired, two-tailed t-test when only two groups were compared at a single time point. Two-way ANOVA with Bonferroni post-test was used for blood pressure, heart rate, and echocardiography analysis. Mann-Whitney tests were used for ranked histological analysis. p value of <0.05 was considered statistically significant.

Results

Figure 12:
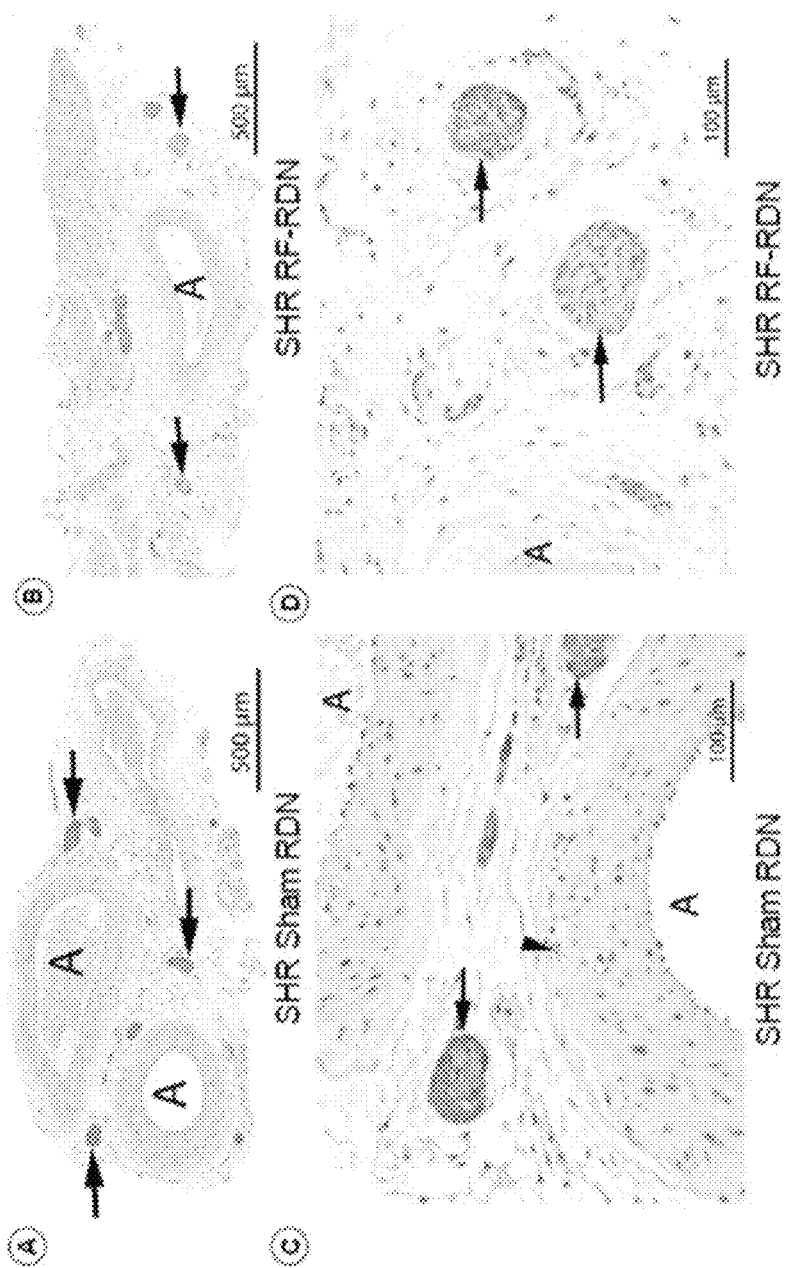
FIG. 12 shows viable renal artery nerve staining and catecholamine spillover following RF-RDN in SHR. Tyrosine hydroxylase staining at the 12-week endpoint following Sham-RDN or RF-RDN. (A) Tyrosine hydroxylase (TH) stain of renal artery section from Sham-RDN treated SHR. Arrows=normal nerves showing score 4 TH staining. A=renal artery. (B) TH stain of renal artery section from RF-RDN treated SHR. Arrows=nerves showing score 1 TH staining. A=renal artery, (C) Magnified image of FIG. 2A. Arrowheads=ganglion cells showing full intensity cytoplasmic TH staining. (D) Magnified image of FIG. 2B. (E) Degree of TH staining. (F) Plasma norepinephrine and (G) epinephrine at the 12 week endpoint. Values are expressed as mean±SEM.
Figure 12:
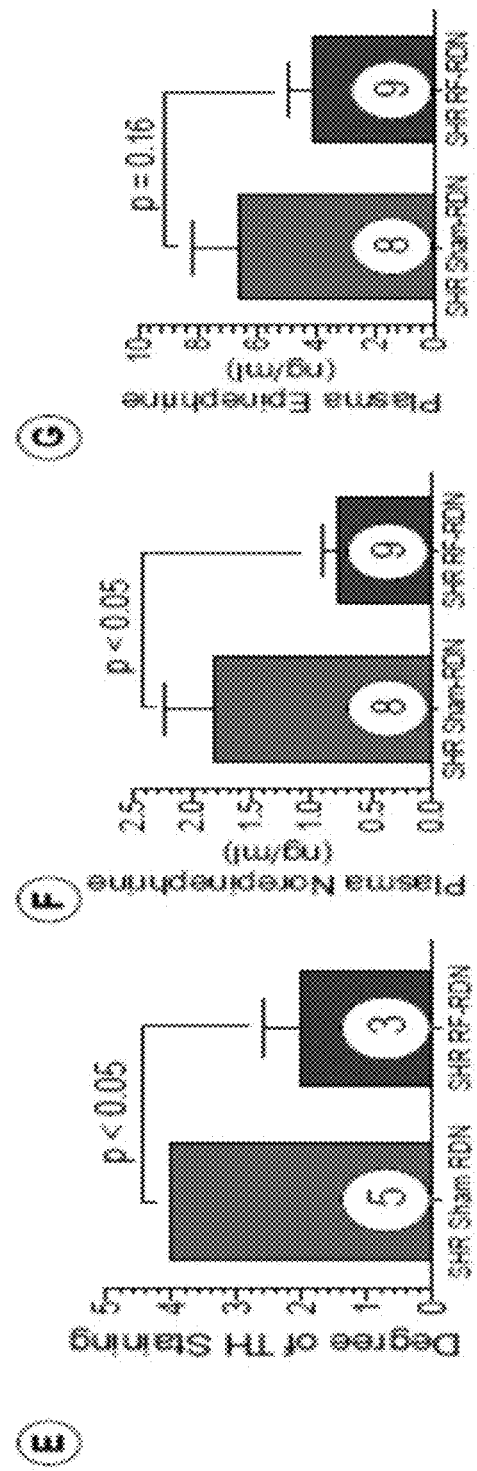
Figure 18:
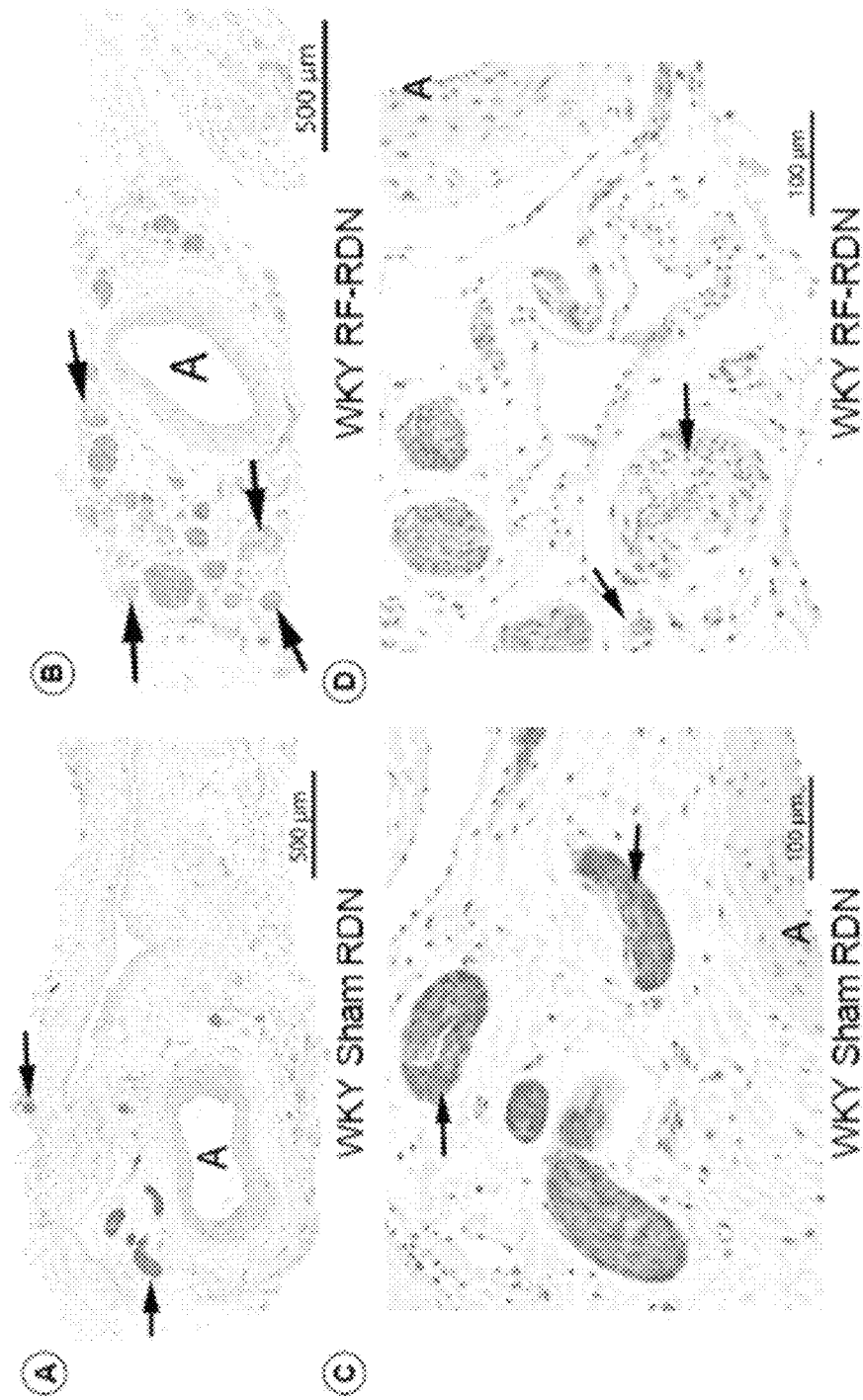
FIG. 18 shows viable renal artery nerve staining and catecholamine spillover following RF-RDN in WKY. Tyrosine hydroxylase staining at the 12-week endpoint following Sham-RDN or RF-RDN. (A) Tyrosine hydroxylase (TH) stain of renal artery section from Sham-RDN treated WKY. Arrows=normal nerves showing score 4 TH staining. A=renal artery. (B) TH stain of renal artery section from RF-RDN treated WKY. Arrows=nerves showing score 1 TH staining. A=renal artery, (C) Magnified image of FIG. 2A. (D) Magnified image of FIG. 2B. (E) Degree of TH staining. (F) Plasma norepinephrine and (G) epinephrine at the 12 week endpoint. Values are expressed as mean±SEM.

Renal Artery Nerve Viability and Catecholamine Levels Following RF-RDN in Heart Failure Renal artery nerve tyrosine hydroxylase (TH) staining at 8 weeks following RF-RDN or Sham-RDN in SHR and WKY rats revealed significantly reduced, but variable reductions in renal nerve viability following RF-RDN as compared to sham-RDN procedures (FIGS. 12 and 18). As a marker of sympathetic outflow, spillover norepinephrine (NE) and epinephrine levels were measured 8 weeks following RF-RDN or Sham-RDN. There was a significant reduction in circulating NE following RF-RDN compared to the sham-RDN in SHR and WKY rats, but there were no significant changes in plasma epinephrine levels. Previously, we reported that RF-RDN reduces TH staining and plasma NE levels 5 weeks following treatment (B17), but this study is the first to report that renal nerves remain denervated 8 weeks following RF-RDN in the setting of heart failure.

Figure 13:
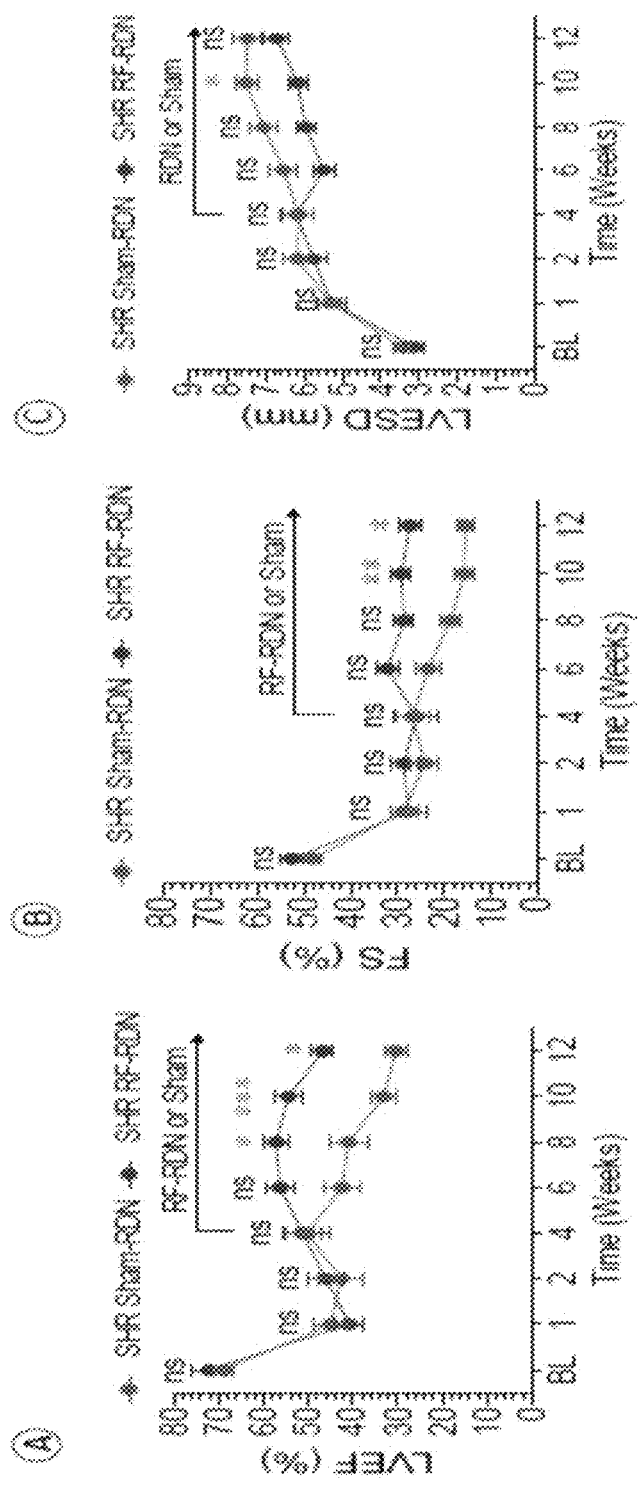
FIG. 13 shows left ventricular function and remodeling in SHR following ischemia-reperfusion injury with delayed treatment with either Sham-RDN or RF-RDN. (A) Left ventricular ejection fraction, (B) fractional shortening, (C) left ventricular end-systolic diameter, (D) left ventricular end-diastolic diameter, (E) systolic interventricular septal diameter (IVSs) and (F) diastolic interventricular septal diameter (IVSd). (G) Left ventricular end-diastolic pressure, (H) left ventricular end-systolic pressure, (I) left ventricular maximum change in pressure per unit time, (J) left ventricular minimum change in pressure per unit time, and (K) left ventricular relaxation constant, tau measured under anesthesia at the 12-week endpoint. Values are expressed as mean±SEM.
Figure 13:
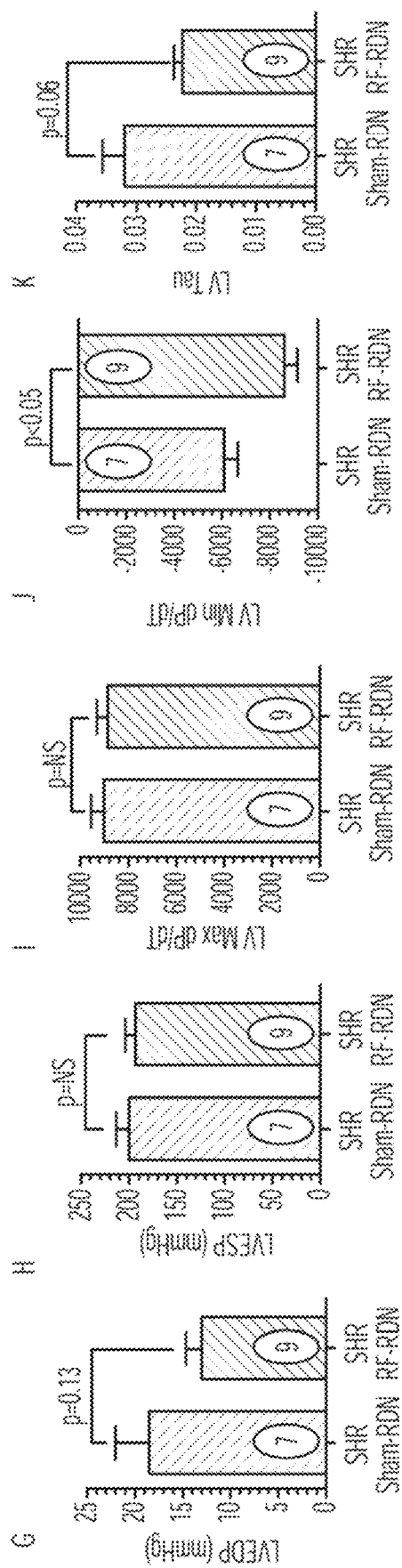

Delayed RF-RDN Therapy Preserves LV Function and Improves Cardiac Remodeling Following I/R Injury in SHR 4 weeks following MI/R injury, SHR were treated with either RF-RDN or Sham-RDN. LF function, as quantified by LV ejection fraction (LVEF) and Fractional Shortening (FS), was markedly improved as early as 4 weeks following therapy and remained superior to the sham treated animals through the 12-week end point (FIG. 13 A, B). Left ventricular end-systolic diameter (LVESD) was significantly reduced at 10 weeks, compared to sham-RDN animals (FIG. 13C). Interestingly, RF-RDN significantly increased the thickness of the interventricular septal wall at end-systole following ischemic injury, indicating that RF-RDN promotes myocardial tissue thickening of the infarcted wall (FIG. 13 E, F). in vivo LV pressure measurements indicate that RF-RDN has no significant effect on LV end systolic pressure (FIG. 13F) or the rate of pressure development during contraction (FIG. 13G). However, the LV rate of decreased pressure during relaxation (LV Min dP/dT) was significantly improved in the RF-RDN treated animals (FIG. 13H). The LV relaxation time constant, Tau, had a trending improvement in the RF-RDN group compared to Sham-RDN treated animals (FIG. 13I).

RF-RDN Modulates Circulating Natriuretic Peptides (NPs) in SHR in Heart Failure

Figure 14:
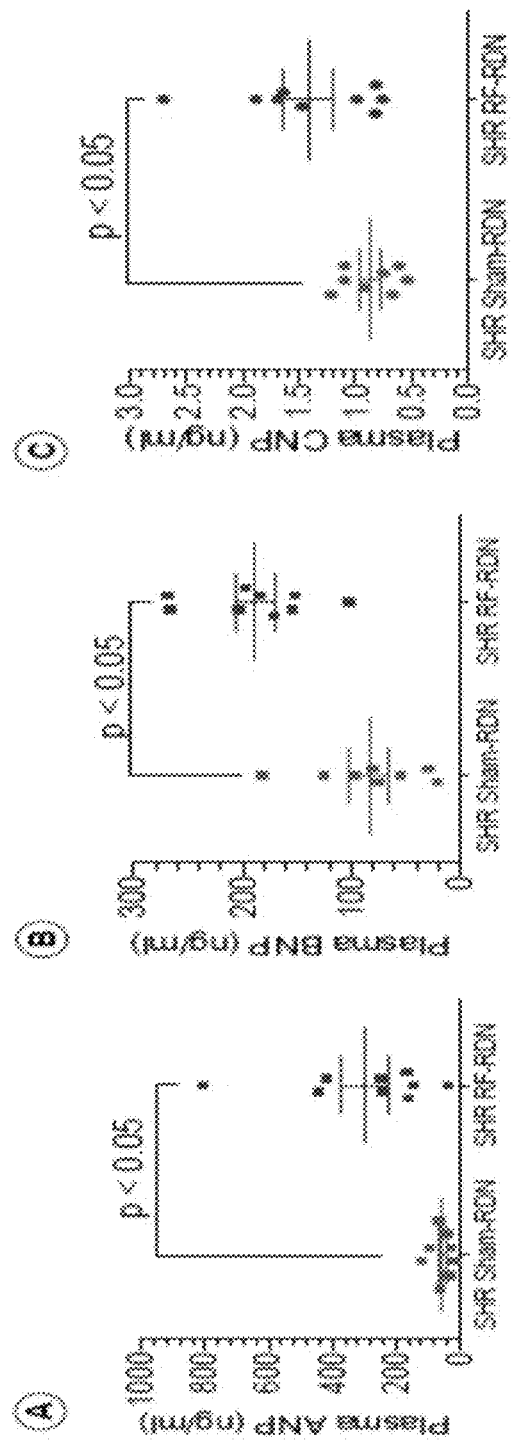
FIG. 14 shows circulating natriuretic peptides and myocardial natriuretic peptide gene expression in SHR following Sham-RDN or RF-RDN in heart failure. (A) Plasma ANP, (B) BNP, and (C) CNP levels at the 12-week endpoint in SHR following Sham-RDN or RF-RDN. (D) Left ventricle ANP mRNA, (E) BNP mRNA, and (F) CNP mRNA levels. (G) Left ventricle N-terminus Pro-BNP and (H) plasma N-terminus Pro-BNP in SHR following Sham-RDN or RF-RDN. Values are expressed as mean±SEM.
Figure 14:
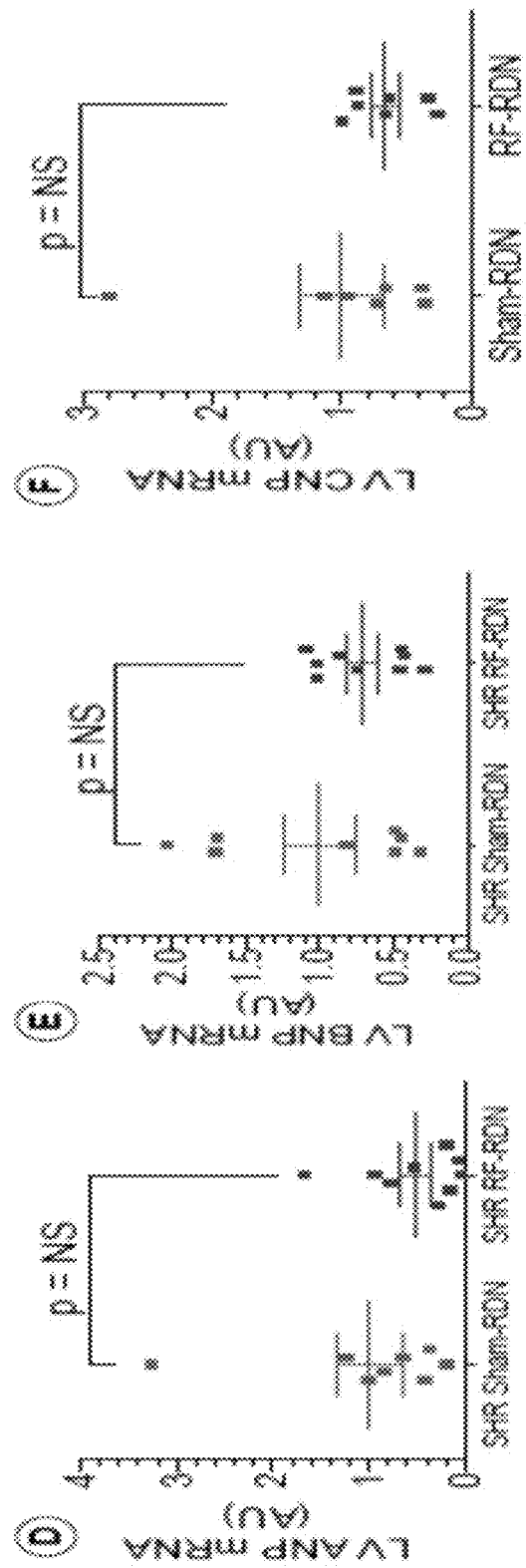

Despite improved LV function and remodeling, 12-week plasma ANP (FIG. 14A), BNP (FIG. 14B), and CNP (FIG. 14C) levels were markedly elevated in the RF-RDN treated group compared to sham. Interestingly, these changes were not due to increased gene transcription of ANP, BNP, and CNP in the myocardium (FIG. 14 D-F). Additionally, NT Pro-BNP levels in the LV and plasma indicate that RF-RDN did not enhance the release of NPs from the myocytes to circulation (FIG. 14 G, H).

RF-RDN Inhibits Renal Neprilysin Activity in SHR in Heart Failure

Figure 15:
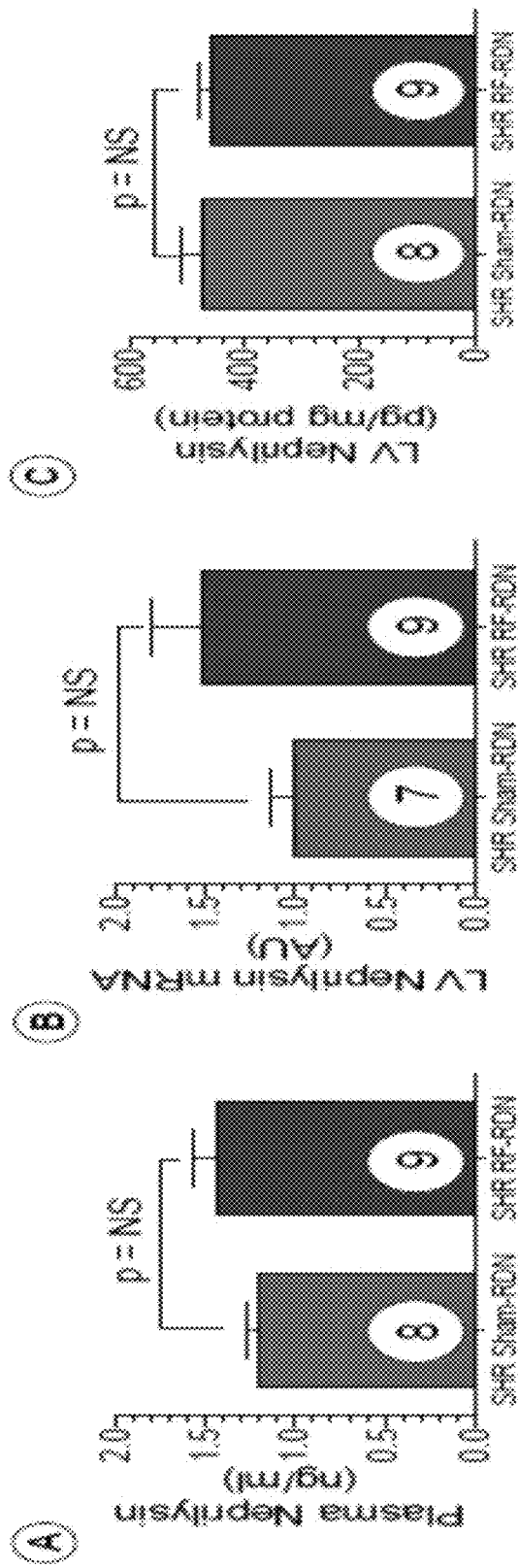
FIG. 15 shows neprilysin activity, natriuretic peptide clearance receptors, and cardioprotective and vasoactive agents in SHR following Sham-RDN or RF-RDN in heart failure. (A) Plasma NEP, (B) left ventricle NEP mRNA, (C) left ventricle NEP protein, and (D) kidney NEP mRNA levels in SHR following Sham-RDN or RF-RDN. (E) Kidney NEP activity at the 12-week endpoint following Sham-RDN or RF-RDN in SHR following ischemic injury. (F) Kidney Natriuretic peptide clearance receptor (NPRC) mRNA levels. (G) Plasma Substance P, (H) plasma Bradykinin, and (I) left ventricular nitrite levels in SHR rats treated with either Sham-RDN or RF-RDN. Values are expressed as mean±SEM.
Figure 15:
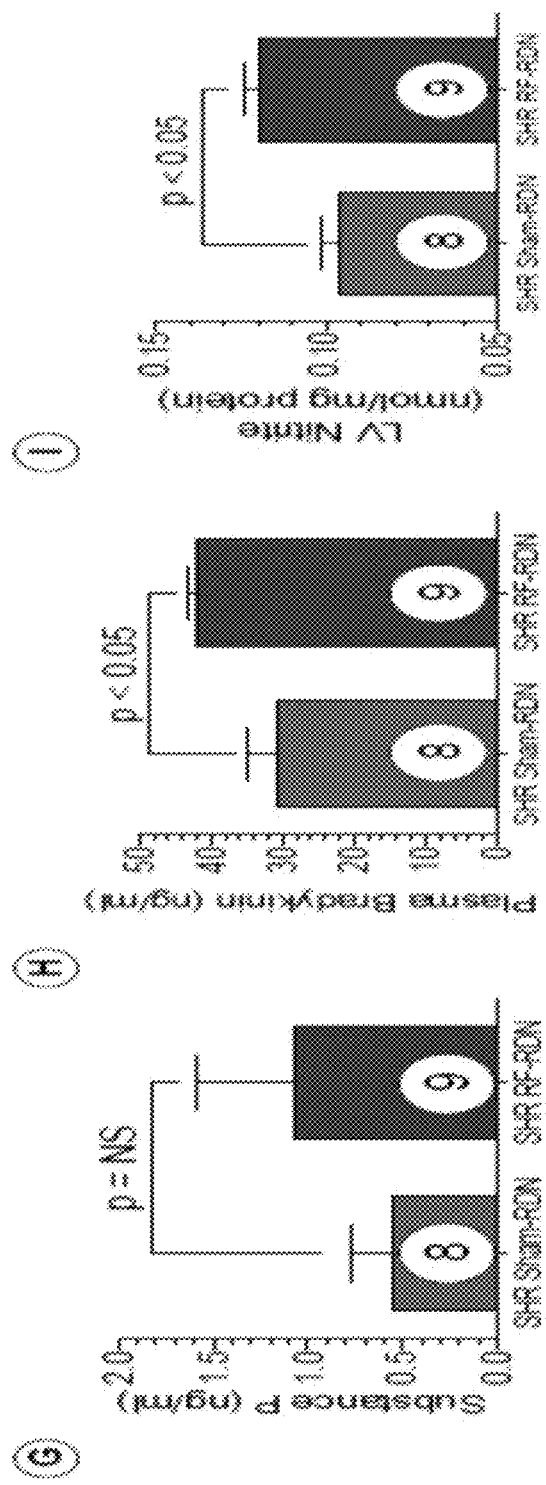

Because gene transcription alterations of NPs in the myocardium were not the cause of augmented NP levels in circulation, we next investigated the clearance and degradation of NPs. NPs are primarily cleared in the kidney via the natriuretic peptide clearance receptor (NPRC)(B20). mRNA levels of NPRC in the kidney following RF-RDN indicate that reduced clearance did not contribute to elevated NPs in circulation (FIG. 15F). NPs are principally degraded into inactive fragments by the metalo-endopeptidase, neprilysin (NEP)(B21). NEP is present in a wide variety of tissues, but is particularly abundant in the kidney. mRNA and protein quantification indicate that RF-RDN does not alter circulating, myocardial, or kidney NEP levels (FIG. 15 A, B, C, D). However, RF-RDN significantly inhibited renal NEP activity (FIG. 15E). Additionally, NEP degrades other cardioprotective and vasculoprotective peptides such as Substance P and Bradykinin (BK)(B22, B23). RF-RDN did not significantly alter circulating Substance P levels (FIG. 15G), but did promote BK levels in circulation (FIG. 15H). It is well established that BK promote nitric oxide (NO) levels by activating endothelial nitric oxide synthase (eNOS) (B24, B25). Increased LV nitrite levels following RF-RDN (FIG. 15I) indicate improved NO signaling and provides another possible mechanism of cardioprotection (B26).

Figure 16:
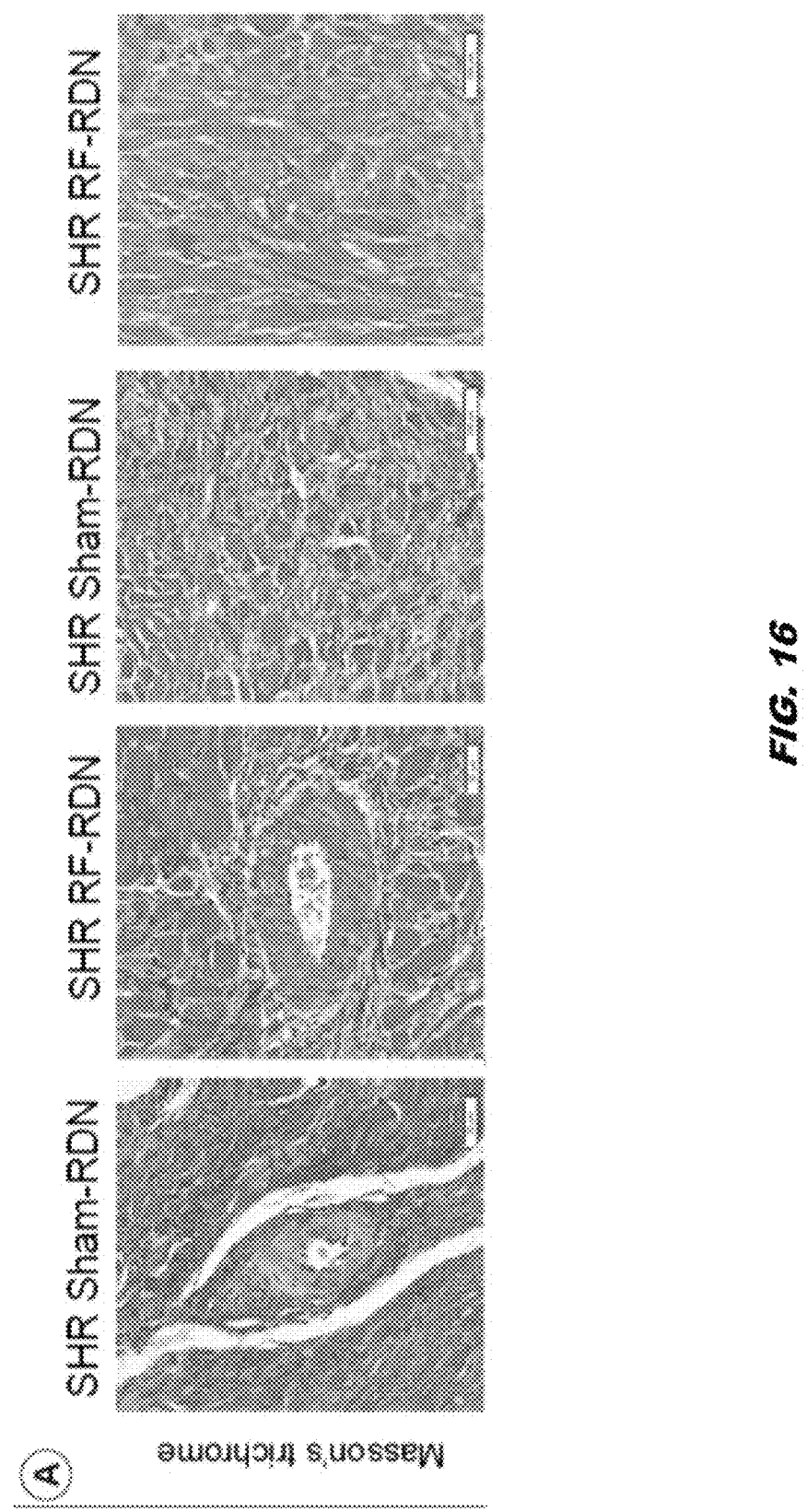
FIG. 16 shows cardiac fibrosis in SHR in heart failure following Sham-RDN or RF-RDN therapy. (A) Representative Masson's trichrome staining of perivascular and interstitial fibrosis in the left ventricle of SHR 12-weeks following ischemia-reperfusion injury. (B) Fibrosis score and (C) percent area fibrotic of the left ventricle. (D) mRNA levels of fibrotic genes collagen type 1 (Col1A1), collagen type 3 (Col3a1), transforming growth factor beta (TGF-beta), interleukin 6 (IL-6), connective tissue growth factor (CTGF), matrix metalloproteinase-2 (MMP-2), metallopeptidase inhibitor 1 (TIMP-1), and metallopeptidase inhibitor-2 (TIMP-2). (E) Representative images of expanded transition zone and (G) expanded transition zone score. Values are expressed as mean±SEM.
Figure 16:
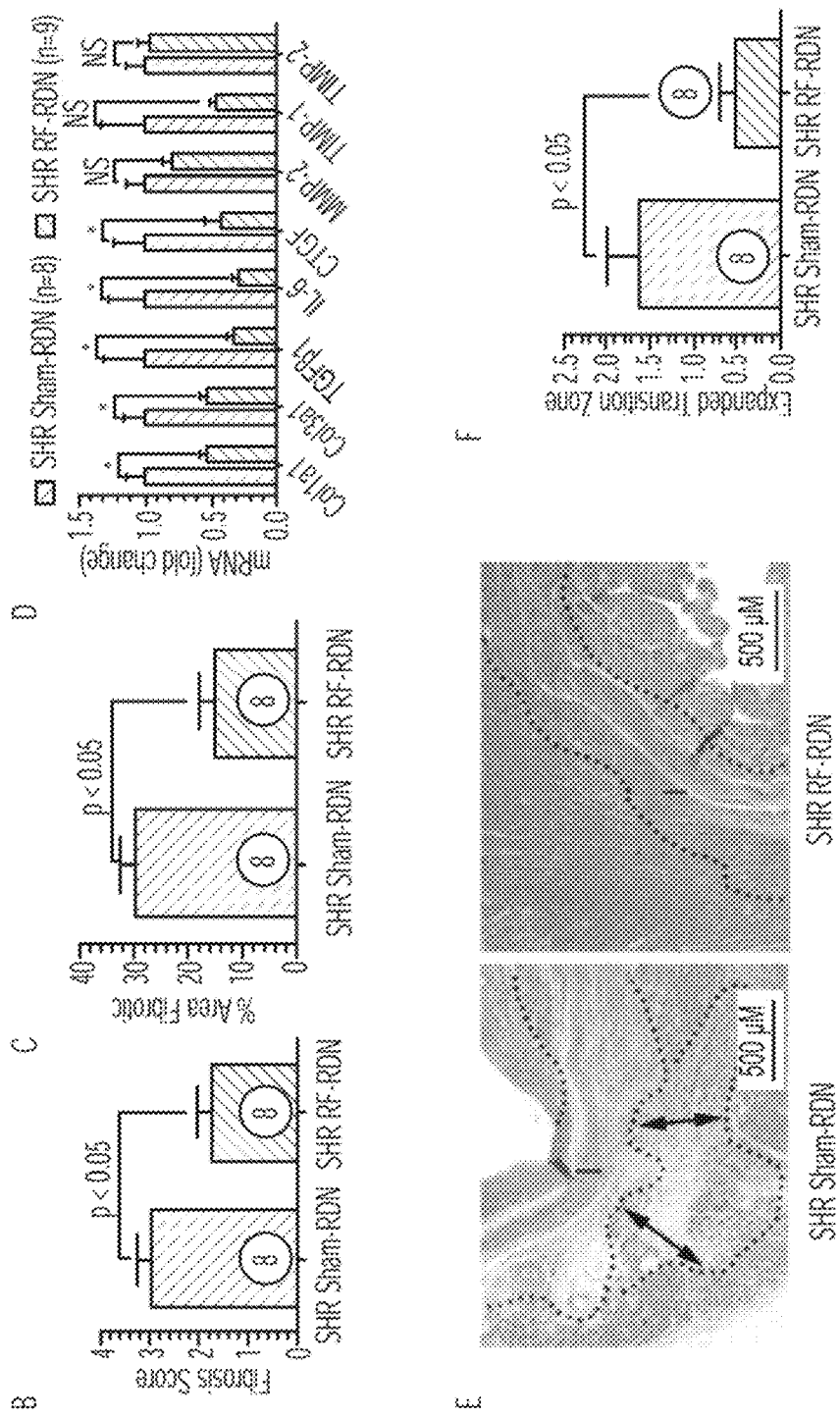

RF-RDN Attenuates Cardiac Fibrosis Pro-Fibrotic Signaling Following Ischemic Injury in SHR RF-RDN reduced left ventricular (LV) fibrosis score and % Area Fibrotic of the LF (29%±2.7 vs. 16%±3.0, p<0.05) at the 12-week endpoint following ischemic injury (FIG. 16B, C). Additionally, RF-RDN inhibited transition zone expansion of the infarcted region compared to sham (FIG. 16 E-F). Gene quantification revealed that RDN mitigated pro-fibrotic signaling, Col1a1, Col3a1, TGF beta1, IL6, and connective tissue growth factor (CTGF) (FIG. 16D). We observed no differences in MMP-2, TIMP-1, or TIMP2 gene expression in the RF-RDN treated group (FIG. 16D).

Figure 17:
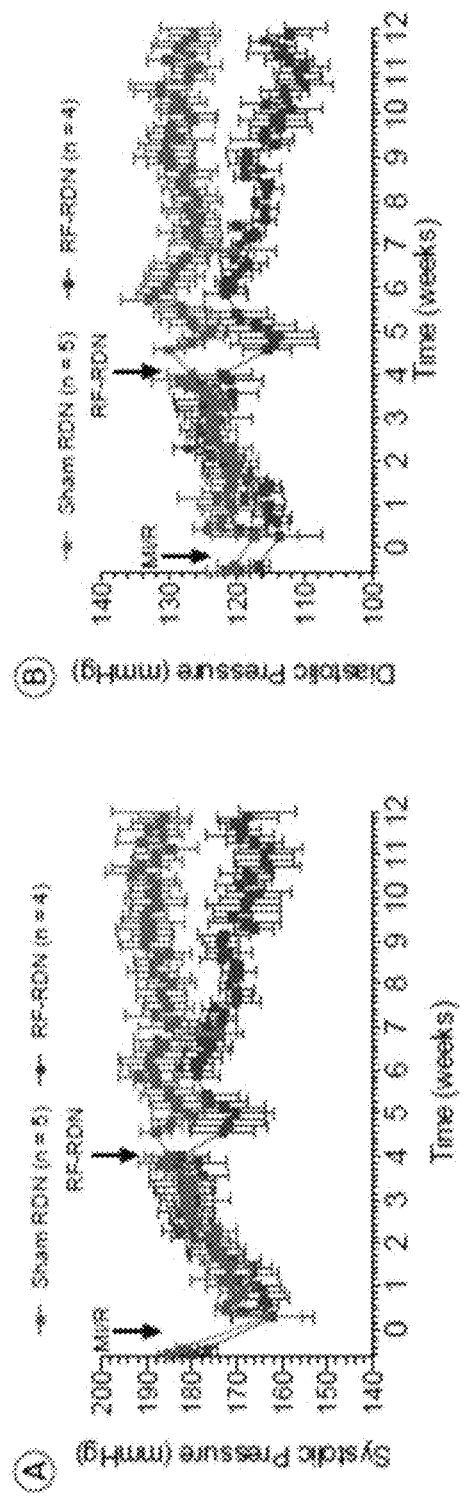
FIG. 17 shows radiotelemetry arterial blood pressure and heart rate measurements in SHR following MI/R injury and either Sham-RDN or RF-RDN therapy. (A) Systolic pressure in mmHg, (B) diastolic pressure, (C) mean arterial pressure, and (D) heart rate. Baseline and 12-week endpoint (E) systolic pressure, (F) diastolic pressure, (G) meant arterial pressure, and (H) heart rate in SHR. Values are expressed as mean±SEM.

RF-RDN has Modest Blood Pressure Lowering Effects Following Ischemic Injury in Hypertensive Animals RF-RDN produced a small, but significant decrease in conscious systolic, diastolic, and mean arterial blood pressure as compared to Sham-RDN at the 12-week endpoint (FIG. 17). However, the RF-RDN treated animals remained hypertensive with a systolic pressure above 150 and diastolic pressure above 110 mmHg (B27). RF-RDN did not significantly alter heart rate (FIG. 17).

Figure 19:
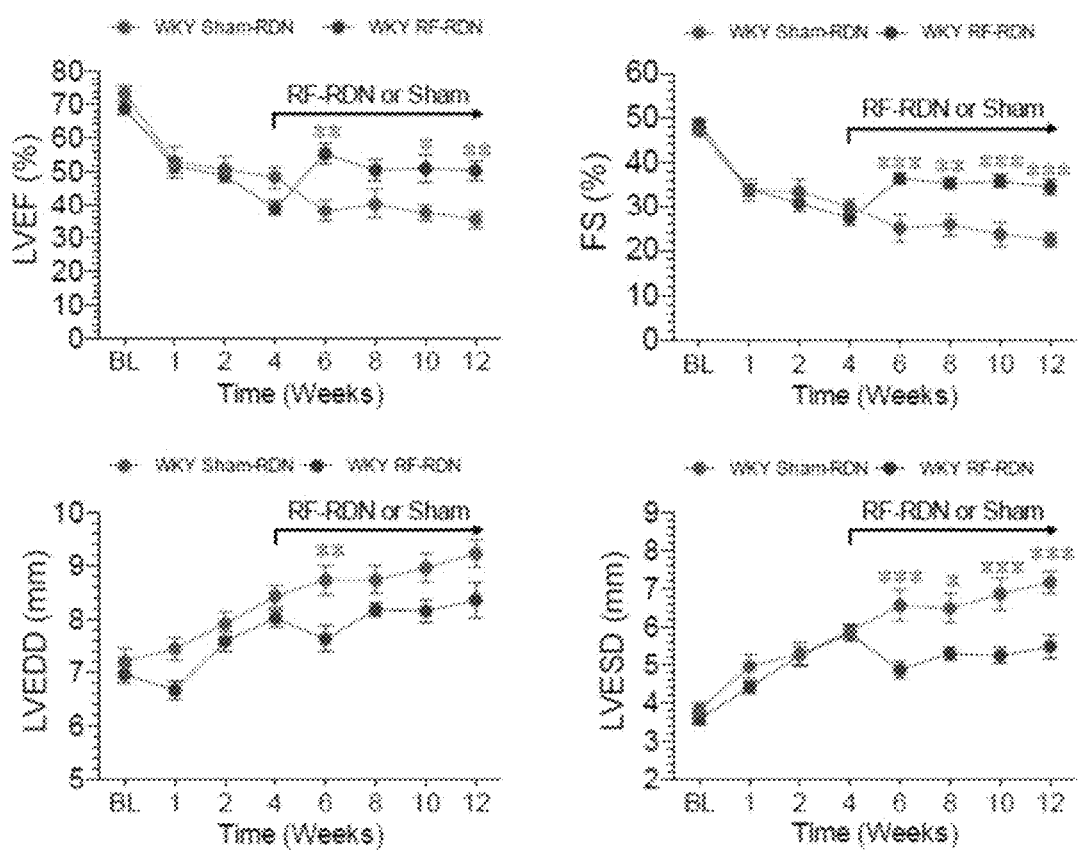
FIG. 19 shows left ventricular function and remodeling in WKY following ischemia-reperfusion injury with delayed treatment with either Sham-RDN or RF-RDN. (A) Left ventricular ejection fraction, (B) fractional shortening, (C) left ventricular end-systolic diameter, and (D) left ventricular end-diastolic diameter. Values are expressed as mean±SEM.

Delayed RF-RDN Therapy Preserves LV Function and Improves Cardiac Remodeling Following I/R Injury in Normotensive WKY Rats Much of the cardioprotective effects of RDN therapy are thought to be due to reduction in pressure, which reduces the afterload of the heart. However, LV function was improved in normotensive animals as early as 2 weeks following therapy and remained superior to the sham treated animals through the 12-week end point (FIG. 19 A, B). RF-RDN also improved cardiac remodeling in WKY. Left ventricular end-diastolic diameter (LVEDD) was significantly reduced at 6 weeks, compared to sham-RDN animals (FIG. 19C) and LVESD was maintained below the Sham-RDN dimension from week 6 through the 12-week endpoint. These results indicate that RDN may have therapeutic potential for HF in both hypertensive and normotensive patients.

RF-RDN Modulates Circulating Natriuretic Peptides (NPs) in WKY in Heart Failure

Figure 20:
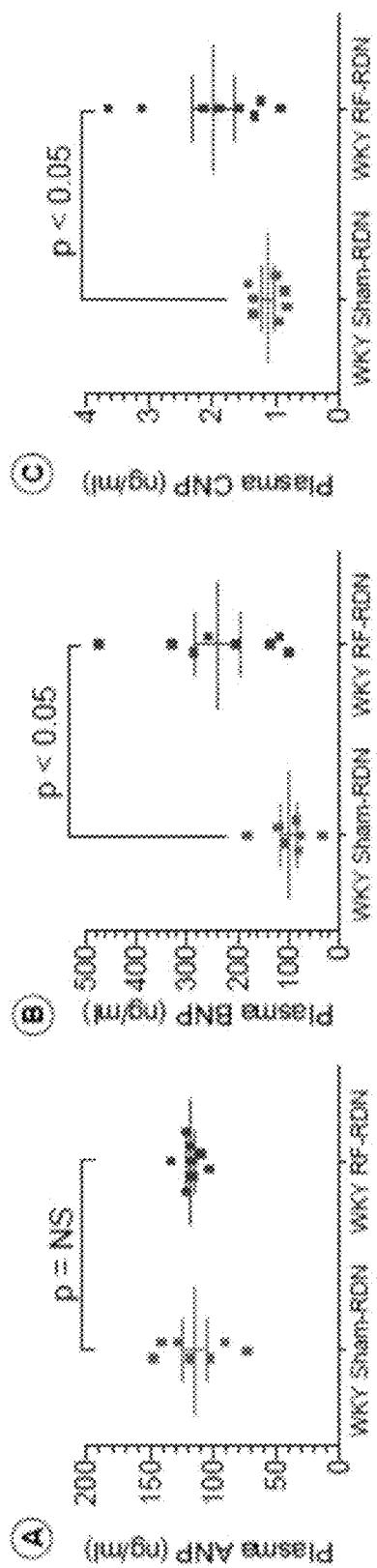
FIG. 20 shows circulating natriuretic peptides and myocardial natriuretic peptide gene expression in WKY rats following Sham-RDN or RF-RDN in heart failure. (A) Plasma ANP, (B) BNP, and (C) CNP levels at the 12-week endpoint in WKY rats following Sham-RDN or RF-RDN. (D) Left ventricle ANP mRNA, (E) BNP mRNA, and (F) CNP mRNA levels. (G) Left ventricle N-terminus Pro-BNP and (H) plasma N-terminus Pro-BNP in WKY rats following Sham-RDN or RF-RDN. (I) Plasma Bradykinin levels in WKY rats at the 12-week endpoint. Values are expressed as mean±SEM.
Figure 20:
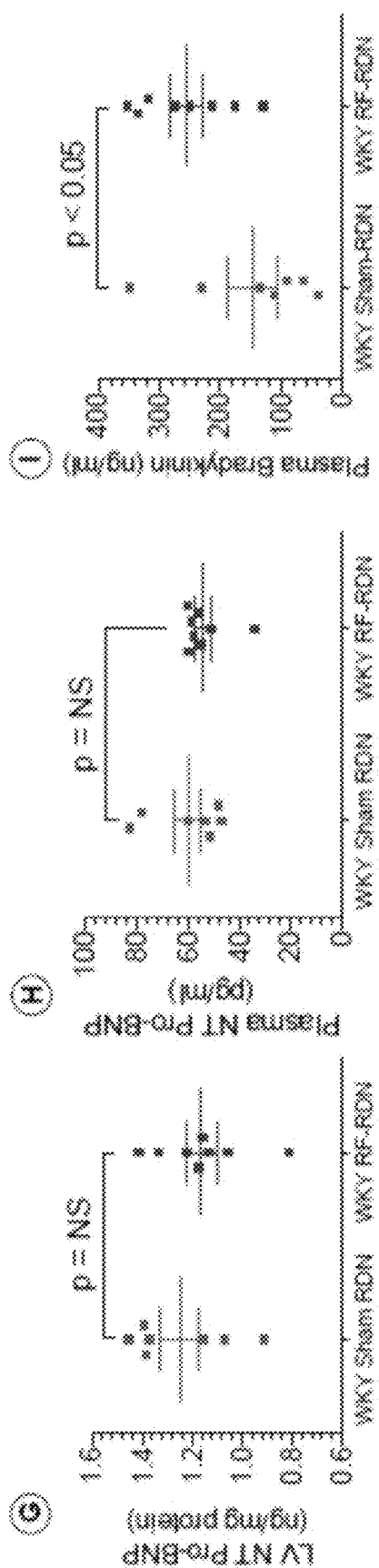
Figure 21:
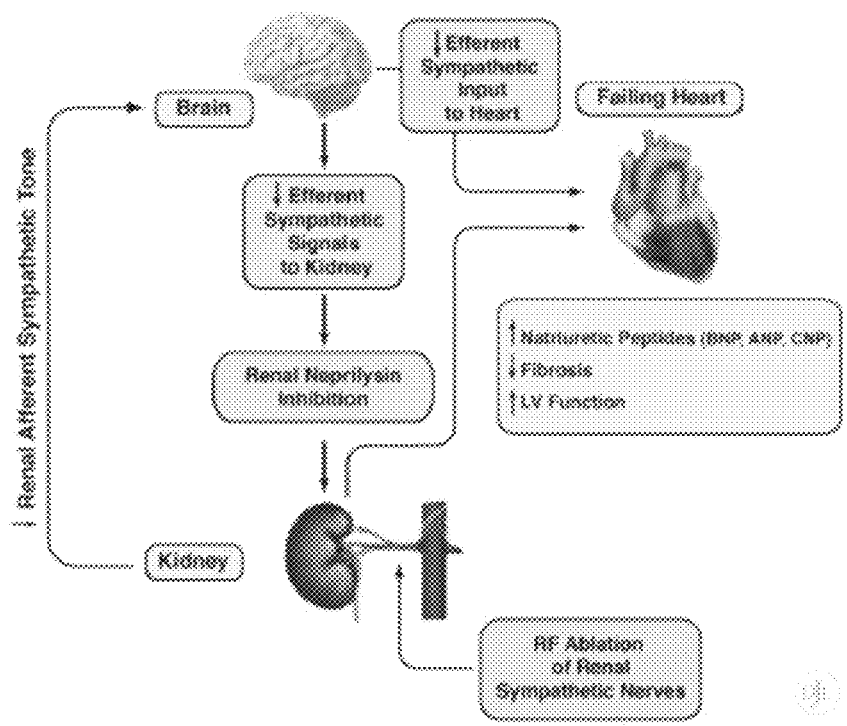
FIG. 21 shows proposed mechanism of cardioprotection by RF-RDN in the setting of heart failure. Radiofrequency ablation of the renal sympathetic nerves suppresses both efferent sympathetic signals to the kidney and afferent sympathetic tone to the brain. Reduced sympathetic tone to the kidney results in renal neprilysin inhibition, augmentation of circulating natriuretic peptides, reduced cardiac fibrosis and improved function. Additionally, repressed renal afferent sympathetic tone modulates efferent sympathetic inputs on the heart, improving cardiac remodeling and function.
Figure 22:
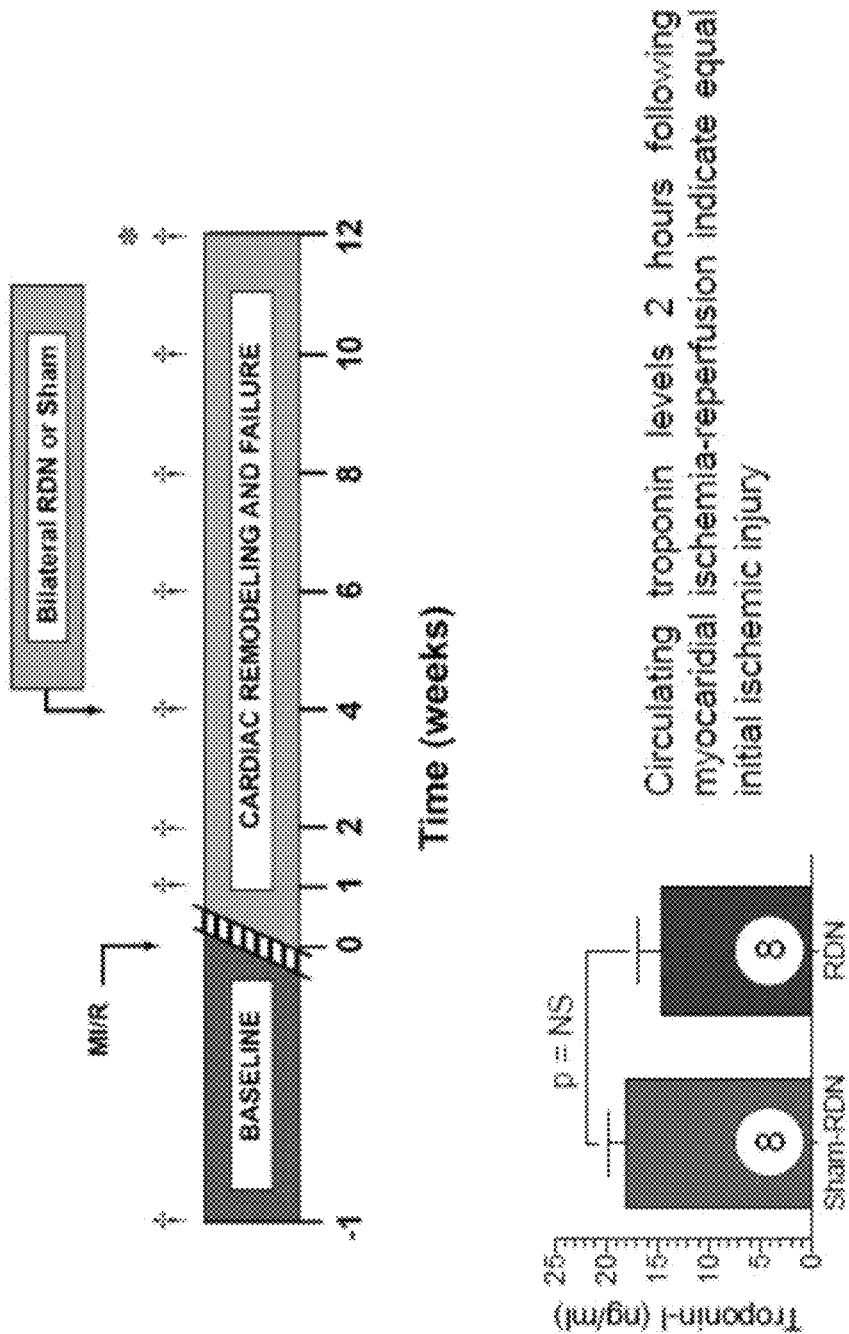
FIG. 22 shows rat ischemic heart failure experimental protocol.
Figure 23:
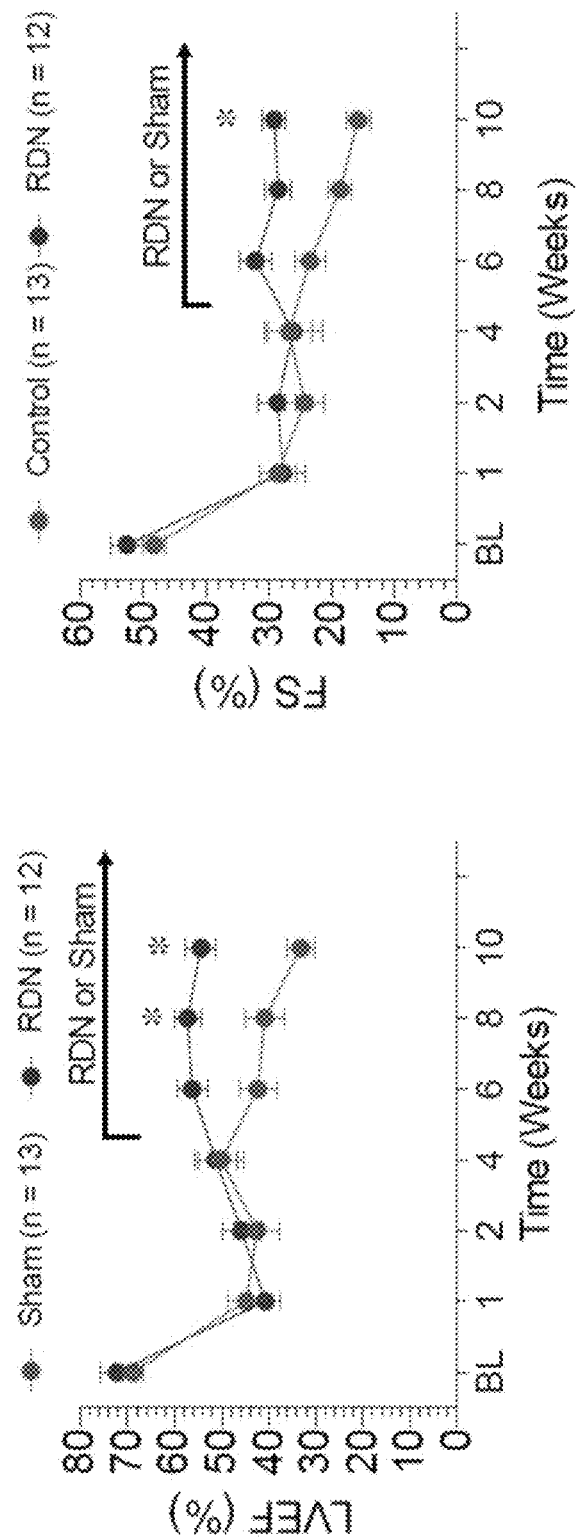
FIG. 23 shows improved LV function following delayed RDN therapy in the setting of ischemic heart failure.
Figure 24:
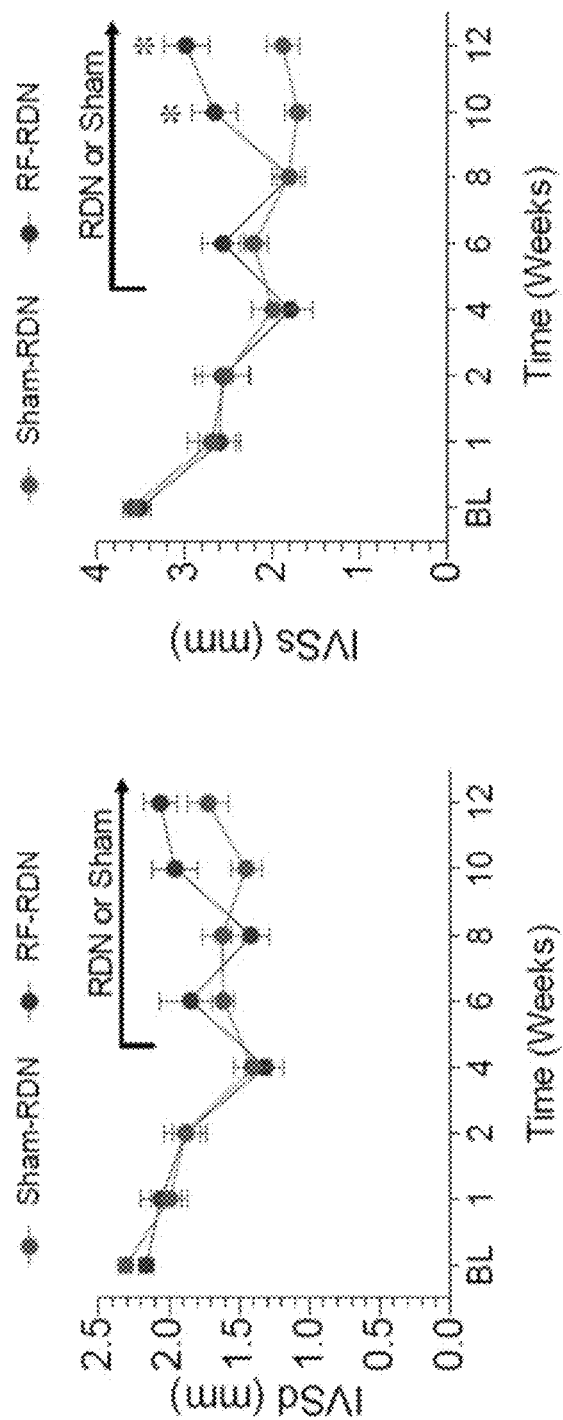
FIG. 24 shows increased septal wall thickness following delayed RDN therapy in the setting of ischemic heart failure.
Figure 25:
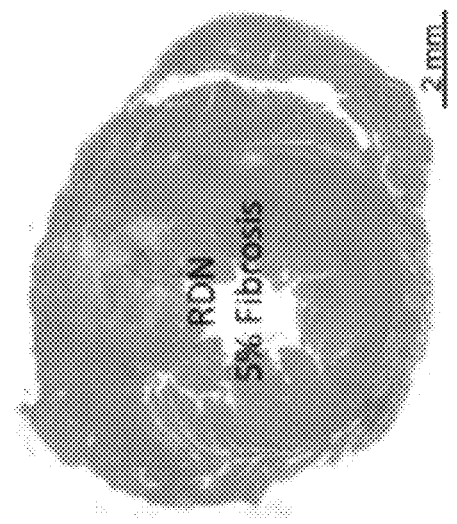
FIG. 25 shows reduced LV fibrosis following delayed RDN therapy in the setting of ischemic heart failure (12 weeks).
Figure 25:
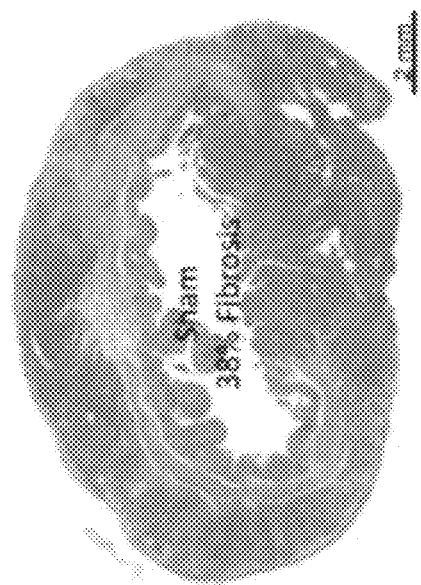
Figure 25:
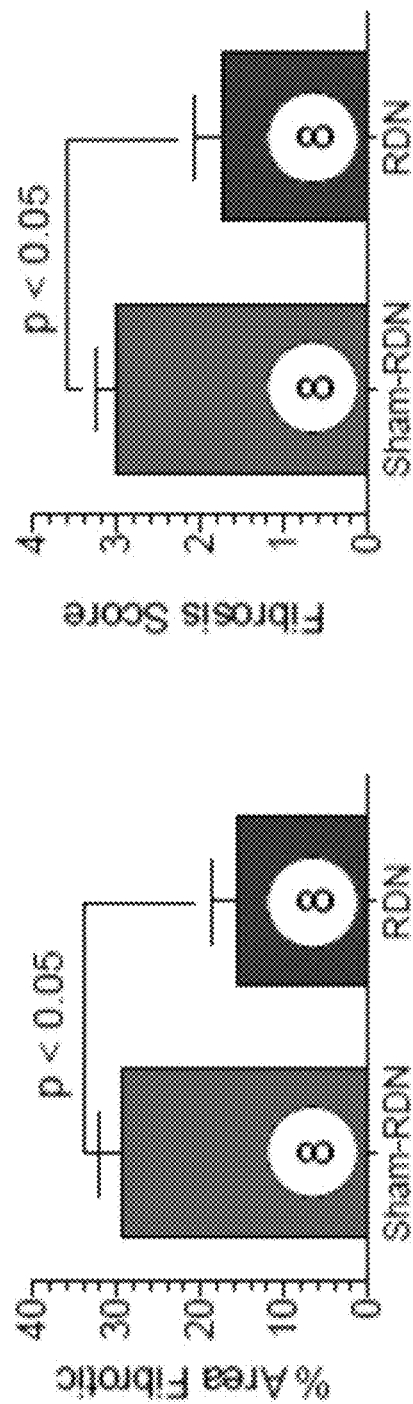
Figure 26:
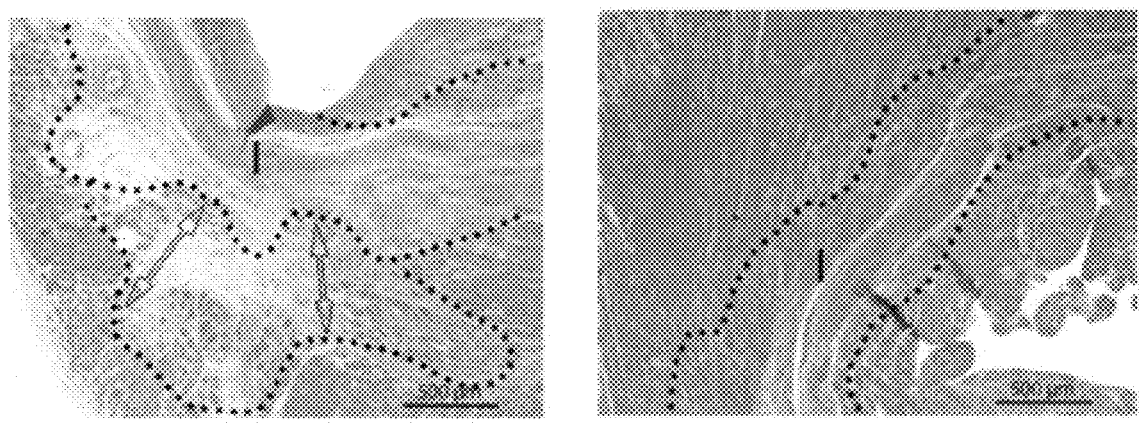
FIG. 26 shows reduced fibrosis transition zone following delayed RDN therapy in the setting of ischemic heart failure (12 weeks).
Figure 26:
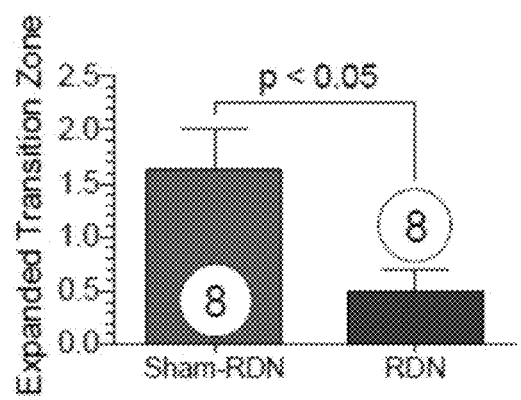
Figure 27:
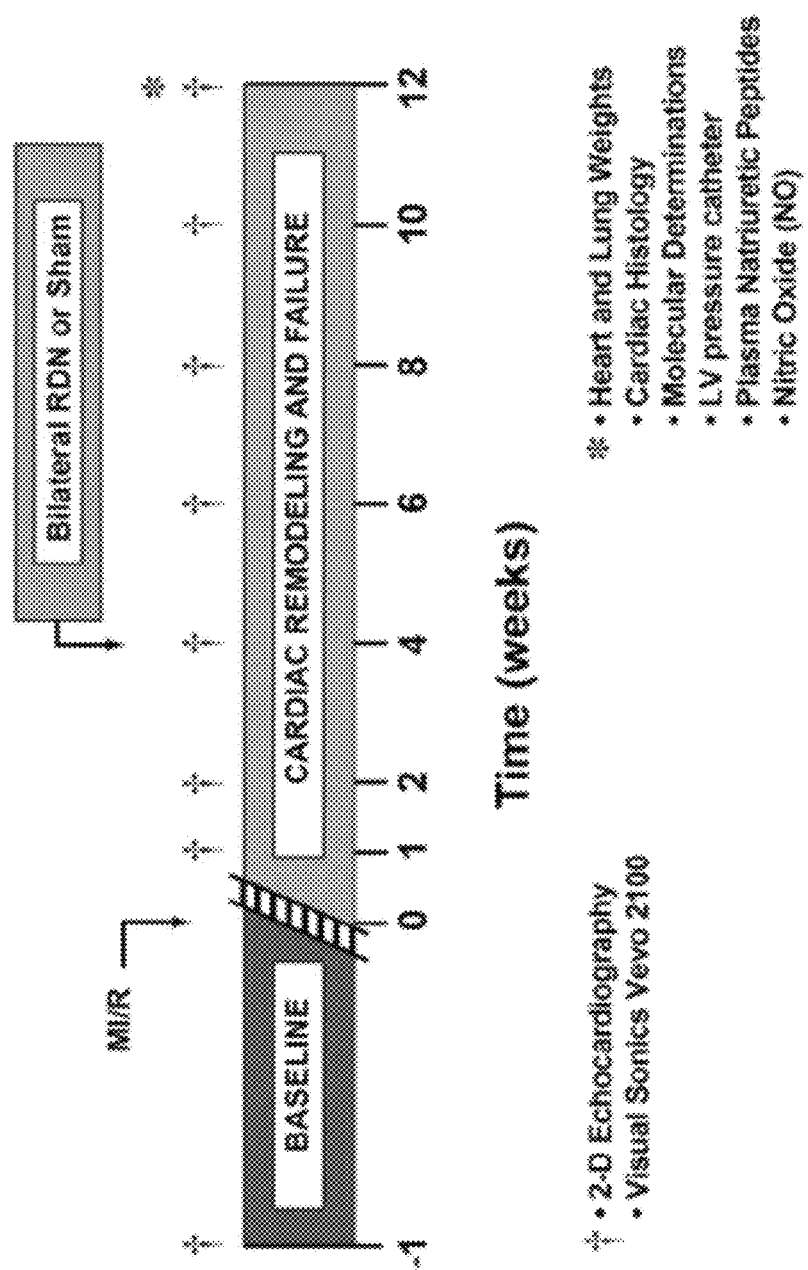
FIG. 27 shows rat ischemic heart failure experimental protocol.
Figure 28:
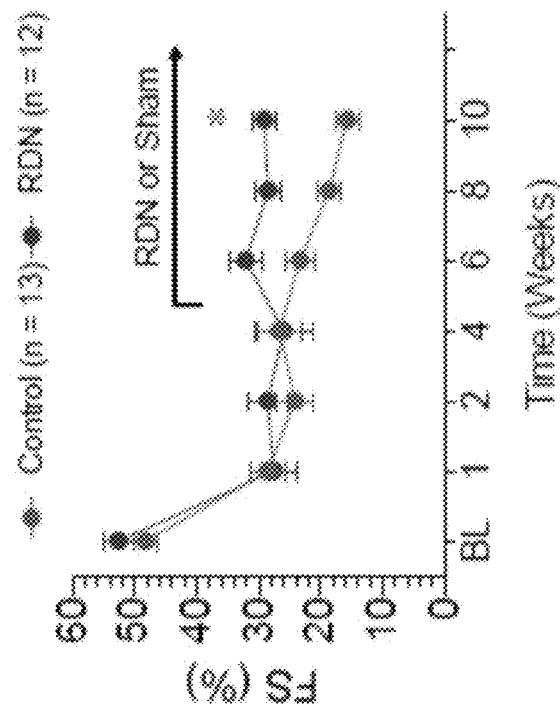
FIG. 28 shows percent LVEF and percent FS.
Figure 28:
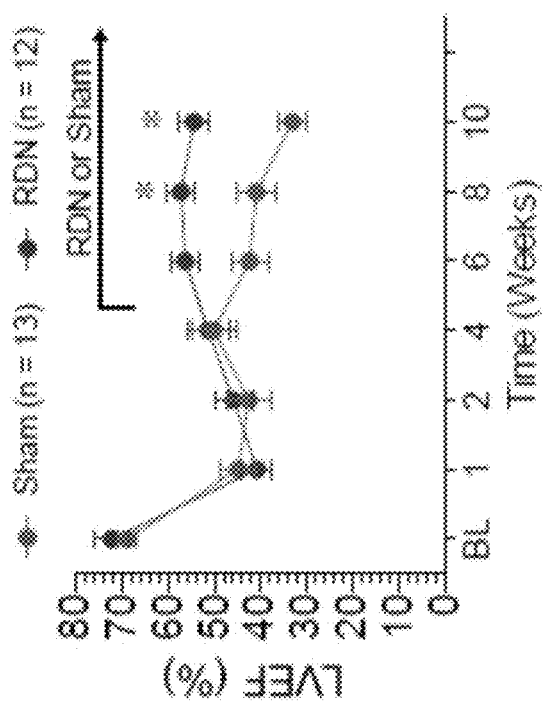
Figure 29:
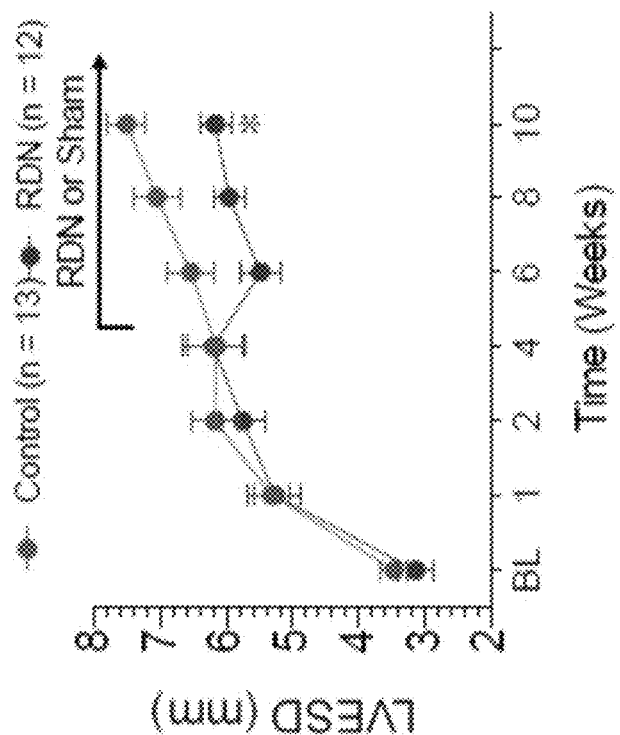
FIG. 29 shows LVEDD and LVESD.
Figure 29:
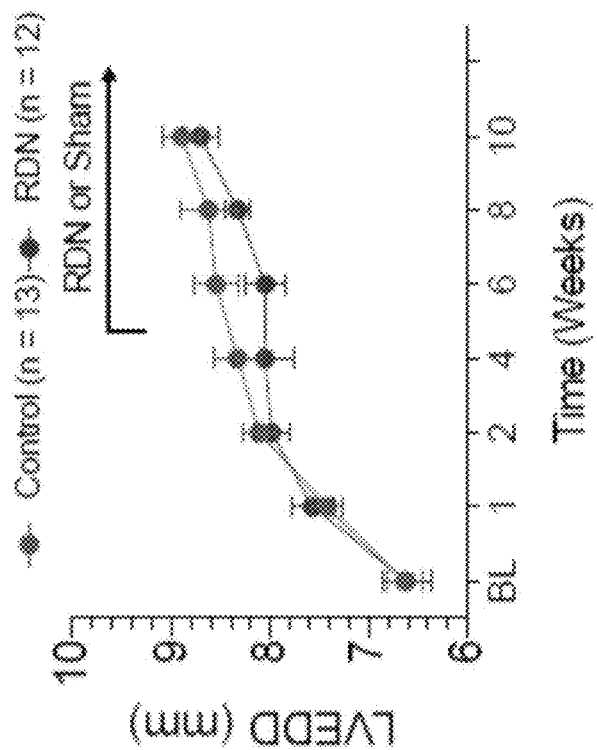
Figure 30:
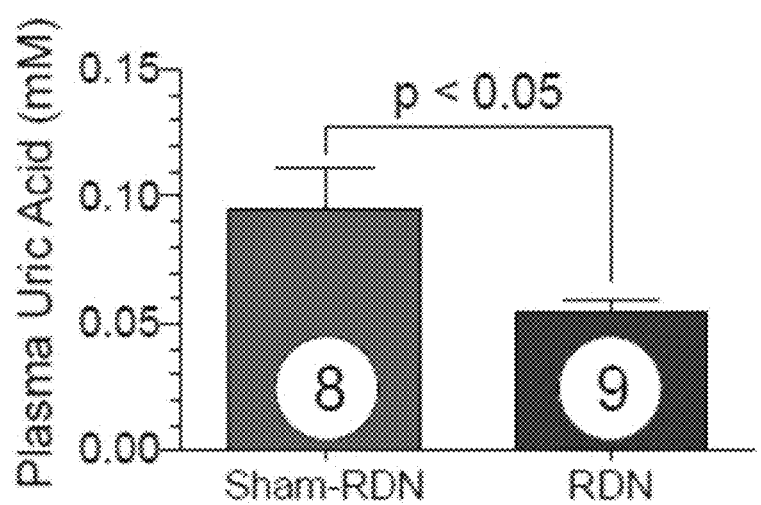
FIG. 30 shows plasma uric acid.
Figure 31:
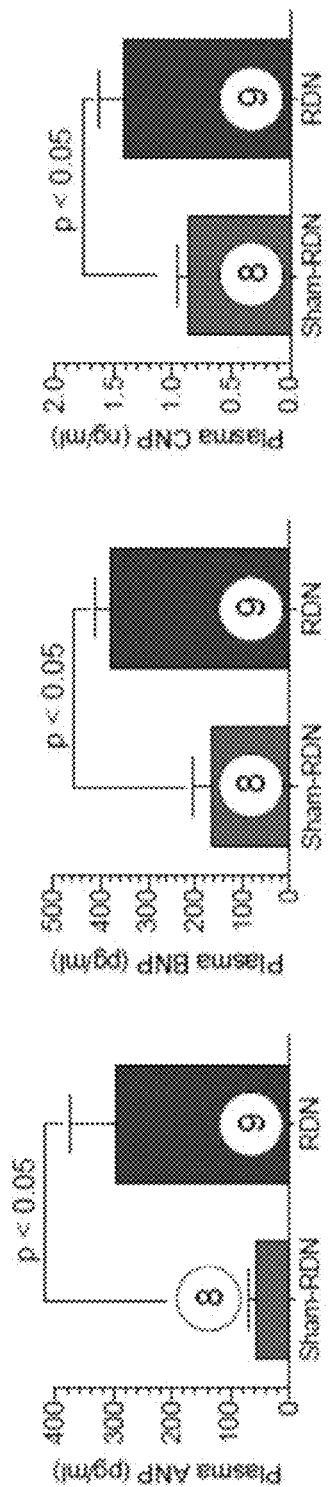
FIG. 31 shows plasma ANP, BNP, and CNP.
Figure 32:
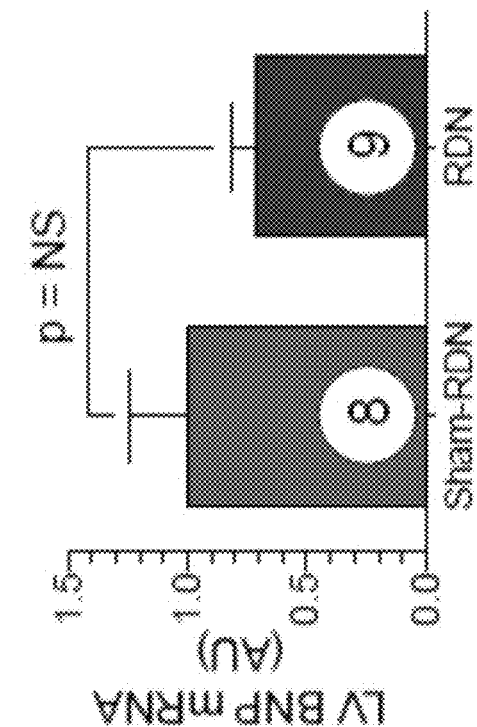
FIG. 32 shows ANP mRNA and BNP mRNA.
Figure 32:
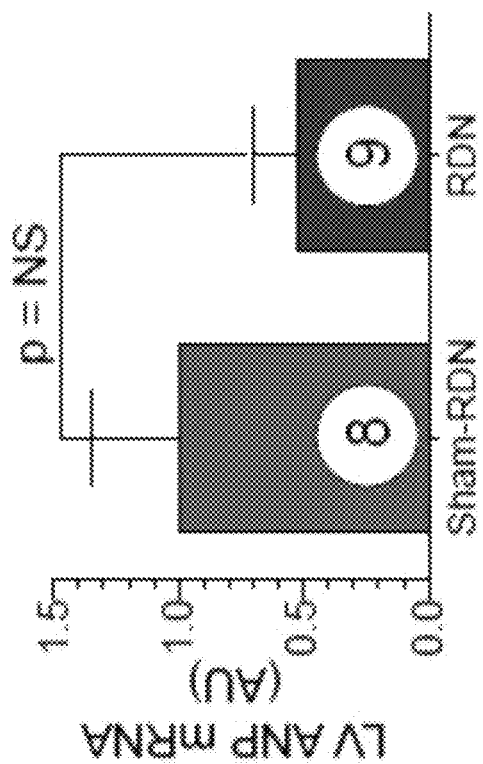
Figure 33:
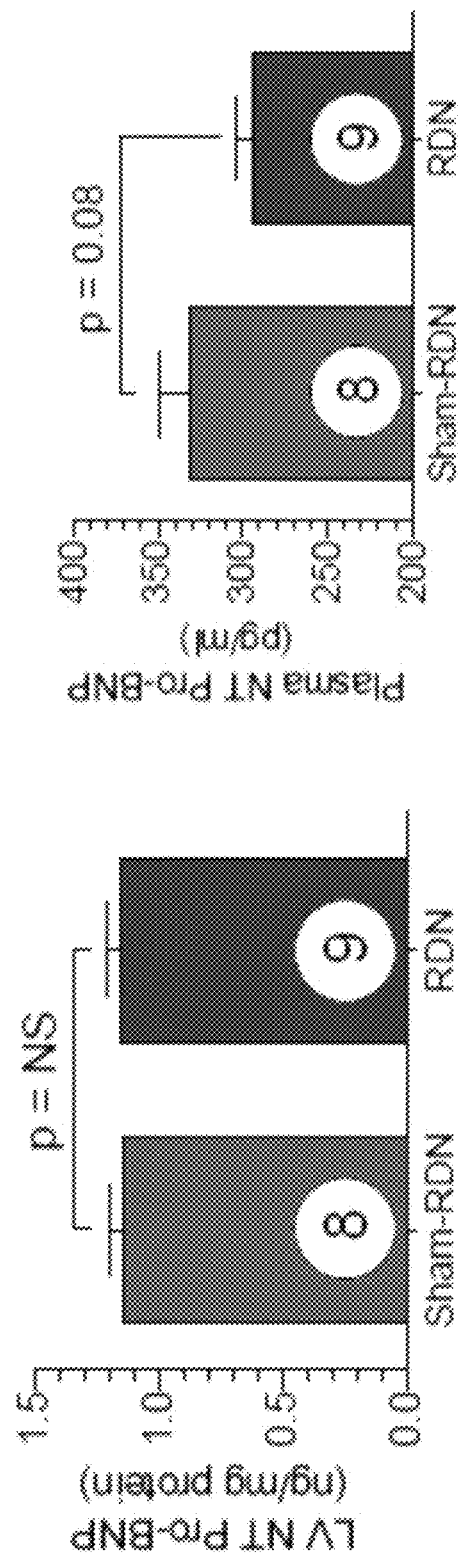
FIG. 33 shows LV NT Pro-BNP, and plasma NT Pro-BNP.
Figure 34:
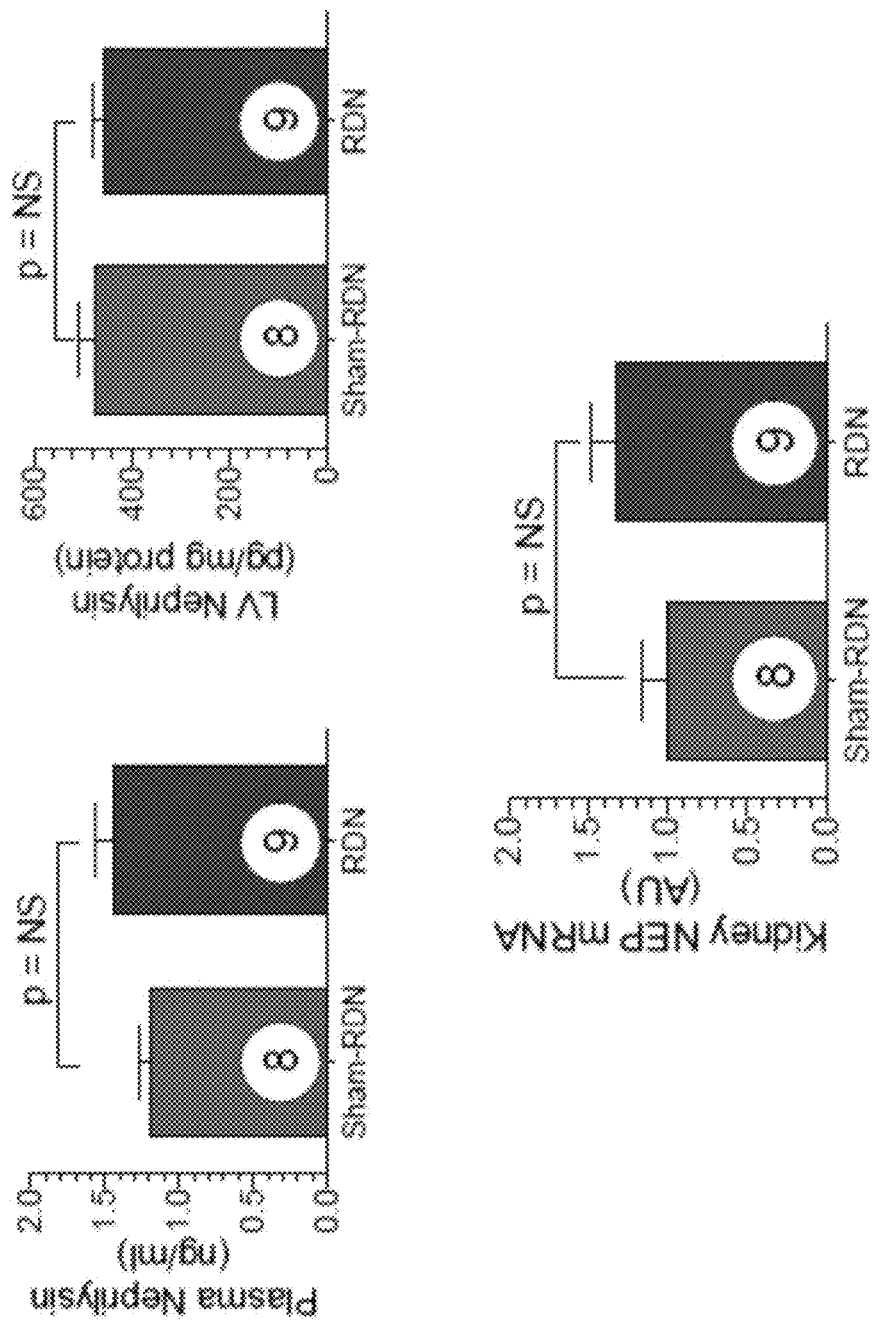
FIG. 34 shows plasma neprilysin, kidney NEP mRNA, and LV neprilysin.
Figure 35:
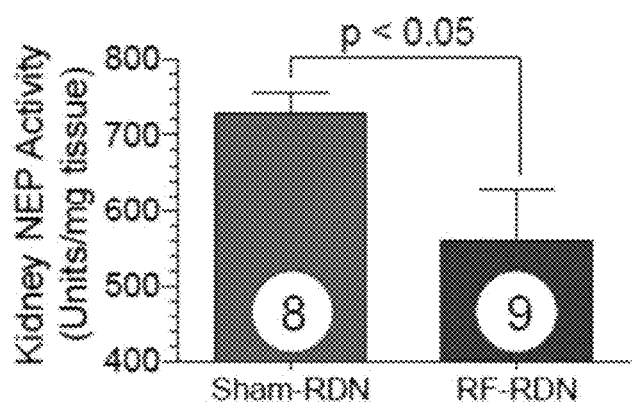
FIG. 35 shows kidney NEP activity.
Figure 36:
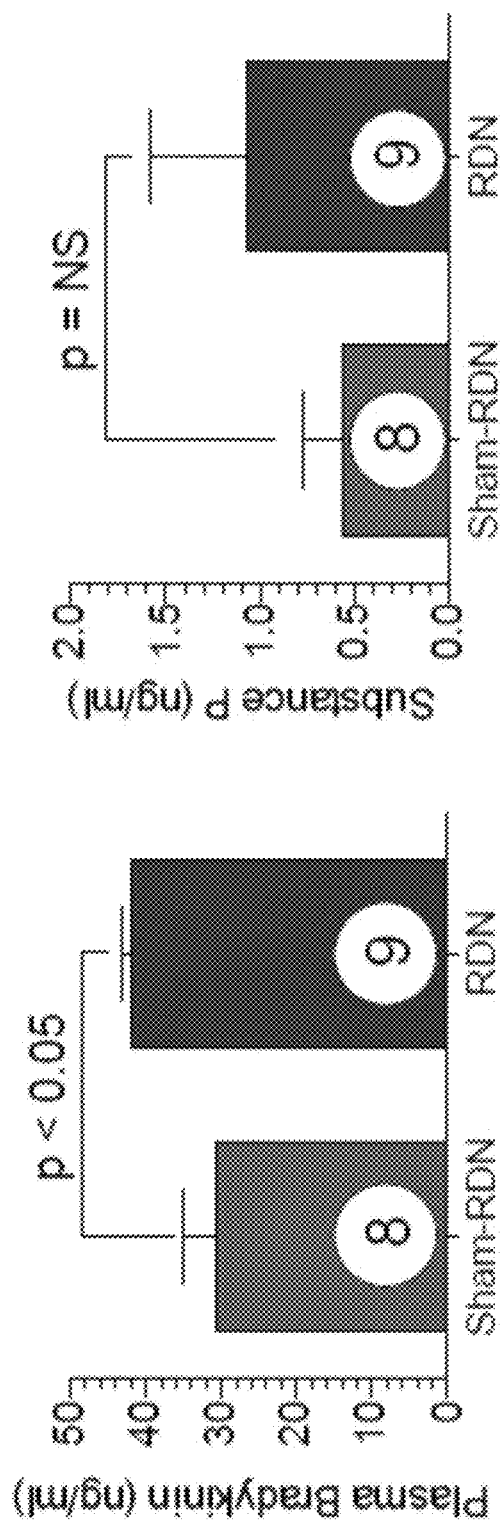
FIG. 36 shows plasma bradykinin and substance P.
Figure 37:
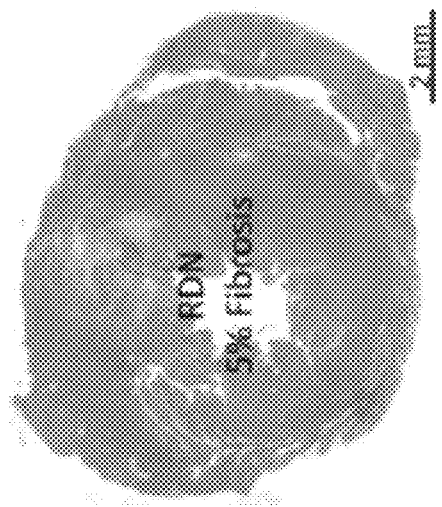
FIG. 37 shows fibrosis and LV COL1 mRNA and LV COL3 mRNA.
Figure 37:
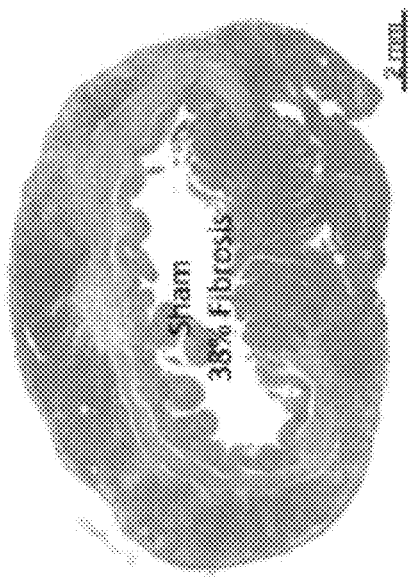
Figure 38:
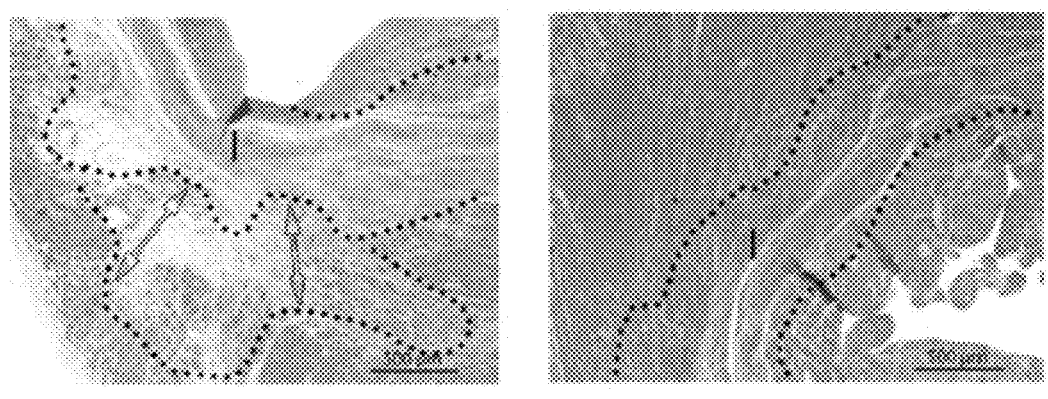
FIG. 38 shows expanded transition zone.
Figure 38:
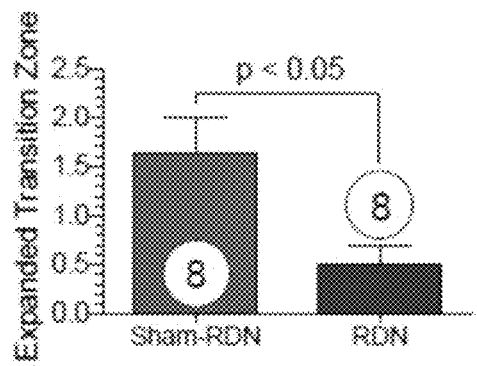
Figure 39:
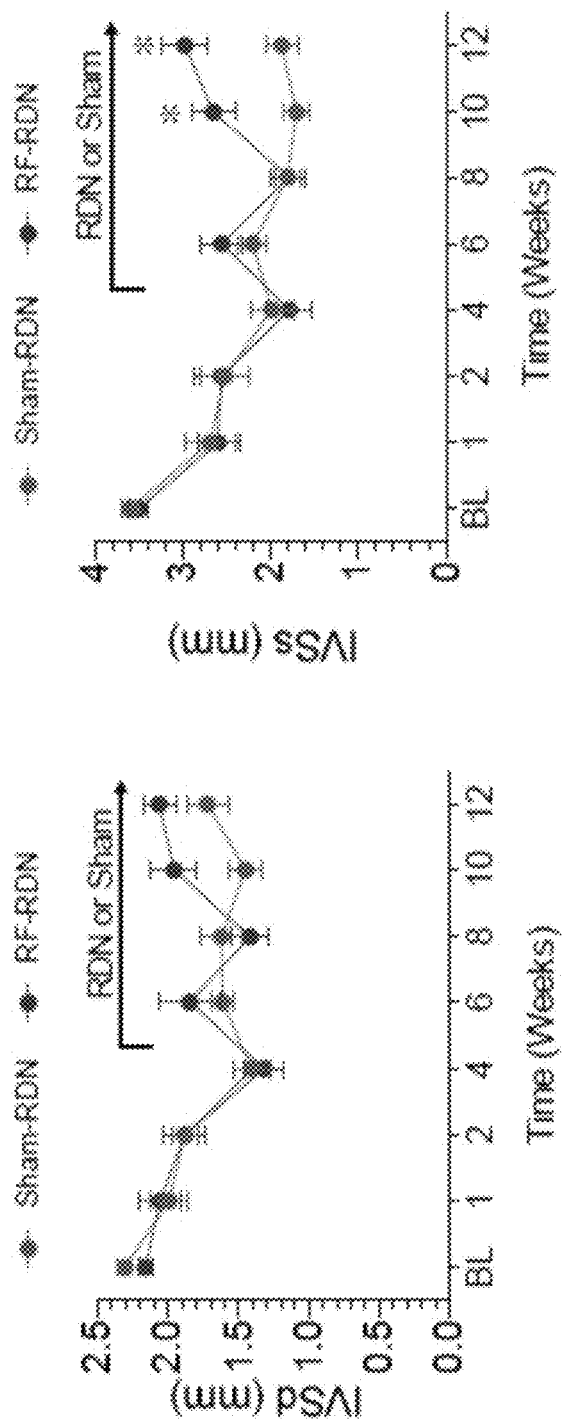
FIG. 39 shows IVSd and IVSs.
Figure 40:
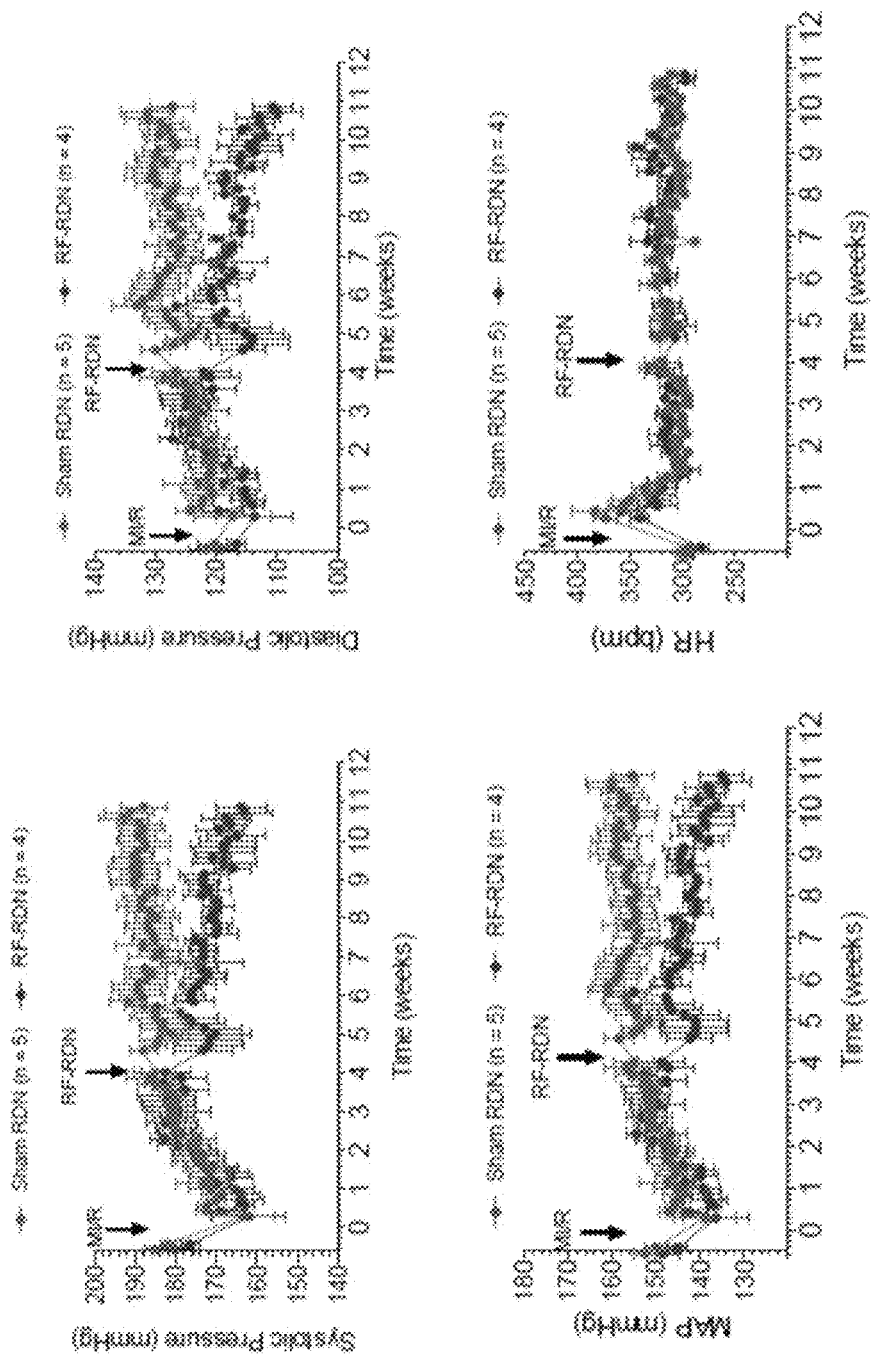
FIG. 40 shows MAP, Systolic Pressure, HR, and Diastolic Pressure.
Figure 41:
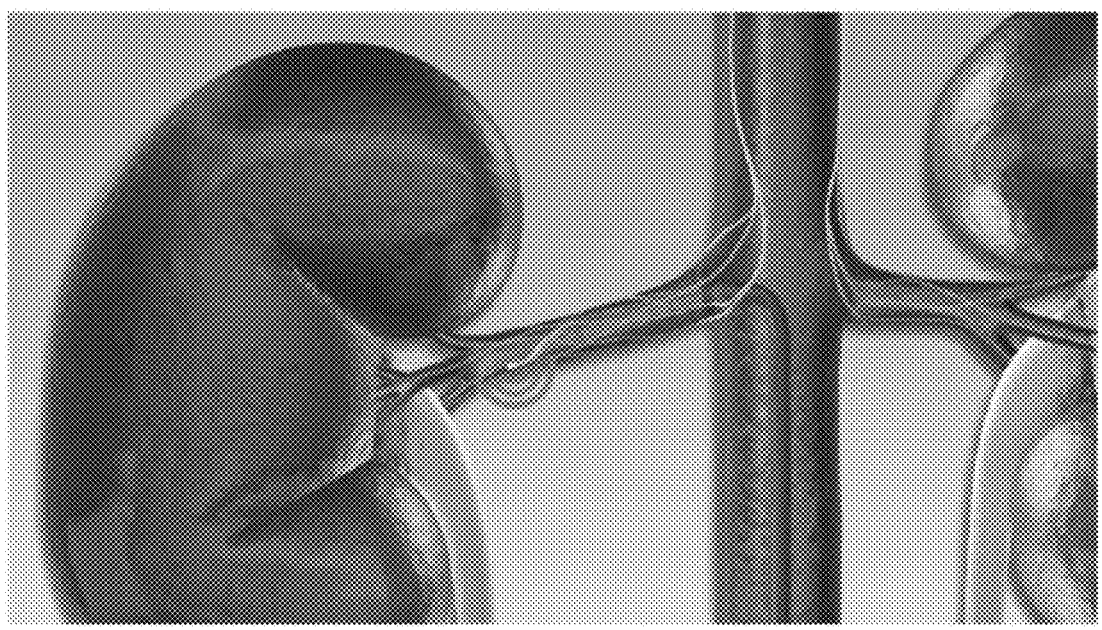
FIG. 41 shows sympathetic renal nerve denervation.
Figure 42:
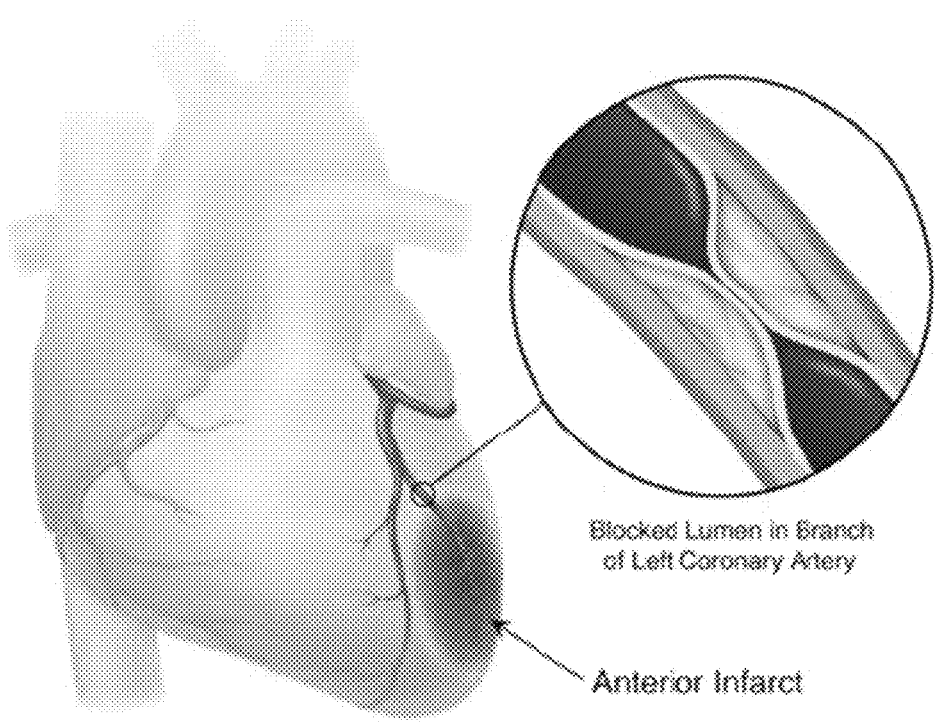
FIG. 42 shows heart disease is the number 1 killer.
Figure 43:
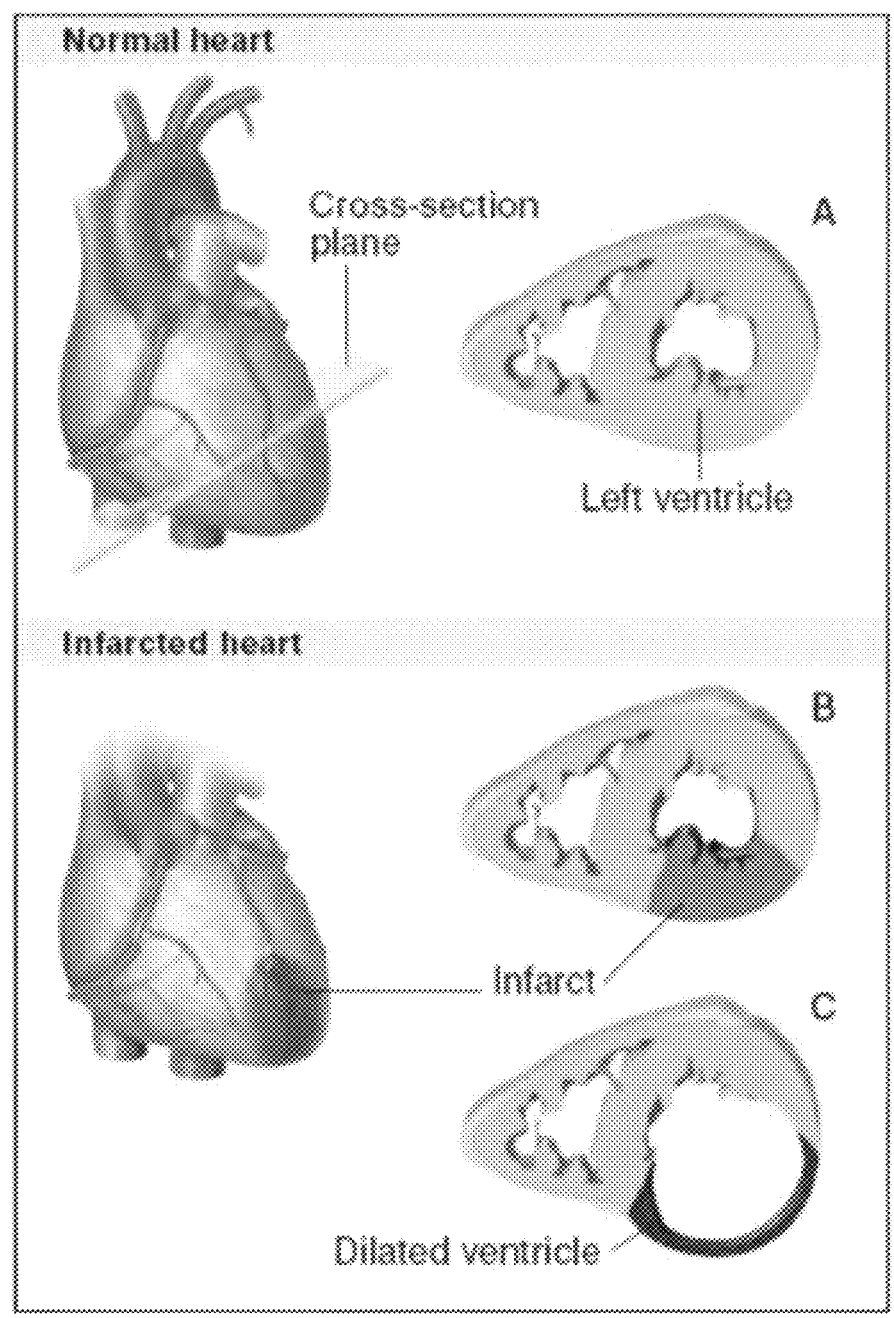
FIG. 43 shows cardiac injury and repair following myocardial infarction.
Figure 44:
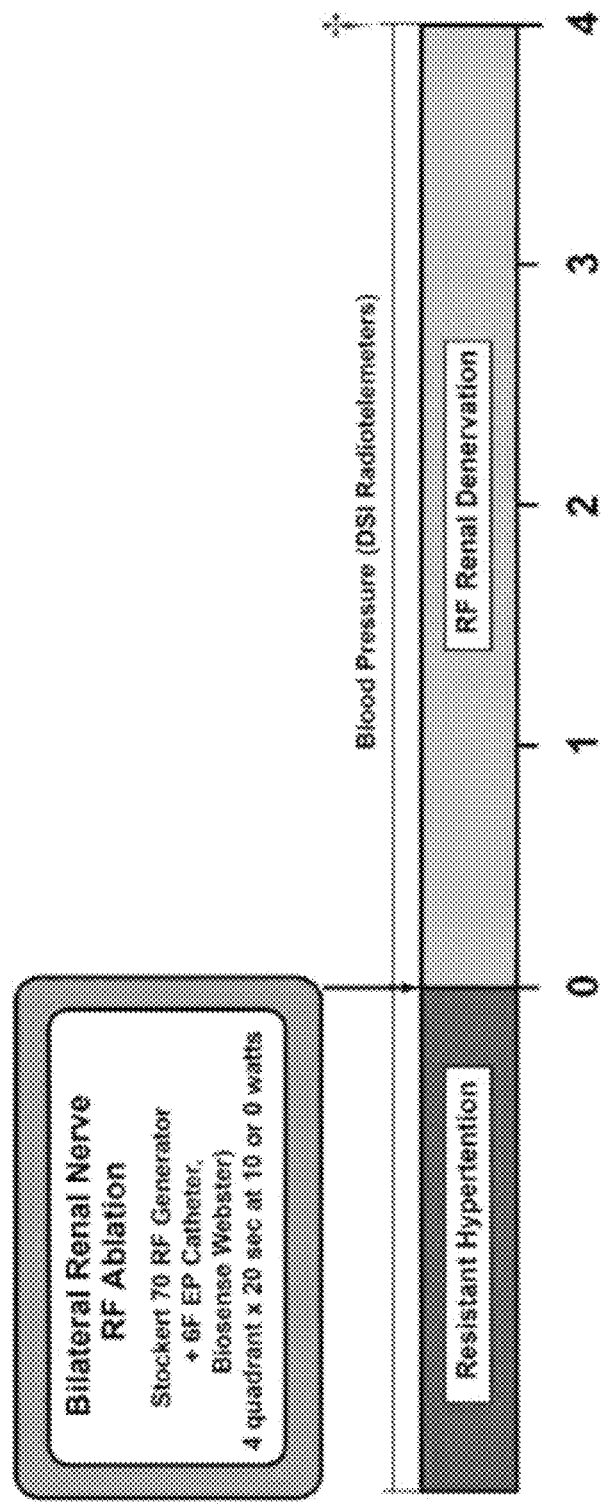
FIG. 44 shows renal nerve RF ablation protocol in SHR rats.
Figure 45:
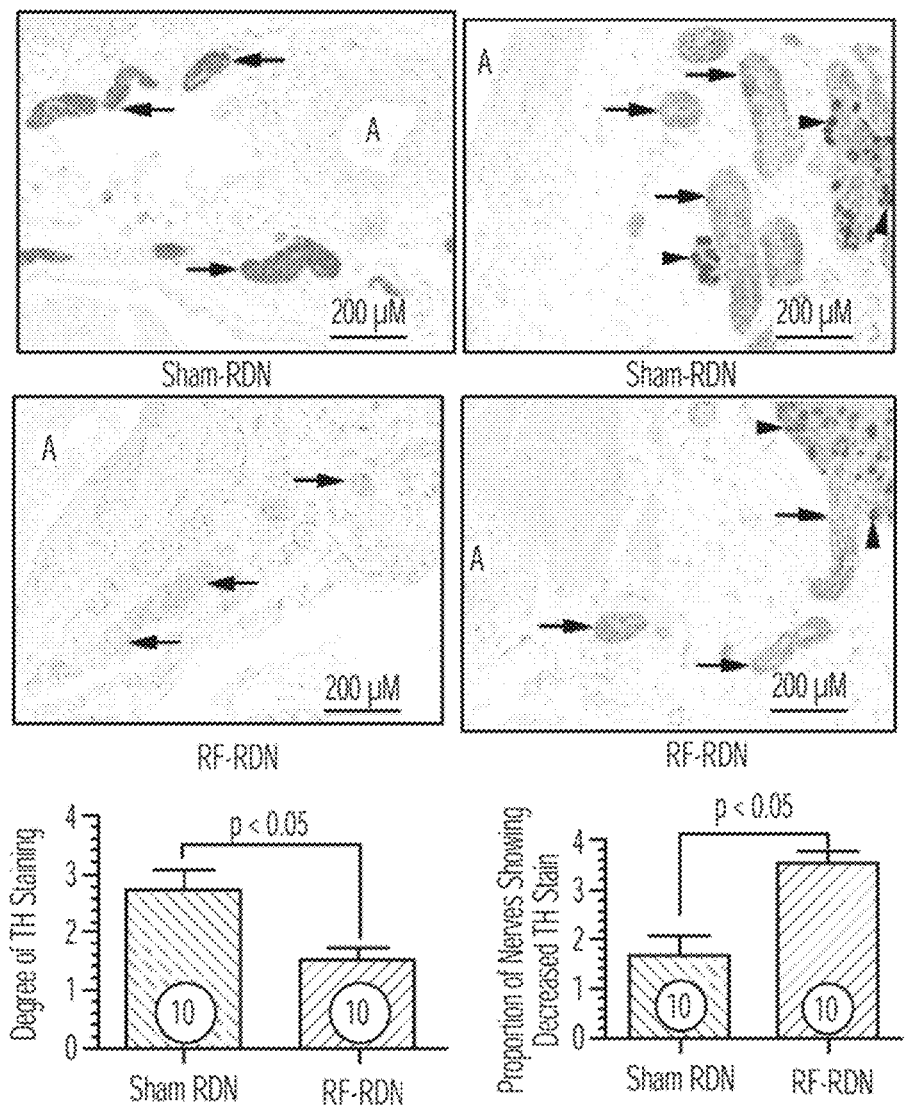
FIG. 45 shows tyrosine hydroxylase stain of renal arteries following RF-RDN.
Figure 46:
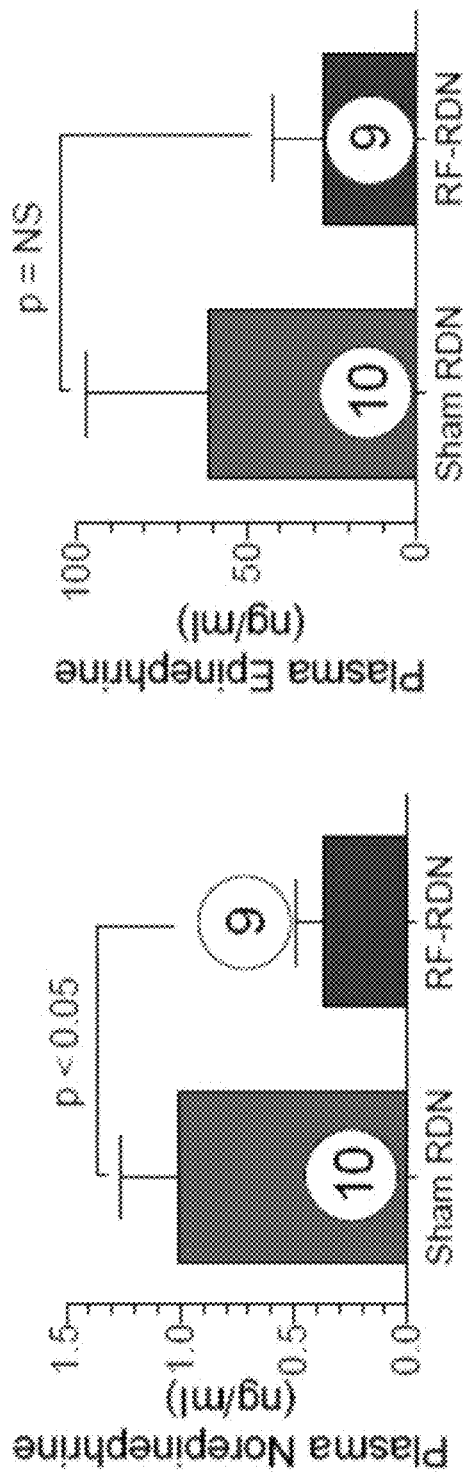
FIG. 46 shows circulating catecholamine levels following RF-RDN.
Figure 47:
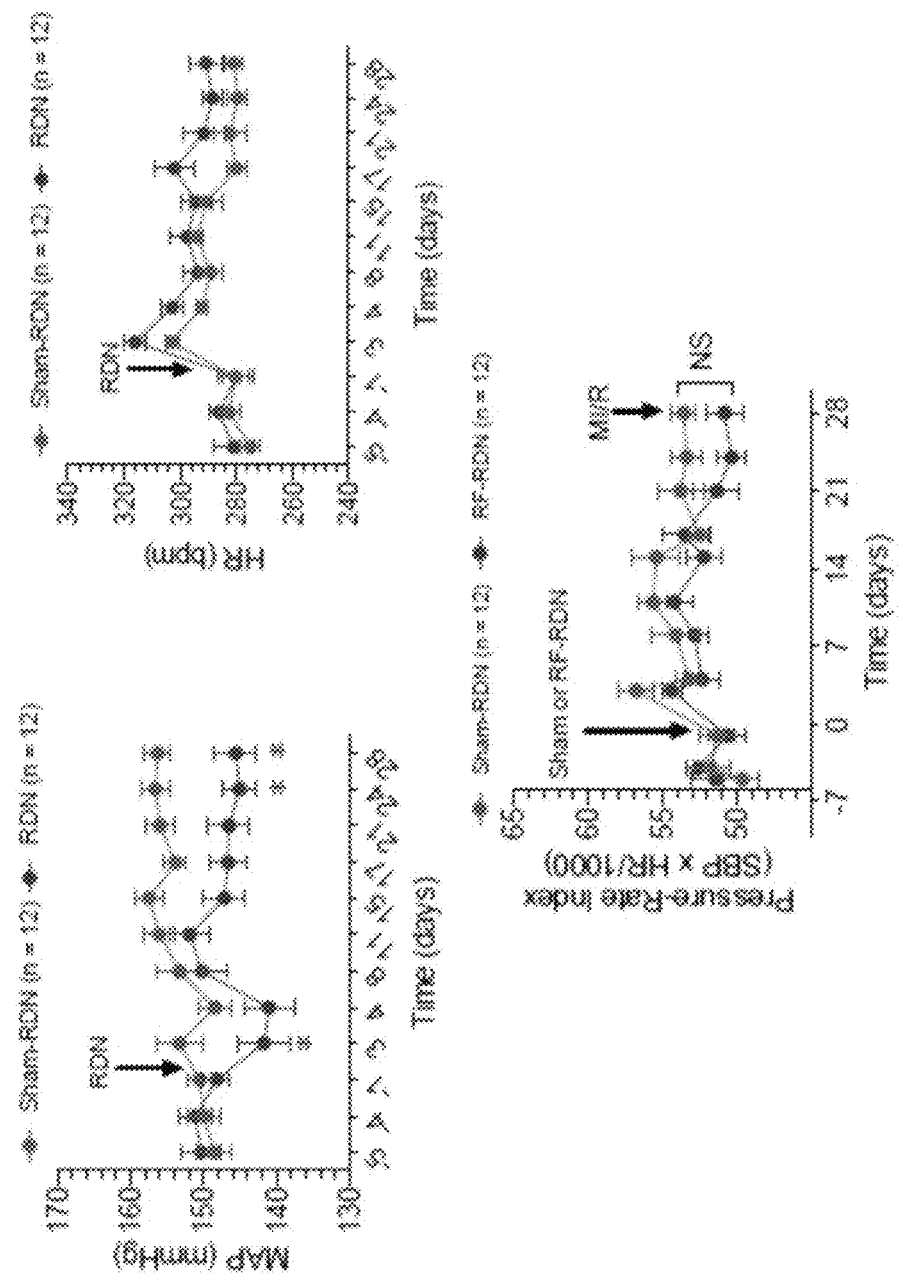
FIG. 47 shows blood pressure and heart rate following RF-RDN.
Figure 48:
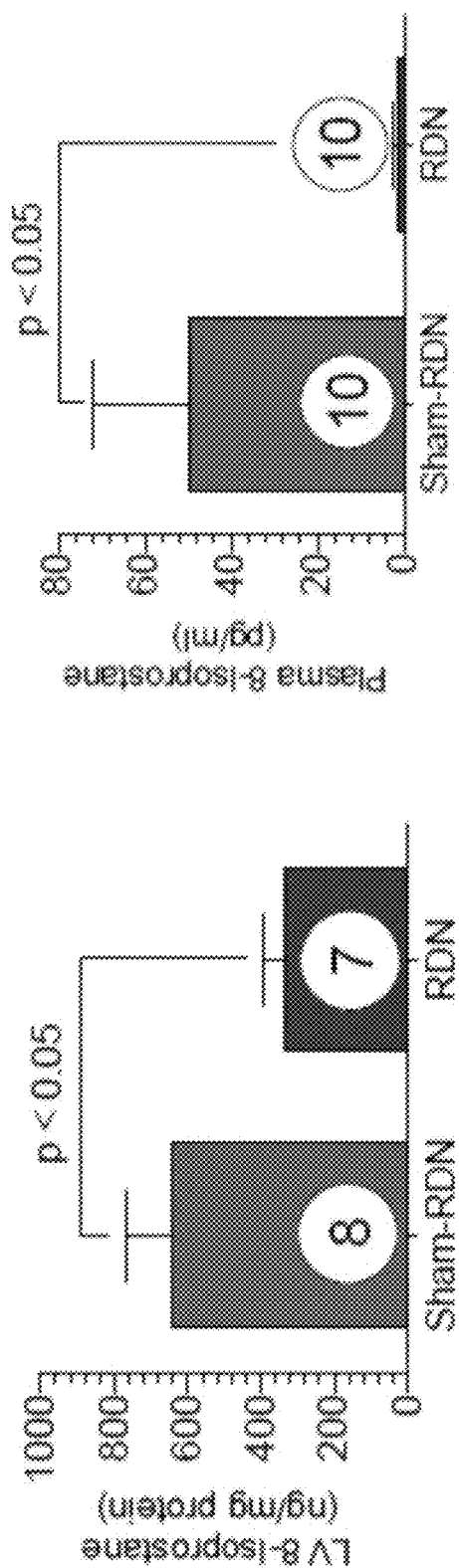
FIG. 48 shows that RF-RDN reduces oxidative stress in SHR.
Figure 49:
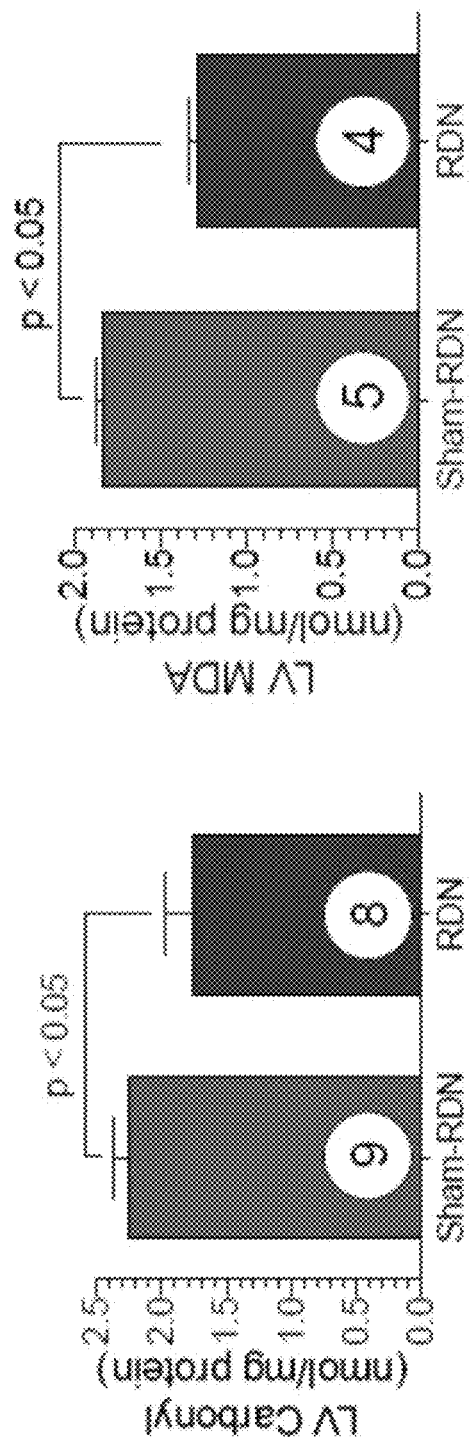
FIG. 49 shows that RF-RDN reduces myocardial oxidative stress in SHR.
Figure 50:
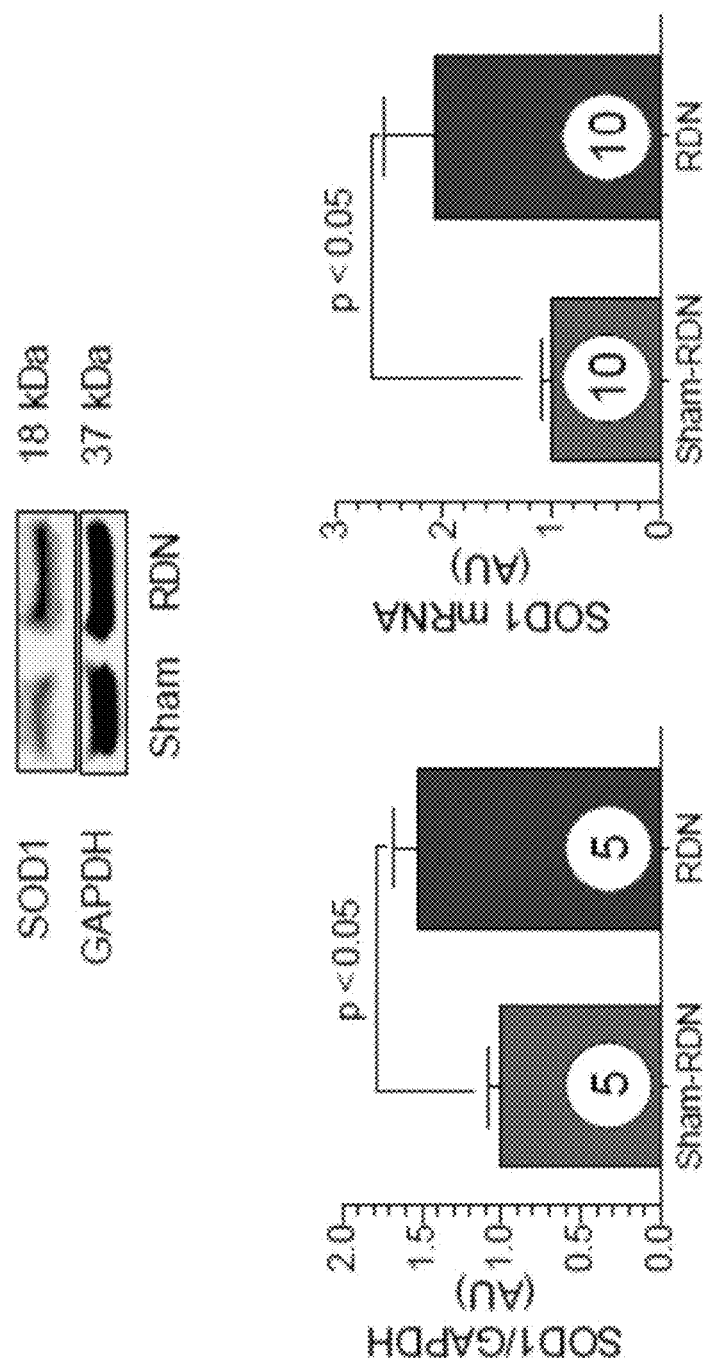
FIG. 50 shows that RF-RDN promotes myocardial antioxidant expression in SHR.
Figure 51:
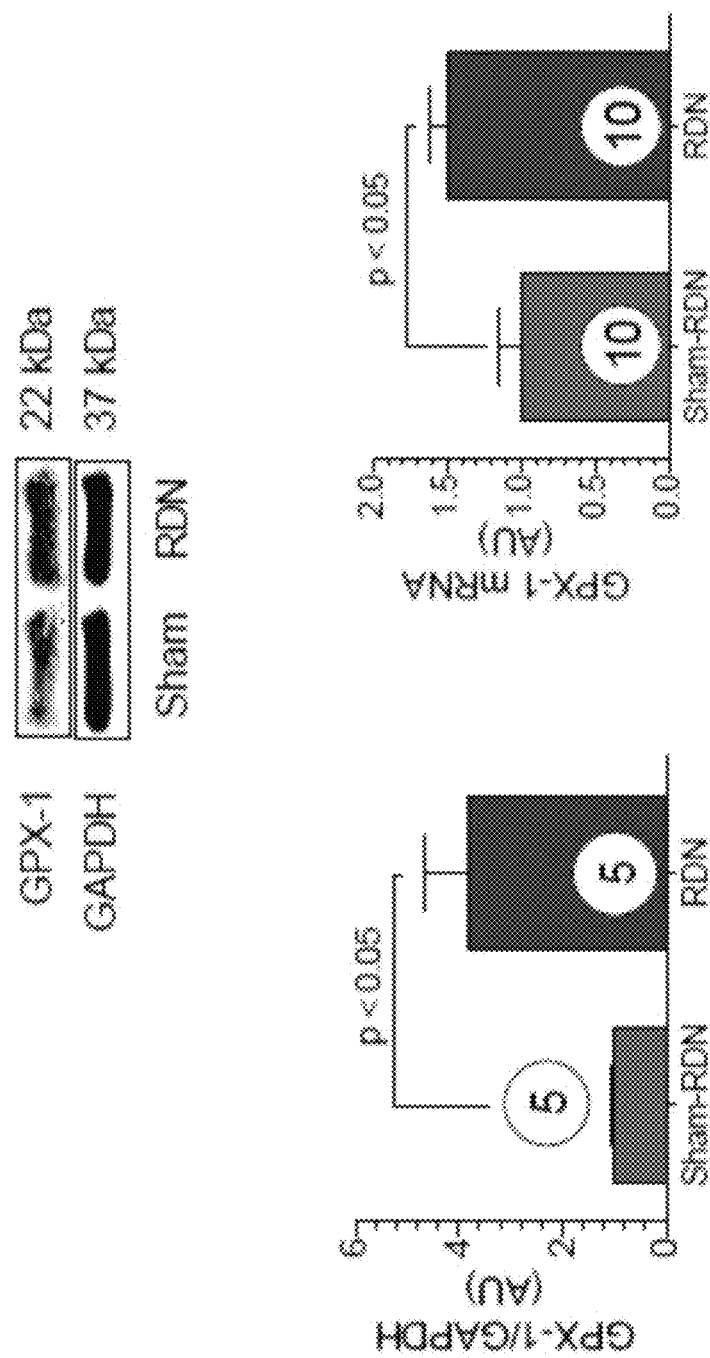
FIG. 51 shows that RF-RDN promotes myocardial antioxidant expression in SHR.
Figure 52:
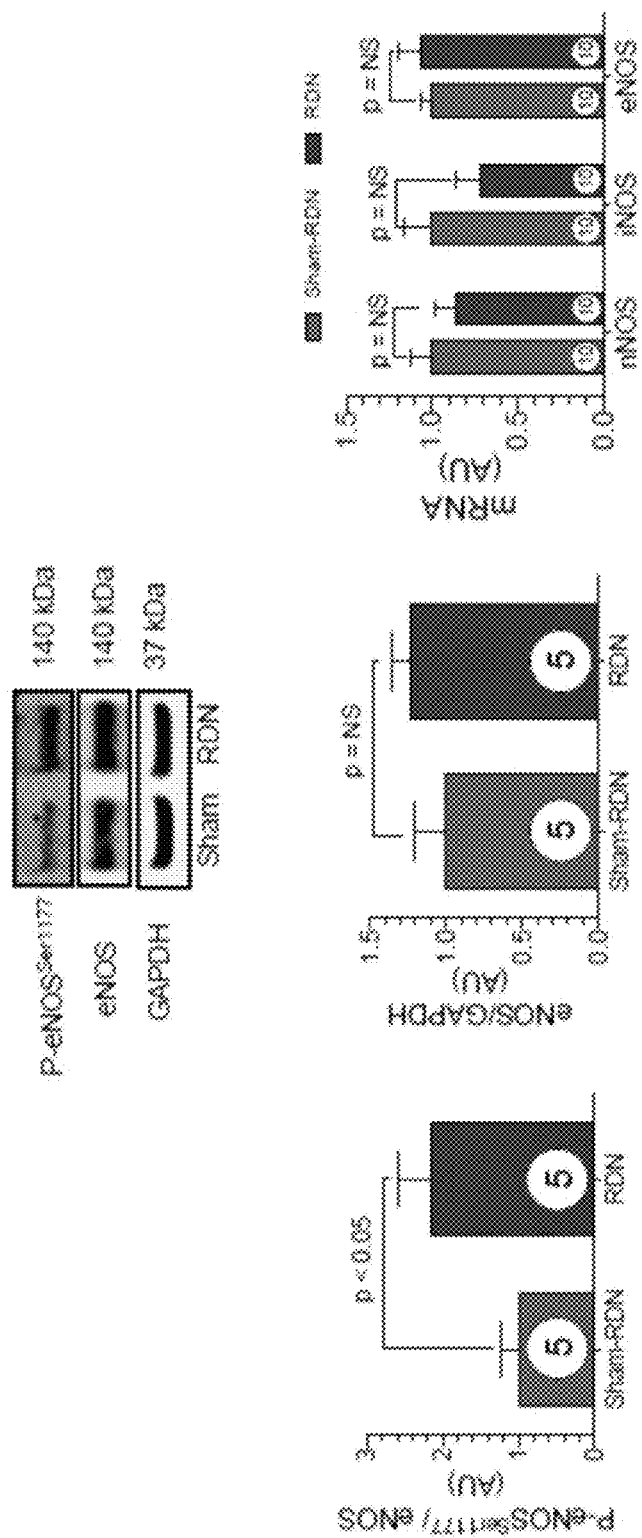
FIG. 52 shows that RF-RDN activates myocardial eNOS in SHR.
Figure 53:
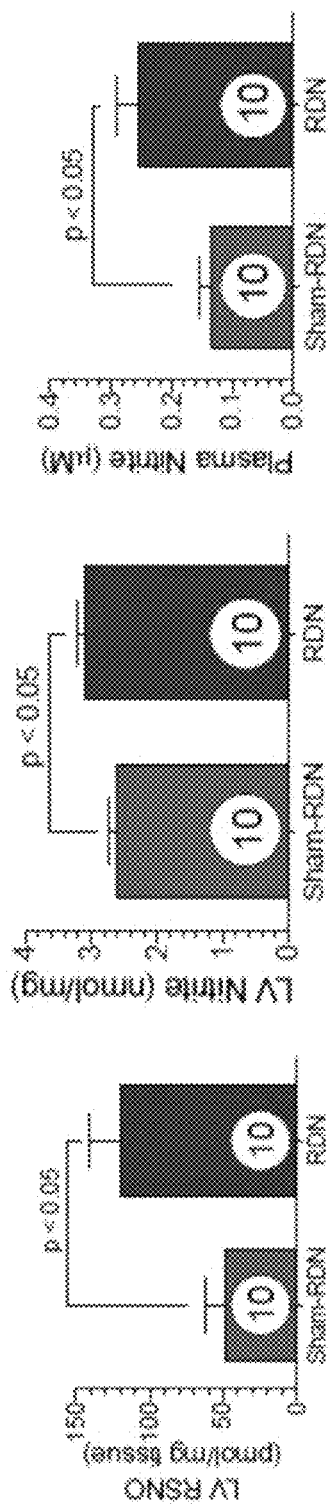
FIG. 53 shows that RF-RDN increases myocardial and vascular nitric oxide (NO) signaling in SHR.
Figure 54:
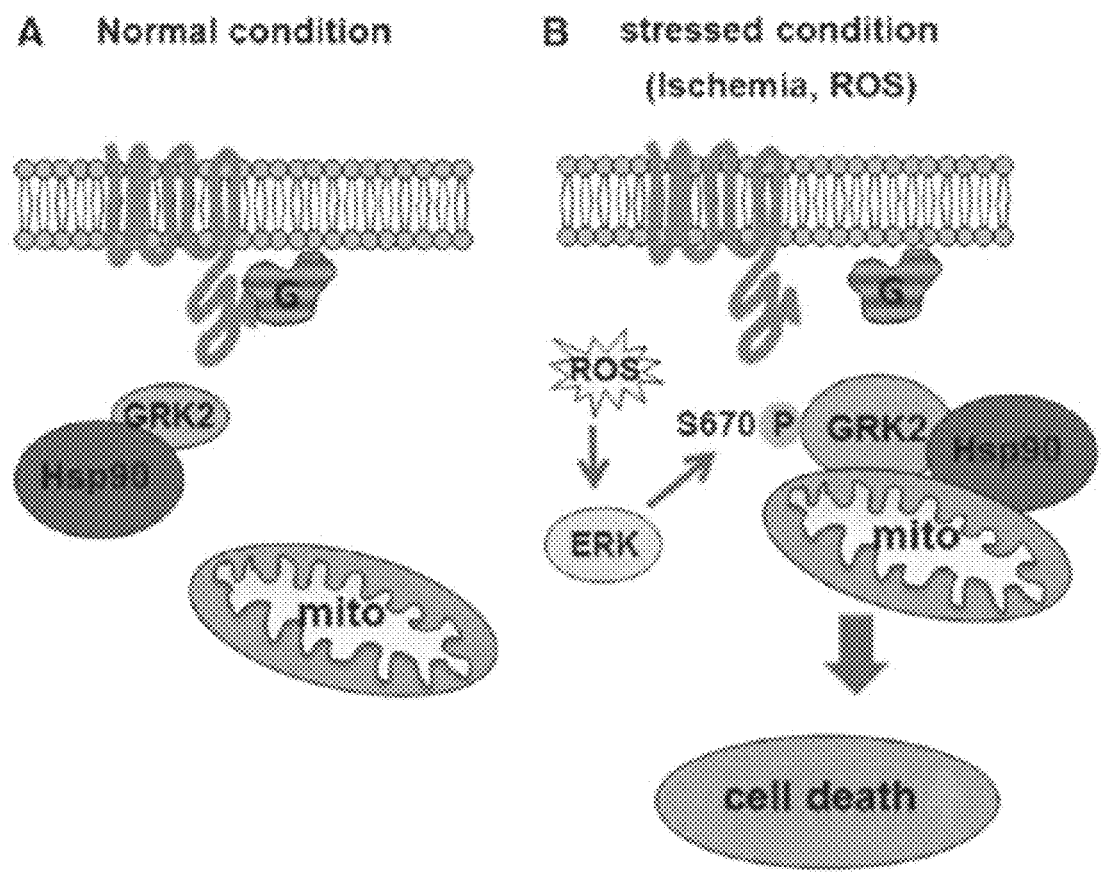
FIG. 54 shows G protein coupled receptor kinase 2 (GRK2.)
Figure 55:
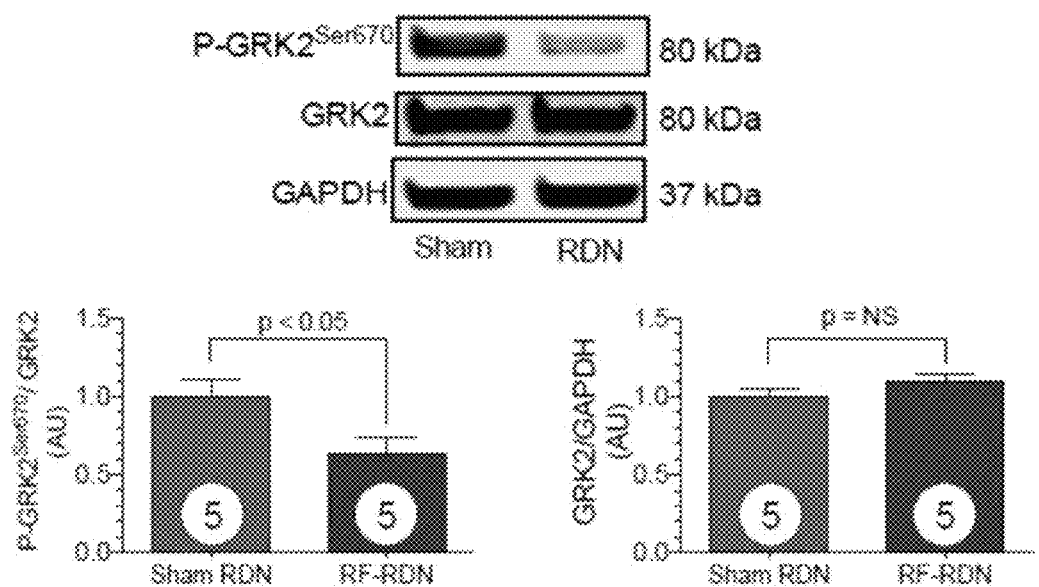
FIG. 55 shows reduced GRK2 signaling following RF-RDN in SHR.
Figure 56:
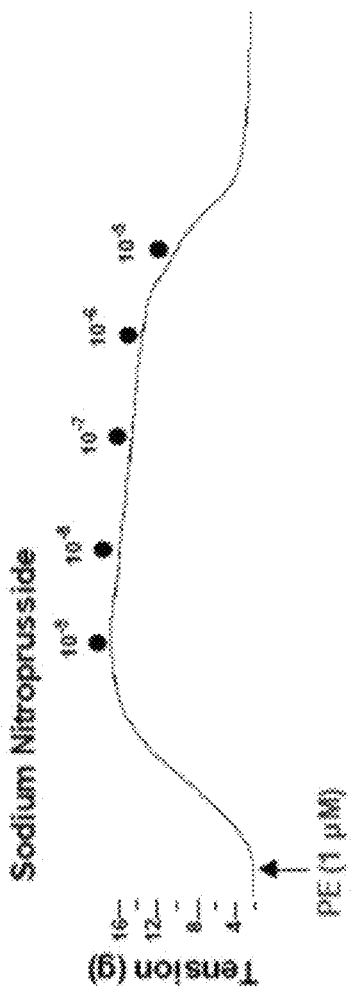
FIG. 56 shows aortic smooth muscle relaxation in SHR following RF-RDN.
Figure 56:
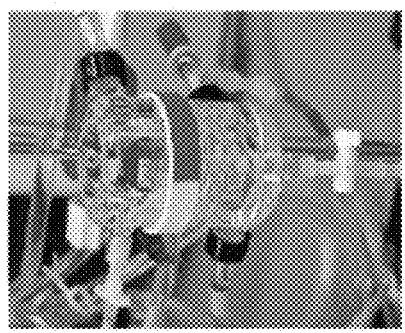
Figure 57:
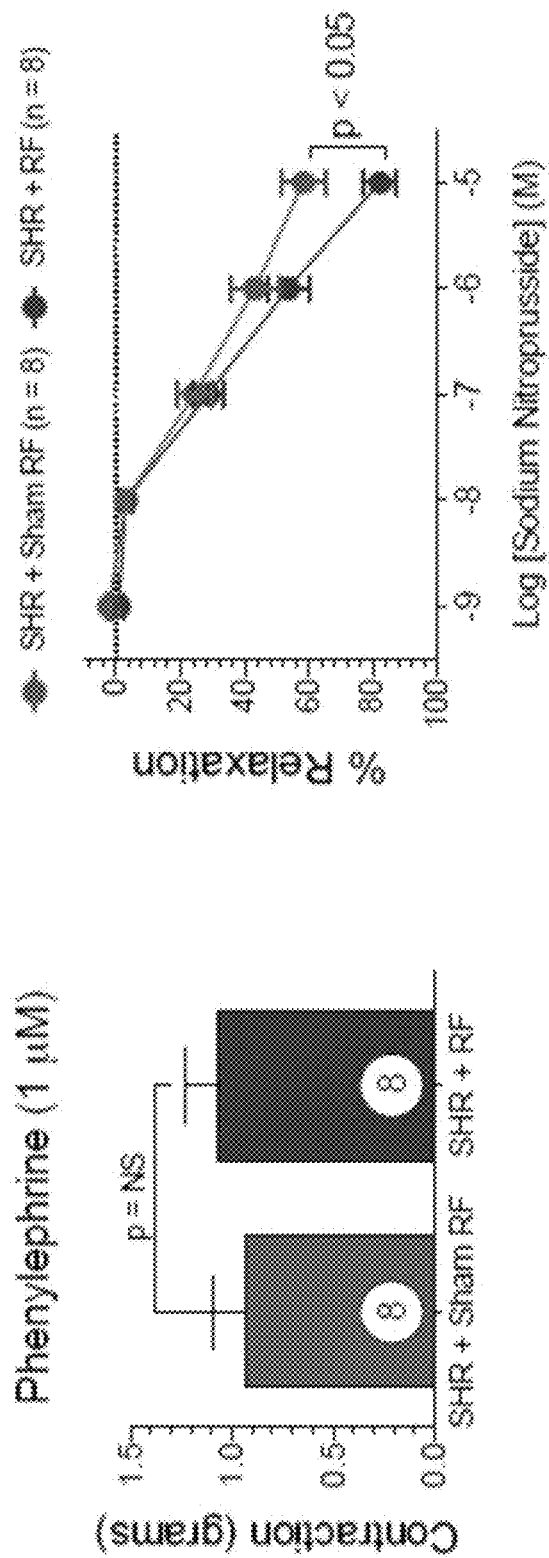
FIG. 57 shows RF-renal nerve ablation and cardiovascular protection in resistant hypertension.
Figure 58:
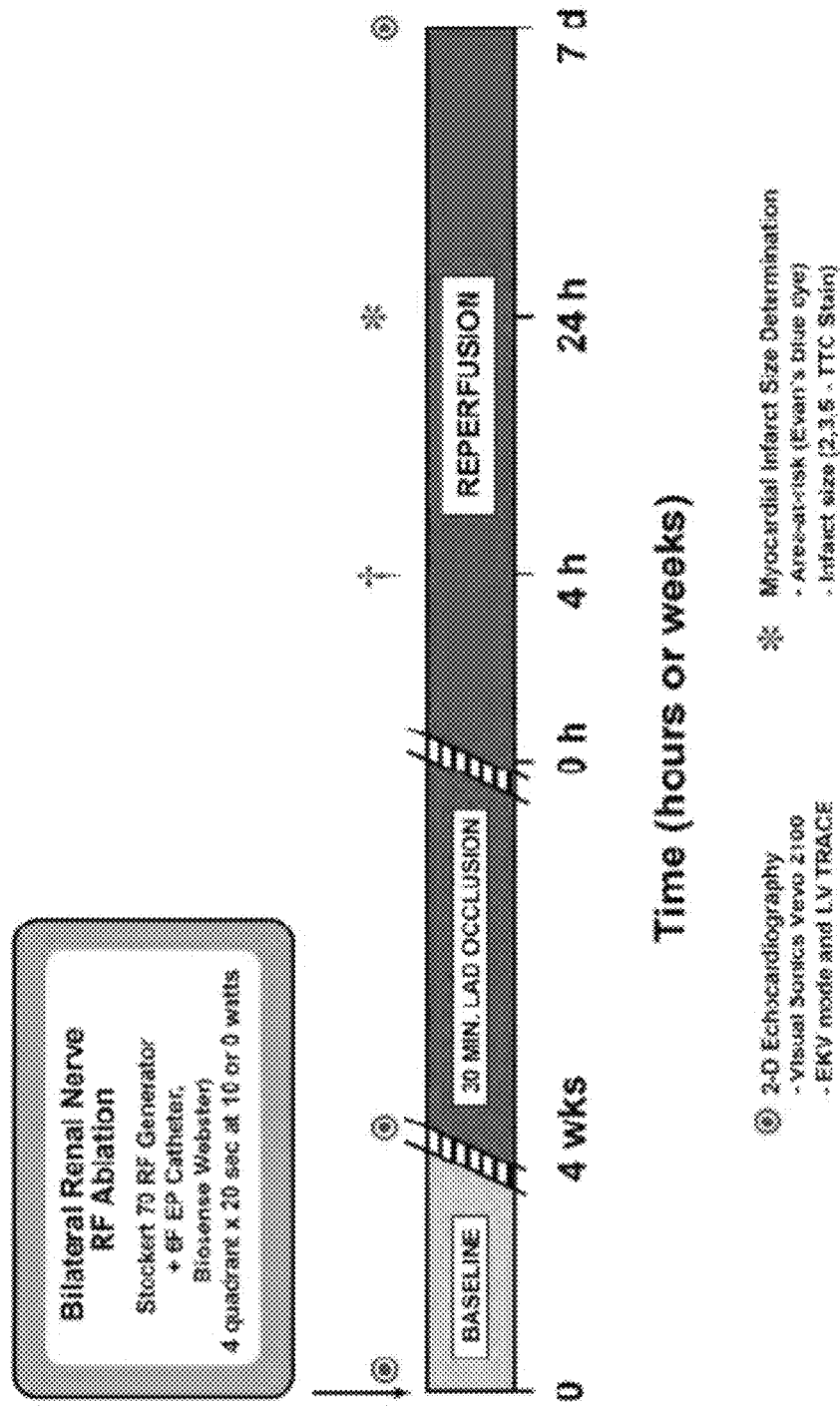
FIG. 58 shows renal nerve RF ablation and MI/R protocol in SHR rats and also WKY rats.
Figure 59:
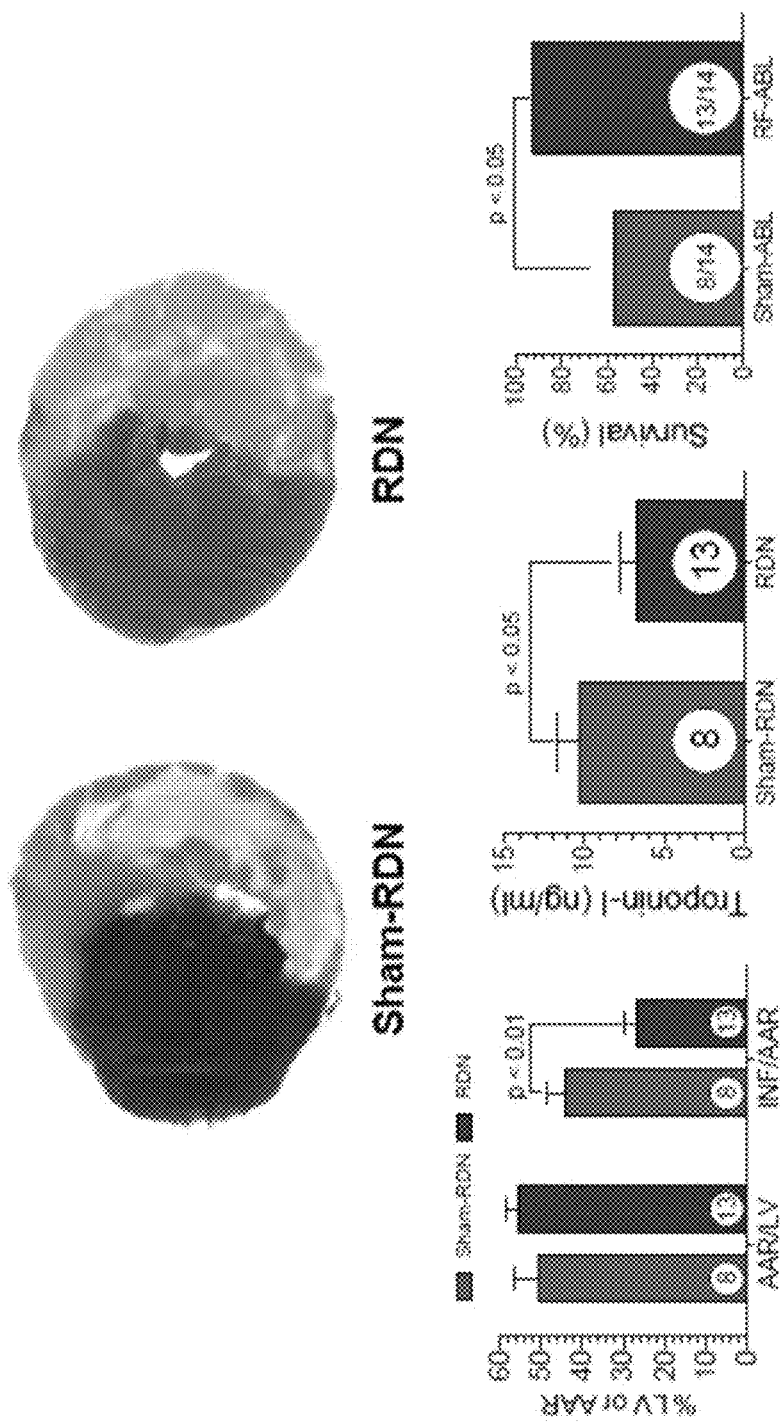
FIG. 59 shows RF-RDN attenuates MI/R injury in hypertensive rats.
Figure 60:
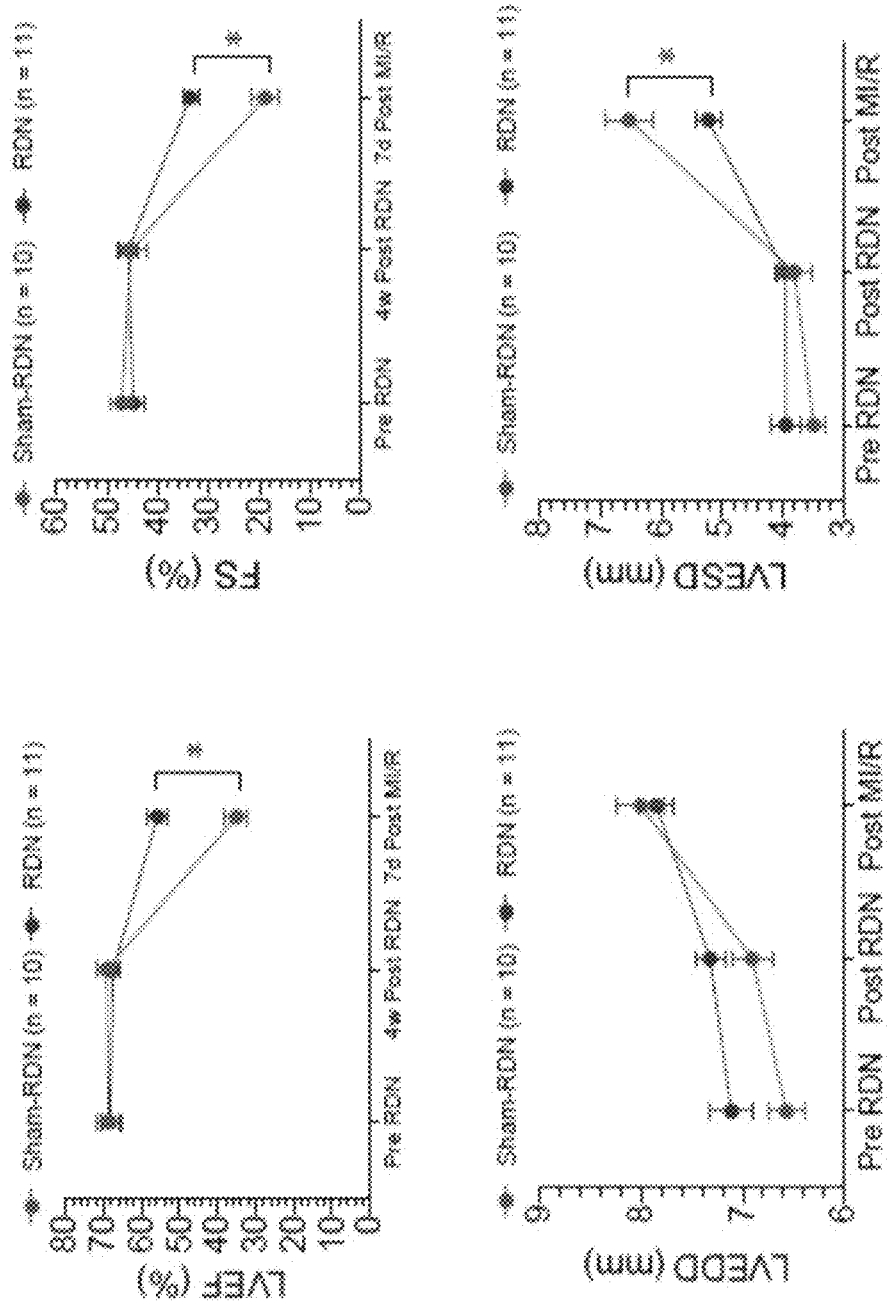
FIG. 60 shows RF-RDN preserves LV function 7 days following MI/R injury.
Figure 61:
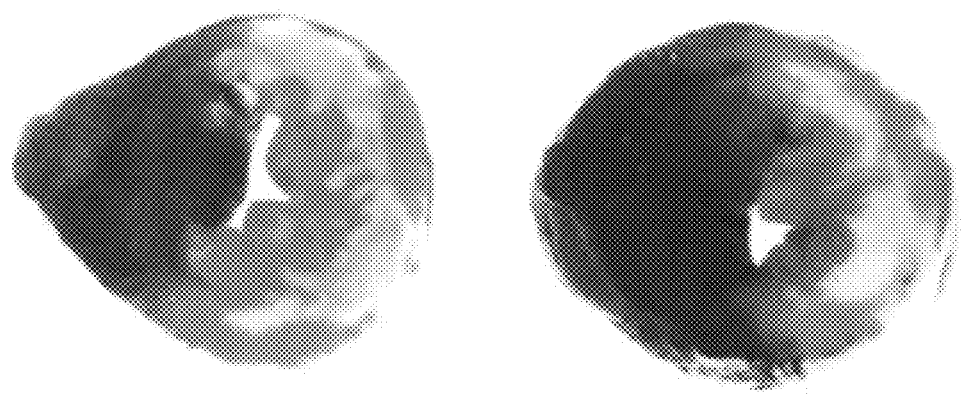
FIG. 61 shows RF-RDN does not attenuate MI/R injury in normotensive WKY rats.
Figure 61:
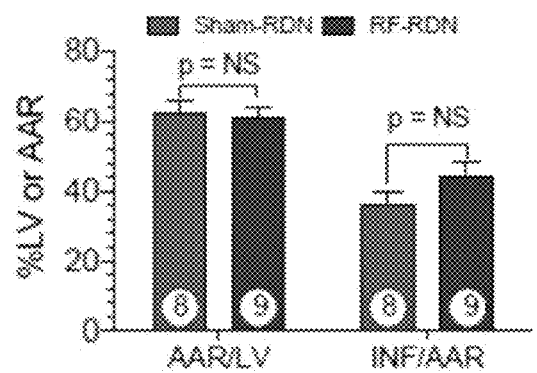
Figure 62:
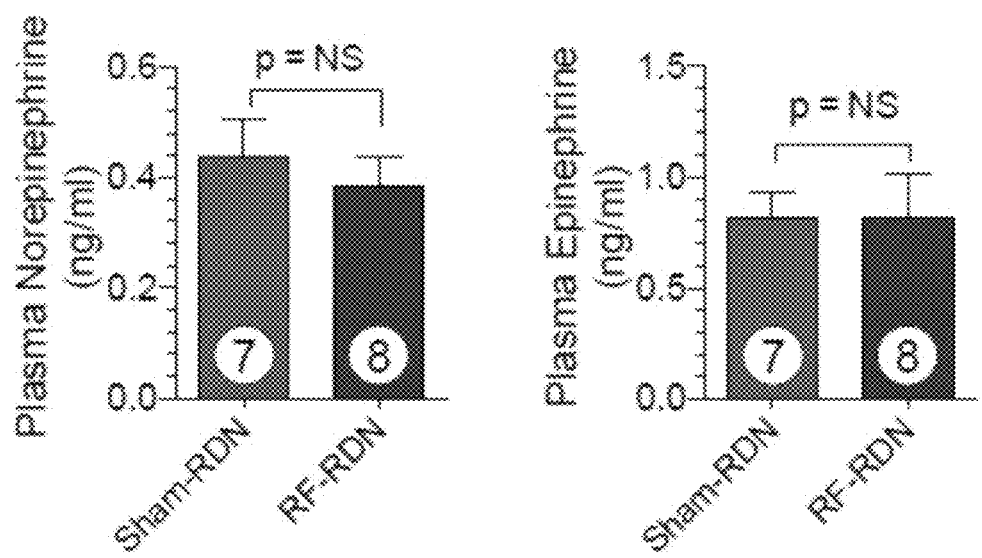
FIG. 62 shows circulating catecholamine levels following RF-RDN in WKY rats.
Figure 63:
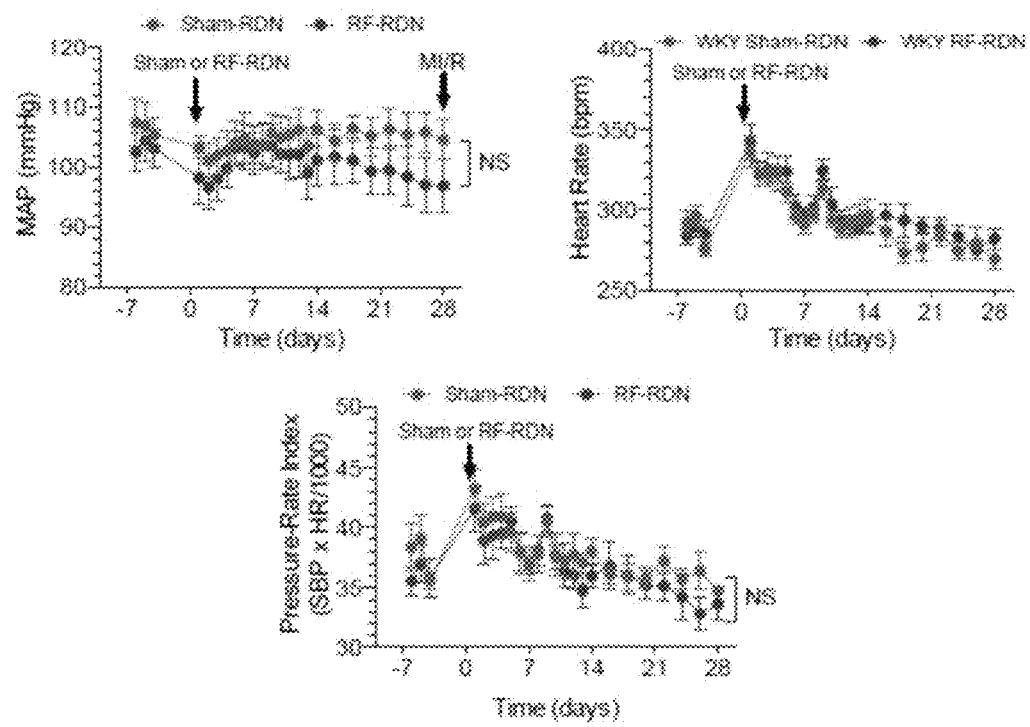
FIG. 63 shows blood pressure and heart rate following RF-RDN in WKY.
Figure 64:
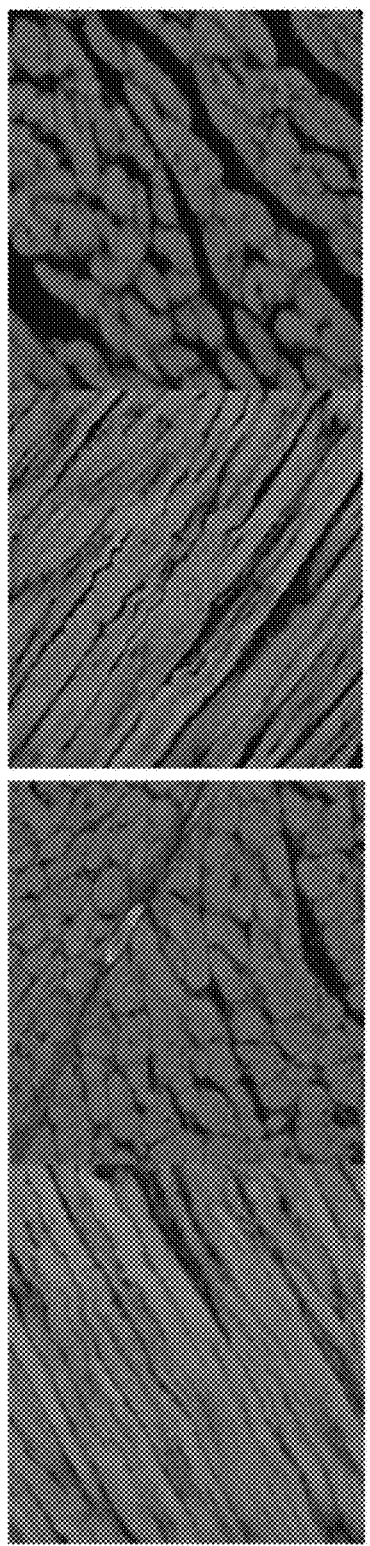
FIG. 64 shows myocardial oxidative stress following RF-RDN in WKY rats.
Figure 64:
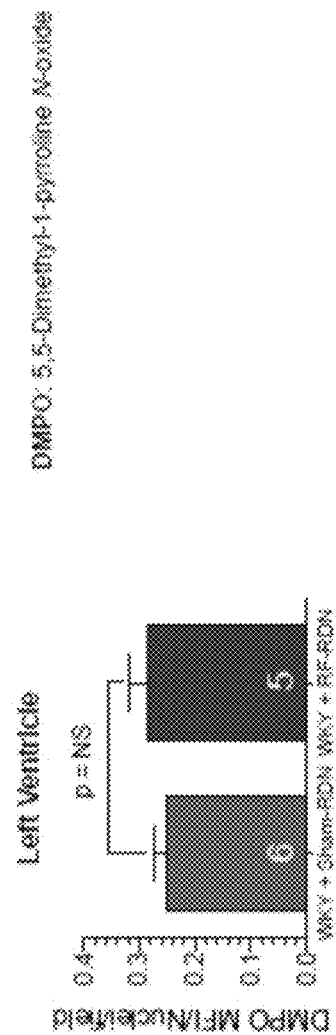
Figure 65:
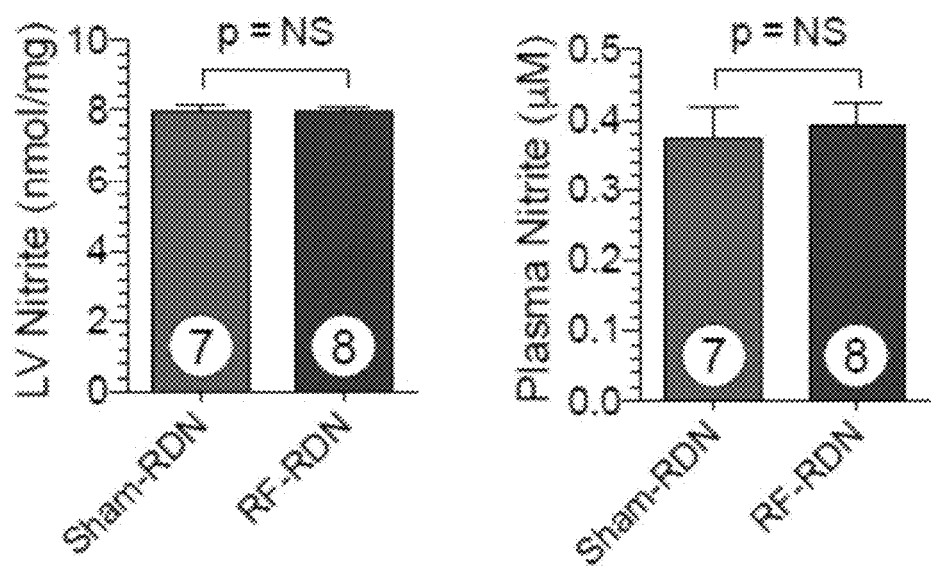
FIG. 65 shows myocardial and vascular nitric oxide (NO) signaling in WKY.
Figure 66:
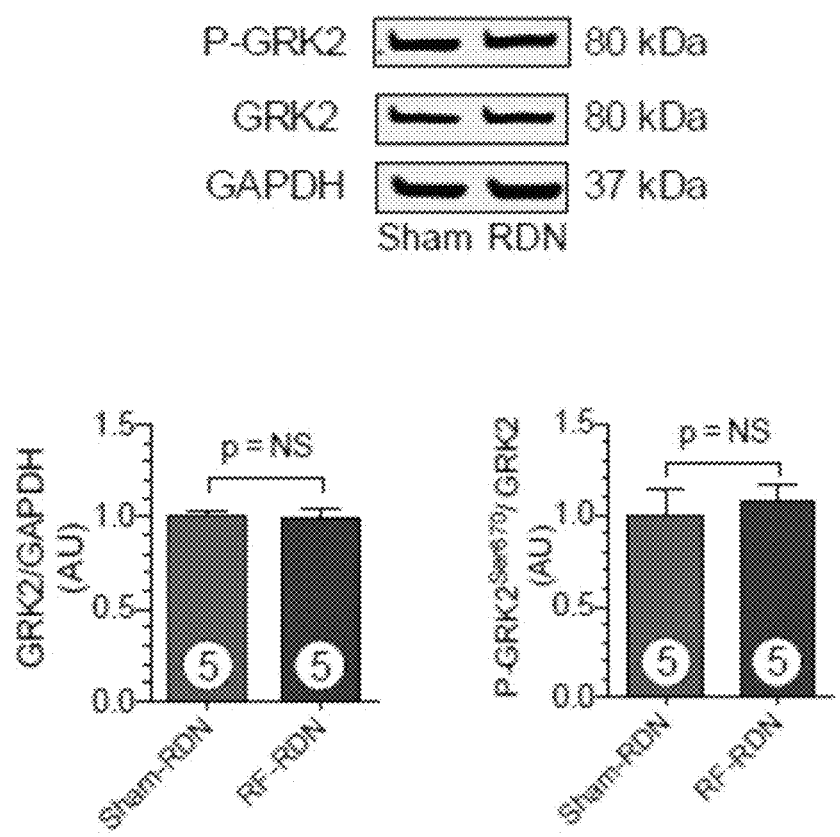
FIG. 66 shows GRK2 signaling following RF-RDN in WKY rats.
Figure 67:
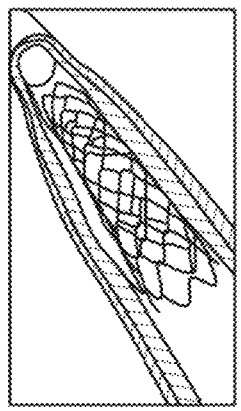
FIG. 67 shows Aim 1 future directions.
Figure 67:
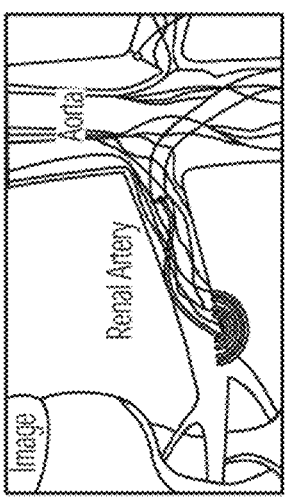
Figure 67:
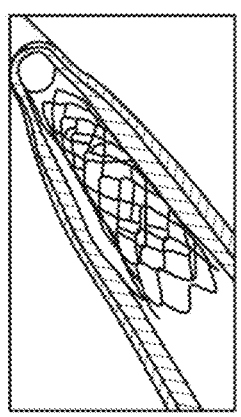
Figure 68:
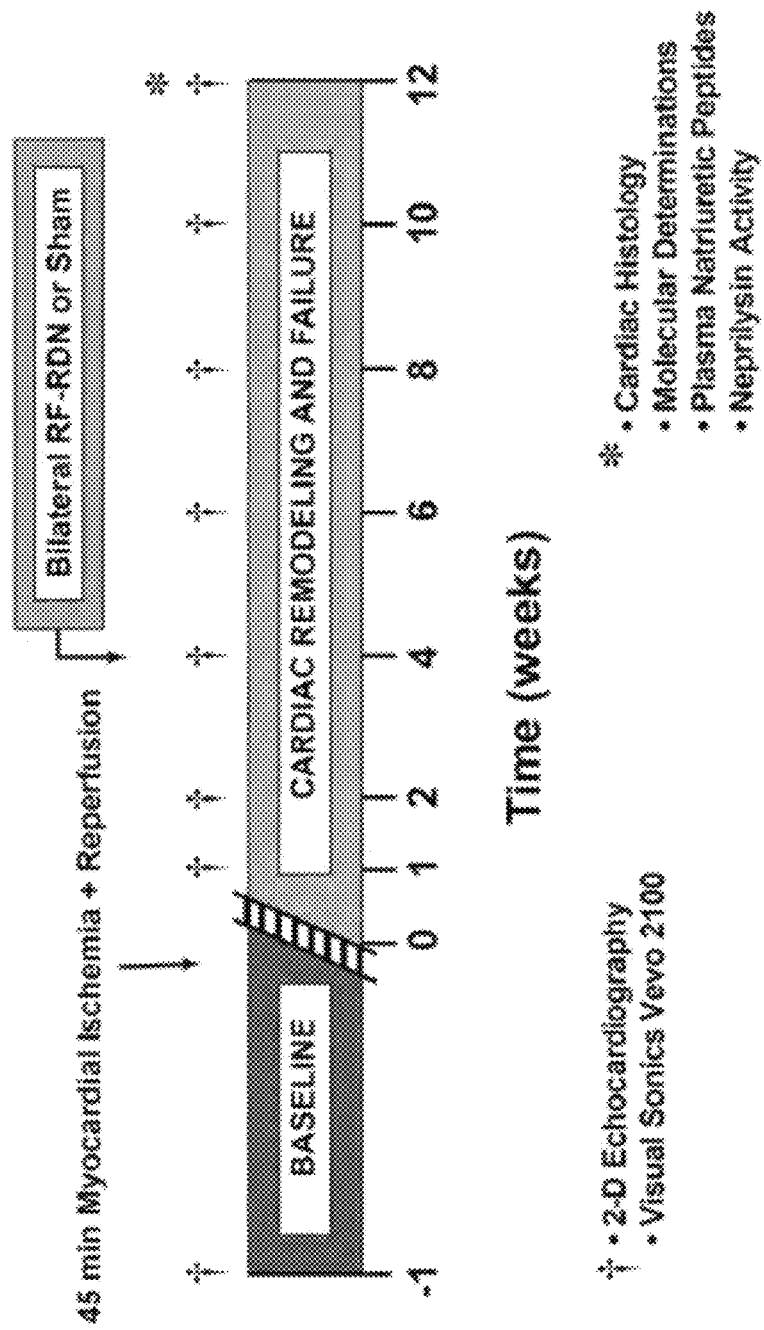
FIG. 68 shows rat ischemic heart failure experimental protocol in hypertensive SHR rats.
Figure 69:
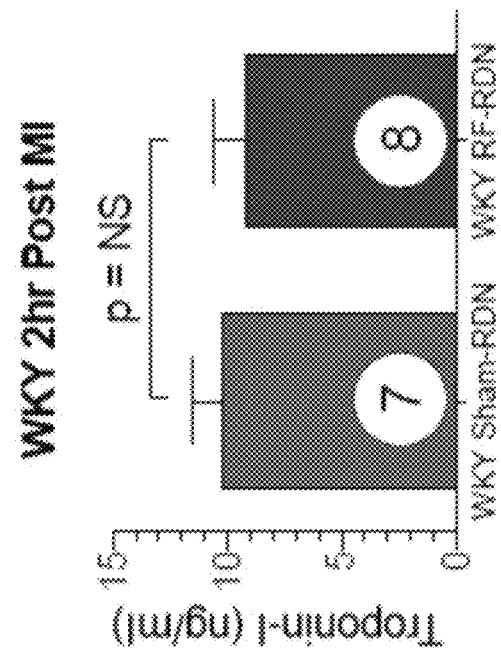
FIG. 69 shows initial ischemic injury in SHR and WKY rats.
Figure 69:
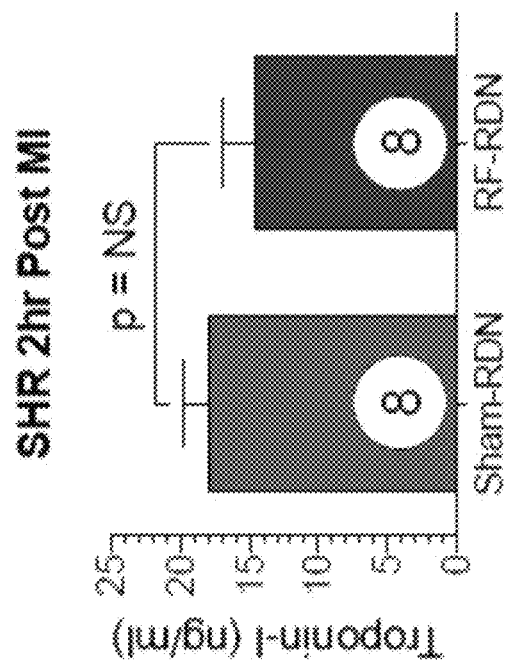
Figure 70:
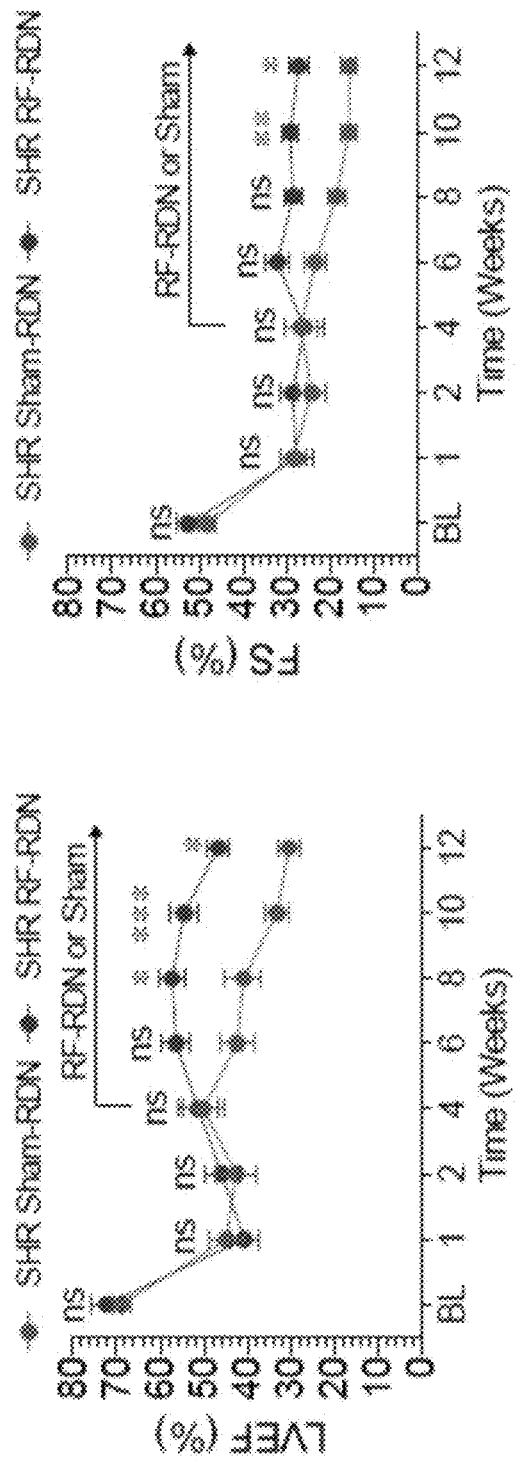
FIG. 70 shows left ventricular function following RF-RDN in SHR.
Figure 71:
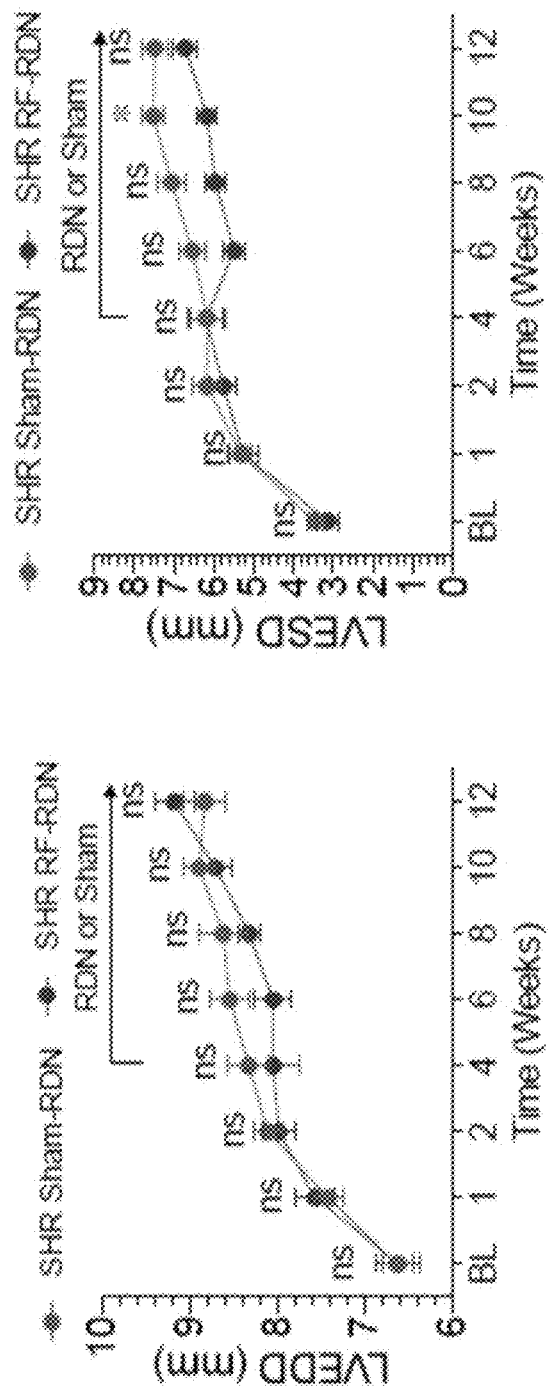
FIG. 71 shows left ventricular remodeling following RF-RDN in SHR.
Figure 72:
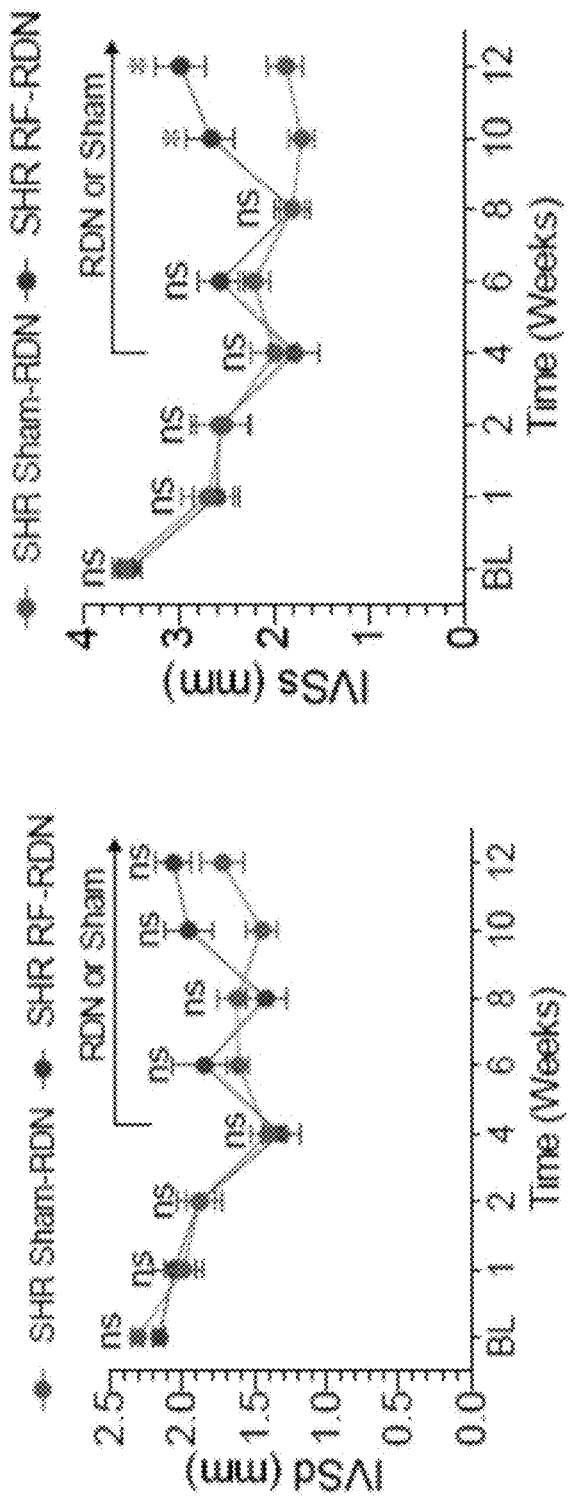
FIG. 72 shows left ventricular remodeling following RF-RDN in SHR.
Figure 73:
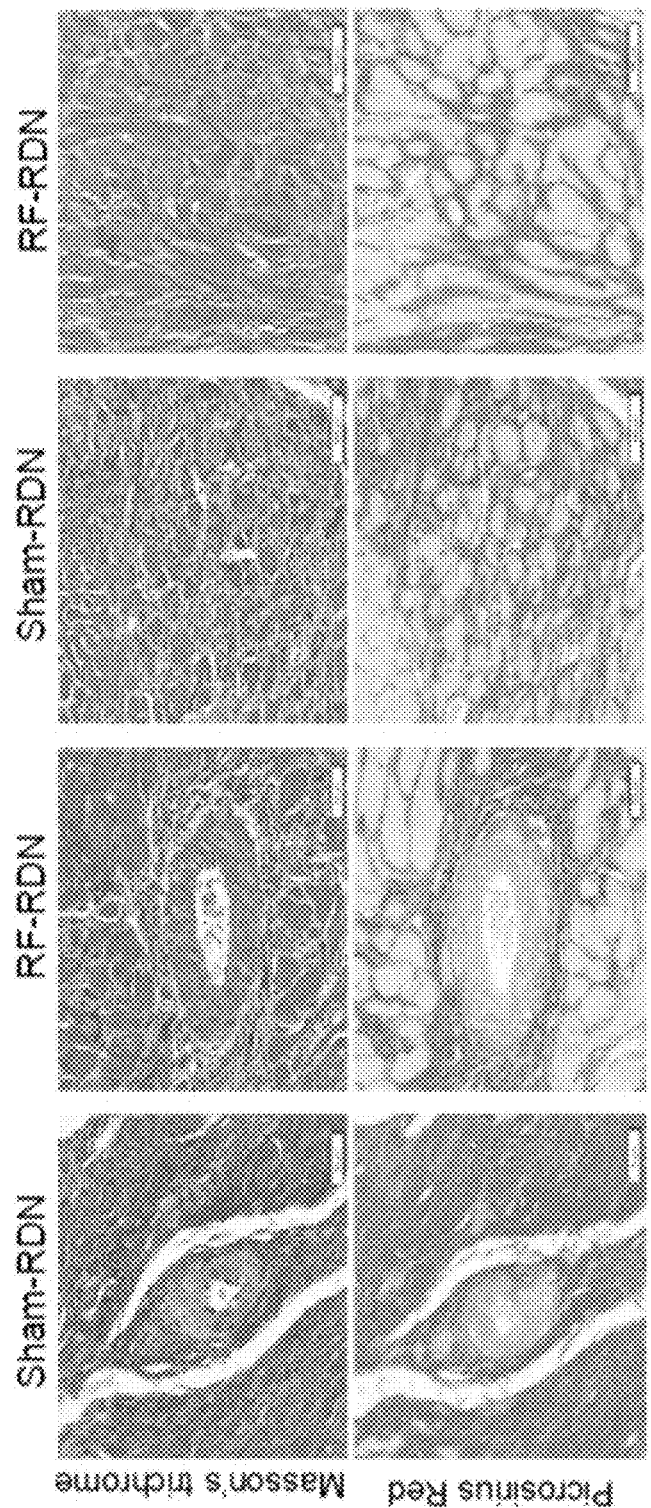
FIG. 73 shows myocardial fibrosis in SHR following RF-RDN.
Figure 74:
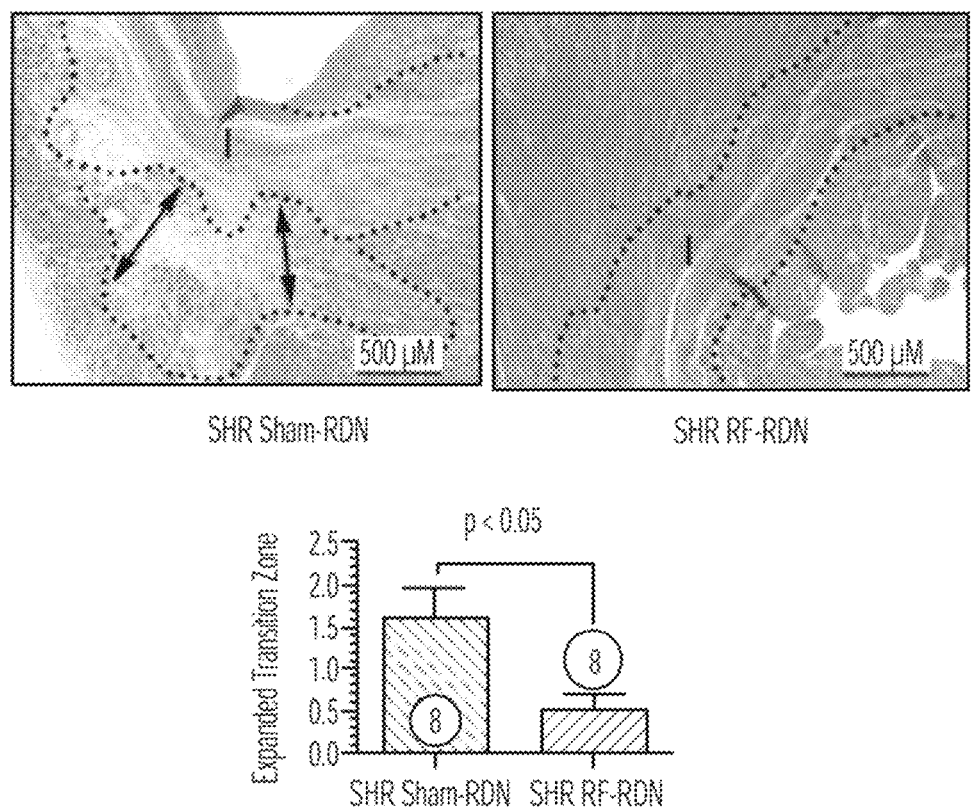
FIG. 74 shows infarct boarder zone expansion in SHR following RF-RDN.
Figure 75:
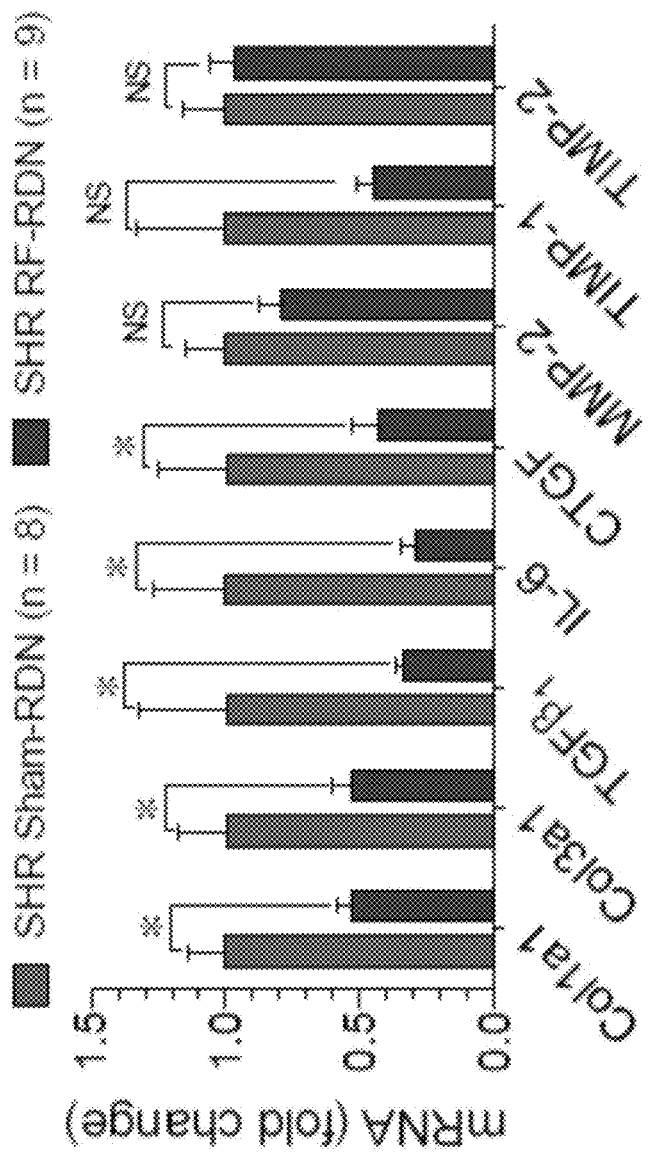
FIG. 75 shows fibrotic gene expression in SHR following RF-RDN.
Figure 76:
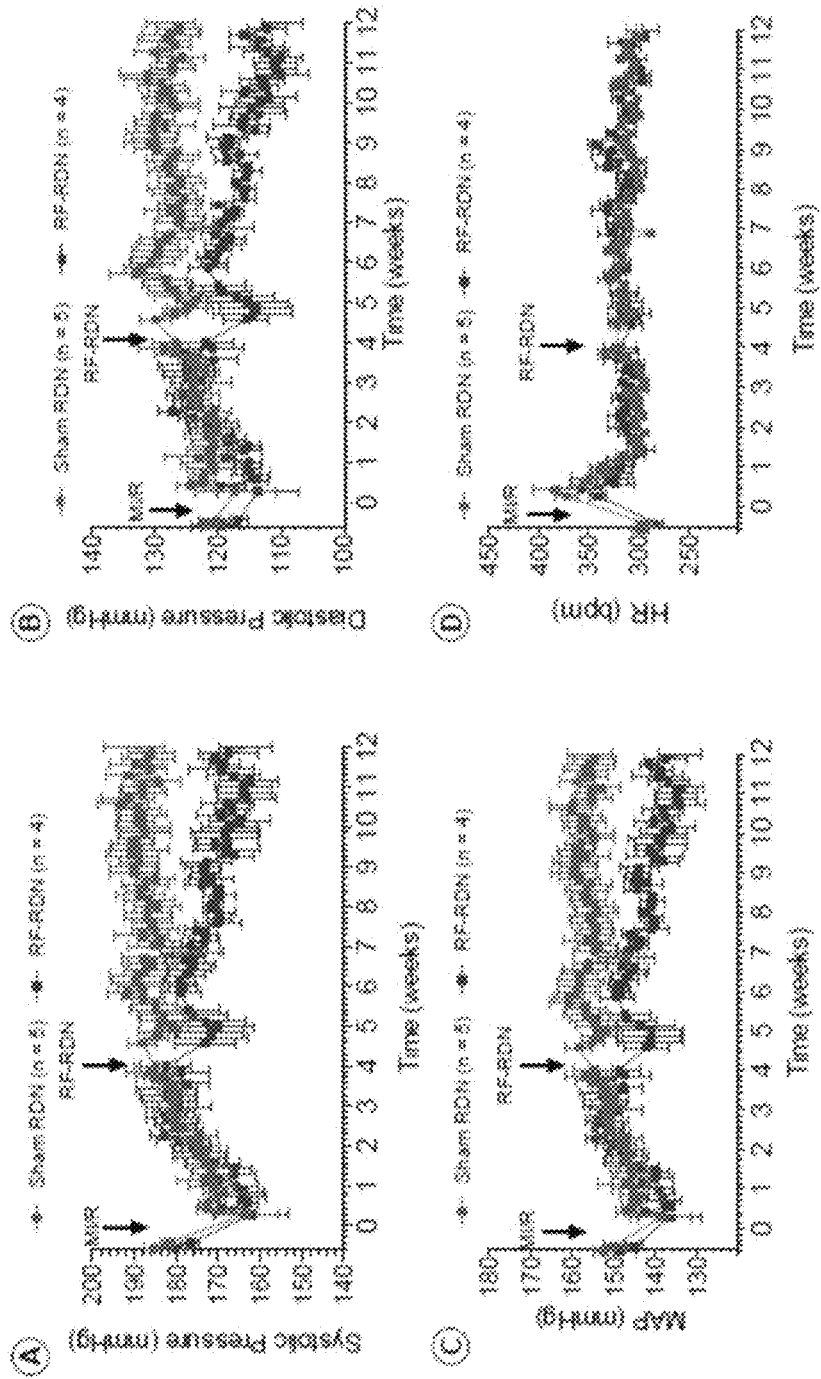
FIG. 76 shows blood pressure and HR in SHR following RF-RDN in heart failure.
Figure 77:
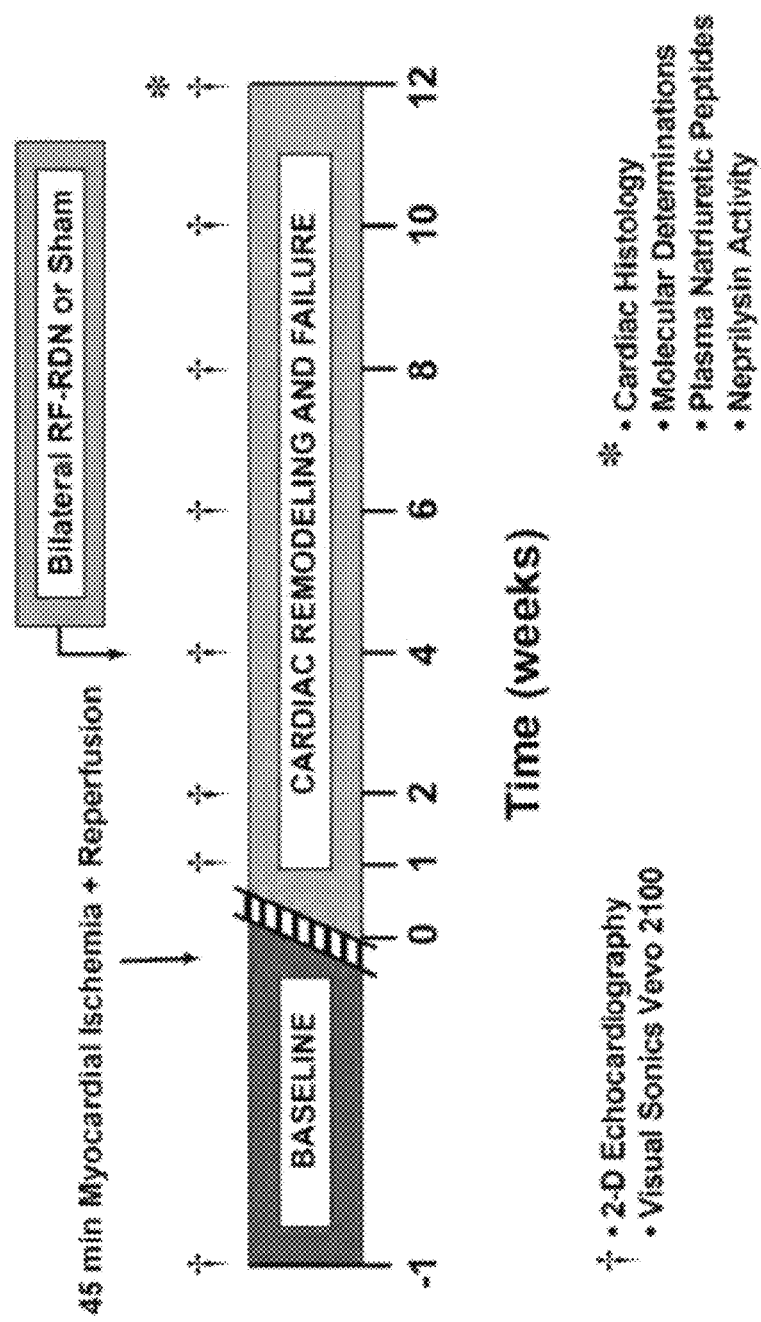
FIG. 77 shows rat ischemic heart failure experimental protocol in normotensive WKY rats
Figure 78:
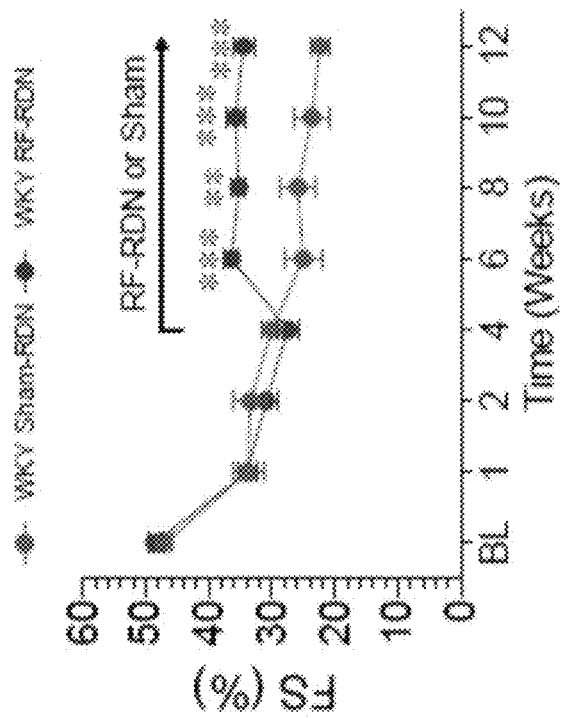
FIG. 78 shows left ventricular function following RF-RDN in normotensive WKY.
Figure 78:
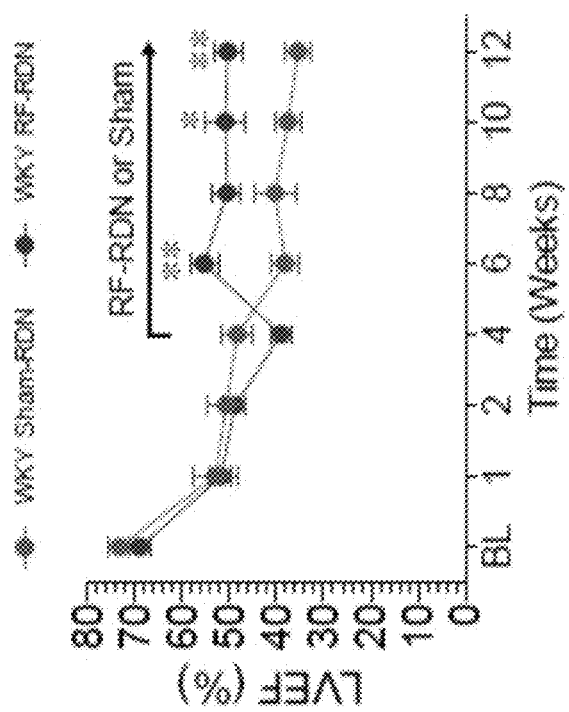
Figure 79:
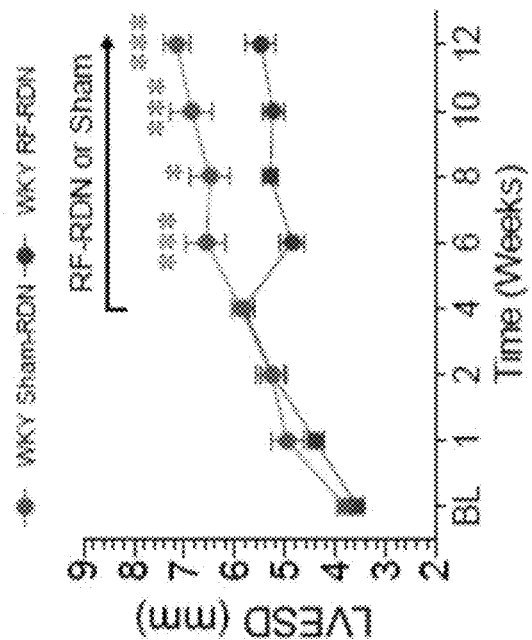
FIG. 79 shows left ventricular remodeling following RF-RDN in normotensive WKY.
Figure 79:
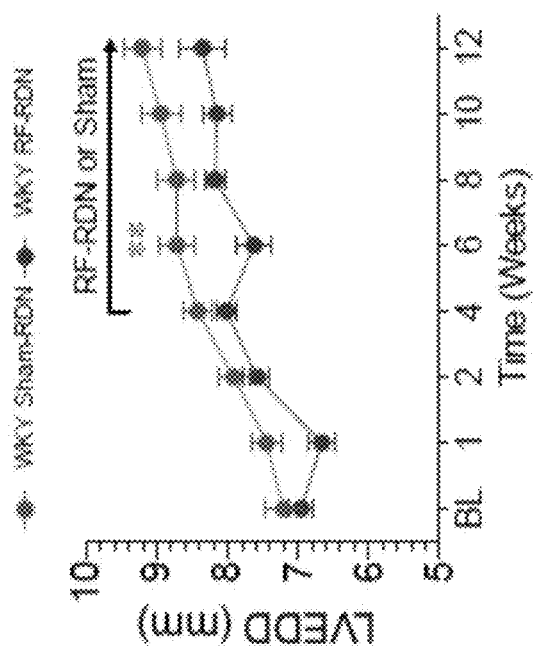
Figure 80:
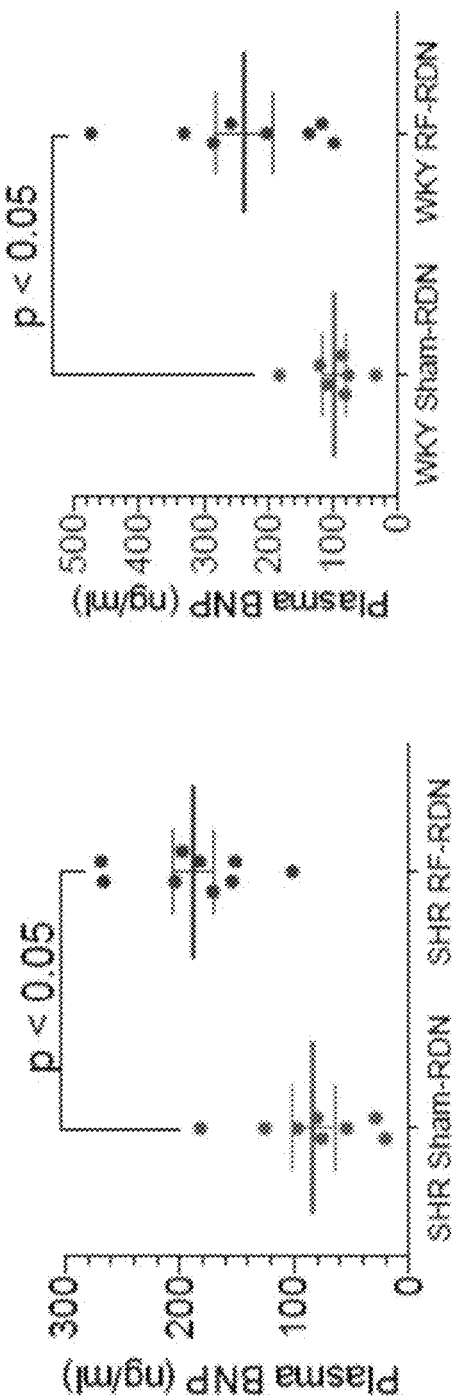
FIG. 80 shows 12 week plasma BNP levels in SHR and WKY following RF-RDN in hear failure
Figure 81:
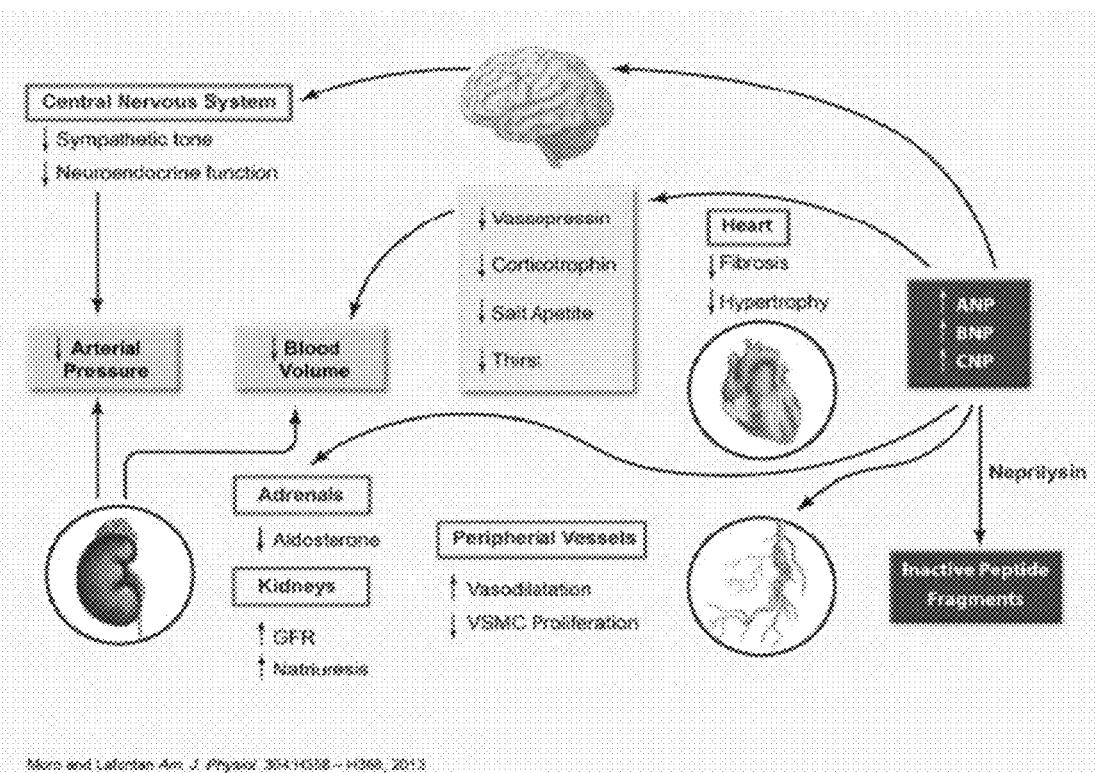
FIG. 81 shows cardioprotection by natriuretic peptides in heart failure
Figure 82:
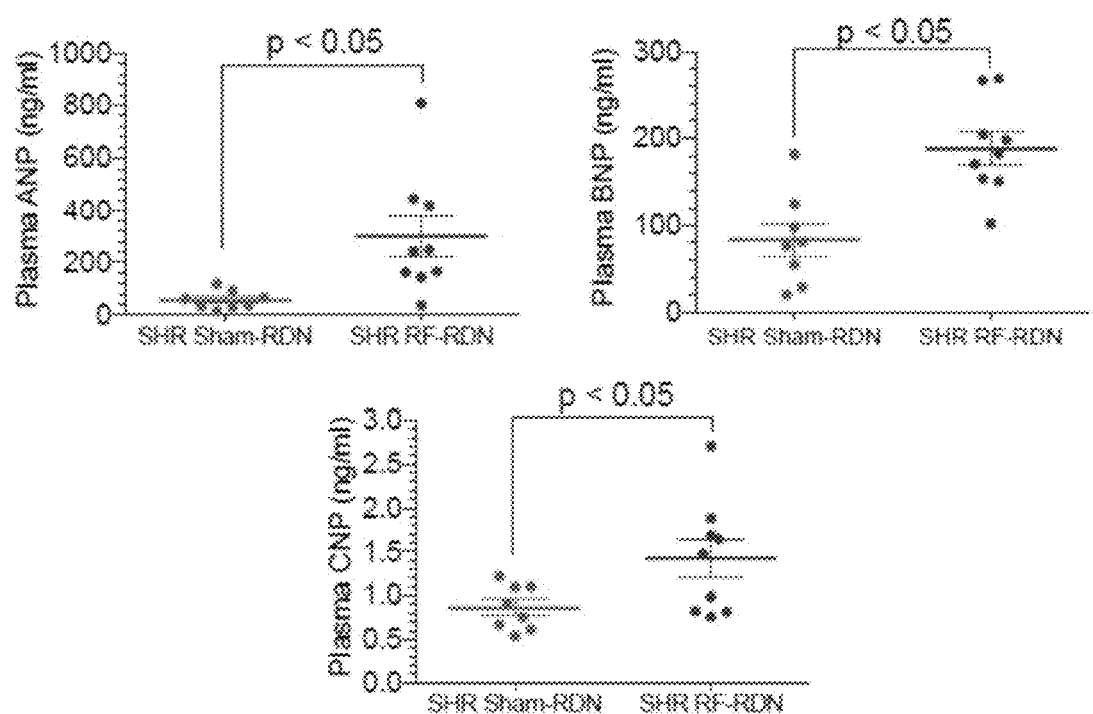
FIG. 82 shows 12 week natriuretic peptide levels in SHR following RF-RDN in heart failure.
Figure 83:
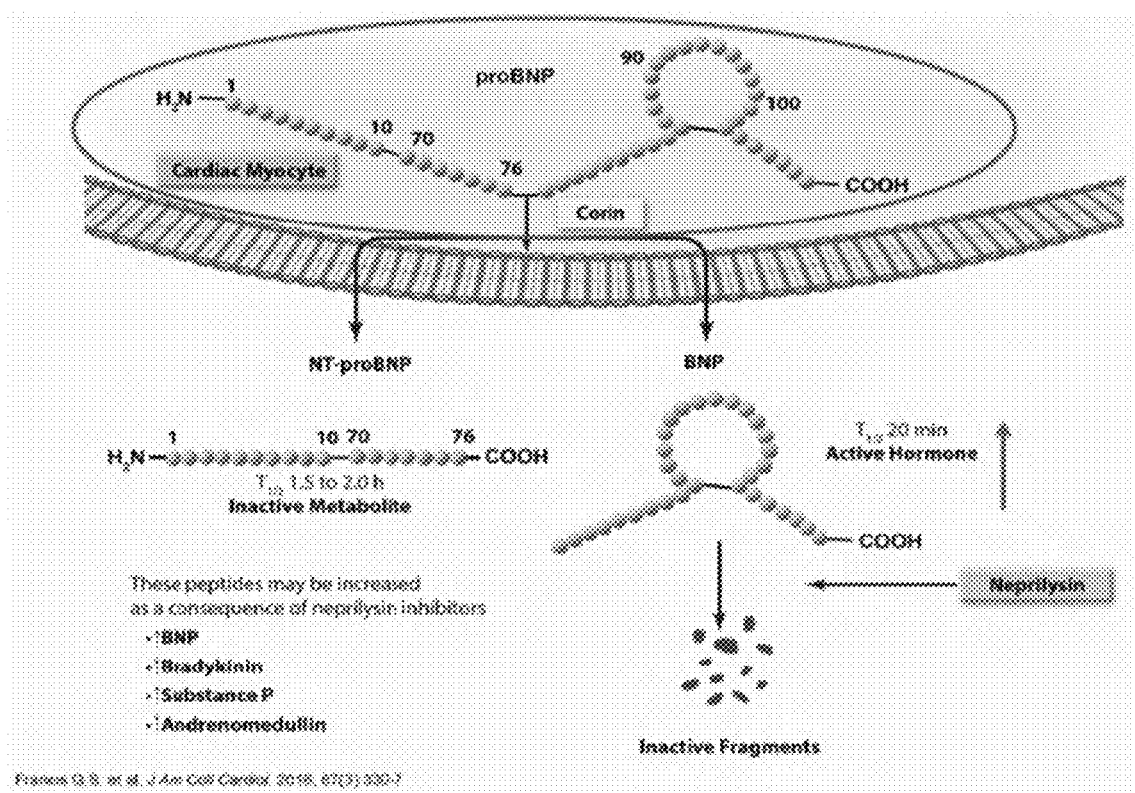
FIG. 83 shows natriuretic peptide in metabolism by neprilysin in heart failure.
Figure 84:
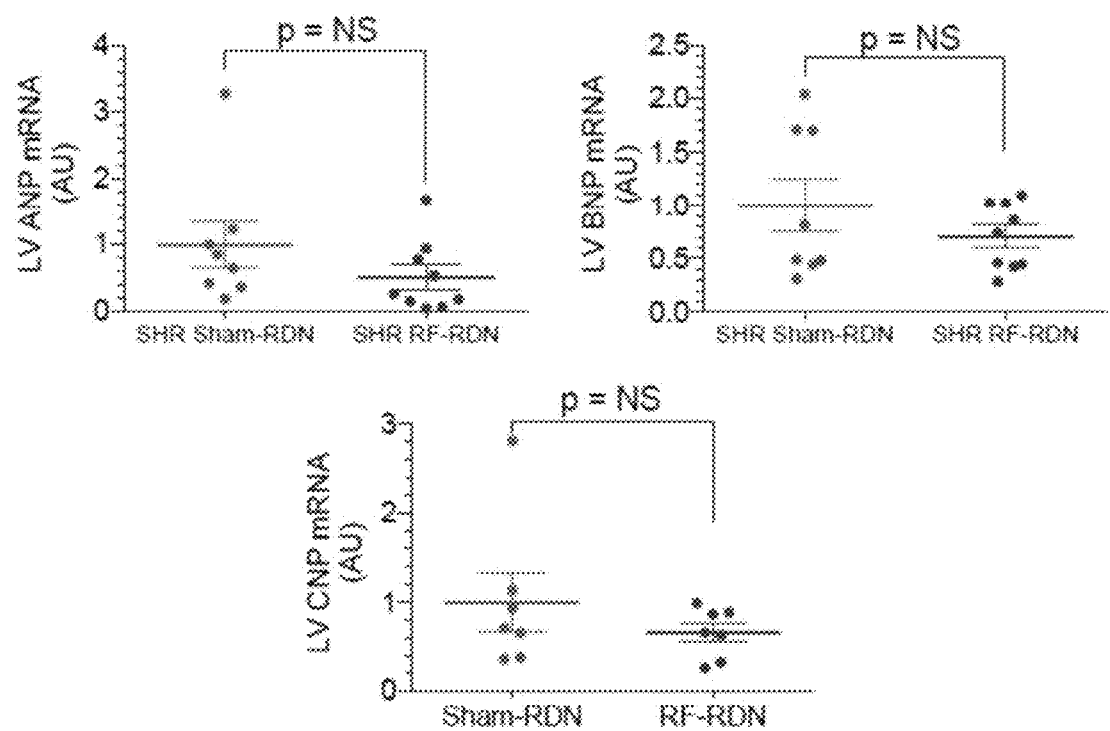
FIG. 84 shows 12 week natriuretic peptide levels in SHR following RF-RDN in heart failure.
Figure 85:
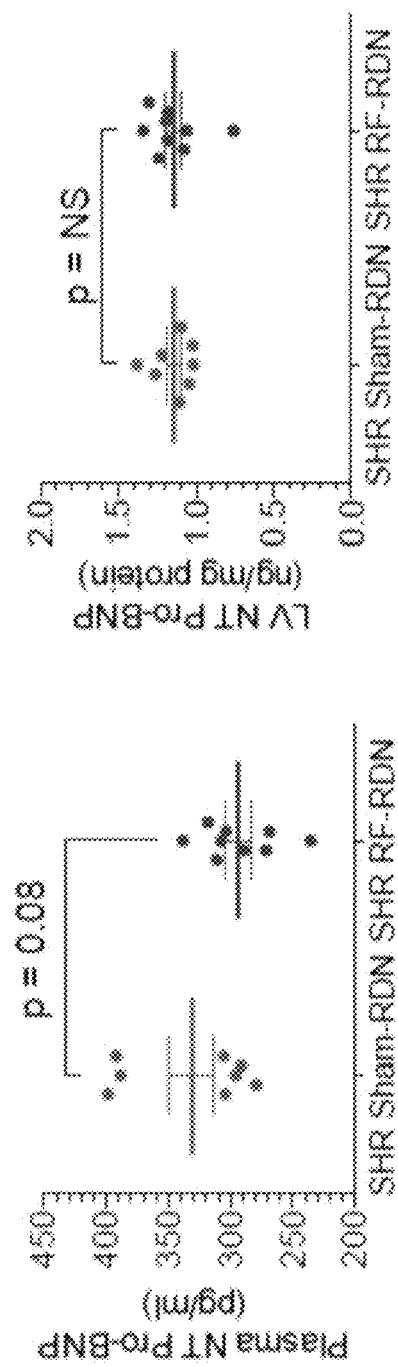
FIG. 85 shows 12 week NT pro-BNP levels in SHR following RF-RDN in heart failure.
Figure 86:
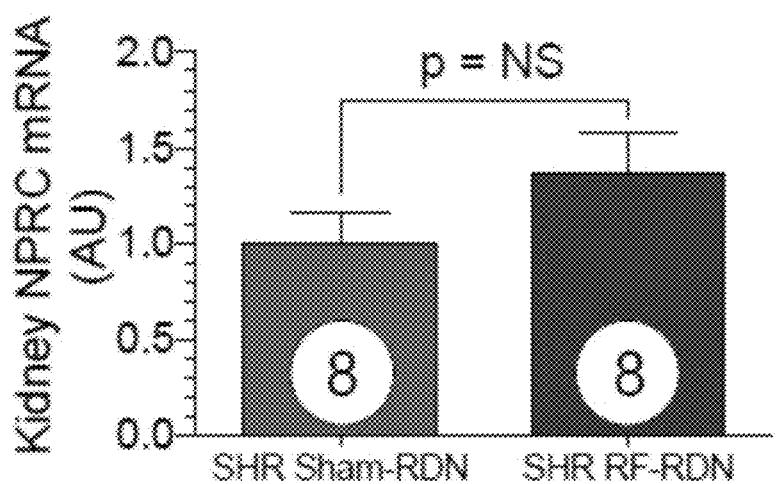
FIG. 86 shows NP clearance receptor mRNA levels in SHR following RF-RDN in heart failure.
Figure 87:
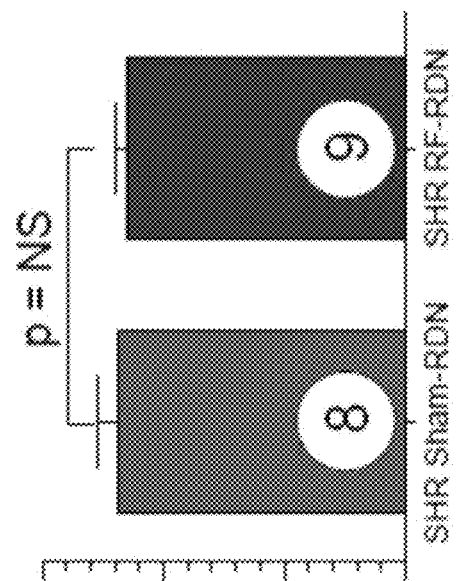
FIG. 87 shows plasma and LV neprilysin levels in SHR following RF-RDN in heart failure.
Figure 87:
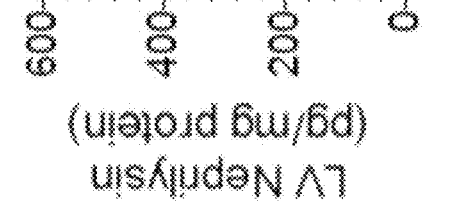
Figure 87:
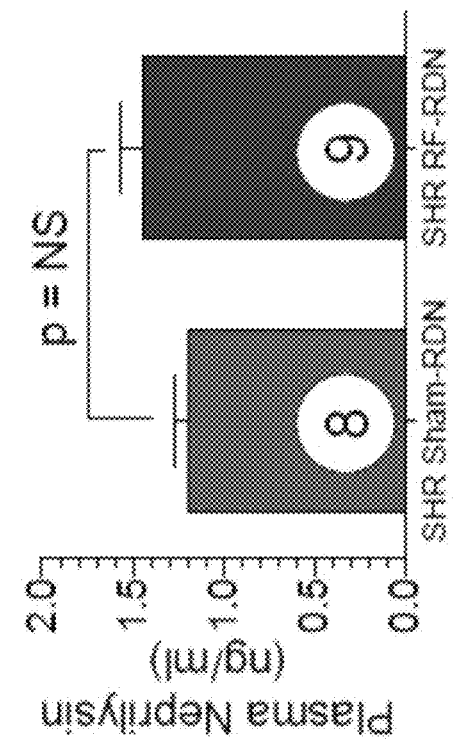
Figure 88:
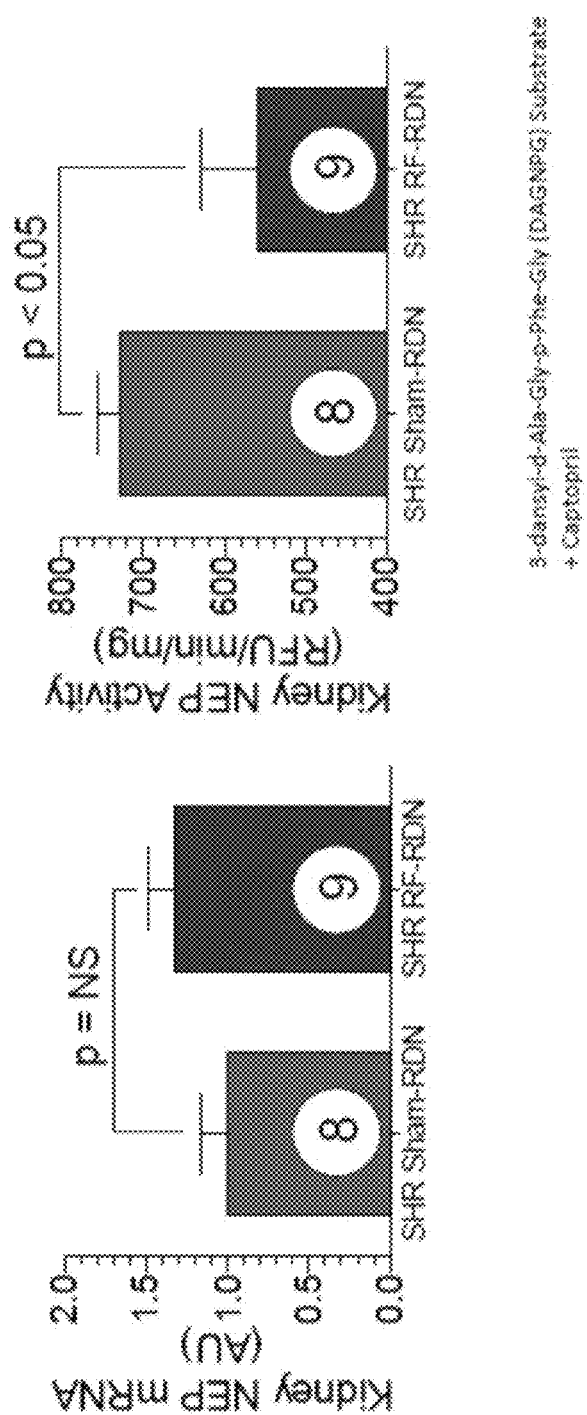
FIG. 88 shows renal neprilysin inhibition by RF-RDN in SHR in heart failure.
Figure 89:
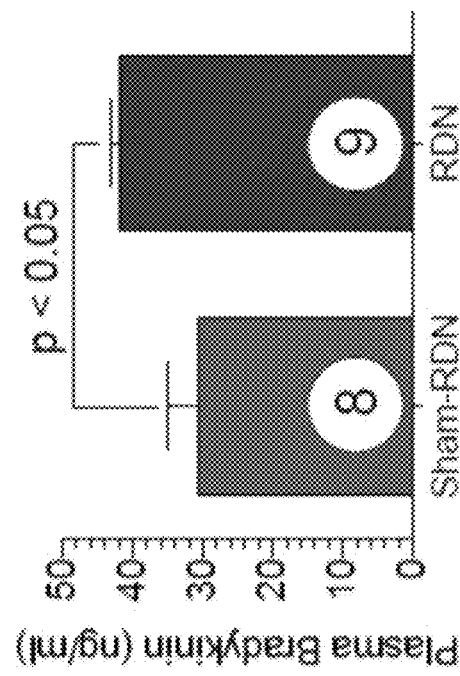
FIG. 89 shows cardioprotective plasma peptide levels in SHR following RF-RDN in heart failure.
Figure 89:
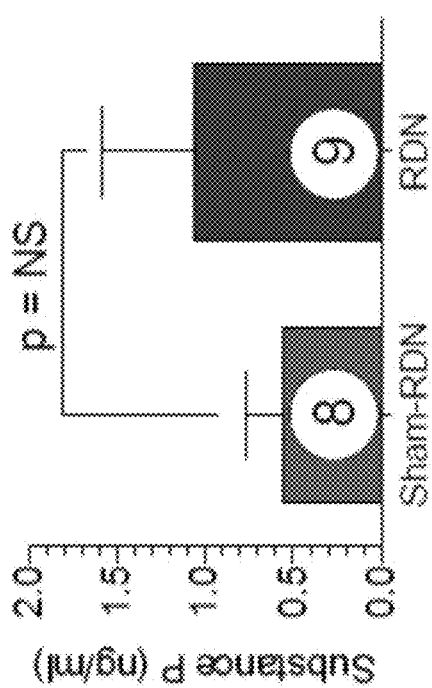
Figure 91:
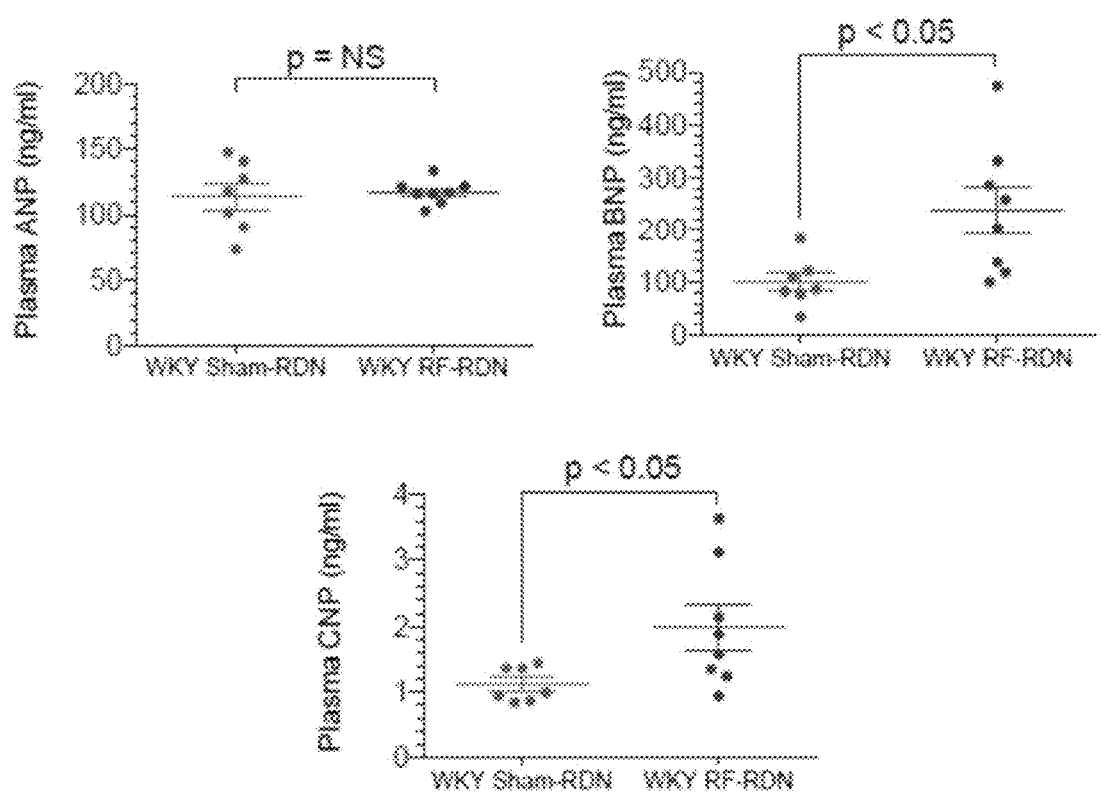
FIG. 91 shows 12 week natriuretic peptide levels in WKY following RF-RDN in heart failure.
Figure 92:
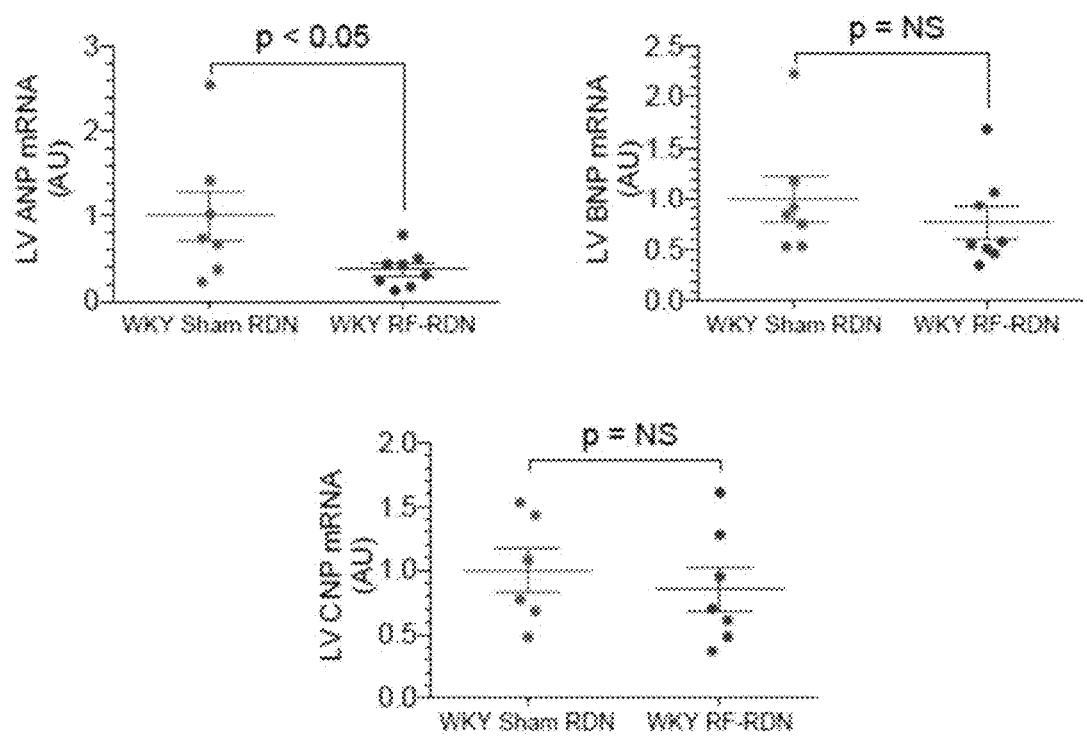
FIG. 92 shows 12 week natriuretic peptide mRNA levels in WKY following RF-RDN in heart failure.
Figure 93:
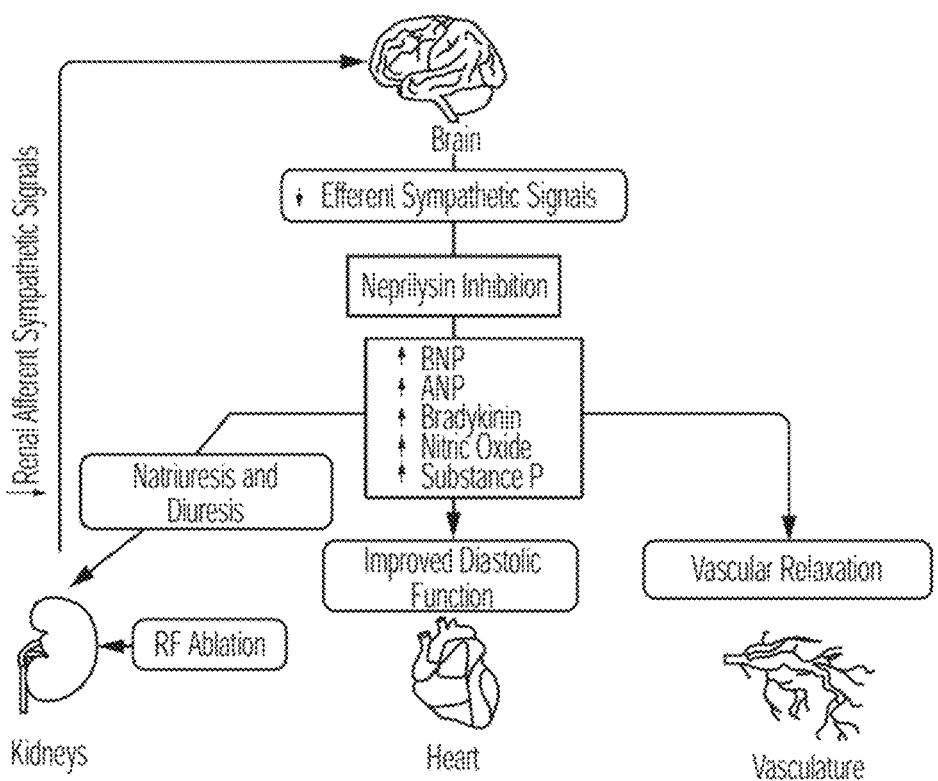
FIG. 93 shows RF-renal nerve ablation and cardioprotection in heart failure.
Figure 94:
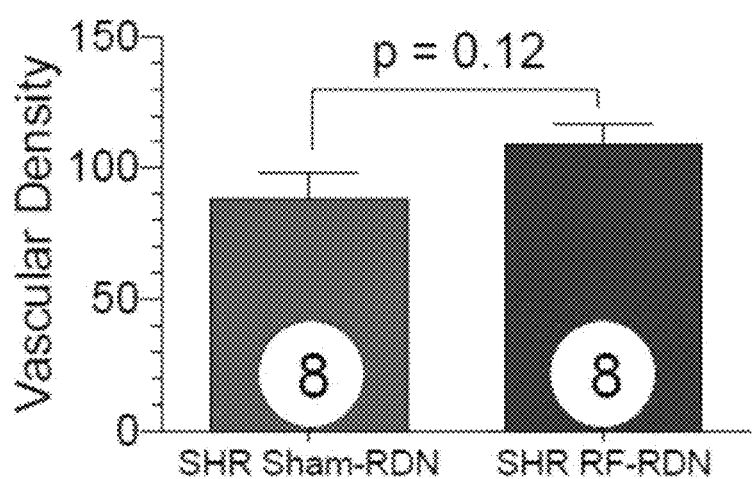
FIG. 94 shows vascular density (CD31) in SHR following RF-RDN in heart failure.
Figure 95:
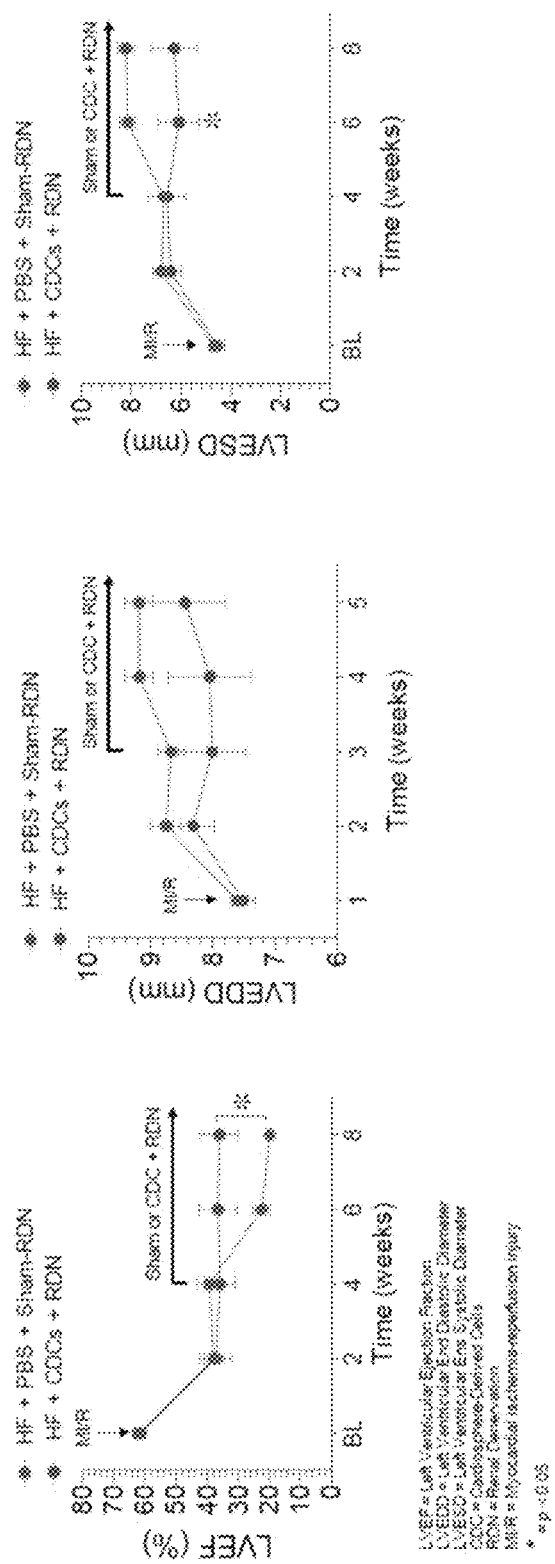
FIG. 95 shows the use of stem cell therapy with renal denervation (RDN) for the treatment of heart failure.
Figure 96:
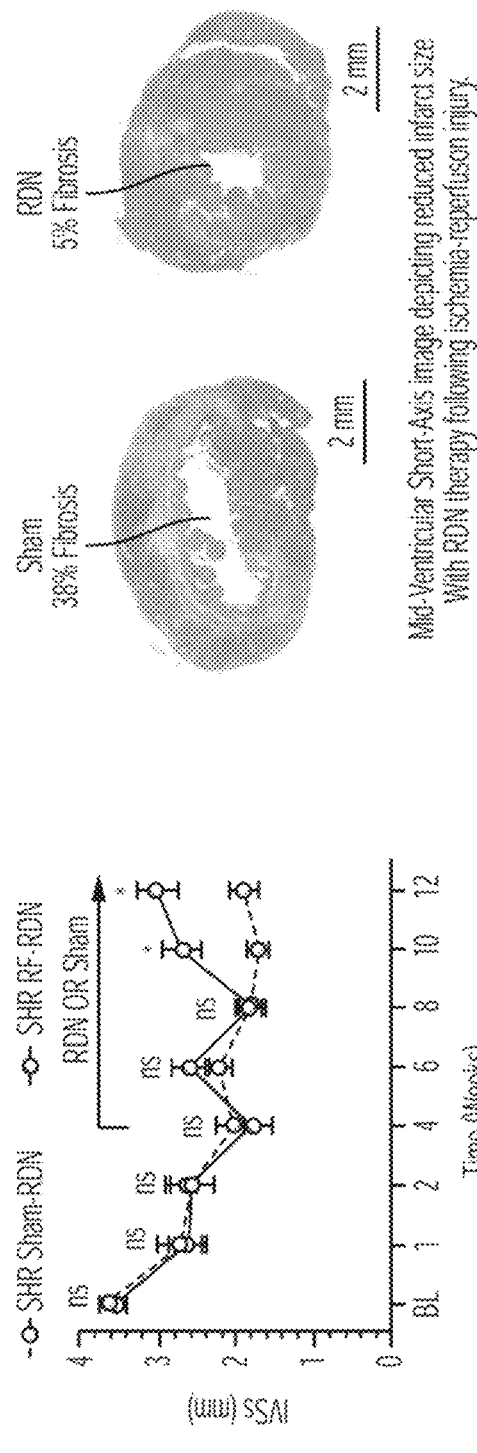
FIG. 96 shows renal denervation promotes septal wall thickening and reduces infarct size following myocardial ischemia-reperfusion injury
Figure 97:
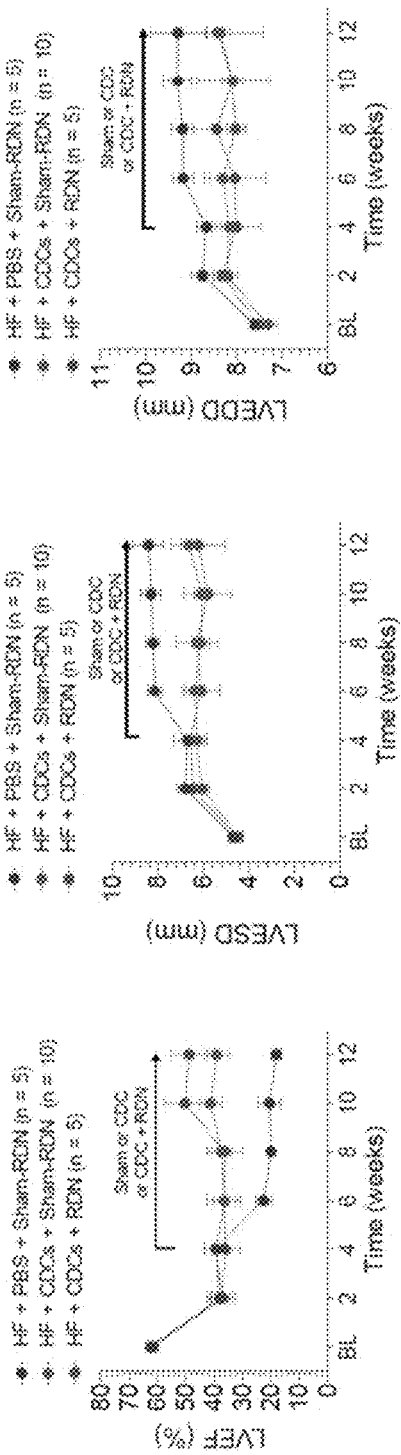
FIG. 97 shows the use of cardiosphere derived cells (CDCs) with Renal Denervation (RDN) for the treatment of heart failure
Figure 98:
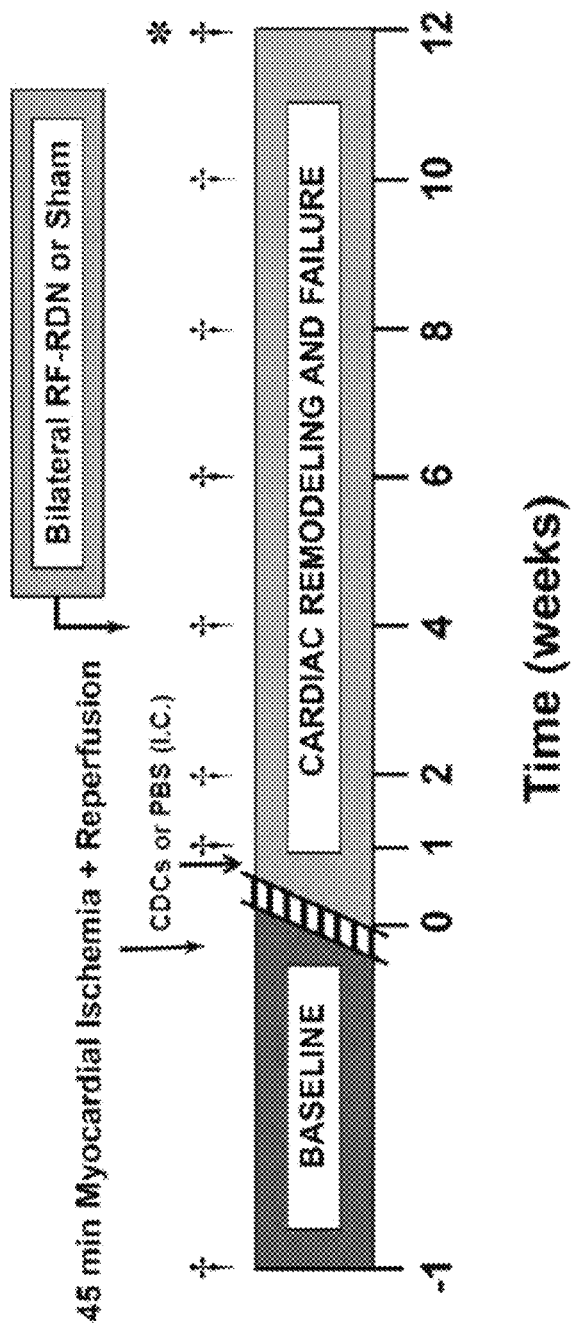
FIG. 98 shows rat ischemic heart failure experimental protocol for embodiments of the invention.
Figure 99:
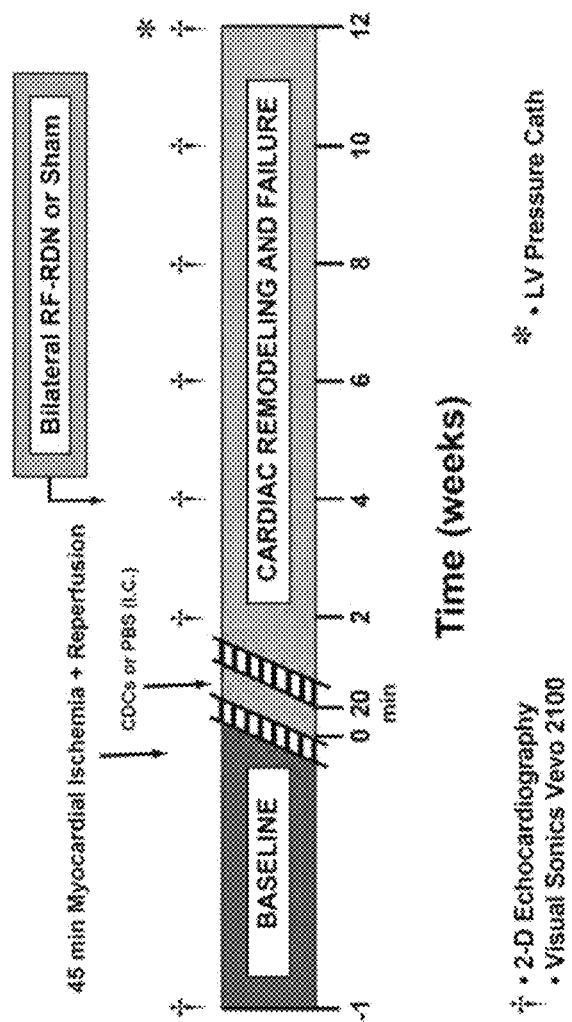
FIG. 99 shows rat ischemic heart failure experimental protocol for embodiments of the invention.
Figure 100:
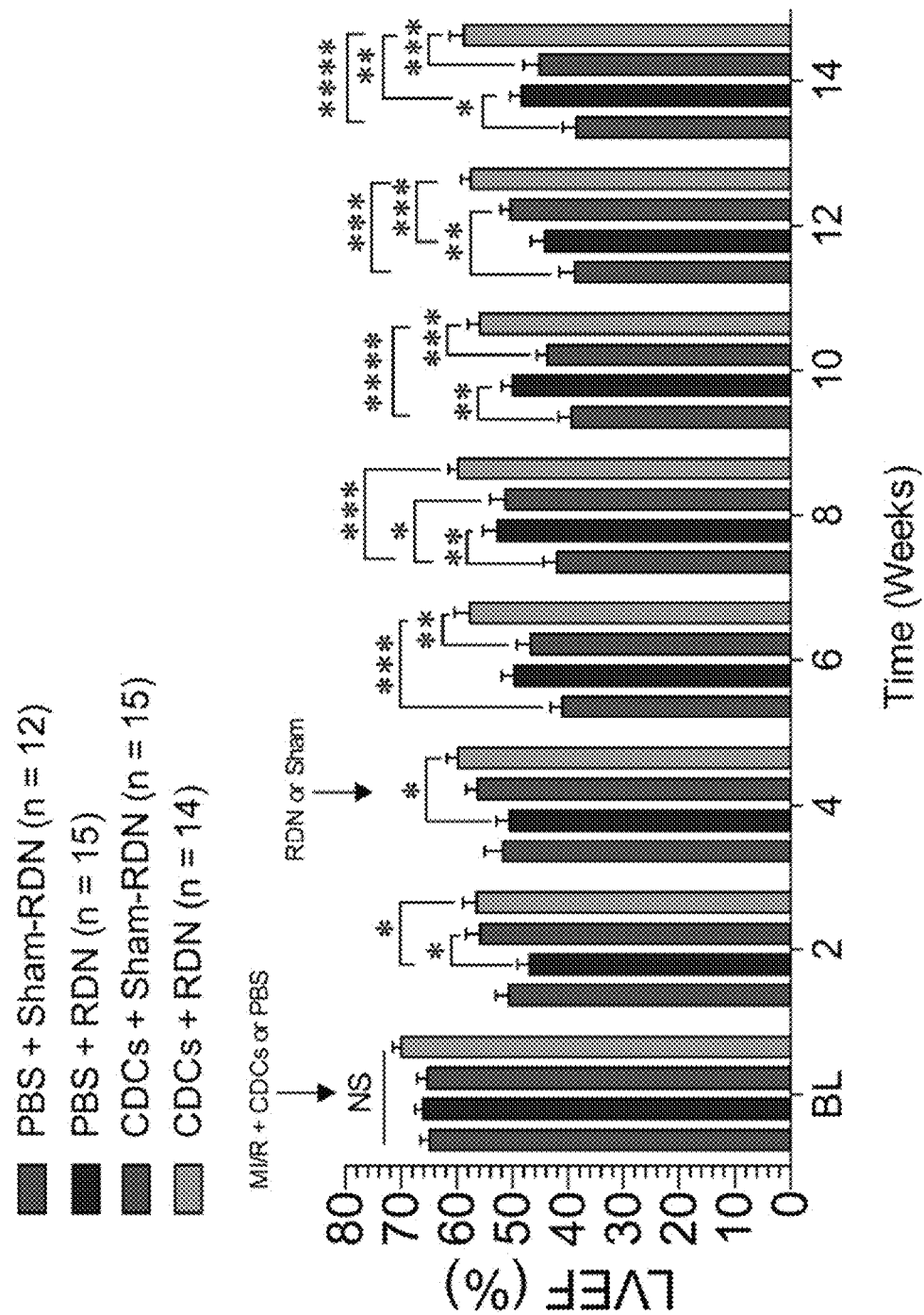
FIG. 100 shows left ventricular function following MI/R.
Figure 101:
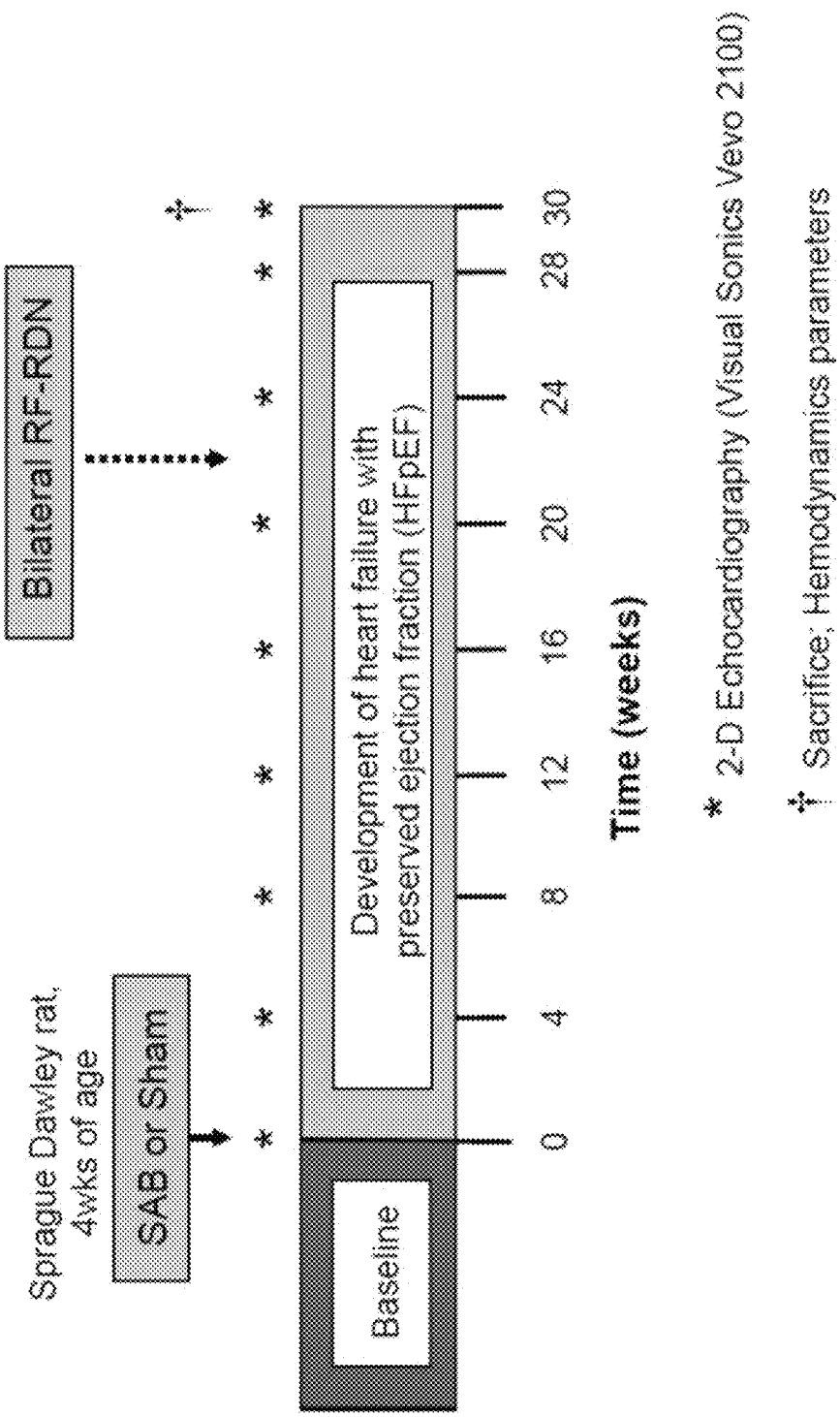
FIG. 101 shows supra-aortic banding (SAB) heart failure with preserved ejection fraction (HFpEF) protocol.
Figure 102:
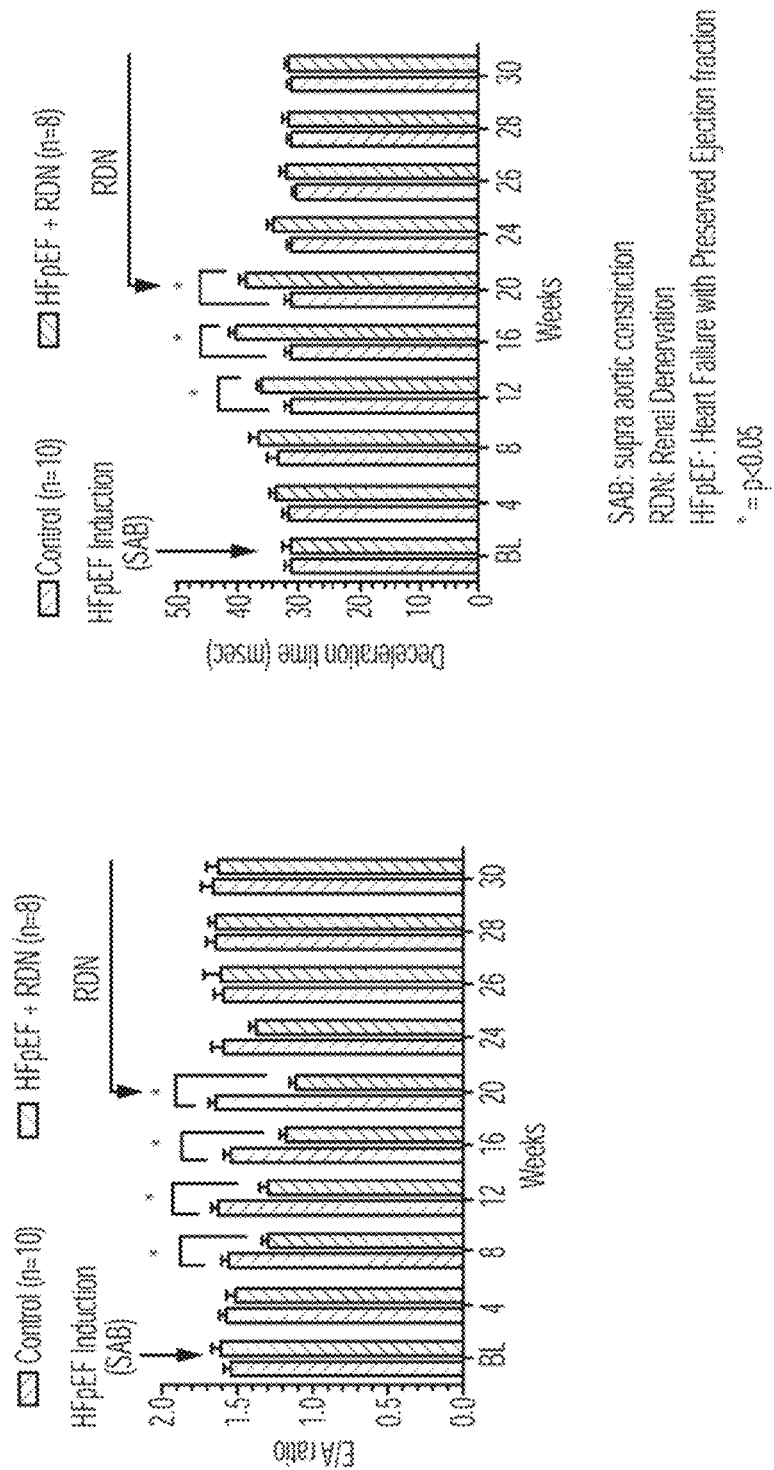
FIG. 102 shows renal denervation (RDN) improves cardiac diastolic function in heart failure with preserved ejection fraction (HFpEF).
Figure 103:
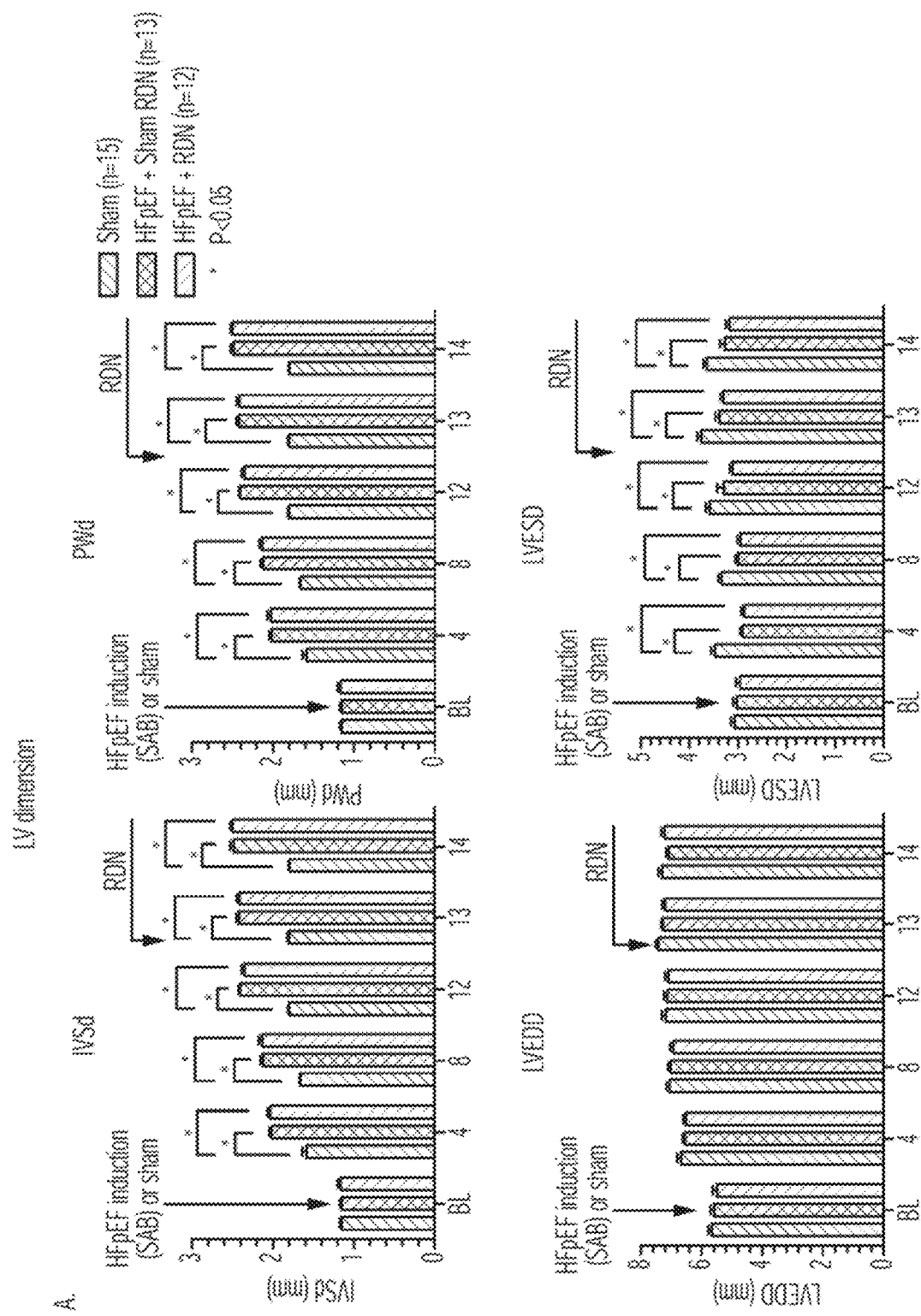
FIG. 103 shows RDN improves diastolic function in a rat model of heart failure with preserved ejection fraction (HFpEF). (A) LV dimension, (B) LV systolic function; (C) LV diastolic function; (D) LV diastolic function.
Figure 104:
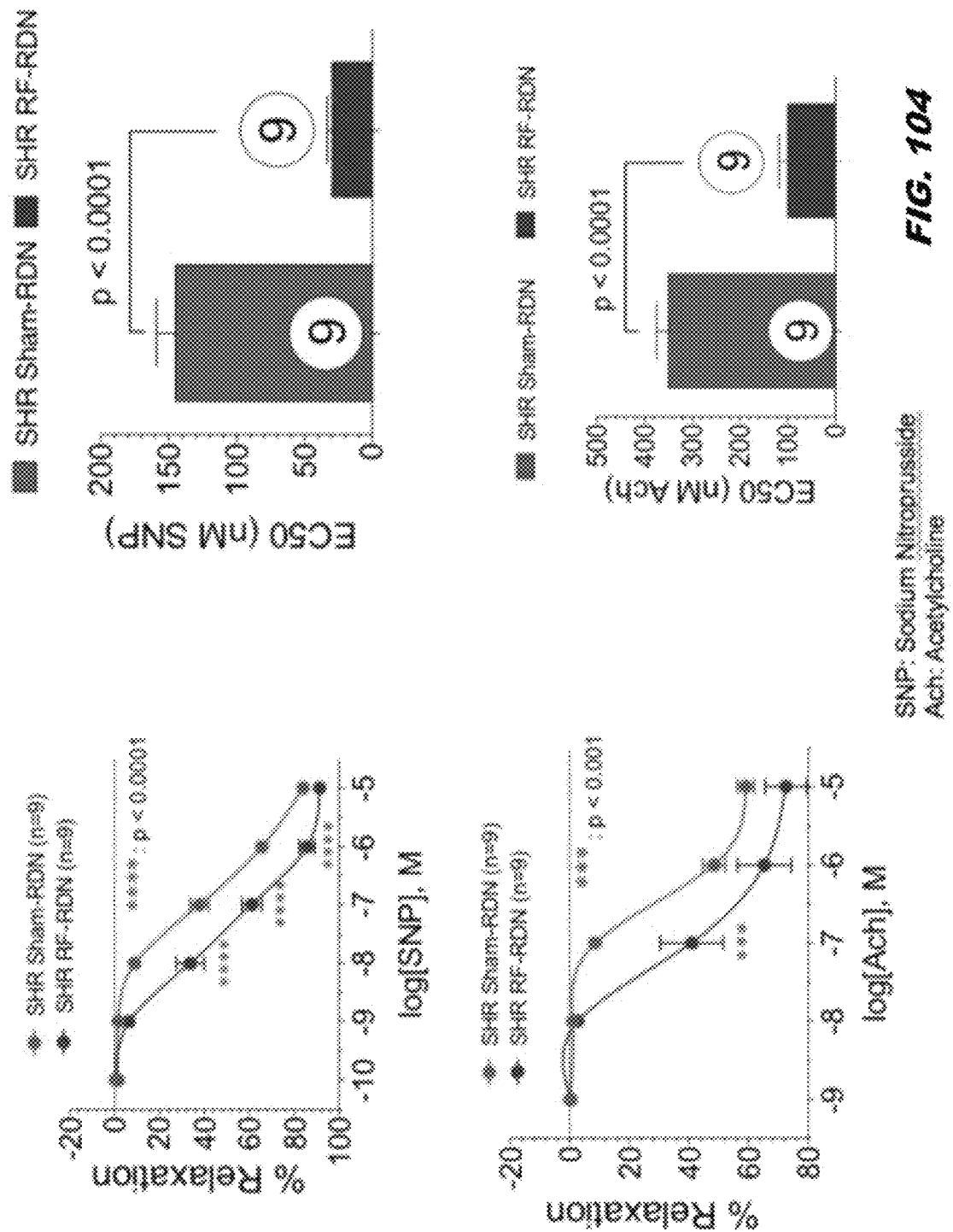
FIG. 104 shows RDN improves smooth muscle and endothelial function in the vessels of rats in heart failure.
Figure 105:
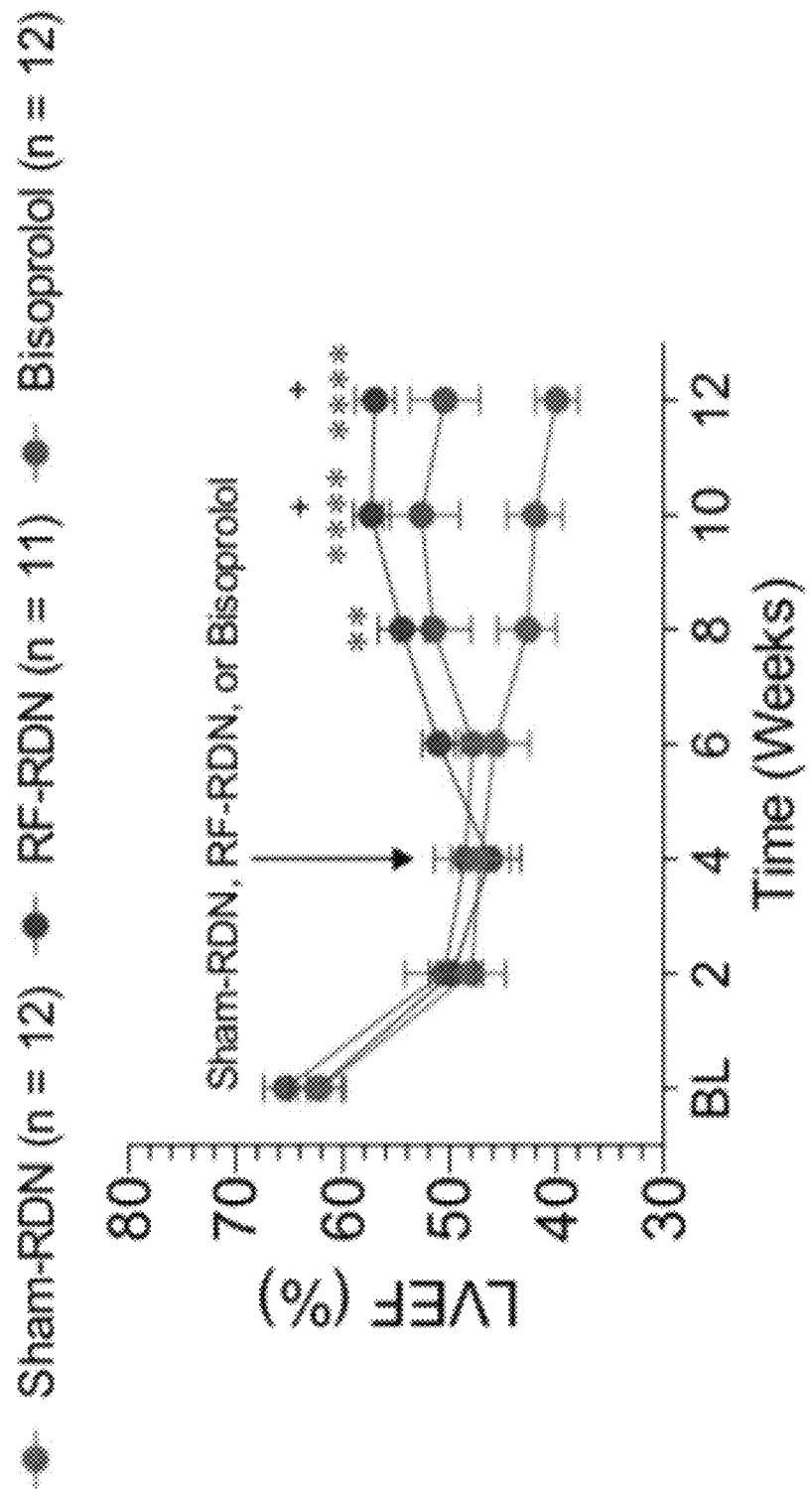
FIG. 105 shows RDN has better effects on ejection fraction than a beta-blocker, bisoprolol. Left ventricular function following RF-RDN or Bisoprolol in normotensive WKY.
Figure 106:
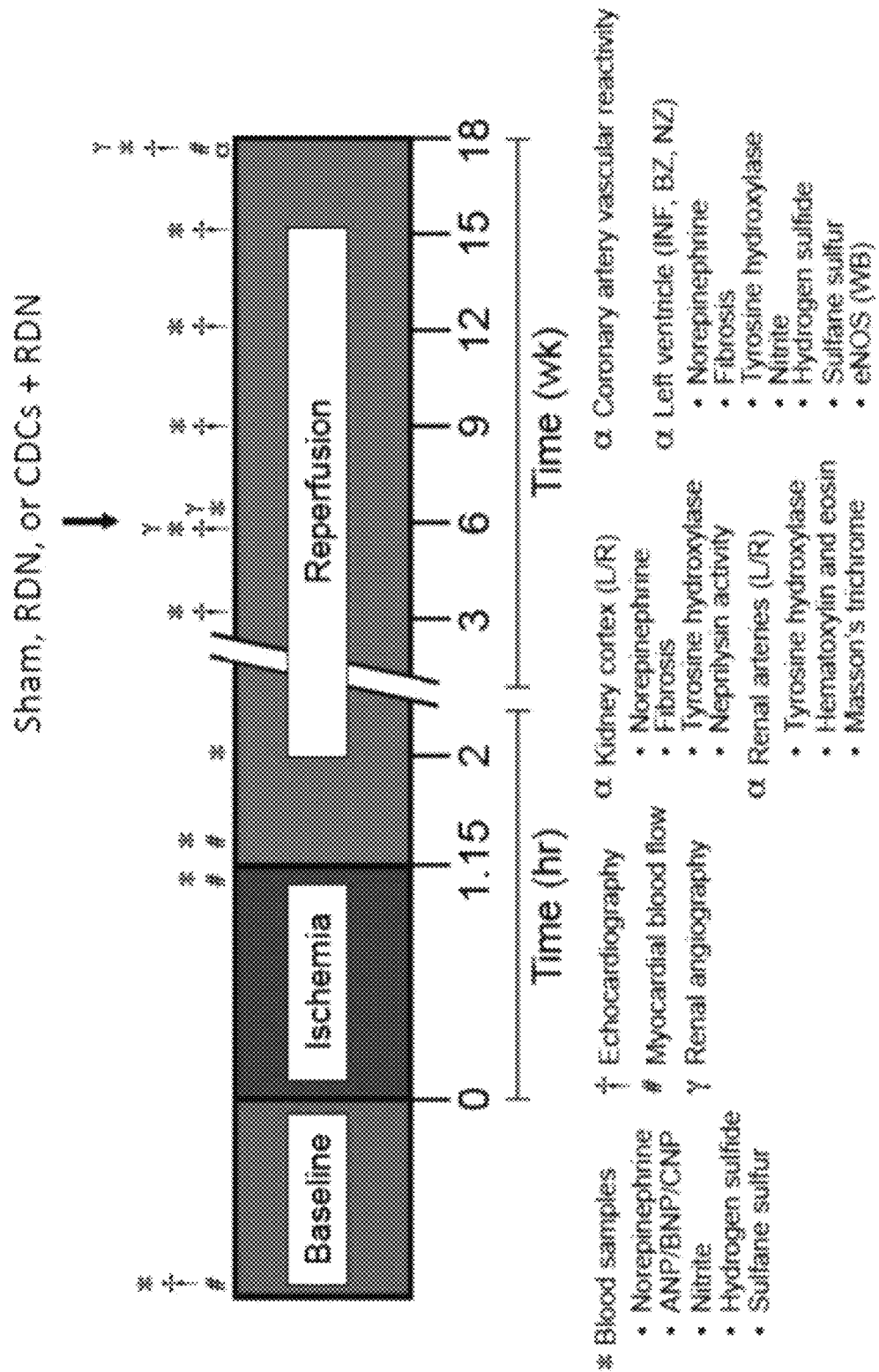
FIG. 106 shows a model heart failure protocol. For example, swine heart failure protocol testing the efficacy of renal denervation and CDCs.

We investigated whether renal sympathetic denervation modifies the endogenous regulation of NPs in normotensive animals in heart failure. Although WKY rats have less sympathetic drive under basal conditions than SHR, ischemic injury promotes the activation of the sympathetic nervous system (B28). In a similar fashion to SHR, despite improved LV function and remodeling, 12-week plasma ANP (FIG. 20A), BNP (FIG. 20B), and CNP (FIG. 20C) levels were markedly elevated in the RF-RDN treated WKY compared to sham. Similarly, these changes were not due to increased gene transcription of ANP, BNP, and CNP in the myocardium (FIG. 20 D-F). NT Pro-BNP levels in the LV and plasma indicate that RF-RDN did not enhance the release of NPs from the myocytes to circulation (FIG. 20 G, H). Likewise, RF-RDN promoted circulating BK levels following in WKY in the setting of HF (FIG. 20I)

Discussion

Modulation of the autonomic nervous system as a treatment for HF has been limited to chronic pharmacologic therapies. We propose that sympathoinhibitory interventional and device-based approaches may have clinical indications for cardiovascular disease beyond the treatment of hypertension. We have previously reported that RF-RDN has direct effects on the myocardium and protects against acute myocardial I/R injury by attenuating myocardial oxidative stress and pro-death signaling pathways (B17). In the current study, we examined the cardioprotective effects of RF-RDN on post-infarction remodeling both in the setting of hypertension (SHR rats) and normal blood pressure (WKY rats). We also examined the interaction of the sympathetic nervous system and the endogenous regulation of natriuretic peptides (NPs) that are well recognized to exert protective effects on cardiac myocytes and the vasculature.

Following MI/R injury, RF-RDN therapy resulted in superior LV function, improved ventricular remodeling, and a thickened intraventricular septal wall compared to sham-operated hypertensive rats. Much of the presumed benefits of RF-RDN in heart failure were due to blood pressure lowering effects and decreased afterload on the heart. However, we observed similar, and in several categories, more substantial cardioprotection by RF-RDN in normotensive animals. These findings suggest that RF-RDN therapy for heart failure is not limited to hypertensive patients and led us to seek out mechanisms of protection beyond blood pressure reduction.

It was not until the 1980s that the heart was recognized as an endocrine organ that secretes a family of hormones called natriuretic peptides (NP)(B29). These peptides primarily act on the vasculature and kidney to produce natriuresis, diuresis, and vasodilation to compensate for increased cardiac wall stress and volume (B30). Ventricular hypertrophy is accompanied by augmented synthesis and release of NPs and therefore, circulating BNP levels are an established biomarker of heart failure severity (B31-33). Nature's ability to compensate for the myocyte stretch that occurs in the failing heart by increasing the synthesis of vasoactive NPs has been a target for heart failure therapeutics. NP analogs such as Nesiritide are often used for acute decompensated heart failure (B34) and inhibitors of NP degradation are at the forefront of chronic HF therapy research (B9, B11, B35).

The processing, metabolism, and clearance of NPs are fairly complex and are regulated by multiple cleavage enzymes and a primary clearance receptor (B36, B37). BNP translation, for example, is stimulated in response to ventricular stretch or ischemia and results in the translation of a 134 amino acid (AA) preproBNP peptide (B38). The prepro form is then cleaved to the 108 AA proBNP and a 26 AA signal peptide. proBNP is then cleaved, primarily by Corin, to an inactive N-terminal proBNP (76 AA) and an active BNP (32 AA) form (B38, B39). BNP and NT-proBNP travel through the circulation and BNP can act on target organs such as the blood vessels, kidney, and heart. NPs are largely cleared by a common clearance receptor, natriuretic peptide C receptor (NPRC) in the kidney (B21). The biologic half-life of active BNP is approximately 20 minutes and is degraded primarily by the endopeptidase, Neprilysin (NEP)(B40, B41). NEP is largely located in the kidney, but is expressed in moderate levels in the lung, brain, heart, and circulation. NEP serves as an endogenous inactivator of multiple peptide hormones, including ANP, BNP, CNP, bradykin, and substance P (B42-B44). Finding ways to regulate the activity of NEP has become a hotly researched topic since Sacubitril and Entresto emerged as promising HF therapeutics. Somatostatin is one of the few endogenous molecules reported to modulate NEP and does so by enhancing activity (B45). To date, there is no known relationship between the sympathetic nervous system and NP regulation.

In the current study, we examined the role of sympathetic nerve denervation (RF-RDN) and the endogenous regulation of NPs. Despite improved LV function, RF-RDN in SHR resulted in increased circulating ANP, BNP, and CNP levels 12 weeks following MI/R injury. Beyond the unconventional positive relationship between NP levels and LV function, elevated NP levels following RF-RDN therapy were maintained 8 weeks following therapy. Unchanged NP mRNA levels in the LV indicate that RF-RDN did not modulate NP levels by signaling for enhanced gene transcription. Furthermore, the cleaved, inactive NT-proBNP levels were unchanged between Sham-RDN and RF-RDN treated groups in the heart and plasma (trending lower in the RF-RDN treated group, p=0.08). Examination of the NP clearance system revealed that RF-RDN had no impact on regulation of the primary clearance receptor in the kidney. Rejecting increased NP synthesis or downregulated NP clearance as possible mechanisms for elevated NP levels following RF-RDN, we then studied the degradation system. RF-RDN did not result in altered mRNA or protein levels of NEP in the kidney, heart, or circulation compared to Sham-RDN treated animals. However, we observed significant reduction in NEP enzyme activity in the RF-RDN treated group. This is of substantial clinical importance because this inhibition was maintained 8 weeks following RF-RDN therapy.

Natriuretic peptides serve as cardioprotective molecules beyond their ability to clear sodium and water and relax smooth muscle. ANP, BNP, and CNP bind to natriuretic peptide receptors-A, B, and C (NPR-A, NPR-B, and NPR-C)(B30). NPR-A and NPR-B are G-protein coupled receptors (GPCRs) that stimulate guanylyl cyclase to generate cGMP and activate protein kinase G (PKG)(B30). Increasing cGMP and activating PKG have been shown to inhibit hypertrophy and to increase intracellular calcium to improve contractility (B46-B48). Moreover BNP has been shown to remarkably reduce TFG-beta-induced effects on cardiac fibroblasts (B49). BNP opposes TGF-beta regulated genes related to fibrosis (collagen 1, CTGF, and TIMP3), myofibroblast conversion, proliferation, and inflammation (COX2, IL6, and TNF-alpha)(B49). In the currently study, we similarly observed regulation of TGF-beta, collagen 1 & 3, CTGF, and IL6 following RF-RDN therapy. The overall result was reduced total ventricular fibrosis, minimized infarct transition zone expansion, and improved LV function.

We propose that RF-RDN inhibits renal afferent sympathetics to the brain and this leads to dampened efferent sympathetic tone to peripheral organs. Sympathoinhibition to the kidney results in renal NEP inhibition and the modulation of cardioprotective NPs. These NPs act on the vasculature and heart to reduce peripheral vascular resistance, reduce cardiac fibrosis, and improve cardiac function. Simultaneous inhibition of efferent sympathetic input to the heart also affords direct protection of the failing heart. Importantly, these actions are sustained long after the RF-RDN procedure.

We have shown for the first time that radiofrequency RDN improves LV function and cardiac remodeling in heart failure and that it does so independently of its minor blood pressure effects in the setting of hypertension. Furthermore, we have identified a link between the sympathetic nervous system and endogenous regulation of NPs. Sympathetic inhibition by RF-RDN obstructs renal NEP activity and leads to prolonged NP elevation, resulting in cardiac and vascular protection in heart failure. We therefore conclude that RF-RDN is worthy of further exploration as a promising minimally invasive strategy for the treatment of cardiac injury and heart failure.

REFERENCES CITED IN THIS EXAMPLE

B1. Mozaffarian, D., Benjamin, E. J., Go, A. S., Arnett, D. K., Blaha, M. J., Cushman, M., de Ferranti, S., Despres, J. P., Fullerton, H. J., Howard, V. J., et al. 2015. Heart disease and stroke statistics—2015 update: a report from the American Heart Association. *Circulation* 131:e29-322.

B2. Voigt, J., Sasha John, M., Taylor, A., Krucoff, M., Reynolds, M. R., and Michael Gibson, C. 2014. A reevaluation of the costs of heart failure and its implications for allocation of health resources in the United States. *Clin Cardiol* 37:312-321.

B3. Watson, A. M., Hood, S. G., and May, C. N. 2006. Mechanisms of sympathetic activation in heart failure. *Clin Exp Pharmacol Physiol* 33:1269-1274.

B4. Brouri, F., Hanoun, N., Mediani, O., Saurini, F., Hamon, M., Vanhoutte, P. M., and Lechat, P. 2004. Blockade of beta 1- and desensitization of beta 2-adrenoceptors reduce isoprenaline-induced cardiac fibrosis. *Eur J Pharmacol* 485:227-234.

B5. Packer, M., Bristow, M. R., Cohn, J. N., Colucci, W. S., Fowler, M. B., Gilbert, E. M., and Shusterman, N. H. 1996. The effect of carvedilol on morbidity and mortality in patients with chronic heart failure. U.S. Carvedilol Heart Failure Study Group. *N Engl J Med* 334:1349-1355.

B6. Garg, R., and Yusuf, S. 1995. Overview of randomized trials of angiotensin-converting enzyme inhibitors on mortality and morbidity in patients with heart failure. Collaborative Group on ACE Inhibitor Trials. *JAMA* 273:1450-1456.

B7. Flather, M. D., Yusuf, S., Kober, L., Pfeffer, M., Hall, A., Murray, G., Torp-Pedersen, C., Ball, S., Pogue, J., Moye, L., et al. 2000. Long-term ACE-inhibitor therapy in patients with heart failure or left-ventricular dysfunction: a systematic overview of data from individual patients. ACE-Inhibitor Myocardial Infarction Collaborative Group. *Lancet* 355:1575-1581.

B8. McMurray, J. J., Ostergren, J., Swedberg, K., Granger, C. B., Held, P., Michelson, E. L., Olofsson, B., Yusuf, S., Pfeffer, M. A., Investigators, C., et al. 2003. Effects of candesartan in patients with chronic heart failure and reduced left-ventricular systolic function taking angiotensin-converting-enzyme inhibitors: the CHARM-Added trial. *Lancet* 362:767-771.

B9. McMurray, J. J., Packer, M., Desai, A. S., Gong, J., Lefkowitz, M. P., Rizkala, A. R., Rouleau, J. L., Shi, V. C., Solomon, S. D., Swedberg, K., et al. 2014. Angiotensin-neprilysin inhibition versus enalapril in heart failure. *N Engl J Med* 371:993-1004.

B10. Fala, L. 2015. Entresto (Sacubitril/Valsartan): First-in-Class Angiotensin Receptor Neprilysin Inhibitor FDA Approved for Patients with Heart Failure. *Am Health Drug Benefits* 8:330-334.

B11. Solomon, S. D., Zile, M., Pieske, B., Voors, A., Shah, A., Kraigher-Krainer, E., Shi, V., Bransford, T., Takeuchi, M., Gong, J., et al. 2012. The angiotensin receptor neprilysin inhibitor LCZ696 in heart failure with preserved ejection fraction: a phase 2 double-blind randomised controlled trial. *Lancet* 380:1387-1395.

B12. Chatterjee, N. A., and Singh, J. P. 2015. Novel Interventional Therapies to Modulate the Autonomic Tone in Heart Failure. *JACC Heart Fail* 3:786-802.

B13. Krum, H., Schlaich, M., Whitbourn, R., Sobotka, P. A., Sadowski, J., Bartus, K., Kapelak, B., Walton, A., Sievert, H., Thambar, S., et al. 2009. Catheter-based renal sympathetic denervation for resistant hypertension: a multicentre safety and proof-of-principle cohort study. *Lancet* 373:1275-1281.

B14. Mahfoud, F., Luscher, T. F., Andersson, B., Baumgartner, I., Cifkova, R., Dimario, C., Doevendans, P., Fagard, R., Fajadet, J., Komajda, M., et al. 2013. Expert consensus document from the European Society of Cardiology on catheter-based renal denervation. *Eur Heart J* 34:2149-2157.

B15. Symplicity, H. T. N. I., Esler, M. D., Krum, H., Sobotka, P. A., Schlaich, M. P., Schmieder, R. E., and Bohm, M. 2010. Renal sympathetic denervation in patients with treatment-resistant hypertension (The Symplicity HTN-2 Trial): a randomised controlled trial. *Lancet* 376:1903-1909.

B16. Bhatt, D. L., Kandzari, D. E., O'Neill, W. W., D'Agostino, R., Flack, J. M., Katzen, B. T., Leon, M. B., Liu, M., Mauri, L., Negoita, M., et al. 2014. A controlled trial of renal denervation for resistant hypertension. *N Engl J Med* 370:1393-1401.

B17. Polhemus, D. J., Gao, J., Scarborough, A., Trivedi, R. K., McDonough, K. H., Goodchild, T. T., Smart, F., Kapusta, D. R., and Lefer, D. J. 2016. Radiofrequency Renal Denervation Protects the Ischemic Heart via Inhibition of GRK2 and Increased Nitric Oxide Signaling. *Circ Res*.

B18. King, A. L., Polhemus, D. J., Bhushan, S., Otsuka, H., Kondo, K., Nicholson, C. K., Bradley, J. M., Islam, K. N., Calvert, J. W., Tao, Y. X., et al. 2014. Hydrogen sulfide cytoprotective signaling is endothelial nitric oxide synthase-nitric oxide dependent. *Proc Natl Acad Sci USA* 111:3182-3187.

B19. Carpenter, T. C., and Stenmark, K. R. 2001. Hypoxia decreases lung neprilysin expression and increases pulmonary vascular leak. *Am J Physiol Lung Cell Mol Physiol* 281:L941-948.

B20. Potter, L. R., Yoder, A. R., Flora, D. R., Antos, L. K., and Dickey, D. M. 2009. Natriuretic peptides: their structures, receptors, physiologic functions and therapeutic applications. *Handb Exp Pharmacol*:341-366.

B21. Potter, L. R. 2011. Natriuretic peptide metabolism, clearance and degradation. *FEBS J* 278:1808-1817.

B22. Deddish, P. A., Marcic, B. M., Tan, F., Jackman, H. L., Chen, Z., and Erdos, E. G. 2002. Neprilysin inhibitors potentiate effects of bradykinin on b2 receptor. *Hypertension* 39:619-623.

B23. Lu, B., Figini, M., Emanueli, C., Geppetti, P., Grady, E. F., Gerard, N. P., Ansell, J., Payan, D. G., Gerard, C., and Bunnett, N. 1997. The control of microvascular permeability and blood pressure by neutral endopeptidase. *Nat Med* 3:904-907.

B24. Cargnoni, A., Comini, L., Bernocchi, P., Bachetti, T., Ceconi, C., Curello, S., and Ferrari, R. 2001. Role of bradykinin and eNOS in the anti-ischaemic effect of trandolapril. *Br J Pharmacol* 133 :145-153.

B25. Linz, W., Wiemer, G., and Scholkens, B. A. 1992. ACE-inhibition induces NO-formation in cultured bovine endothelial cells and protects isolated ischemic rat hearts. *J Mol Cell Cardiol* 24:909-919.

B26. Bhushan, S., Kondo, K., Polhemus, D. J., Otsuka, H., Nicholson, C. K., Tao, Y. X., Huang, H., Georgiopoulou, V. V., Murohara, T., Calvert, J. W., et al. 2014. Nitrite therapy improves left ventricular function during heart failure via restoration of nitric oxide-mediated cytoprotective signaling. *Circ Res* 114:1281-1291.

B27. James, P. A., Oparil, S., Carter, B. L., Cushman, W. C., Dennison-Himmelfarb, C., Handler, J., Lackland, D. T., LeFevre, M. L., MacKenzie, T. D., Ogedegbe, O., et al. 2014. 2014 evidence-based guideline for the management of high blood pressure in adults: report from the panel members appointed to the Eighth Joint National Committee (JNC 8). *JAMA* 311:507-520.

B28. Karlsberg, R. P., Penkoske, P. A., Cryer, P. E., Corr, P. B., and Roberts, R. 1979. Rapid activation of the sympathetic nervous system following coronary artery occlusion: relationship to infarct size, site, and haemodynamic impact. *Cardiovasc Res* 13:523-531.

B29. Wang, T. J. 2012. The natriuretic peptides and fat metabolism. *N Engl J Med* 367:377-378.

B30. Nishikimi, T., Maeda, N., and Matsuoka, H. 2006. The role of natriuretic peptides in cardioprotection. *Cardiovasc Res* 69:318-328.

B31. Troughton, R. W., Frampton, C. M., Yandle, T. G., Espiner, E. A., Nicholls, M. G., and Richards, A. M. 2000. Treatment of heart failure guided by plasma aminoterminal brain natriuretic peptide (N-BNP) concentrations. *Lancet* 355:1126-1130.

B32. Seino, Y., Ogawa, A., Yamashita, T., Fukushima, M., Ogata, K., Fukumoto, H., and Takano, T. 2004. Application of NT-proBNP and BNP measurements in cardiac care: a more discerning marker for the detection and evaluation of heart failure. *Eur J Heart Fail* 6:295-300.

B33. Vodovar, N., Seronde, M. F., Laribi, S., Gayat, E., Lassus, J., Boukef, R., Nouira, S., Manivet, P., Samuel, J. L., Logeart, D., et al. 2014. Post-translational modifications enhance NT-proBNP and BNP production in acute decompensated heart failure. *Eur Heart J* 35:3434-3441.

B34. Colucci, W. S., Elkayam, U., Horton, D. P., Abraham, W. T., Bourge, R. C., Johnson, A. D., Wagoner, L. E., Givertz, M. M., Liang, C. S., Neibaur, M., et al. 2000. Intravenous nesiritide, a natriuretic peptide, in the treatment of decompensated congestive heart failure. Nesiritide Study Group. *N Engl J Med* 343:246-253.

B35. Packer, M., McMurray, J. J., Desai, A. S., Gong, J., Lefkowitz, M. P., Rizkala, A. R., Rouleau, J. L., Shi, V. C., Solomon, S. D., Swedberg, K., et al. 2015. Angiotensin receptor neprilysin inhibition compared with enalapril on the risk of clinical progression in surviving patients with heart failure. *Circulation* 131:54-61.

B36. Ruskoaho, H. 1992. Atrial natriuretic peptide: synthesis, release, and metabolism. *Pharmacol Rev* 44:479-602.

B37. Hunt, P. J., Espiner, E. A., Nicholls, M. G., Richards, A. M., and Yandle, T. G. 1997. The role of the circulation in processing pro-brain natriuretic peptide (proBNP) to amino-terminal BNP and BNP-32. *Peptides* 18:1475-1481.

B38. Palazzuoli, A., Gallotta, M., Quatrini, I., and Nuti, R. 2010. Natriuretic peptides (BNP and NT-proBNP): measurement and relevance in heart failure. *Vasc Health Risk Manag* 6:411-418.

B39. Levin, E. R., Gardner, D. G., and Samson, W. K. 1998. Natriuretic peptides. *N Engl J Med* 339:321-328.

B40. Stephenson, S. L., and Kenny, A. J. 1987. The hydrolysis of alpha-human atrial natriuretic peptide by pig kidney microvillar membranes is initiated by endopeptidase-24.11. *Biochem J* 243 :183-187.

B41. Weber, M., and Hamm, C. 2006. Role of B-type natriuretic peptide (BNP) and NT-proBNP in clinical routine. *Heart* 92:843-849.

B42. Pankow, K., Wang, Y., Gembardt, F., Krause, E., Sun, X., Krause, G., Schultheiss, H. P., Siems, W. E., and Walther, T. 2007. Successive action of meprin A and neprilysin catabolizes B-type natriuretic peptide. *Circ Res* 101:875-882.

B43. Yamaguchi, T., Kido, H., and Katunuma, N. 1992. A membrane-bound metallo-endopeptidase from rat kidney. Characteristics of its hydrolysis of peptide hormones and neuropeptides. *Eur J Biochem* 204:547-552.

B44. Pereira, N. L., Aksoy, P., Moon, I., Peng, Y., Redfield, M. M., Burnett, J. C., Jr., Wieben, E. D., Yee, V. C., and Weinshilboum, R. M. 2010. Natriuretic peptide pharmacogenetics: membrane metallo-endopeptidase (MME): common gene sequence variation, functional characterization and degradation. *J Mol Cell Cardiol* 49:864-874.

B45. Saito, T., Iwata, N., Tsubuki, S., Takaki, Y., Takano, J., Huang, S. M., Suemoto, T., Higuchi, M., and Saido, T. C. 2005. Somatostatin regulates brain amyloid beta peptide Abeta42 through modulation of proteolytic degradation. *Nat Med* 11:434-439.

B46. Oliver, P. M., Fox, J. E., Kim, R., Rockman, H. A., Kim, H. S., Reddick, R. L., Pandey, K. N., Milgram, S.L., Smithies, O., and Maeda, N. 1997. Hypertension, cardiac hypertrophy, and sudden death in mice lacking natriuretic peptide receptor A. *Proc Natl Acad Sci USA* 94:14730-14735.

B47. Booz, G. W. 2005. Putting the brakes on cardiac hypertrophy: exploiting the NO-cGMP counter-regulatory system. *Hypertension* 45:341-346.

B48. Mohan, P., Brutsaert, D. L., Paulus, W. J., and Sys, S. U. 1996. Myocardial contractile response to nitric oxide and cGMP. *Circulation* 93:1223-1229.

B49. Kapoun, A. M., Liang, F., O'Young, G., Damm, D. L., Quon, D., White, R. T., Munson, K., Lam, A., Schreiner, G. F., and Protter, A. A. 2004. B-type natriuretic peptide exerts broad functional opposition to transforming growth factor-beta in primary human cardiac fibroblasts: fibrosis, myofibroblast conversion, proliferation, and inflammation. *Circ Res* 94:453-461.

Example 4

Sympathetic Renal Nerve Denervation

Endovascular intervention originally targeted to manage BP in patients with resistant hypertension
RDN inhibits activity of renal sympathetic efferent and afferent nerves that lie within and immediately adjacent to the wall of the renal artery
Preliminary catheter based RDN trials successful (Medtronic: SYMPLICITY HTN 1&2. St. Jude: EnligHTN 1, Boston Scientific: Vessix V2)
SYMPLICITY HTN-3: first randomized, sham-controlled trial failed to show systolic BP reductions compared to sham
Dozens of ongoing clinical trials Renal Denervation and Distant Organ Protection (Polhemus Presentation Therapeutic potential beyond blood pressure reduction?
Heart is critically regulated by autonomic nervous system
sympathetic nervous system plays a role in the pathogenesis of myocardial infarction and heart failure
sustained sympathetic overdrive results in oxidative stress and overactive beta-Adrenergic receptor signaling Heart Disease is the #1 Killer of Human Beings An MI occurs every 25 seconds in the US (~50% fatal)
5 million Americans suffer from heart failure
the incidence of heart failure exceeds all combined cancers
heart failure therapy=inadequate
drugs: beta-blockers, ACE inhibitors, MRAs, etc.
Devices: LVADS, pacemakers, etc.

Cardiac Injury and Repair Following Myocardial Infarction human LV has 2-4 billion heart muscle cells
MI can kill 25% of these cells in a few hours
adult mammals generate minimal new cardiac muscle cells
fibrotic cells replace cardiac myocytes
result is diminished contractile and relaxation function of the LV→HF
Specific Aim 1: To investigate the protective effects of RF-RDN on acute myocardial ischemia-reperfusion (MI/R) injury and survival in the setting of hypertension. We hypothesize that by decreasing sympathetic outflow globally, and specifically to the heart, RF-RDN has infarct sparing effects by improving redox balance, inhibiting pro-death signaling, and restoring NO signaling deficiencies associated with chronic hypertension.

Aim 1 Summary and Directions

RF-RDN reduces systemic and myocardial oxidative stress, inhibits of GRK2 signaling, and enhanced eNOS-NO signaling in SHR
RF-RDN protects against myocardial I/R injury in the setting of established hypertension by inhibiting pro-death signaling pathways that are associated with an overactive sympathetic outflow
RF-RDN does not reduce myocardial infarct size in normotensive WKY rats
The absence of myocardial protection afforded by RF-RDN in WKY is explained by low baseline GRK2 signaling and limited to eNOS dysfunction
Does RF-RDn reduce infarct size if given at the time of reperfusion?
a. current paradigm for AMI treatment: reflow with coronary angioplasty
b. clinical significance for treating AMI with percutaneous intervention
Specific Aim 2: To determine protective effects of RF-RDN on ventricular structure and function in a rat model of ischemic heart failure. We hypothesize that delayed RF-RDN treatment improves cardiac remodeling and ventricular function following ischemic injury, in part, by inhibiting myocardial fibrosis. WKY and SHR rats are treating with RF-RDN or SHAm-RDN 4 weeks following IM/R and monitored for 12 weeks.
Specific Aim 3: To investigate the interaction of renal sympathetic denervation and endogenous regulation of cardioprotective NPs. We have identified a possible link between the sympathetic nervous system and endogenous regulation of NPs. We examine the mechanisms by which RF-RDN modulates circulating NPs, with particular focus on the metabolism, excretion, and translation of these peptides following RF-RDN and SHR and WKY rats.

Aim 2 & 3 Summary and Directions

RF-RDN Preserves LV function and improves cardiac remodeling in the setting of ischemic heart failure in SHR and WKY.
RF-RDN Inhibits myocardial Fibrosis in ischemic heart failure.
RF-RDN modifies the endogenous regulation of cardioprotective NPs by inhibiting renal Neprilysin Activity.
Neprilysin inhibition results in increased levels of circulating cardioprotective and vasculoprotective peptides.
RDN-based therapeutics many prove beneficial for the treatment of heart failure
How does neprilysin inhibi4on in WKY compare to SHR in HF?
Does RF-RDN modulate NPs and inhibit neprilysin in essen4al hypertension without cardiac injury?
Does RF-RDN inhibit neprilysin in distant organs? Kidney specific?

G Protein-Coupled Receptor Kinase 2 (GRK2)

canonical GRK2 signaling: phosphorylates and desensitizes GPCRs
GRK2 is most abundant GRK in the myocardium
persistent binding of catecholamines to the βAR results in GRK-mediated cytotoxic cellular signaling pathways
phosphorylation at Ser670 results in GRK2 mitochondrial translocation and cell death induced by mitochondrial permeability transition pore opening Natriuretic Peptides and Heart Failure 1980s: The heart was recognized as an endocrine organ that secretes a family of hormones called natriuretic peptides
NPs primarily act on the vasculature and kidney to produce natriuresis, diuresis, and vasodilation to compensate for increased cardiac wall stress and volume Ventricular hypertrophy a augmented synthesis and release of NPs circulating BNP levels are an established biomarker of heart failure severity NP analogs such as Nesiritide (BNP) are often used for acute decompensated heart failure Example 5

Heart failure with preserved ejection fraction (HFpEF) accounts for approximately half of all prevalent heart failure. To date, we are not aware of any approved therapies available for reducing mortality or hospitalization rates in these patients.

The use of renal denervation (RDN) provides a safe and minimally invasive approach to reduce blood pressure. It acts, at least in part, by modulating the sympathetic nerves traveling to and away from the kidney. We have found that renal denervation (RDN) has remote protective actions on the heart, specifically in the setting of HFpEF.

Embodiments as described herein comprise the use of RDN in patients with HFpEF.

Embodiments as described herein, such as the use of RDN as an effective treatment for HFpEF, are unexpected, as other pharmacologic therapies that target the sympathetic nervous system are ineffective in patients with HFpEF.

One embodiment comprises the use of RDN at the time of diagnosis of HFpEF. At present, hypertension is the sole indication for RDN therapy. Without wishing to be bound by theory, RDN therapy could be used in patients with normal or high blood pressure with HFpEF to improve mortality and hospitalization rates.

Example 6

Repeated Cell Transplantation and Adjunct Renal Denervation in Ischemic Heart Failure: Exploring Modalities for Improving Cell Therapy Efficacy Background and Objectives: Enthusiasm for cell therapy for myocardial injury has waned due to equivocal benefits in clinical trials. In an attempt to improve efficacy, we investigated repeated cell therapy and adjunct renal denervation (RDN) as strategies for augmenting cardioprotection with cardiosphere-derived cells (CDCs). Without wishing to be bound by theory, combining CDC post-conditioning with repeated CDC doses or delayed RDN therapy would result in superior function and remodeling.

Wistar-Kyoto Rats (WKY) or Spontaneously Hypertensive Rats (SHR) were subjected to 45 minutes of coronary artery ligation followed by reperfusion for 12-14 weeks. In the first study arm, SHR rats were treated with CDCs (0.5×106 I.C.) or PBS 20 minutes following reperfusion, or additionally treated with CDCs (1.0×106 I.V.) at 2, 4, and 8 weeks. In the second arm, at 4 weeks following myocardial infarction (MI), SHR rats received CDCs (0.5×106 I.C.) or CDCs+RDN. In the third arm, WKY rats were treated with I.C. CDCs administered 20 minutes following reperfusion and RDN or a sham at 4 weeks. Multiple dosing (i.e. early I.C.+multiple I.V dosing), but not single I.C. dosing, of CDCs improved long-term left ventricular (LV) function, but not remodeling. Delayed CDC+RDN therapy was not superior to single dose delayed CDC therapy. Early CDC+ delayed RDN therapy improved LV ejection fraction and remodeling compared to both CDCs alone and RDN alone.

Our findings motivate further translation targeting a heart failure indication with combined approaches.

Introduction

The current paradigm for treating myocardial infarction (MI) is timely reperfusion. Unless reperfusion is prompt, ischemic and reperfusion-induced injury lead to scar formation, wall thinning, and adverse cardiac remodeling. Many strategies to reduce infarct size and provide long-term structural and functional benefit have failed (1). Specifically, treatment with stem and progenitor cells has been pursued with the ultimate goal of cardiac regeneration. However, enthusiasm for cell-based therapies for cardiac injury has been stifled by inconsistent or undetectable benefits in single-dose clinical trials (2-4). The lack of efficacy of cell therapy has been suggested to be due to poor engraftment of stem/progenitor cells and the limitations of single-dose administration. Several lines of evidence suggests that repeated doses of transplanted cells result in enhanced myocardial protection or recovery (5,6). Protection is likely due to the paracrine effects of the transplanted cells, which produce a host of protective factors (7-9). Cell engraftment is limited and transient, at levels <3% by 35 days, and regenerative capacity by canonical stem cell mechanisms is likely below levels that reach clinical significance (10).

Both cell therapy and renal denervation (RDN) have shown some promise, particularly in preclinical settings, but both have met setbacks in clinical testing (11-16). Cell therapy has been proposed as a means to offset loss of functional muscle, while RDN blocks secondary maladaptive autonomic pathways that perpetuate and exacerbate post-MI heart failure. Here, we investigated potential modalities for improving cell-therapy following MI. First, we investigated the efficacy of repeated cell administrations. Secondly, because cell therapy and RDN target different steps in the pathophysiology of heart failure, therapy with cardiosphere-derived cells (CDCs) during early reperfusion, coupled with delayed RDN, may provide more robust and durable effects on cardiac structure and function than either therapy alone. The advantage for combining cell therapy with RDN, as opposed to pharmacologic agents is that neither therapy requires pretreatment or dependence on patient adherence, increasing the clinical viability of the combination.

Here, we demonstrate, in a rodent model of MI, that treatment with CDCs soon after reperfusion has short-term benefits in systolic function, which attenuate over time. This improvement in function, however, is sustained with follow-up doses of IV infusions of CDCs. Moreover, while single-dose CDC administration soon after reperfusion only improves short-term function and has no impact on long-term remodeling, RDN prevents late-stage cardiac dilation and systolic dysfunction. When combined, we find that the two approaches lead to enhanced lasting improvements of systolic function, as well as salutary changes in structural remodeling.

Methods

Experiment Animals—Male Wistar-Kyoto rats (WKY) or spontaneously hypertensive rats (SHR) 19-20 weeks of age (Charles River Laboratories) were used in the study. All animals were housed in a temperature-controlled animal facility with a 12-hour light/dark cycle, with water and rodent chow provided ad libitum. All animals received humane care in compliance with the Principles of Laboratory Animal Care formulated by the National Society of Medical Research and the Guide for the Care and Use of Laboratory Animals published by the NIH (8th Edition, Revised 2011). The LSUHSC New Orleans IACUC approved all animal procedures.

Myocardial Ischemia/Reperfusion—Myocardial ischemia-reperfusion was performed as described previously by our group (24). Following 45 minutes of ischemia, rats underwent coronary reperfusion and were maintained on study for 12 or 14 weeks. During this time cardiac structure and function were assessed using two-dimensional echocardiography. Animals were excluded from the study protocol if there was <15% reduction in LVEF at 2 weeks in the SHR studies and <10% reduction in LVEF at 2 weeks in WKY studies.

Cardiosphere Derived Cells (CDCs) Administration—CDCs from WKY rats were derived, expanded, and prepared as previously described [7]. At 20 minutes of reperfusion, the aorta was cross-clamped for 15 seconds during which time $0.5\times10^6$ cells or PBS were injected with a 30-gauge needle into the LV lumen to achieve effective intracoronary delivery [12]. In the multiple dosing study, $1.0\times10^6$ cells or PBS were also injected with a 30-gauge needle into the tail vein at the 2, 4, and 8-week timepoints.

Radiofrequency Renal Denervation Procedure—SHR and WKY were randomly divided into either a RF-RDN or sham-RDN group 4 weeks after ischemia-reperfusion. RF-RDN was performed as previously described (24).

Echocardiography—Prior to MI, baseline parasternal long axis, two-dimensional and M-mode echocardiography was performed using MS250 13-24-MHz probe on a Vevo 2100 (Visualsonics) under anesthesia with isoflurane (1%) supplemented with 100% O2. Serial echocardiography was also performed in the same manner. LV end diastolic dimension (LVEDD) and LV end systolic dimension (LVESD) were analyzed from EKV™ (ECG-Gated Kilohertz Visualization) generated M-mode long-axis images. LV ejection fraction (LVEF) was determined using LV Trace from an EKV™ generated long axis B-mode image.

Biofluorescence Imaging—CDCs ($1\times10^6$) were labeled with the liposomal dye DiD (ThermoScientific) and then delivered intravenously (tail vein infusion) following myocardial ischemia-reperfusion. Two hours later, organs (heart, lungs, liver, kidneys, spleen) were excised, rinsed in PBS, and then imaged for biofluorescence (Xenogen IVIS Lumina, PerkinElmer). CDC biofluorescence was normalized against organ-specific autofluorescence by acquiring CDC-treated and control organs within the same field.

Left Ventricular and Arterial Blood Pressure Measurements—At 14 weeks, LV end-diastolic pressure and carotid pressures were determined using a pressure catheter (Transonic Scisense Pressure Measurement system) under 1.0% isoflurane supplemented with 100% O2. Analysis was performed using LabChart Pro software.

Assessment of Cardiac Fibrosis—At the 12 or 14-week endpoints, hearts were arrested in diastole (potassium chloride), fixed in zinc formalin, embedded in paraffin, sectioned at one level, cut twice and stained for Masson's Trichrome to detect fibrosis. In a blinded fashion, infarct area of LV was calculated as total fibrotic area/myocardium area×100. Infarct expansion scores were determined in a blinded fashion (Alizee Pathology LLC, Thurmont, Md., USA) as previously described [25]. 0=the solid fibrous scar has a well-defined external border without evidence of interstitial fibrosis extending into the surrounding myocardium. 1=the solid fibrous scar has a well-defined external border with evidence of interstitial fibrosis extending slightly (up to ~300 microns) into the surrounding myocardium in few areas with most areas having 100 microns or less of border zone expansion. 2=the solid fibrous scar has poorly defined external borders with interstitial fibrosis extending greater than 300 microns but less than 500 microns in numerous areas surrounding the solid scar. 3=the solid fibrous scar has poorly defined external borders with widespread extension of interstitial fibrosis (greater than 500 microns) in multiple areas surrounding the solid scar.

Kidney Norepinephrine measurement—At the 14-week endpoint, kidney cortex was homogenized and norepinephrine levels were measured using ELISA technique according to the manufacturer's recommendations (Abnova Co.)

Plasma Angiotensin II and Aldosterone measurements—At the 14-week endpoint, plasma concentrations of angiotensin II and aldosterone were determined using ELISA technique according to the manufacturers recommendations (Enzo Life Sciences).

Statistical Analyses—All pooled data are expressed as the mean±SEM. A repeated measure two-way ANOVA with matched values and Bonferroni post-test were used for echocardiography analyses. Multiple Mann-Whitney tests were used for ranked histological analysis. p values of <0.05 were considered statistically significant. Unmarked p-values indicate no statistical difference between groups.

Results

Biodistribution of CDCs Following I. V. Dosing

Following MI/R, rats were infused intravenously with either PBS or CDCs (DiD-labeled, $1\times10^6$). Organs were harvested two hours later to examine CDC distribution in various organs following I.V. delivery. CDCs were primarily concentrated in the lungs and liver (FIG. 1B) with 3500-fold higher concentration of CDCs in the lungs than the heart. CDCs were undetectable in the kidneys at this timepoint.

Figure 107:
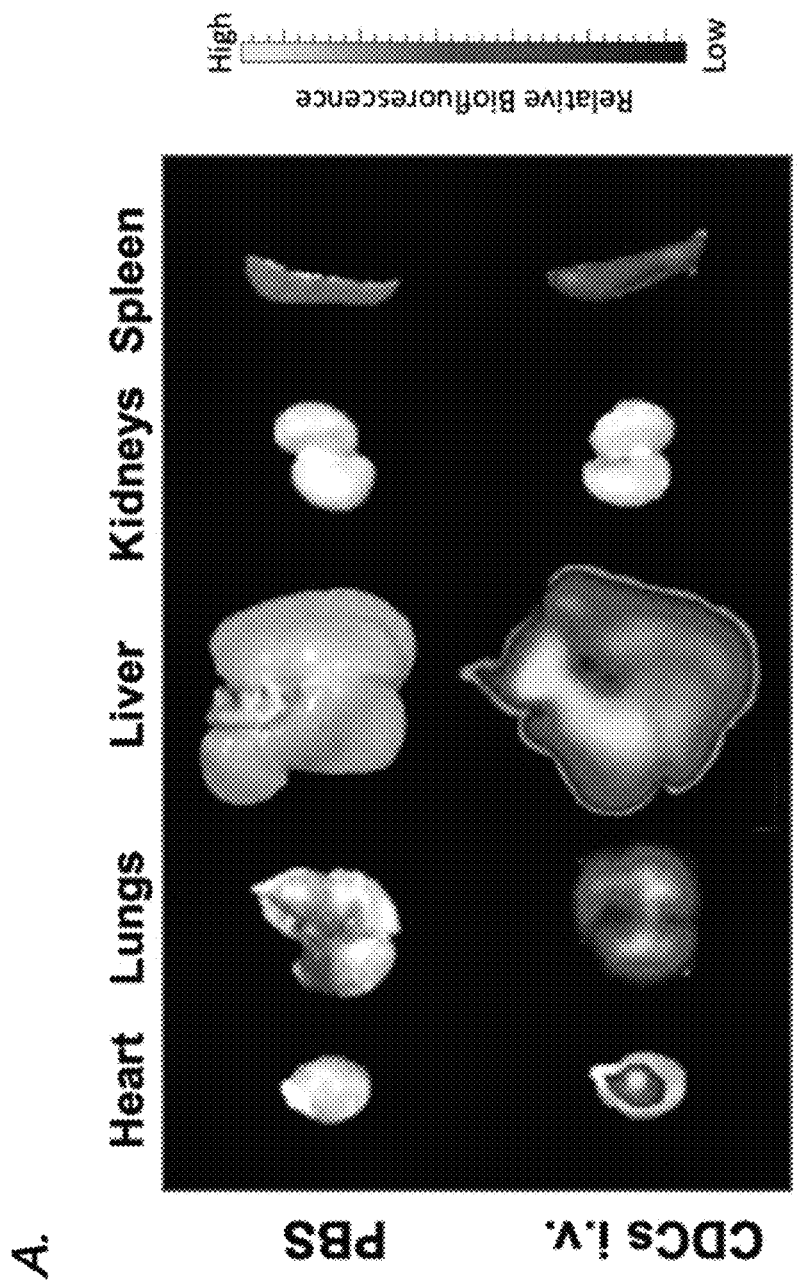
FIG. 107 shows (A) Cardiosphere-derived cell (CDC) biodistribution following MI. Representative biofluorescence images of organs harvested from rats treated intravenously with PBS or CDCs (Did-labeled; $1.0 \times 10^6$) post-MI. (B) Quantification of total CDC biofluorescence relative to control tissue (n=4). (C) Ischemic heart failure protocol. Myocardial ischemic reperfusion injury protocol in SHR rats. Rats were subjected to 45 minutes of coronary artery ligation followed by 12 weeks of reperfusion. SHR were treated with either PBS or $0.5 \times 10^6$ CDCs via intracardiac delivery with aortic crossclamp 20 minutes into reperfusion. SHR were then treated with either PBS or $1.0 \times 10^6$ CDCs via tail vein injection at 2, 4, and 8 weeks. (D) LV ejection fraction, (E) LV end-diastolic dimensions, and (F) LV end-systolic dimensions. Mean is represented +/−SEM. *=p<0.05 compared to PBS, =p<0.01 compared to PBS, *=p<0.001 compared to PBS, and ****=p<0.001 compared to PBS.
Figure 115:
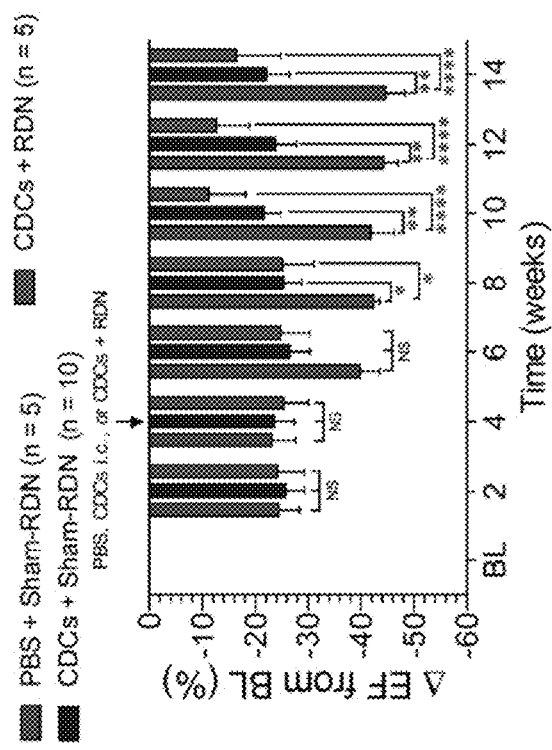
FIG. 115 shows (A) SHR were subjected to 45 minutes of complete coronary artery occlusion followed by 12 weeks of reperfusion. Rats were treated with either PBS or $0.5 \times 106$ CDCs via intracardiac delivery into the left ventricular lumen with aortic cross-clamp at 20 minutes following reperfusion. SHR were then treated with either PBS or $1.0 \times 106$ CDCs via tail vein injection at 2, 4, and 8 weeks following ischemia and reperfusion. The Graph represents the change in LV ejection fraction relative to baseline levels for each study group. (B) SHR rats were subjected to 45 minutes of coronary artery ligation followed by 14 weeks of reperfusion. Rats were treated with either PBS or $0.5 \times 106$ CDCs via intracardiac delivery with aortic cross-clamp at 4 weeks following reperfusion. Rats were also treated with either Sham-RDN or bilateral radiofrequency (RF)-RDN at 4 weeks into reperfusion. Graph represents the absolute change LV in ejection fraction relative to baseline levels. (C) Normotensive WKY rats were subjected to 45 minutes of coronary artery ligation followed by 14 weeks of reperfusion. WKY were treated with either PBS or $0.5 \times 10^6$ CDCs via intracardiac delivery with aortic cross-clamp at 20 minutes into reperfusion. WKY were then treated with either Sham-RDN or bilateral radiofrequency (RF)-RDN at 4 weeks post-reperfusion. Graph represents the change in LV ejection fraction relative to baseline levels.

Early I.C. CDCs+Repeated I.V. CDC Therapy has Superior Sustaining Improvements on LV Ejection Fraction Compared to Single Dose I.C. CDCs CDCs were administered at 20 minutes after reperfusion into the LV lumen under aortic cross-clamp, or additionally by IV infusion at 2, 4, and 8 weeks following myocardial ischemia-reperfusion injury in SHR rats (FIG. 107, panel C). Single dose injection of CDCs soon after MI yielded trending transient improvements in EF compared to control (FIG. 107, panel D). In contrast, multiple-dose treatment resulted in improvements in EF beginning as early as 4 weeks, and these benefits were maintained throughout the study (FIG. 107, panel D). Delta EF relative to baseline values are shown in FIG. 115, panel A. Neither single- nor multiple-dose treatments of CDCs improved cardiac dilation; and all improvements in ejection fraction were due to a reduction in end-systolic dimensions compared to control (FIG. 107, panels E-F).

Cardiac Fibrosis Following CDC Therapy for Myocardial Infarction

Figure 108:
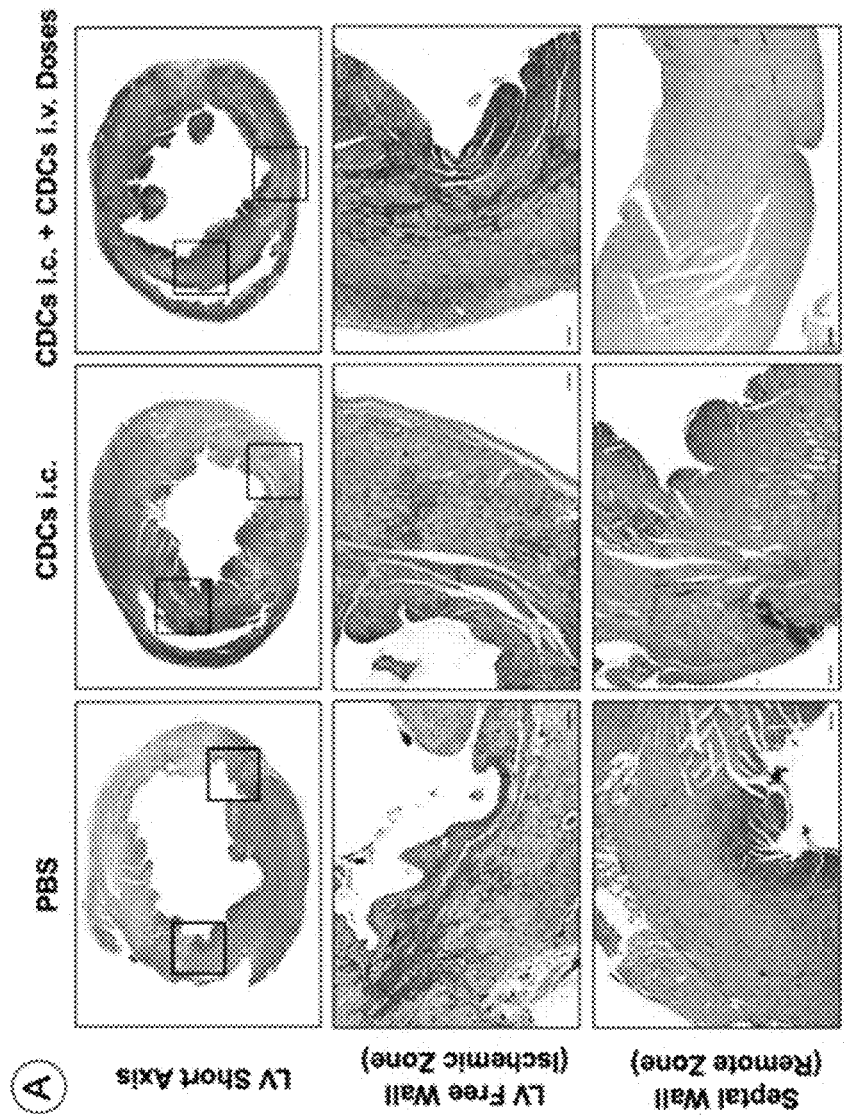
FIG. 108 shows cardiac fibrosis at 12 weeks following ischemic injury in SHR rats. (A) Representative images stained with Masson's Trichrome of the mid-ventricular short axis LV, free wall (ischemic zone) and the remote zone of the septum. (B) Total LV, LV free wall, and septal fibrosis in the PBS, CDCs I.C., and CDCs I.C.+CDC IV Doses groups. Mean is represented +/−SEM. *=p<0.05 compared to PBS and **=p<0.01 compared to PBS

Analysis of cardiac fibrosis at the study endpoint revealed that single I.C. injection of CDCs at reperfusion did not reduce cardiac fibrosis compared to PBS when quantified as total LV fibrosis, infarct zone fibrosis (LV free wall), or remote zone fibrosis (septal wall) in SHR rats (FIG. 108). However, multiple-dose treatment reduced total LV fibrosis compared to the PBS and single-dose treatment groups, reduced infarct zone fibrosis compared to the single-dose group, and lowered remote zone fibrosis compared to the PBS and single dose groups (FIG. 108). The remote protection distant from the infarct injury shows that repeated CDC therapy has cardioprotective actions which extend beyond tissue repair of ischemic myocardial cells.

Figure 109:
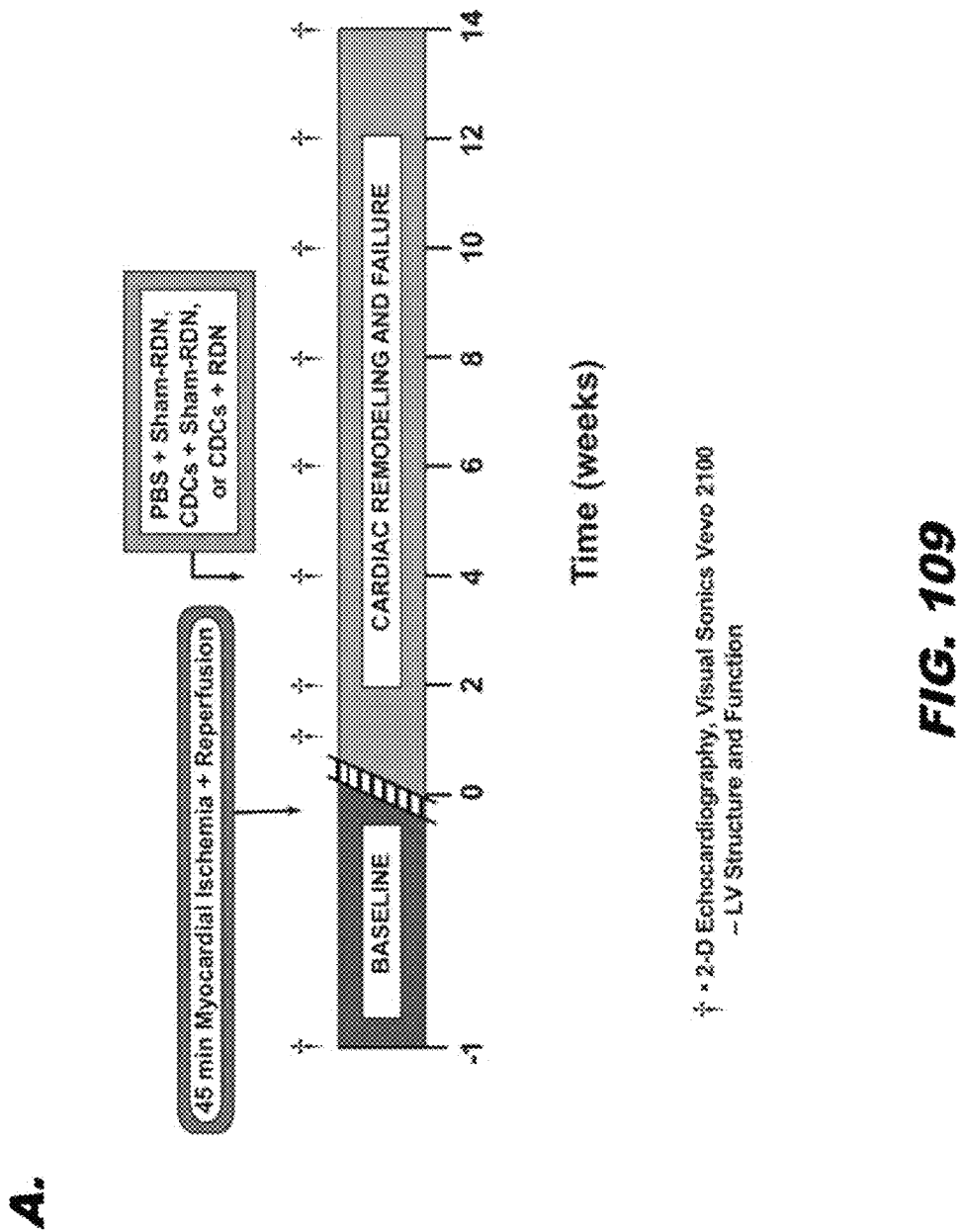
FIG. 109 shows (A) Ischemic heart failure protocol. Myocardial ischemic reperfusion injury protocol in SHR rats. Rats were subjected to 45 minutes of coronary artery ligation followed by 14 weeks of reperfusion. SHR were treated with either PBS or $0.5 \times 10^6$ CDCs via intracardiac delivery with aortic crossclamp 4 weeks into reperfusion. SHR were also treated with either Sham-RDN or bilateral radiofrequency (RF)-RDN at 4 weeks into reperfusion. (B) LV ejection fraction, (C) LV end-diastolic dimensions, and (D) LV end-systolic dimensions. Mean is represented +/−SEM. *=p<0.05 compared to PBS, =p<0.01 compared to PBS, and *=p<0.001 compared to PBS.

Delayed CDC+RDN Therapy Improves Ventricular Function but is Not Superior to Delayed CDC Treatment CDC or CDC+RDN therapies were given at 4 weeks following myocardial ischemia-reperfusion injury in SHR rats (FIG. 109, panel A). Delayed single-dose i.c. injection of CDCs post-MI yielded lasting improvements in EF compared to control (FIG. 109, panel B). Additionally, delayed CDC+RDN treatment resulted in lasting improvements in EF compared to control, but not beyond those of independent CDC therapy. LVEF improvements were observed as early as 2-4 weeks after treatments. Delta EF relative to baseline values are shown in FIG. 115, panel B. Both CDC and CDC+RDN similarly improved LV end-systolic diameter compared to control (FIG. 109, panel D. Neither CDCs alone nor CDC+RDN significantly mitigated cardiac dilation as measured by LV end-diastolic diameter, although there was a trending improvement in both treatment groups (FIG. 109 panel C).

Figure 11:
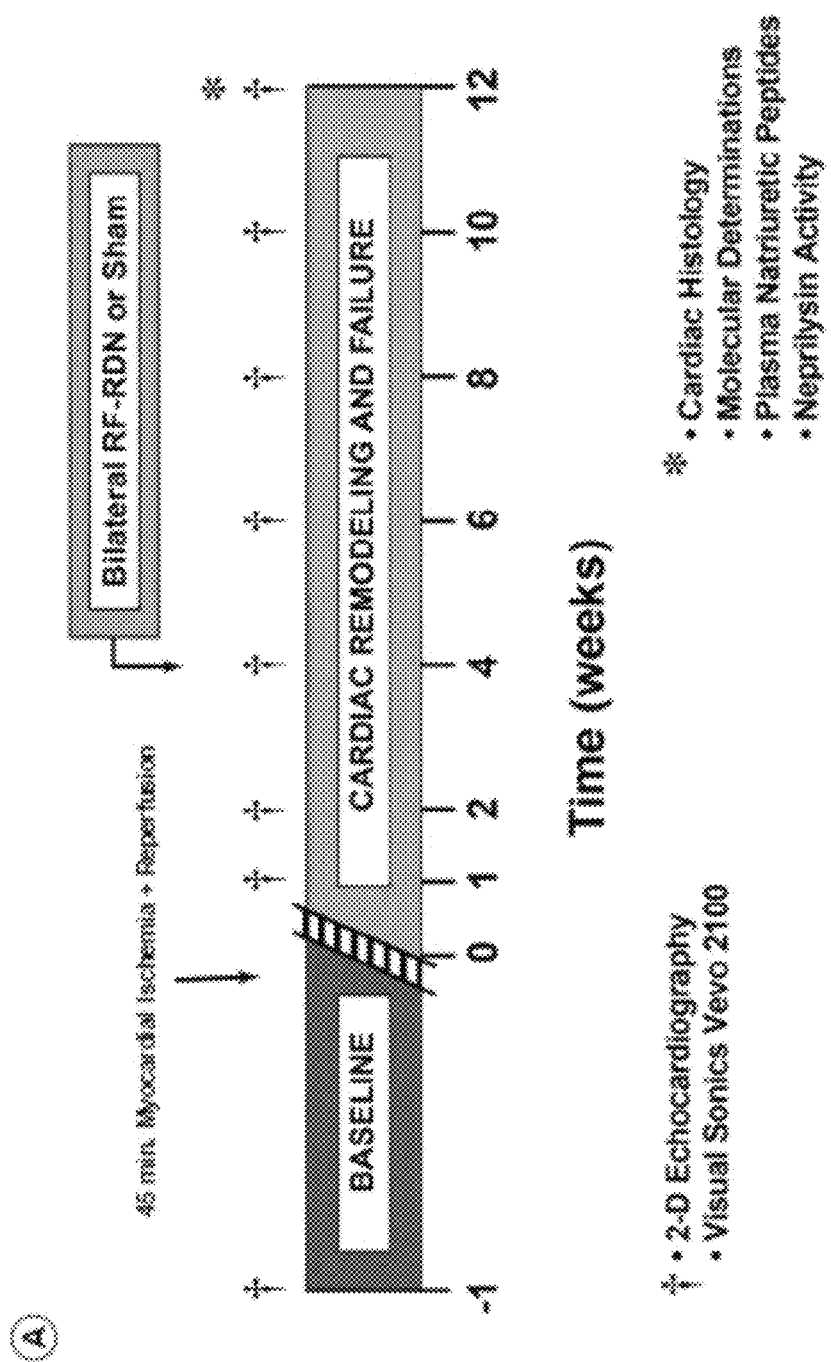
FIG. 11 shows ischemic heart failure experimental protocol with delayed RF-RDN therapy. (A) Experimental HF protocol for SHR and WKY rats. Rats were subjected to 45 minutes of ischemia following by 12 weeks of reperfusion. 4 weeks following FR injury, SHR and WKY rats were treated with either Sham-RDN or RF-RDN. Echocardiography was performed at baseline, 1, 2, 4, 6, 8, 10, and 12 weeks. Tissue was collected at the 12 week endpoint for analysis. (B) Plasma cardiac troponin-I levels 2 hours after reperfusion displaying equal ischemic injury in Sham-RDN and RF-RDN treated SHR and (C) WKY rats. Values are expressed as mean±SEM.
Figure 110:
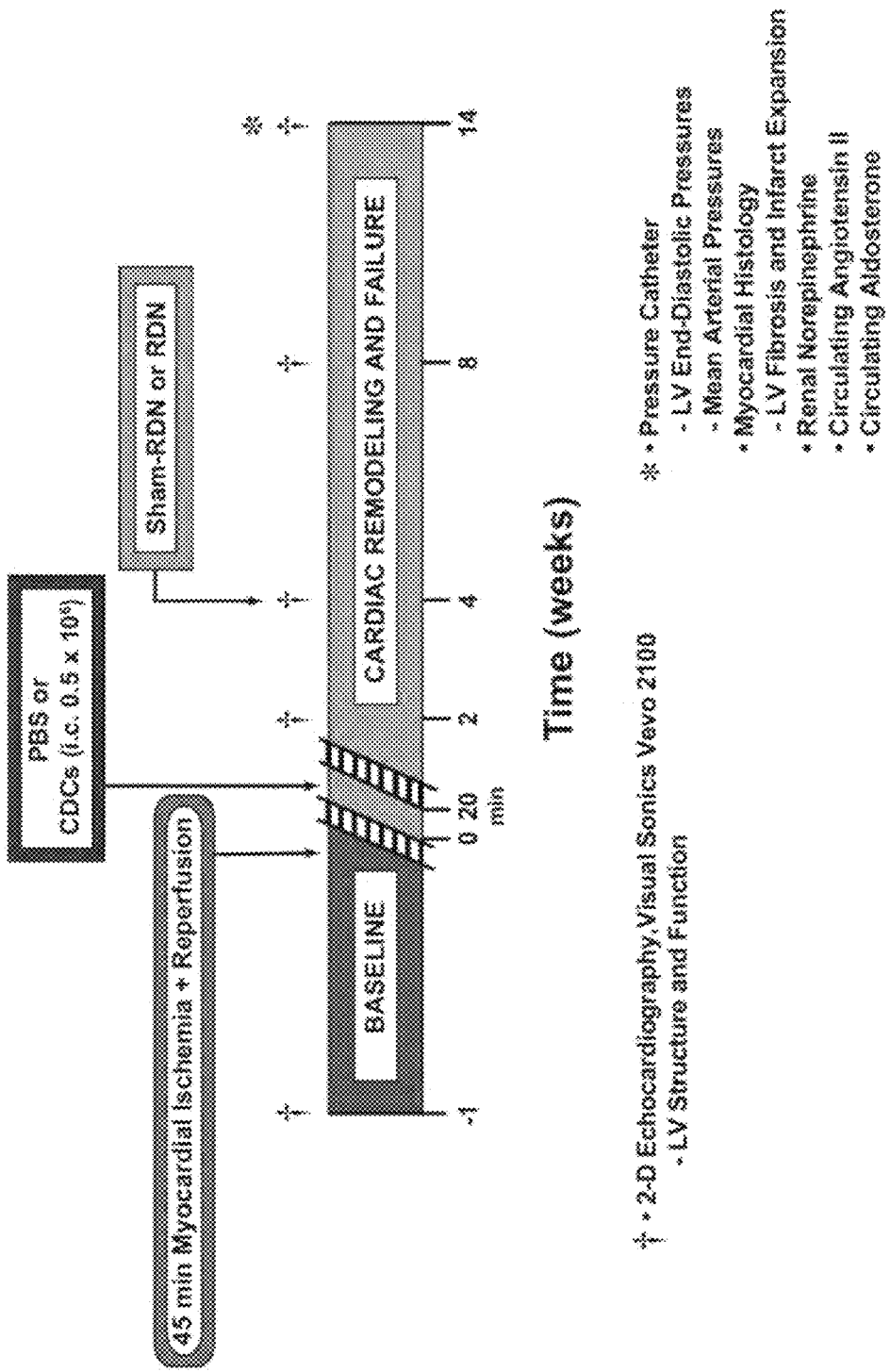
FIG. 110 shows ischemic heart failure protocol. Myocardial ischemic reperfusion injury protocol in WKY rats. Rats were subjected to 45 minutes of coronary artery ligation followed by 14 weeks of reperfusion. WKY were treated with either PBS or $0.5 \times 10^6$ CDCs via intracardiac delivery with aortic crossclamp 20 minutes into reperfusion. WKY were then treated with either Sham-RDN or bilateral radiofrequency (RF)-RDN at 4 weeks into reperfusion.

CDCs Improve Short-Term Ejection Fraction while RDN Preserves Long-Term Function Given the lack of additional benefit of combining CDCs+RDN therapy at 4-weeks of reperfusion compared to single therapy, we modified the treatment protocol to administer CDCs early into reperfusion followed by RDN at 4 weeks post-reperfusion treatment timepoint in normotensive WKY rats (FIG. 110). CDC therapy alone, given 20 minutes into reperfusion, preserved LVEF through the 2, 4, and 8-week time points (FIG. 11 panel A). However, by 14 weeks, the systolic function improvements in CDC-treated WKY diminished such that LVEF was no longer significantly superior to PBS+Sham-RDN. Improvements in LVEF in the RDN treated rats were observed as early as 4 weeks after denervation and were maintained above the PBS+Sham-RDN treated rats throughout the 14-week experiment. At 8 weeks, LVEF in CDC+RDN treated rats trended to be superior to either CDCs or RDN alone. These differences were statistically significant by 14-weeks, when LVEF with combined CDC+RDN treatment was 22% and 30% greater than RDN and CDCs alone, respectively. Delta EF relative to baseline values are shown in FIG. 115, panel C.

Figure 111:
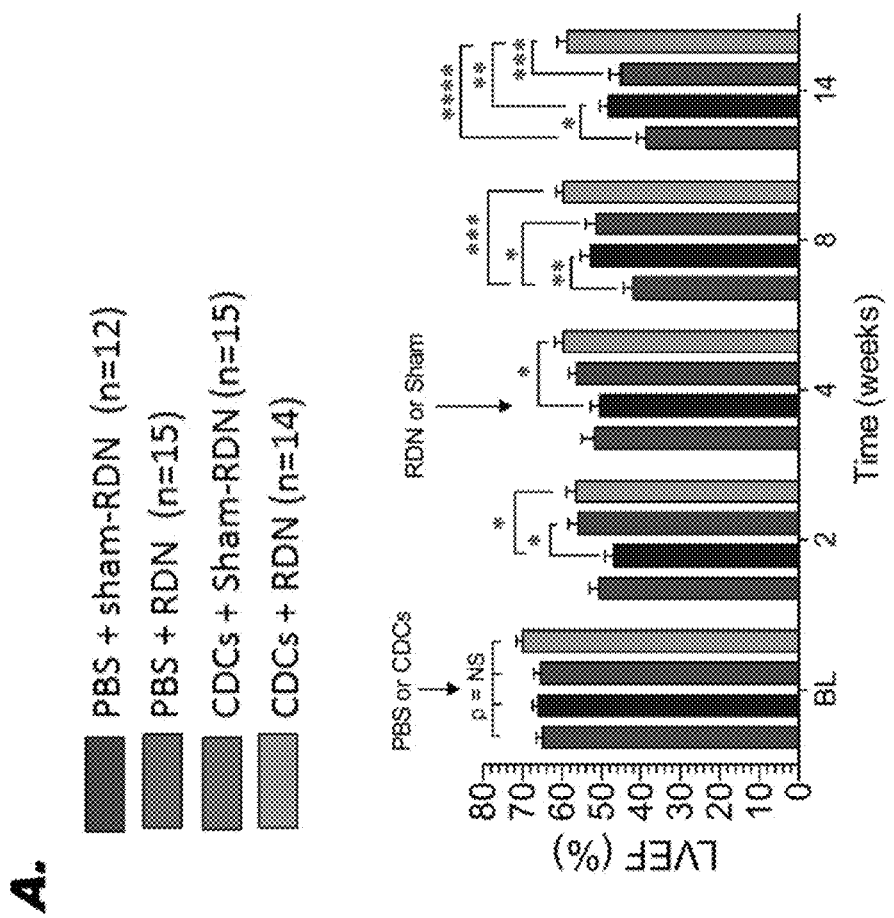
FIG. 111 shows cardiac structure and function following CDC and RDN Therapy in WKY rats. (A) LV ejection fraction, (B) LV end-diastolic dimensions, (C) LV end-systolic dimensions, and (D) intraventricular septal diameter at systole. Mean is represented +/−SEM. *=p<0.05, =p<0.01, *=p<0.001, and ****=p<0.001.

RDN, but Not CDC, Therapy Improves Ventricular Dilation Following Ischemic Injury Left ventricular dimensions at end-diastole (FIG. 11, panel B) and end-systole (FIG. 111, panel C) revealed that ventricular dilation in the CDC therapy progressed similar to the PBS+Sham-RDN treated rats by the study end-points. Conversely, RDN attenuated remodeling and statistical improvements compared to PBS+Sham-RDN and CDC+Sham-RDN were reached by 14 weeks. There were no greater reductions in dilation in the CDC+RDN group compared to PBS+RDN, indicating that all improvements in remodeling were due to RDN treatment. Wall thickness, as measured by interventricular septal diameter at systole (IVSs) indicated that wall thickness was preserved in the CDC+Sham-RDN group through 8 weeks but was lost by the 14-week endpoint (FIG. 111, panel D). However, the CDC+RDN group had a significantly IVSs at 14-weeks compared to CDC+Sham-RDN, indicating that the addition of RDN therapy preserved both structure and function compared to cell-therapy alone.

Effects of RDN on the Sympathetic Nervous System

Figure 112:
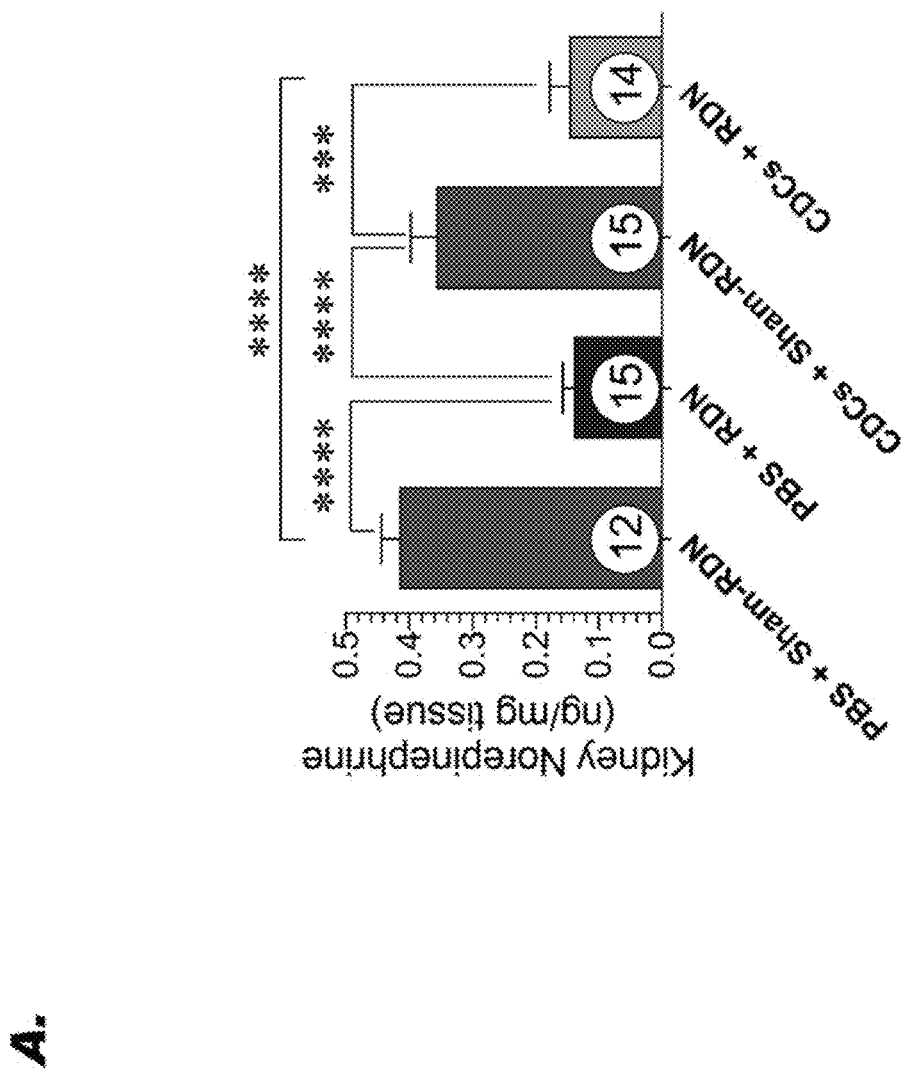
FIG. 112 shows renal sympathetic tone in Sham-RDN and RDN treated WKY rats 8 weeks after treatment. (A) Kidney norepinephrine content, (B) plasma angiotensin II and (C) plasma aldosterone levels at the 14-week timepoint. Mean is represented +/−SEM. *=p<0.05, =p<0.01, *=p<0.001, and ****=p<0.001.
Figure 112:
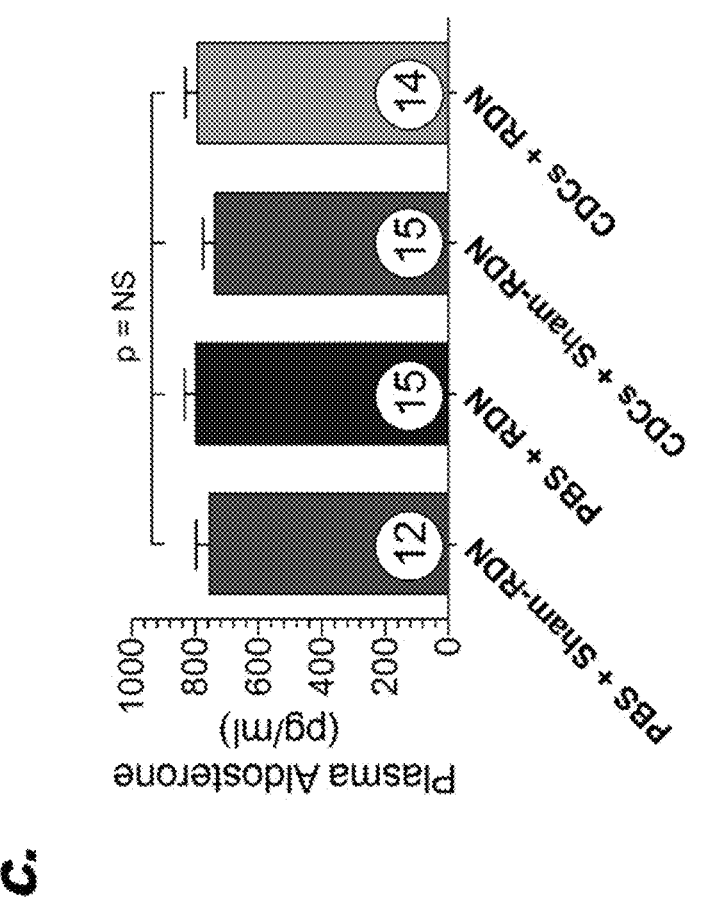

As we have previously reported, renal denervation exerts sustained effects on the renal sympathetic activation state following ischemia-reperfusion injury. PBS+RDN and CDC+RDN treatments equally reduced kidney norepinephrine levels (NE), which indicates equivalent reductions in renal sympathetic nerve activity (FIG. 112, panel A). CDC+Sham-RDN failed to reduce kidney NE content below PBS+Sham-RDN levels, indicating that CDCs do not alter renal sympathetic nerve activity. In a similar fashion, PBS+RDN and CDC+RDN groups had significantly lower circulating angiotensin II levels compared to PBS+Sham-RDN at 14-weeks (FIG. 112, panel B). There was no difference in plasma angiotensin II concentrations between the PBS+Sham-RDN and CDCs+Sham-RDN groups. The alterations in angiotensin II levels resulting from RDN treatment did no extend to modifications in plasma aldosterone. There were no differences in aldosterone concentrations among study groups at 14-weeks (FIG. 112, panel C).

Arterial Blood Pressure and LV Pressure Following CDC and RDN

Figure 113:
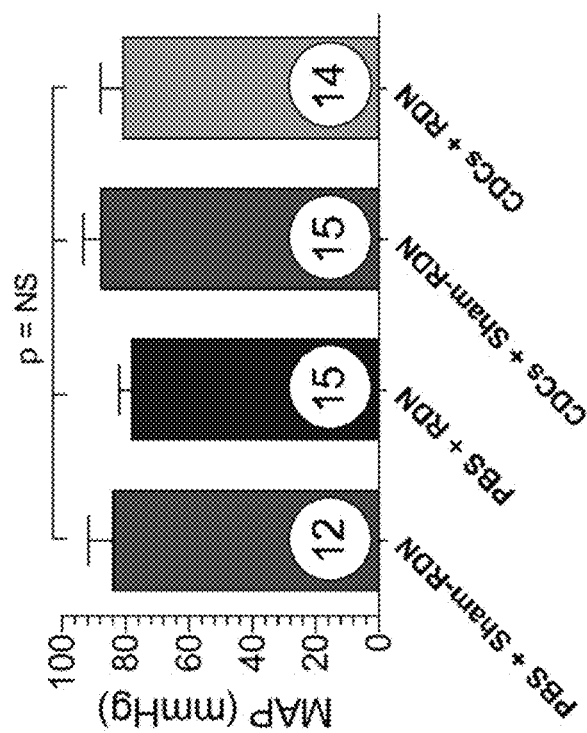
FIG. 113 shows hemodynamics and ventricular pressures in WKY rats at 14-weeks. (A) Carotid artery mean arterial pressures and (B) LV end-diastolic pressures at the 14-week endpoint. Mean is represented +/−SEM. *=p<0.05

RDN was developed for and is currently in clinical trials for the treatment of resistant hypertension (3). Clinical studies have shown that RDN decreases systolic and diastolic blood pressure in both patients on and off antihypertensive medications (2, 16, 30). However, we have previously demonstrated that in normotensive animals, RDN does not have any blood pressure lowering effects or heart rate altering effects (24). In the present study, we confirmed that CDCs and RDN do not have any significant impact on arterial pressure in the setting of post-ischemic injury in normotensive WKY rats (FIG. 113, panel A). Following ischemic injury, LV end-diastolic pressures rise, which can cause pulmonary congestion. All treatment combinations reduced LVEDP compared to the control PBS+Sham-RDN group, but the combination of CDCs+RDN was not greater than either treatment alone (FIG. 113, panel B).

Cardiac Fibrosis Following Ischemic Injury in CDC and RDN Treated Rats

Figure 114:
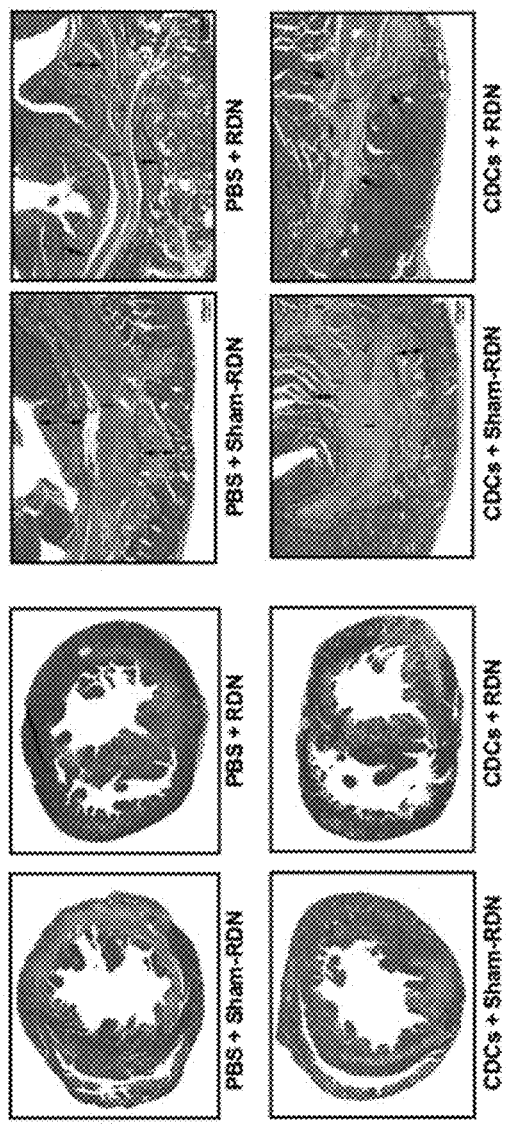
FIG. 114 shows cardiac fibrosis following ischemic injury in WKY. Representative images in LV stained with Masson's Trichrome of the (A) mid-ventricular short axis and (B) the solid fibrous infarct (I) and the infarct expansion zone (dotted lines with arrows) at 14 weeks following myocardial infarction in animals treated with PBS+Sham-RDN, PBS+RDN, CDCs+Sham-RDN, and CDCs+RDN. (C) Total LV fibrosis relative to the LV and (F) Infarct expansion score. Mean is represented +/−SEM. *=p<0.05, **=p<0.01.
Figure 114:
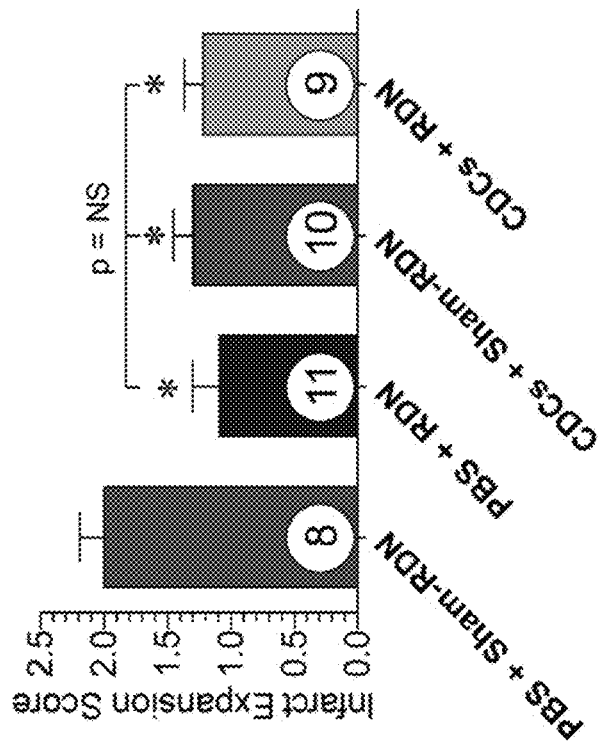

CDC and RDN treatments both independently reduced LV fibrosis area compared to the control PBS+Sham-RDN group (FIG. 114, panel C). The combination of these treatments, however, did not further reduce cardiac fibrosis relative to the LV. Similarly, CDC and RDN independently inhibited infarct expansion, and comparable reductions were observed in the CDC+RDN treated animals following ischemia-reperfusion injury (FIG. 113, panel D).

Discussion

Cell therapy for cardiac injury, in particular heart failure following MI, has largely failed to meet early hopes and expectations of myocardial regeneration and long-term functional improvements. Although hotly debated, poor clinical efficacy is likely due, in part, to the inability of sufficient cell engraftment, poor cell survival, non-localized cell delivery, and/or improper dosing strategies (22).

We investigated multiple strategies for improving cell therapy effects on post-infarction function and remodeling. In this pursuit, we utilized a thoroughly-investigated cell therapy product, CDCs, whose bioactivity and protective mechanisms have been elucidated by >45 independent laboratories (19). CDCs secrete vesicles called exosomes, which are packed with signaling RNAs and proteins that modulate macrophages, fibroblasts, endothelial cells, and cardiomyocytes (6, 9, 18). Modification of resident macrophages dampens the host's innate immune response to ischemia-reperfusion injury and results in infarct size reduction (7, 19). Late phase effects of CDCs include alteration in polarization of infiltrating macrophages, increased clearance of necrotic debris, and preservation of structural and functional myocardium (19). Recently, CDCs have been tested in patients with LV dysfunction and a remote MI (>1.5 months) in 2 distinct clinical trials (CADUCEUS [Cardiosphere-Derived Autologous Stem Cells to Reverse Ventricular Dysfunction](21) and ALLSTAR [Allogeneic Heart Stem Cells to Achieve Myocardial Regeneration] (5)). In both trials, the cells were safe, and showed signs of efficacy in improving LV structure and function post-MI, when delivered through the infarct-related coronary artery in chronically-injured hearts.

In the first arm of the study, we examined the efficacy of repeated CDC therapy following MI (FIG. 107 and FIG. 108). As has been consistent with numerous clinical trials, single CDC therapy, when given early into reperfusion did not have lasting improvements on ventricular function or structure. Conversely, early CDC therapy followed with IV CDC doses at 2, 4, and 8 weeks yielded lasting improvements on LV ejection fraction. This is an important finding because not only was a multiple administration strategy efficacious, but also it indicates that I.V. delivery of cells peripherally can lead to a biological response in the myocardium. Consistent with previous work, the major effect of the second injections of CDCs appears to be maintenance of benefit, rather than incremental improvement [26]. Additionally, multiple doses of CDCs reduced cardiac fibrosis in the infarct zone as well as the remote zone of the LV. This attenuation of fibrosis was not observed in the single-treatment group. These findings have far reaching clinical implications for patients who may be able to receive cell therapy efficaciously in a far less invasive I.V. delivery.

The sympathetic nervous system contributes to the pathophysiology of cardiac remodeling and failure in post-MI patients (31). Because of this, drugs that regulate downstream effects of the sympathetic nervous system (i.e., beta blockers, ACE inhibitors, ARBs) are regularly used, with much success, in this patient population. These drugs have several limitations, including off-target side effects, significant cost burden, and patient non-adherence. Meanwhile, their 5-year mortality rate is at an inadequate rate of 50%. We have previously explored the use of RDN as a means to dampen SNS activity in ischemia-induced heart failure and potentially replace or supplement current HF pharmacotherapies on the market. We found that delayed RDN therapy has lasting improvements on LV function and structure, augments protective circulating natriuretic peptide levels, and reduces cardiac fibrosis (25, 29). The protective actions of RDN are independent of blood pressure lowering effects. These findings were reaffirmed in the present study that illustrates that RDN has lasting effects on LVEF and cardiac dilation, with sustained reductions in renal sympathetic nerve activity. Because there is no evidence of CDCs, or cell therapy, modulate the pathological actions of the sympathetic nervous system in HF, we proposed combining these complementary treatment strategies that are less susceptible to patient non-adherence.

We first examined the combination of delayed CDC therapy at the same time as delayed RDN following myocardial ischemia-reperfusion injury (FIG. 109). This protocol mimics a treatment regimen for a heart failure patient suffering from chronic heart failure. In this model, single-dose CDCs that were delivered 4 weeks following reperfusion resulted in preserved LV function compared to the declining LVEF in the HF control group. However, the addition of RDN with CDC therapy, when both given at 4 weeks, did not further improve cardiac function beyond CDC treatment levels.

In the third arm, we delivered CDCs 20 minutes into reperfusion in an attempt to recruit early cardioprotection (FIGS. 110-114). CDC treatment had early benefits on EF (up to 8 weeks), but the benefit was lost by 14 weeks. Interestingly, CDCs did not prevent LV dilation at any time point. Despite this, CDC treatment alone reduced myocardial fibrosis as effectively as any of the other active treatments, indicating a disconnect between cardiac fibrosis and remodeling. CDC treated rats had significantly improved LVEDP compared to the PBS+Sham-RDN group indicating long-term improvements in diastolic function, but only short-term improvements in systolic function. Given the efficacy of CDCs to prevent immediate decline in cardiac function following ischemic injury, we investigated combining this post-conditioning treatment with another single-procedure therapy that maintains cardiac function and structure following ischemic injury: RDN (25). The reduction of cardiac fibrosis by single CDC therapy can be contrasted to the lack of reduction in fibrosis by single CDC therapy in the first arm of the study. In the first arm we utilized a hypertensive SHR rat, while in the third arm, we utilized a normotensive WKY. It is possible that the pathological effects of long-standing hypertension underline this discrepancy, however, further studies will determine the role of hypertension on cell therapy efficacy.

Combining these therapies targets the early inflammatory response as shown in previous CDC MI studies (7,26) that contributes to infarct development, and also mitigates the later-phase detrimental effects of the SNS on cardiac structure and fibrosis. Previous preclinical studies report that CDCs improve cardiac function and structure, but the tested ischemia-reperfusion protocols do not extend to 14 weeks as was the case in the present study (6, 7, 9). We found, in fact, that early CDC therapy did not improve long-term ventricular dilation following MI. Moreover, systolic function, as quantified by LVEF, was not significantly superior to the PBS+Sham-RDN control group at this 14-week endpoint, indicating that CDC therapy is not independently sufficient for improving long-term cardiac performance. Alternatively, RDN mitigated MI-induced LV dilatation and preserved EF above PBS+Sham-RDN at all time points following treatment. The combination of CDCs+RDN did not further reduce dilation compared the PBS+RDN, indicating that improvements in remodeling were independently due to RDN. However, the combination of CDCs and RDN improved LVEF beyond either treatment alone. All treatments equally reduced total cardiac fibrosis and infarct expansion, demonstrating that fibrosis reductions were not the cause of late term improvements in EF and dilation. Without wishing to be bound by theory, the early infarct-reducing, anti-inflammatory actions of CDC therapy coupled with sympathetic modulation of maladaptive changes with RDN (FIG. 111) resulted in lasting effects on systolic function and remodeling that were not seen with either independent therapy.

Further, treating with CDCs and RDN simultaneously at the time of reperfusion may prove highly effective to attenuate the development of heart failure with reduced ejection fraction. Future studies will thoroughly examine and optimize the various combinations and timing; however, it is important to note that, clinically, both treatments can be administered via minimally invasive endovascular techniques and may be performed during the same percutaneous procedure. In the first two arms we utilized the SHR to more closely mimic multifactorial cardiovascular disease state and investigate cell therapy efficacy in hypertension. We then utilized normotensive WKY rats in the third arm to reaffirm our previous work detailing that improvements in LV function and remodeling following RDN therapy is blood pressure-independent and not strictly due to ventricular unloading. Hemodynamics and cardiomyocyte signaling, particularly beta-adrenergic signaling is different in WKY and SHR rats (1, 20). Therefore, there may be mechanistic differences associated with remodeling changes in the studies using SHR and WKY rats. Large animal and clinical results attest to the safety and efficacy of CDCs and RDN therapies individually (9, 19), and large animal studies will validate our present findings with combined therapy. For example, additional studies will validate the use of embodiments such as a clinical, endovascular RDN catheter and/or the extravascular radiofrequency RDN technique, such as that described herein. The major objective of the current study was to see if there were additive or synergistic effects of the two therapies. Follow-up studies will focus on mechanistic causes of early versus late remodeling differences between the two therapies.

We have introduced an alternative approach for improving cell therapy following MI. Specifically, we report the superiority of early I.C. delivery in combination with a repeated I.V. dosing regimen with cardiac-derived stem cells compared to single-dose I.C. treatment. We also investigated, for the first time, the combination of CDC cell therapy with RDN. Our findings reveal that CDCs improve early systolic function, while RDN maintains late-stage function and remodeling. Interestingly, when both therapies were given, LVEF was maintained at a higher level than either CDCs or RDN alone. Given the numerous limitations of current HF pharmacotherapies, combining these strategies may have therapeutic potential in treating post-infarction injury to attenuate cardiac remodeling and HF progression.

Perspective

Clinical Implication—Myocardial injury, such as myocardial infarction, can result in cell death and ultimately maladaptive remodeling and cardiac failure. Cell-based therapies have been investigated in humans following myocardial infarction and results from these trials suggest modest to no lasting effect. Attenuation of pathological sympathetic nervous system signaling via pharmacologic tools have been shown to decrease mortality in patients with myocardial injury and heart failure. Renal denervation is clinically tested endovascular technique that ablates renal sympathetic nerves that coarse along the renal arteries. Our results indicate that combining cell-based therapy with renal denervation has lasting improvements on function and structure in the post-infarcted heart. While the current paradigm for treating myocardial infarction is timely reflow, the findings from the current study have the potential to extend our treatment options to improve long-term outcomes.

Translational Outlook—Although the work in the present study was performed in a rodent model of myocardial infarction, the findings have substantial translational implications because both therapies have been tested independently in man. Importantly, both therapies are safe and well-tolerated in healthy subjects and subjects with cardiovascular disease. These results motivate clinical translation targeting a post-myocardial injury indication with combined approaches.

REFERENCES CITED IN THIS EXAMPLE

1. Anand-Srivastava M B (1992) Enhanced expression of inhibitory guanine nucleotide regulatory protein in spontaneously hypertensive rats. Relationship to adenylate cyclase inhibition. Biochem J 288 (Pt 1):79-85
2. Azizi M, Schmieder R E, Mahfoud F, Weber M A, Daemen J, Davies J, Basile J, Kirtane A J, Wang Y, Lobo M D, Saxena M, Feyz L, Rader F, Lurz P, Sayer J, Sapoval M, Levy T, Sanghvi K, Abraham J, Sharp A S P, Fisher N D L, Bloch M J, Reeve-Stoffer H, Coleman L, Mullin C, Mauri L (2018) Endovascular ultrasound renal denervation to treat hypertension (RADIANCE-HTN SOLO): a multicentre, international, single-blind, randomised, sham-controlled trial. Lancet 391:2335-2345 doi: 10.1016/s0140-6736(18)31082-1
3. Bhatt D L, Kandzari D E, O'Neill W W, D'Agostino R, Flack J M, Katzen B T, Leon M B, Liu M, Mauri L, Negoita M, Cohen S A, Oparil S, Rocha-Singh K, Townsend R R, Bakris G L, Investigators SH-(2014) A controlled trial of renal denervation for resistant hypertension. N Engl J Med 370:1393-1401 doi:10.1056/NEJMoa1402670
4. Bolli R (2017) Repeated Cell Therapy: A Paradigm Shift Whose Time Has Come. Circ Res 120:1072-1074 doi: 10.1161/CIRCRESAHA.117.310710
5. Chakravarty T, Makkar R R, Ascheim D D, Traverse J H, Schatz R, DeMaria A, Francis G S, Povsic T J, Smith R R, Lima J A, Pogoda J M, Marban L, Henry T D (2017) ALLogeneic Heart STem Cells to Achieve Myocardial Regeneration (ALLSTAR) Trial: Rationale and Design. Cell Transplant 26:205-214 doi:10.3727/096368916x692933
6. de Couto G, Gallet R, Cambier L, Jaghatspanyan E, Makkar N, Dawkins J F, Berman B P, Marban E (2017) Exosomal MicroRNA Transfer Into Macrophages Mediates Cellular Postconditioning. Circulation 136:200-214 doi:10.1161/CIRCULATIONAHA.116.024590
7. de Couto G, Liu W, Tseliou E, Sun B, Makkar N, Kanazawa H, Arditi M, Marban E (2015) Macrophages mediate cardioprotective cellular postconditioning in acute myocardial infarction. J Clin Invest 125:3147-3162 doi:10.1172/JCI81321
8. Fisher S A, Doree C, Mathur A, Martin-Rendon E (2015) Meta-analysis of cell therapy trials for patients with heart failure. Circ Res 116:1361-1377 doi:10.1161/CIRCRESAHA.116.304386
9. Gallet R, Dawkins J, Valle J, Simsolo E, de Couto G, Middleton R, Tseliou E, Luthringer D, Kreke M, Smith R R, Marban L, Ghaleh B, Marban E (2017) Exosomes secreted by cardiosphere-derived cells reduce scarring, attenuate adverse remodelling, and improve function in acute and chronic porcine myocardial infarction. Eur Heart J 38:201-211 doi:10.1093/eurheartj/ehw240

10. Guo Y, Wysoczynski M, Nong Y, Tomlin A, Zhu X, Gumpert A M, Nasr M, Muthusamy S, Li H, Book M, Khan A, Hong K U, Li Q, Bolli R (2017) Repeated doses of cardiac mesenchymal cells are therapeutically superior to a single dose in mice with old myocardial infarction. Basic Res Cardiol 112:18 doi:10.1007/s00395-017-0606-5

11. Gyongyosi M, Wojakowski W, Lemarchand P, Lunde K, Tendera M, Bartunek J, Marban E, Assmus B, Henry T D, Traverse J H, Moye L A, Surder D, Corti R, Huikuri H, Miettinen J, Wohrle J, Obradovic S, Roncalli J, Malliaras K, Pokushalov E, Romanov A, Kastrup J, Bergmann M W, Atsma D E, Diederichsen A, Edes I, Benedek I, Benedek T, Pejkov H, Nyolczas N, Pavo N, Bergler-Klein J, Pavo I J, Sylven C, Berti S, Navarese E P, Maurer G, Investigators A (2015) Meta-Analysis of Cell-based CaRdiac stUdiEs (ACCRUE) in patients with acute myocardial infarction based on individual patient data. Circ Res 116:1346-1360 doi:10.1161/CIRCRESAHA.116.304346

12. Hajjar R J, Schmidt U, Matsui T, Guerrero J L, Lee K H, Gwathmey J K, Dec G W, Semigran M J, Rosenzweig A (1998) Modulation of ventricular function through gene transfer in vivo. Proc Natl Acad Sci USA 95:5251-5256

13. Hodgkinson C P, Bareja A, Gomez J A, Dzau V J (2016) Emerging Concepts in Paracrine Mechanisms in Regenerative Cardiovascular Medicine and Biology. Circ Res 118:95-107 doi:10.1161/CIRCRESAHA.115.305373

14. Hong K U, Guo Y, Li Q H, Cao P, Al-Maqtari T, Vajravelu B N, Du J, Book M J, Zhu X, Nong Y, Bhatnagar A, Bolli R (2014) c-kit+ Cardiac stem cells alleviate post-myocardial infarction left ventricular dysfunction despite poor engraftment and negligible retention in the recipient heart. PloS one 9:e96725 doi: 10.1371/journal.pone.0096725

15. Janssens S, Dubois C, Bogaert J, Theunissen K, Deroose C, Desmet W, Kalantzi M, Herbots L, Sinnaeve P, Dens J, Maertens J, Rademakers F, Dymarkowski S, Gheysens O, Van Cleemput J, Bormans G, Nuyts J, Belmans A, Mortelmans L, Boogaerts M, Van de Werf F (2006) Autologous bone marrow-derived stem-cell transfer in patients with ST-segment elevation myocardial infarction: double-blind, randomised controlled trial. Lancet 367: 113-121 doi:10.1016/S0140-6736(05)67861-0

16. Kandzari D E, Bohm M, Mahfoud F, Townsend R R, Weber M A, Pocock S, Tsioufis K, Tousoulis D, Choi J W, East C, Brar S, Cohen S A, Fahy M, Pilcher G, Kario K (2018) Effect of renal denervation on blood pressure in the presence of antihypertensive drugs: 6-month efficacy and safety results from the SPYRAL HTN-ON MED proof-of-concept randomised trial. Lancet 391:2346-2355 doi: 10.1016/s0140-6736(18)30951-6

17. Khan M, Nickoloff E, Abramova T, Johnson J, Verma S K, Krishnamurthy P, Mackie A R, Vaughan E, Garikipati V N, Benedict C, Ramirez V, Lambers E, Ito A, Gao E, Misener S, Luongo T, Elrod J, Qin G, Houser S R, Koch W J, Kishore R (2015) Embryonic stem cell-derived exosomes promote endogenous repair mechanisms and enhance cardiac function following myocardial infarction. Circ Res 117:52-64 doi:10.1161/circresaha.117.305990

18. Lapchak P A, Boitano P D, de Couto G, Marban E (2018) Intravenous xenogeneic human cardiosphere-derived cell extracellular vesicles (exosomes) improves behavioral function in small-clot embolized rabbits. Exp Neurol 307:109-117 doi:10.1016/j.expneurol.2018.06.007

19. Lefer D J, Marban E (2017) Is Cardioprotection Dead? Circulation 136:98-109 doi:10.1161/CIRCULATIONAHA.116.027039

20. Limas C, Limas C J (1978) Reduced number of beta-adrenergic receptors in the myocardium of spontaneously hypertensive rats. Biochem Biophys Res Commun 83:710-714

21. Malliaras K, Makkar R R, Smith R R, Cheng K, Wu E, Bonow R O, Marban L, Mendizabal A, Cingolani E, Johnston P V, Gerstenblith G, Schuleri K H, Lardo A C, Marban E (2014) Intracoronary cardiosphere-derived cells after myocardial infarction: evidence of therapeutic regeneration in the final 1-year results of the CADUCEUS trial (CArdiosphere-Derived aUtologous stem CElls to reverse ventricUlar dySfunction). J Am Coll Cardiol 63:110-122 doi:10.1016/j.jacc.2013.08.724

22. Marban E (2018) A mechanistic roadmap for the clinical application of cardiac cell therapies. Nature Biomedical Engineering 2:353-361 doi:10.1038/s41551-018-0216-z 23. Martin-Rendon E, Brunskill S J, Hyde C J, Stanworth S J, Mathur A, Watt S M (2008) Autologous bone marrow stem cells to treat acute myocardial infarction: a systematic review. Eur Heart J 29:1807-1818 doi:10.1093/eurheartj/ehn220

24. Polhemus D J, Gao J, Scarborough A L, Trivedi R, McDonough K H, Goodchild T T, Smart F, Kapusta D R, Lefer D J (2016) Radiofrequency Renal Denervation Protects the Ischemic Heart via Inhibition of GRK2 and Increased Nitric Oxide Signaling. Circ Res 119:470-480 doi:10.1161/circresaha.115.308278

25. Polhemus D J, Trivedi R K, Gao J, Li Z, Scarborough A L, Goodchild T T, Varner K J, Xia H, Smart F W, Kapusta D R, Lefer D J (2017) Renal Sympathetic Denervation Protects the Failing Heart Via Inhibition of Neprilysin Activity in the Kidney. J Am Coll Cardiol 70:2139-2153 doi:10.1016/j.jacc.2017.08.056

26. Reich H, Tseliou E, de Couto G, Angert D, Valle J, Kubota Y, Luthringer D, Mirocha J, Sun B, Smith R R, Marban L, Marban E (2016) Repeated transplantation of allogeneic cardiosphere-derived cells boosts therapeutic benefits without immune sensitization in a rat model of myocardial infarction. J Heart Lung Transplant 35:1348-1357 doi:10.1016/j.healun.2016.05.008

27. Ripa R S, Jorgensen E, Wang Y, Thune J J, Nilsson J C, Sondergaard L, Johnsen H E, Kober L, Grande P, Kastrup J (2006) Stem cell mobilization induced by subcutaneous granulocyte-colony stimulating factor to improve cardiac regeneration after acute ST-elevation myocardial infarction: result of the double-blind, randomized, placebo-controlled stem cells in myocardial infarction (STEMMI) trial. Circulation 113:1983-1992 doi:10.1161/CIRCULATIONAHA.105.610469

28. Sanganalmath S K, Bolli R (2013) Cell therapy for heart failure: a comprehensive overview of experimental and clinical studies, current challenges, and future directions. Circ Res 113:810-834 doi:10.1161/CIRCRESAHA.113.300219

29. Sharp T E, Polhemus D J, Li Z, Spaletra P, Jenkins J S, Reilly J P, White C J, Kapusta D R, Lefer D J, Goodchild T T (2018) Renal Denervation Prevents Heart Failure Progression Via Inhibition of the Renin-Angiotensin System. J Am Coll Cardiol 72:2609-2621 doi:10.1016/j.jacc.2018.08.2186

30. Townsend R R, Mahfoud F, Kandzari D E, Kario K, Pocock S, Weber M A, Ewen S, Tsioufis K, Tousoulis D, Sharp A S P, Watkinson A F, Schmieder R E, Schmid A, Choi J W, East C, Walton A, Hopper I, Cohen D L, Wilensky R, Lee D P, Ma A, Devireddy C M, Lea J P, Lurz P C, Fengler K, Davies J, Chapman N, Cohen S A, DeBruin V, Fahy M, Jones D E, Rothman M, Bohm M (2017) Catheter-based renal denervation in patients with uncontrolled hypertension in the absence of antihypertensive medications (SPYRAL HTN-OFF MED): a randomised, sham-controlled, proof-of-concept trial. Lancet 390:2160-2170 doi:10.1016/s0140-6736(17)32281-x 31. Triposkiadis F, Karayannis G, Giamouzis G, Skoularigis J, Louridas G, Butler J (2009) The sympathetic nervous system in heart failure physiology, pathophysiology, and clinical implications. J Am Coll Cardiol 54:1747-1762 doi:10.1016/j.jacc.2009.05.015

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. A method of treating a subject suffering from heart disease in need thereof, wherein the method comprises attenuating at least one nerve of the renal artery of the subject; and administering to the subject a therapeutically effective amount of cardiac-derived stem cells.

2. The method of claim 1, wherein the method comprises attenuating the activity of the sympathetic nervous system of the subject.

3. The method of claim 2, wherein attenuating comprises vagal nerve stimulation (VNS), spinal cord stimulation (SCS), baroreceptor stimulation, renal denervation, tragus stimulation, endovascular stimulation, endovascular cardiac plexus stimulation or a combination thereof.

4. The method of claim 2, wherein attenuating is measured by microneurography, positron emission tomography (PET), heart rate, heart rate viability, heart rate recovery following exercise, baroreflex sensitivity, or a combination thereof.

5. The method of claim 1, wherein the nerve comprises a sympathetic nerve.

6. The method of claim 1, wherein attenuating at least one nerve of the renal artery comprises attenuation of at least one sympathetic nerve of the renal artery, wherein attenuation comprises ablation, radiofrequency denervation, ultrasound, chemical ablation, or a combination thereof.

7. The method of claim 1, wherein the administering of the cells occurs prior to or subsequent to nerve attenuation.

8. The method of claim 1, wherein the cells are administered intracoronarilly, intramyocardially, intravenously, intraarterially, or any combination thereof.

9. The method of claim 1, wherein the cells are autologous cells, homologous cells, allogenic cells, heterologous cells, or any combination thereof.

10. The method of claim 1, wherein the heart disease comprises a myocardial injury, myocardial infarction, heart failure, a congenital heart defect, a structural heart disease, an inflammation-mediated heart disease, hypertension-induced heart failure, or any combination thereof.

11. The method of claim 10, wherein heart failure comprises heart failure with reduced ejection fraction (HFrEF) or heart failure with preserved ejection fraction (HFpEF).

12. The method of claim 10, wherein the heart failure is metabolic-syndrome induced, artificially induced from a composition administered to a subject, naturally occurring, or a combination thereof.

13. The method of claim 12, wherein the composition comprises an anti-cancer agent.

14. The method of claim 1, further comprising the step of measuring cardiac function of the subject.

15. The method of claim 14, wherein the cardiac function comprises left ventricular ejection fraction, left ventricular diastolic function, or a combination thereof.

16. The method of claim 15, wherein an increase in the left ventricular ejection fraction indicates an improved cardiac function.

17. The method of claim 14, wherein the measuring comprises measuring a myocardial peptide marker, a circulating peptide marker, a heart pump function, a heart gross morphology, an enzymatic activity, or a combination thereof.

18. The method of claim 17, wherein heart pump function is measured by echocardiogram.

19. The method of claim 1, wherein myocardial injury results from heart failure, myocardial infarction, ischemia/reperfusion, or a combination thereof.

20. A method for improving cardiac function of a subject suffering from heart disease, the method comprising ablating at least one nerve of the renal artery; and administering to the subject a therapeutically effective amount of cardiac-derived stem cells.

* * * * *